United States Patent
Pepperberg et al.

(10) Patent No.: US 9,399,145 B2
(45) Date of Patent: Jul. 26, 2016

(54) NANOSCALE NEUROMODULATING PLATFORM FOR RETINA NEURON ACTIVATION APPARATUS AND METHOD

(71) Applicants: David R. Pepperberg, Chicago, IL (US); Karol Bruzik, Naperville, IL (US); Lan Yue, Chicago, IL (US); Michal Pawlowski, Chicago, IL (US); Haohua Qian, Vienna, VA (US)

(72) Inventors: David R. Pepperberg, Chicago, IL (US); Karol Bruzik, Naperville, IL (US); Lan Yue, Chicago, IL (US); Michal Pawlowski, Chicago, IL (US); Haohua Qian, Vienna, VA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 285 days.

(21) Appl. No.: 13/662,138

(22) Filed: Oct. 26, 2012

(65) Prior Publication Data
US 2013/0237899 A1 Sep. 12, 2013
US 2016/0129277 A9 May 12, 2016

Related U.S. Application Data

(63) Continuation-in-part of application No. 11/912,754, filed as application No. PCT/US2006/016232 on Apr. 28, 2006, now abandoned.

(60) Provisional application No. 60/675,600, filed on Apr. 28, 2005, provisional application No. 61/551,806, filed on Oct. 26, 2011.

(51) Int. Cl.
*A61K 31/655* (2006.01)
*A61N 5/06* (2006.01)
*C07C 245/08* (2006.01)
*C07D 207/452* (2006.01)

(52) U.S. Cl.
CPC .............. *A61N 5/062* (2013.01); *A61K 31/655* (2013.01); *A61N 5/0622* (2013.01); *C07C 245/08* (2013.01); *C07D 207/452* (2013.01)

(58) Field of Classification Search
None
See application file for complete search history.

(56) References Cited

U.S. PATENT DOCUMENTS

2004/0023952 A1* 2/2004 Leventhal ............ 514/221
2007/0054319 A1 3/2007 Boyden et al.

OTHER PUBLICATIONS

Amin, Jahanshah and Weiss, David S.; "GABAa receptor needs two homologous domains of the beta subunit for activation by GABA but not pentobarbital." Nature (1993) 366 p. 565-569.*
Wolf, Harold H. et al; "Anticonvulsant properties of some N-substituted hydantoins." J. Pharma. Sci. (1962) 51(1) p. 74-76.*
Gragoudas, Evangelos S. et al; "Pegaptanib for neovascular age related macular degeneration." N. Engl. J. Med. (2004) 351 p. 2805-2816.*
Yue, L. et al; "Light modulated activation of gabaa receptors by a propofol-azobenzene conjugate." Program 338.21, Neuroscience 2010 40th annual meeting, San Diego, CA, presented Nov. 15, 2010.*
Elul, R.; "Fixed charge in the cell membrane." J. Physiol (1967) 189 p. 351-365.*
Yue, Lan et al; "Photo-regulated activity of a teathered propofol derivative at gabaa receptors." Invest. Opthalmol. Vis. Sci. 52 (2011) ARVO E-abstract 1166, presented May 1, 2011.*
Rasmussen, Peter A. et al; "Propofol inhibits epileptiform activity in rat hippocampal slices." Epilep. Res. (1996) 25 p. 169-175.*
Purohit,Y. et al., "Block of muscle nicotinic receptors by choline suggests that the activation and desensitization gates act as distinct molecular entities," 2006, J Gen. Physiol., 127:703-717.
Purohit, Y. et al., "Estimating binding affinities of the nicotinic receptor for low-efficacy ligands using mixture of agonists and two-dimensional concentration-response relationships," 2006, J Gen. Physiol., 127:719-735.
Ragozzino D. et al., "Design and in vitro pharmacology of a selective y-aminobutyric acidc receptor antagonist," 1996, Molec. Pharmacol. 50:1024-1030.
Ramsey, D.J., "Streptozotocin-induced diabetes modulates GABA receptor activity of rat retinal neurons," 2007, Exp. Eye Res., 85:413-422.
Rossetti, A.O. et al, "Management of refractory status epilepticus in adults: still more questions than answers," 2011, Lancet Neural. 10:922-930.
Rotolo, T.C. et al., "Evidence for glycine, GABAA and GABAB receptors on rabbit OFF-alpha ganglion cells," 2003, Vis. Neurosci., 20:285-296.
Sadovski. 0. et al., "Spectral tuning of azobenzene photoswitches for biological applications," 2009, Angew. Chem. Int. Ed., 48:1484-1486.
Santhakumar, V. et al., "Contributions of the GABAA receptor α6 subunit to phasic and tonic inhibition revealed by a naturally occurring polymorphism in the α6 gene," 2006, J Neurosci., 26:3357-3364.
Segal et al., "Toward controlling gene expression at will: Selection and design of zinc finger domains recognizing each of the 5'-GNN-3' DNA target sequences," 1999, 96: 2758-2763.
Siegwart, R. et al., Molecular determinants for the action of general anesthetics at recombinant a2β3γ2 γ-aminobutyric acidA receptors, 2002, J Neurochem., 80:140-148.
Smith, S.L. et al., "Persistent chances in spontaneous firing of Purkinje neurons triggered by the nitric oxide signaling cascade," 2003, J Neurosci., 23:367-372.
Standaert, R.F. et al., "Abc amino acids: design, synthesis and properties of new photo elastic amino acids," 2006, J Org. Chem., 71:7952-7966.
Tan, KR et al., "Hooked on benzodiazepines: GABAA receptor subtypes and addiction," 2011, Trends Neurosci., 34:188-197.

(Continued)

Primary Examiner — Maury Audet
Assistant Examiner — Fred Reynolds
(74) Attorney, Agent, or Firm — McDonnell Boehnen Hulbert & Berghoff LLP

(57) ABSTRACT

The present invention relates to methods and compositions for modulating receptors in postsynaptic neurons of damaged or diseased retinas. The invention also related to methods for using the compositions set forth herein for treatment of diseases of hyperexcitability such as epilepsy.

26 Claims, 55 Drawing Sheets

(56) References Cited

OTHER PUBLICATIONS

Trapani, G. et al., "Propofol analogues. Synthesis, relationships between structure and affinity at GABAA receptor in rat brain, and differential electrophysiological profile at recombinant human GABAA receptors," 1998, J Med. Chem., 41:1846-1854.
Ueno, S. et al., "Bicuculline and gabazine are allosteric inhibitors of channel opening of the GABAA receptor," 1997, J Neurosci., 17:625-634.
Velazquez JL et al., Distribution and lateral mobility of GABA/benzodiazepine receptors on nerve cells, 1989, J Neurosci., 9:2163-2169.
Volgraf, M. et al., "Allosteric control of an ionotropoic glutamate receptor with an optical switch," 2006, Nature Chem. Biol., 2:47-52.
Vu, TQ et al., "Activation of membrane receptors by a neurotransmitter conjugate designed for surface attachment," 2005, Biomaterials, 26:1895-1903.
Wässle, H. et al., "Glycine and GABA receptors in the mammalian retina," 1998, Vision Res., 38:1411-1430.
Wisden, W. et al., "The cerebellum: a model system for studying GABAA receptor diversity," 1996, Neuropharmacol., 35:1139-1160.
Wulff, P. et al., "From synapse to behavior: rapid modulation of defined neuronal types with engineered GABAA receptors," 2007, Nature Neurosci. 10:923-929.
Xie, A. et al., "Propofol potentiates GABA-elicited responses of bipolar and ganglion cells in rat retina," 2010, Invest. Ophthalmol. Vis. Sci., 51: ARVO E-abstract 1865.
Xie A. et al., Enhancement of GABA-elicited responses of retinal ganglion cells by a photo-isomerizable compound, 2011, Invest. Ophthalmal. Vis. Sci., 52:ARVO E-abstract 1610.
Xie, A. et al., "2-Aminoethyl methylphosphonate (2-AEMP), a potent and rapidly acting antagonist of GABAA-p1 receptors," 2011, Molec. Pharmacol., Epub ahead of print.
Yizhar, 0. et al., "Optogenetics in neural systems," 2011, Neuron 71:9-34.
Yue L. et al., "Light-modulated activation of GABAA receptors by a propofol-azobenzene conjugate," Program No. 338.21. 2010 Neuroscience Meeting Planner, San Diego, CA: Society for Neuroscience, 2010. Online.
Yue L. et al., "Potentiating action of propofol at GABAA receptors of retinal bipolar cells," 2011, Invest. Ophthalmol. Vis. Sci., 52:2497-2509.
Yue L. et al., "Photo-regulated activity of a tethered propofol derivative at GABAA receptors," 2011, Invest. Ophthalmol. Vis. Sci. 52: ARVO E-abstract 1166.
Zemelman et al., "Selective Photostimulation of Genetically ChARGed Neurons," 2002, Neuron, 33:15-22.
Adamian, L. et al., "Structural model of p1 GABAc receptor based on evolutionary analysis: Testing of predicted protein-protein interactions involved in receptor assembly and function," 2009, Protein Sci., 18:2371-2383.
Adodra, S. et al., "Potentiation, activation and blockade of GABAA receptors of clonal murine hypothalamic GT 1-7 neurones by propofol," 1995, Br. J Pharmacol. 115: 953-960.
Amin, J. et al., "GABAA receptor needs two homologous domains of the β-subunit for activation by GABA but not by pentobarbital," 1993, Nature, 366:565-569.
Amin J. et al., "Two tyrosine residues on the a subunit are crucial for benzodiazepine binding and allosteric modulation of γ-aminobutyric acidA receptors," 1997, Mol. Pharmacol., 51:833-841.
Bali, M. et al., "The location of a closed channel gate in the GABAA receptor Channel," 2007, J Gen. Physiol., 129:145-159.
Bali, M. et al., "GABAA-induced intersubunit conformational movement in the GABAA receptor αIMI-β2M3 transmembrane subunit interface: experimental basis for homology modeling of an intravenous anesthetic binding site," 2009, J Neurosci., 29:3083-3092.
Banghart, M. et al., "Light-activated ion channels for remote control of neuronal firing," 2004, Nature Neurosci., 7:1381-1386.
Baulac, S. et al, "First genetic evidence of GABAA receptor dysfunction in epilepsy: a mutation in the y2-subunit gene," 2001, Nature Genetics, 28:46-48.
Beharry, A.A. et al., "Azobenzene photoswitches for biomolecules," 2011, Chem. Soc. Rev. 40:4422-4437.
Belelli, D. et al., "The interaction of the general anesthetic etomidate with the γ-aminobutyric acid type A receptor is influenced by a single amino acid," 1997, Proc. Natl. Acad. Sci. USA, 94:11031-11036.
Campagna-Slater, V. et al., "Anaesthetic binding sites for etomidate and propofol on a GABAA receptor model," 2007, Neurosci. Lett., 418:28-33.
Campagna-Slater, V. et al., "Molecular modelling of the GABAA ion channel protein," 2007, J Mol. Graph. Model., 25:721-730.
Chang, C.S. et al., "A single M1 residue in the ~2 subunit alters channel gating of GABAA receptor in anesthetic modulation and direct activation," 2003, J Biol. Chem., 278:42821-42828.
Colquhoun, D. et al., "The principles of the stochastic interpretation of ion-channel mechanisms," 1995, In Single Channel Recordings, 2nd Edition; Plenum Press, NY; pp. 397-482.
Drexler, B. et al., "Distinct actions of etomidate and propofol at β3-containing γ-aminobutyric acid type a receptors," 2009, Neuropharmacol., 57:446-455.
Farrant, M. et al., "Variations on an inhibitory theme: phasic and tonic activation of GABAA receptors," 2005, Nature. Rev. Neurosci., 6:215-229.
Fischer, K.F. et al., "Age-dependent and cell class-specific modulation of retinal ganglion cell bursting activity by GABA.," 1998, J Neurosci.,18: 3767-3778.
Firtschy, J.-M. et al., Differential dependence of axo-dendritic and axo-somatic GABAergic synapses on GABAA receptors containing the α1 subunit in Purkinje cells, 2006, J Neurosci., 26:3245-3255.
Forman, S., Clinical and molecular pharmacology of etomidate, 2011, Anesthesiology, 114:695-707.
Goodkin, H.P. et al, "Subunit-specific trafficking of GABAA receptors during status epilepticus," 2008, J Neurosci., 28:2527-2538.
Gorostiza, P. et al., "Optical switches for remote and noninvasive control of cell Signaling," 2008, Science, 322:395-399.
Gussin, HA, et al., "Binding of muscimol-conjugated quantum dots to GABAc receptors," 2006, J Amer. Chem. Soc., 128:15701-15713.
Gussin HA, "Quantum dot conjugates of GABA and muscimol: binding to GABAA and GABAc receptors," 2009, Annual Meeting, Society for Neuroscience. Abstract No. 114.4.
Gussin HA, et al., "GABAc receptor binding of quantum-dot conjugates of variable ligand valency," 2010, Bioconjugate Chem., 21:1455-1464.
Gussin, HA, et al., "Subunit-specific polyclonal antibody targeting human p1 GABAc receptor," 2011, Exp. Eye Res. 93:59-64.
Hausser, M. et al., "Tonic synaptic inhibition modulates neuronal output pattern and spatiotemporal synaptic integration," 1997, Neuron 19:665-678.
Husain, SS, et al., "p-Trifluoromethyldiazirinyl-etomidate: a potent photoreactive general anesthetic derivative of etomidate that is selective for ligand-gated cationic ion channels," 2010, J Med. Chem., 53:6432-6444.
Ishida, A.T. et al., "GABA-activated whole-cell currents in isolated retinal ganglion Cells," 1988, J Neurophysiol., 60:381-396.
Iyer, V.N. et al, Propofol infusion syndrome in patients with refractory status epilepticus: an 11-year clinical experience, 2009, Crit. Care Med., 37:3024-3030.
Janovjak, H. et al., "A light-gated, potassium-selective glutamate receptor for the optical inhibition of neuronal firing," 2010, Nature Neurosci., 13:1027-1032.
Jencks WR., "On the attribution and additivity of binding energies," 1981, Proc. Natl. Acad. Sci. USA, 78:4046-4050.
Jones, M.V. et al., "Defining affinity with the GABAA receptor," 1998, J Neurosci., 18:8590-8604.
Jurd, R. et al. "General anesthetic actions in viva strongly attenuated by a point mutation in the GABAA receptor β3 subunit," 2003, FASEB J, 17:250-252.
Krasowski, MD et al., "Propofol and other intravenous anesthetics have sites of action on the γ-aminobutyric acid type A receptor distinct from that for isoflurane," 1998, Molec. Pharmacol., 53:530-538.

(56) References Cited

OTHER PUBLICATIONS

Krasowski, MD et al., "Methionine 286 in transmembrane domain 3 of the GABAA receptor β subunit controls a binding cavity for propofol and other alkylphenol general anesthetics," 2001, Neuropharrnacol. 41:952-964.

Kucken, A.M. et al., "Identification of benzodiazepine binding site residues in the γ2 subunit of the γ-aminobutyric acid A receptor," 2000, Molec. Pharmacol., 57:932-939.

Kucken, A.M. et al., "Structural requirements for imidazobenzodiazepine binding to GABAA receptors," 2003, Molec. Pharmacol., 63: 289-296.

Lema, GM et al., "Modes and models of GABAA receptor gating," 2006, J Physiol., 572:183-200.

Macdonald, R.L. et al, "Mutations in GABAA receptor subunits associated with genetic epilepsies," 2010, J Physiol., 588:1861-1869.

Maciagiewicz, I. et al. "Design and synthesis of propofol analogs as new anesthetic agents," 2007, ACS National Meeting, Chicago, Illinois, Apr. 24-28, 2007.

Meera, P. et al., "Etomidate, propofol and the neurosteroid THDOC increase the GABA efficacy of recombinant α4β3δ and α4β3 GABAA receptors expressed in HEK cells," 2009, Neuropharmacology 56:155-160.

Mihic, S.J. et al., "Inhibition of PI receptor GABAergic currents by alcohols and volatile anesthetics," 1996, J Pharmacol. Exp. Ther., 277:411-416.

Moraga-Cid G. et al., "A single phenylalanine residue in the main intracellular loop of α1 γ-aminobutyric acid type A and glycine receptors influences their sensitivity to propofol," 2011, Anesthesiol., 115:464-473.

Mortensen, M. et al., "Distinct activities of GABA agonists at synaptic- and extrasynaptic-type GABAA receptors," 2010, J Physiol., 588:1251-1268.

Muni, NJ et al., "Activation of membrane receptors by neurotransmitter released from temperature-sensitive hydrogels.," 2006, J Neurosci. Meth., 151:97-105.

Muroi, Y. et al., "Distinct structural changes in the GABAA receptor elicited by pentobarbital and GABA," 2009, Biophys. J., 96:499-509.

Olsen, R.W., et al., "GABAA receptors: subtypes provide diversity of function and Pharmacology," 2009, Neuropharmacology, 56:141-148.

Pajouhesh, H. et al., "Medicinal chemical properties of successful central nervous system drugs," 2005, NeuroRx 6:541-553.

Palma, E. et al, "Abnormal GABAA receptors from the human epileptic hippocampal subiculum microtransplanted to Xenopus oocytes," 2005, Proc. Natl. Acad. Sci. USA, 102:2514-2518.

Power, K.N. et al, "Propofol treatment in adult refractory status epilepticus. Mortality risk and outcome," 2011, Epilepsy Res., 94:53-60.

\* cited by examiner

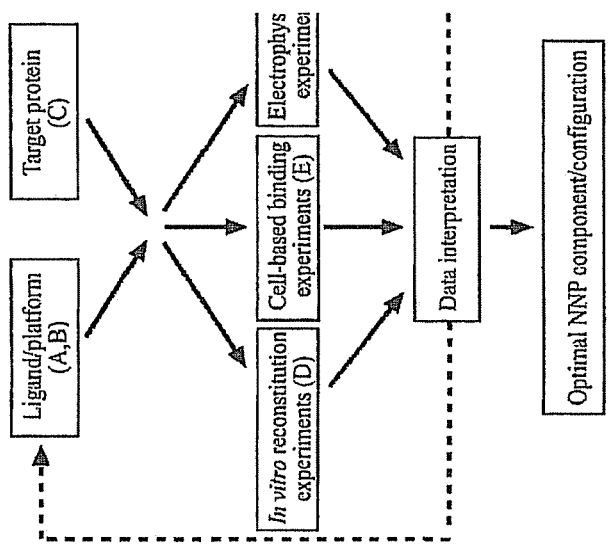

FIG. 10

```
      AchBP  (SEQ ID NO:1) DRADI  VNIRQTSRPDVI  TQHDREVA  SVSLKFINILEVNEITNEVDVVFNQQT   S  R   AWNSSHS--PDQV
       G-A α1 (SEQ ID NO:2) VFTRI  DRLLDGYDNRLR  GLGERVTE  KTDIFVTSFGPVSDHDMEYTIDVFFRQS  E  L  KFKEPMTV-LRLN
   Human-Rho1 (SEQ ID NO:3) TKSEQ  LRIDD-HDFSMR  GFGGPAIP  GVDVQVESLDSISEVDMDFTWTLYLRHY  ER  SFPSTNNLSMTFD
   Perch-rho1B (SEQ ID NO:4) TKTEK  LRIED-HDFTMR  GFGGRAVK  GVDVQVESLDAISEVDMDFTWTLYLRHY  ER  SFRSNTNQSMTFD AchBP              SVPISSL  P  LAAYNAI---SRPEVLTPQLA  VVS  E  VL  MPSIRQRFS  DVSGVDTESG-AT  RIKIG  WTR
        G-A α1              NLMASKI  P  FFFKNGKKSVARNMTMPNKLI  ITR  TI  L  TWRLTVRAE  PMRLEDFPMDAHA  PLKFG  YAY
    Human-Rho1              GRLVKKI  V  MFFVRSKRSFIRDTTTDNVML  VYP  DC  KVL  SLRVTVTAM  NMDFSRFPLDTQT  SLEIS  KAY
   Perch-rho1B              SRLVKKI  V  INFFVRSKKSFTHDTTTDNVMI  VYP  DC  KVL  SLRVTVTAM  SMDLSRFPLDTQT  SLEIS  KAY AchBP              HSREISVDPTTE-----NSDDSEYFSQYSRFEILDVTQKKNSVTY  CCPEA-  EDVEVSLNERK
        G-A α1              TRAEVVYEWTREPARSVVVAEDGS-RINQYDLLGQTVDSGIVQS  ----TGE  VVMTTHFRLKR
    Human-Rho1              TEDDLMLYWKKG-----NDSLKTDERISLSQFLIQEFHTTTRLAFY  S--STGW  NRLYINFTLRR
   Perch-rho1B              TDDDLMLYWKEG-----NRSLNTDERISLSQFLIKEFRTTTKLAFY  S--STGW  NRLYINFTLRR
```

FIG. 27
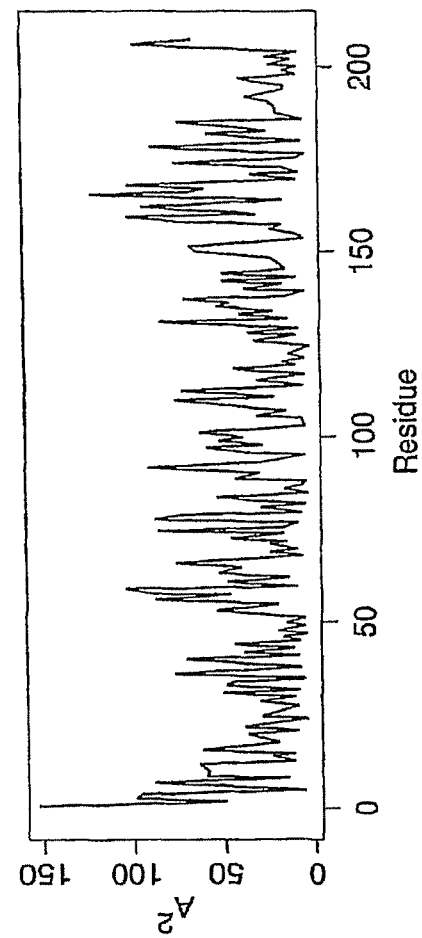
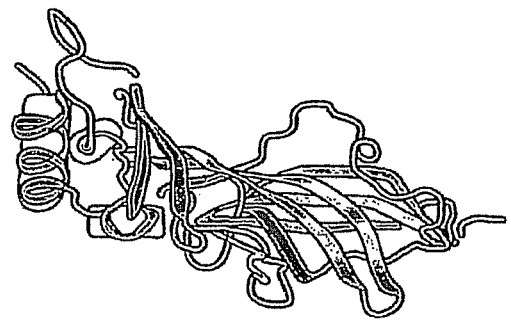

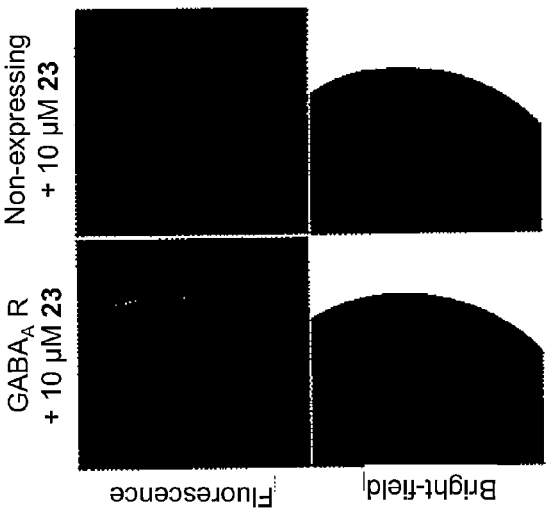
Figure 62
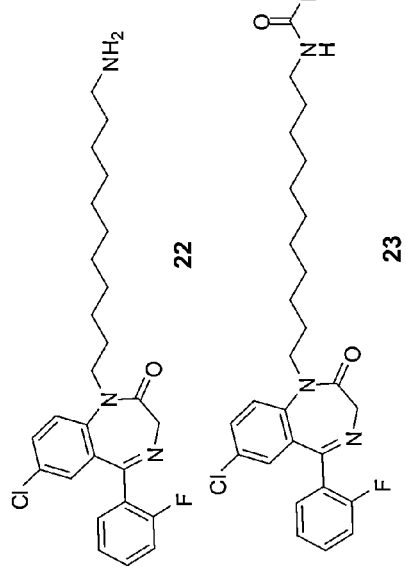
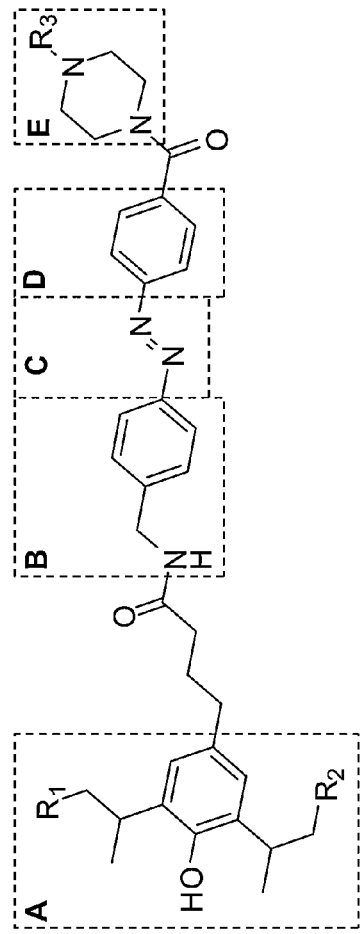
Figure 63

SEQUENCE LISTING

```
<160> NUMBER OF SEQ ID NOS: 8

<210> SEQ ID NO 1
<211> LENGTH: 202
<212> TYPE: PRT
<213> ORGANISM: snail

<400> SEQUENCE: 1

Asp Arg Ala Asp Ile Leu Tyr Asn Ile Arg Gln Thr Ser Arg Pro Asp
1               5                   10                  15

Val Ile Pro Thr Gln Arg Asp Arg Pro Val Ala Val Ser Val Ser Leu
            20                  25                  30

Lys Phe Ile Asn Ile Leu Glu Val Asn Glu Ile Thr Asn Glu Val Asp
        35                  40                  45

Val Val Phe Trp Gln Gln Thr Thr Trp Ser Asp Arg Thr Leu Ala Trp
    50                  55                  60

Asn Ser Ser His Ser Pro Asp Gln Val Ser Val Pro Ile Ser Ser Leu
65                  70                  75                  80

Trp Val Pro Asp Leu Ala Ala Tyr Asn Ala Ile Ser Lys Pro Glu Val
                85                  90                  95

Leu Thr Pro Gln Leu Ala Arg Val Val Ser Asp Gly Glu Val Leu Tyr
            100                 105                 110

Met Pro Ser Ile Arg Gln Arg Phe Ser Cys Asp Val Ser Gly Val Asp
        115                 120                 125

Thr Glu Ser Gly Ala Thr Cys Arg Ile Lys Ile Gly Ser Trp Thr His
    130                 135                 140

His Ser Arg Glu Ile Ser Val Asp Pro Thr Thr Glu Asn Ser Asp Asp
145                 150                 155                 160

Ser Glu Tyr Phe Ser Gln Tyr Ser Arg Phe Glu Ile Leu Asp Val Thr
                165                 170                 175

Gln Lys Lys Asn Ser Val Thr Tyr Ser Cys Cys Pro Glu Ala Tyr Glu
            180                 185                 190
```

Asp Val Glu Val Ser Leu Asn Phe Arg Lys
    195                  200

<210> SEQ ID NO 2
<211> LENGTH: 208
<212> TYPE: PRT
<213> ORGANISM: Homo sapiens

<400> SEQUENCE: 2

Val Phe Thr Arg Ile Leu Asp Arg Leu Asp Gly Tyr Asp Asn Arg
1             5              10            15

Leu Arg Pro Gly Leu Gly Glu Arg Val Thr Glu Val Lys Thr Asp Ile
          20             25            30

Phe Val Thr Ser Phe Gly Pro Val Ser Asp His Asp Met Glu Tyr Thr
        35             40            45

Ile Asp Val Phe Phe Arg Gln Ser Trp Lys Asp Glu Arg Leu Lys Phe
    50               55            60

Lys Gly Pro Met Thr Val Leu Arg Leu Asn Asn Leu Met Ala Ser Lys
65            70             75            80

Ile Trp Thr Pro Asp Thr Phe Phe His Asn Gly Lys Lys Ser Val Ala
        85             90            95

His Asn Met Thr Met Pro Asn Lys Leu Leu Arg Ile Thr Glu Asp Gly
          100           105          110

Thr Leu Leu Tyr Thr Met Arg Leu Thr Val Arg Ala Glu Cys Pro Met
        115           120          125

His Leu Glu Asp Phe Pro Met Asp Ala His Ala Cys Pro Leu Lys Phe
    130              135           140

Gly Ser Tyr Ala Tyr Thr Arg Ala Glu Val Val Tyr Glu Trp Thr Arg
145           150            155          160

Glu Pro Ala Arg Ser Val Val Ala Glu Asp Gly Ser Arg Leu Asn
          165           170          175

Gln Tyr Asp Leu Leu Gly Gln Thr Val Asp Ser Gly Ile Val Gln Ser
        180           185          190

Ser Thr Gly Glu Tyr Val Val Met Thr Thr His Phe His Leu Lys Arg
    195              200           205

<210> SEQ ID NO 3
<211> LENGTH: 207
<212> TYPE: PRT
<213> ORGANISM: Homo sapiens

<400> SEQUENCE: 3

Thr Lys Ser Glu Gln Leu Leu Arg Ile Asp Asp His Asp Phe Ser Met
1             5              10            15

Arg Pro Gly Phe Gly Gly Pro Ala Ile Pro Val Gly Val Asp Val Gln
          20             25            30

Val Glu Ser Leu Asp Ser Ile Ser Glu Val Asp Met Asp Phe Thr Met
        35             40            45

Thr Leu Tyr Leu Arg His Tyr Trp Lys Asp Glu Arg Leu Ser Phe Pro
    50               55            60

Ser Thr Asn Asn Leu Ser Met Thr Phe Asp Gly Arg Leu Val Lys Lys
65            70             75            80

Ile Trp Val Pro Asp Met Phe Phe Val His Ser Lys Arg Ser Phe Ile
        85             90            95

His Asp Thr Thr Thr Asp Asn Val Met Leu Arg Val Gln Pro Asp Gly
          100           105          110

```
Lys Val Leu Tyr Ser Leu Arg Val Thr Val Thr Ala Met Cys Asn Met
        115                 120                 125

Asp Phe Ser Arg Phe Pro Leu Asp Thr Gln Thr Cys Ser Leu Glu Ile
130                 135                 140

Glu Ser Tyr Ala Tyr Thr Glu Asp Asp Leu Met Leu Tyr Trp Lys Lys
145                 150                 155                 160

Gly Asn Asp Ser Leu Lys Thr Asp Glu Arg Ile Ser Leu Ser Gln Phe
                165                 170                 175

Leu Ile Gln Glu Phe His Thr Thr Lys Leu Ala Phe Tyr Ser Ser
            180                 185                 190

Thr Gly Trp Tyr Asn Arg Leu Tyr Ile Asn Phe Thr Leu Arg Arg
        195                 200                 205

<210> SEQ ID NO 4
<211> LENGTH: 207
<212> TYPE: PRT
<213> ORGANISM: Perch

<400> SEQUENCE: 4

Thr Lys Thr Glu His Leu Leu Arg Ile Glu Asp His Asp Phe Thr Met
1               5                   10                  15

Arg Pro Gly Phe Gly Gly Pro Ala Val Pro Val Gly Val Asp Val Gln
                20                  25                  30

Val Glu Ser Leu Asp Ala Ile Ser Glu Val Asp Met Asp Phe Thr Met
            35                  40                  45

Thr Leu Tyr Leu Arg His Tyr Trp Lys Asp Glu Arg Leu Ser Phe Arg
    50                  55                  60

Ser Asn Thr Asn Gln Ser Met Thr Phe Asp Ser Arg Leu Val Lys Lys
65                  70                  75                  80

Ile Trp Val Pro Asp Met Phe Phe Val His Ser Lys Lys Ser Phe Thr
                85                  90                  95

His Asp Thr Thr Thr Asp Asn Val Met Leu Arg Val Tyr Pro Asp Gly
            100                 105                 110

Lys Val Leu Tyr Ser Leu Arg Val Thr Val Thr Ala Met Cys Ser Met
        115                 120                 125

Asp Leu Ser Arg Phe Pro Leu Asp Thr Gln Thr Cys Ser Leu Glu Ile
130                 135                 140

Glu Ser Tyr Ala Tyr Thr Asp Asp Leu Met Leu Tyr Trp Lys Glu
145                 150                 155                 160

Gly Asn Arg Ser Leu Asn Thr Asp Glu Arg Ile Ser Leu Ser Gln Phe
                165                 170                 175

Leu Ile Trp Glu Phe His Thr Thr Lys Leu Ala Phe Tyr Ser Ser
            180                 185                 190

Thr Gly Trp Tyr Asn Arg Leu Tyr Ile Asn Phe Thr Leu Arg Arg
        195                 200                 205

<210> SEQ ID NO 5
<211> LENGTH: 12
<212> TYPE: PRT
<213> ORGANISM: artificial sequence
<220> FEATURE:
<223> OTHER INFORMATION: phage clones 9, 20 and 22

<400> SEQUENCE: 5

His Glu Thr Ala Val Arg Gln Thr Ser Pro Pro Met
1               5                   10
```

```
<210> SEQ ID NO 6
<211> LENGTH: 12
<212> TYPE: PRT
<213> ORGANISM: artificial sequence
<220> FEATURE:
<223> OTHER INFORMATION: phage clone 11

<400> SEQUENCE: 6

His Glu Thr Ala Cys Arg Gln Thr Ser Pro Pro Met
1               5                   10

<210> SEQ ID NO 7
<211> LENGTH: 12
<212> TYPE: PRT
<213> ORGANISM: artificial sequence
<220> FEATURE:
<223> OTHER INFORMATION: phage clone 6

<400> SEQUENCE: 7

His Pro Lys Gln Ser Leu His Phe Pro Asp Leu Ser
1               5                   10

<210> SEQ ID NO 8
<211> LENGTH: 12
<212> TYPE: PRT
<213> ORGANISM: artificial sequence
<220> FEATURE:
<223> OTHER INFORMATION: phage clones 4 and 6-1

<400> SEQUENCE: 8

His Pro Tyr Asp Ser Leu His Phe Pro Arg Met Ser
1               5                   10
```

NANOSCALE NEUROMODULATING PLATFORM FOR RETINA NEURON ACTIVATION APPARATUS AND METHOD

CROSS-REFERENCE TO RELATED APPLICATIONS

This application is a continuation-in-part of U.S. patent application Ser. No. 11/912,754, filed Jun. 12, 2008, which is a US national phase of International Application No. PCT/US06/16232 filed on Apr. 28, 2006 which claims the benefit of priority to U.S. provisional application Ser. No. 60/675,600 filed Apr. 28, 2005. This application also relates to and claims the benefit of priority to provisional application Ser. No. 61/551,506, filed Oct. 26, 2011. The disclosures of each of the above applications are incorporated herein by reference in their entireties.

STATEMENT REGARDING FEDERALLY SPONSORED RESEARCH

The present invention is supported by R03 grant numbers EY13693, EY016094, EY001792 from the National Institutes of Health. The U.S. Government has certain rights in the invention.

BACKGROUND OF THE INVENTION

1. Field of the Invention

The present invention relates to methods and compositions for modulating receptors in postsynaptic neurons of damaged or diseased retinas. The invention also related to methods for using the compositions set forth herein for treatment of diseases of hyperexcitability such as epilepsy.

2. Related Art

Retinal degenerative diseases such as age-related macular degeneration (ARMD) involve progressive dysfunction and deterioration of rod and cone photoreceptors (e.g., Jackson et al., 2002). There is evidence that photoreceptor loss can lead directly or indirectly to diminished function of proximal, i.e., post-photoreceptor, retinal neurons (e.g., Strettoi et al., 2003). However, in certain cases these proximal neurons appear largely to retain their capacity for neural signaling (Medeiros & Curcio, 2001; Varela et al., 2003; Marc et al., 2003; Strettoi et al., 2003; Cuenca et al., 2004); the retina's loss of visual function follows from the inability of deteriorating rods and cones to stimulate postsynaptic membrane receptor proteins of post-photoreceptor neurons. Recent research aimed at developing therapies for ARMD and related blinding diseases includes efforts based on photoreceptor rescue/replacement through genetic engineering, cell transplantation, and provision of growth factors and protective biochemical agents (LaVail et al., 1998; Hauswirth & Lewin, 2000; Acland et al., 2001; Gouras & Tanabe, 2003; Wang et al., 2004). However, these approaches have not yielded a robust and effective therapy for ARMD to date.

Thus, there is a need to achieve restoration of visual function resulting from ARMD and otherwise. Alternative possible treatment modalities include using a prosthetic device that electrically stimulates retinal neurons (Peachey & Chow, 1999; Humayun & de Juan, 1998; Rizzo et al., 2001; Zrenner, 2002; Margalit et al., 2002; Humayun et al., 2003) or focally delivers neurotransmitters within the retina (Iezzi et al., 2002; Gasperini et al., 2003; Peterman et al., 2003, 2004). Common to current designs of retinal prostheses is a macroscopic structure (i.e., dimensions in millimeters or greater) intended for implantation and interfacing with remaining healthy post-photoreceptor neurons. However, a major hurdle inherent in these approaches is the difficulty of achieving, with a macroscopic implanted device, microlocalization and specificity of neuronal stimulation, attributes that are recognized as critical for the retina's spatial resolution of visual stimuli.

In normal photoreception, visual signaling in rod and cone photoreceptors of the vertebrate retina begins with photoisomerization of the 11-cis retinal chromophore of visual pigment in the rod and cone outer segments. This photoisomerization event converts the retinal to the all-trans form and initiates activating conformational changes of the protein (opsin) moiety of the pigment. Pigment photoactivation in turn initiates a chain of biochemical reactions that generate an electrical response. These activating stages of phototransduction, and reactions including those that deactivate the pigment and downstream transduction intermediates, determine the peak amplitude and time course of the electrical response to light (Burns & Baylor, 2001; Arshaysky et al., 2002). Complete recovery of the transduction machinery after illumination, i.e., complete dark adaptation of the photoreceptor, requires the action of metabolic and transport reactions that remove the all-trans retinal chromophore from opsin and provide resynthesized 11-cis retinal that binds to opsin, thereby regenerating photosensitive pigment (Saari, 2000; McBee et al., 2001). The photoreceptor electrical response transiently down-regulates the release of L-glutamate neurotransmitter at chemical synapses formed with retinal horizontal and bipolar cells. Resulting changes in the activity of postsynaptic membrane receptors of the bipolar cells produce a bipolar cell electrical response, thereby conveying visual signals initiated in the photoreceptors to neurons of the inner retina (Dowling, 1987; Wu & Maple, 1998; Thoreson & Witkovsky, 1999; Nawy, 2000).

There is a need to develop further, more robust and effective methods for treating ARMD and other diseases of sight, which have significant negative effects on patient health and well-being, as well as negative economic consequences for individuals and society in general.

SUMMARY OF THE INVENTION

The invention provides compositions that can selectively attach to the extracellular face of postsynaptic membrane receptor proteins in second-order neurons of the human retina, and, by modulating the receptor's activity in response to light, restore visual signaling in retina damaged by photoreceptor degenerative disease.

In one aspect, the disclosure provides compounds of formula (I)

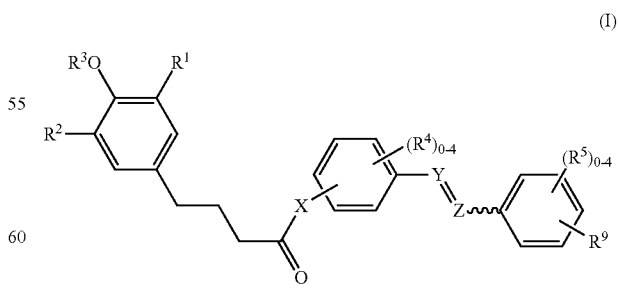

and pharmaceutically acceptable salts thereof, wherein
$R^1$ and $R^2$ are independently $C_1$-$C_{12}$ alkyl, halo($C_1$-$C_{12}$ alkyl), $C_2$-$C_{12}$ alkenyl, or $C_2$-$C_{12}$ alkynyl, each optionally substituted with 1, 2, 3 or 4 substituents selected from halogen, —CN, —NO$_2$, —OR$^6$, —NR$^6_2$, —CO$_2$R$^6$, —CONR$^6_2$, C$_3$-C$_8$ cycloalkyl, C$_3$-C$_8$ cycloalkenyl, aryl, heteroaryl, and heterocycle, wherein each cycloalkyl, cycloalkenyl, aryl, heteroaryl, and heterocycle is optionally substituted with 1, 2, 3 or 4 R$^7$;

R$^3$ is hydrogen, C$_1$-C$_6$ alkyl, or halo(C$_1$-C$_6$ alkyl);

R$^4$ and R$^5$ are independently halogen, —CN, —NO$_2$, C$_1$-C$_6$ alkyl, halo(C$_1$-C$_6$ alkyl), —OR$^6$, —NR$^6_2$, —CO$_2$R$^6$, or —CONR$^6_2$;

X is —N(R$^8$)—, —N(R$^8$)CH$_2$—, —N(R$^8$)CHR$^8$—, —N(R$^8$)(CHR$^8$)$_{2-5}$—, or —O—;

Y=Z is —N=N— or —C(R$^8$)=C(R$^8$)—; and

R$^9$ is hydrogen, —CHR$^{6a}$, —OR$^{6a}$, —NR$^{6a}_2$, —CO$_2$R$^{6a}$, —CONR$^{6a}_2$, —CON(R$^8$)—(CH$_2$)$_{1-6}$—NR$^{6a}_2$, —N(R$^8$)CO—(CH$_2$)$_{1-6}$—NR$^{6a}_2$, —CON(R$^8$)—(CH$_2$)$_{1-6}$—N(R$^8$)COR$^{6a}$, —N(R$^8$)CO—(CH$_2$)$_{1-6}$—N(R$^8$)COR$^{6a}$, —CON(R$^8$)—(CH$_2$)$_{1-6}$—N(R$^8$)COR$^{10}$, or —N(R$^8$)CO—(CH$_2$)$_{1-6}$—N(R$^8$)COR$^{10}$, wherein R$^{10}$ is —CH$_2$CH$_2$(OCH$_2$CH$_2$)$_{2-50}$—N(R$^8$)COR$^{6a}$;

where each R$^6$ independently is hydrogen, C$_1$-C$_6$ alkyl or halo(C$_1$-C$_6$ alkyl), wherein each alkyl is optionally substituted with 1, 2, 3 or 4 R$^7$, or two R$^6$ with the nitrogen to which they are attached form a heterocycle optionally substituted with 1, 2, 3 or 4 R$^7$;

where each R$^{6a}$ independently is hydrogen, C$_1$-C$_6$ alkyl, halo(C$_1$-C$_6$ alkyl), C$_3$-C$_8$ cycloalkyl, aryl, heteroaryl, heterocycle, aryl(C$_1$-C$_6$ alkyl)-, C$_3$-C$_8$cycloalkyl(C$_1$-C$_6$ alkyl)-, aryl(C$_1$-C$_6$ alkyl)-, heteroaryl(C$_1$-C$_6$ alkyl)-, or heterocycle(C$_1$-C$_6$ alkyl)-, wherein each alkyl, cycloalkyl, aryl, heteroaryl, and heterocycle is optionally substituted with 1, 2, 3 or 4 R$^7$, or two R$^6$ with the nitrogen to which they are attached form a heterocycle optionally substituted with 1, 2, 3 or 4 R$^7$;

where each R$^7$ independently is halogen, —CN, —NO$_2$, —N$_3$, C$_1$-C$_6$ alkyl, halo(C$_1$-C$_6$ alkyl), C$_1$-C$_6$ alkoxy, amino, C$_1$-C$_6$alkylamino, diC$_1$-C$_6$alkylamino, —CO$_2$H, —COH, —CO$_2$R$^8$, or —CON(R$^8$)$_2$; and wherein each R$^8$ is independently hydrogen or C$_1$-C$_6$ alkyl.

In particular embodiments, the disclosure provides compounds as described above with reference to formula (I) or (II), wherein R$^3$ is hydrogen.

In other embodiments, the disclosure provides compounds as described above with any reference to formula (I) or (II), wherein R$^1$ and R$^2$ are independently C$_1$-C$_{12}$ alkyl, optionally substituted with one to four substituents selected from halogen, —CN, —NO$_2$, C$_1$-C$_6$ alkyl, halo(C$_1$-C$_6$ alkyl), —OR$^6$, —NR$^6_2$, —CO$_2$R$^6$, —CONR$^6_2$, C$_3$-C$_8$ cycloalkyl, C$_3$-C$_8$cycloalkenyl, aryl, heteroaryl, and heterocycle. In another embodiment, R$^1$ and R$^2$ are independently C$_1$-C$_{12}$ alkyl, optionally substituted with one to four substituents selected from halogen, —CN, —NO$_2$, C$_1$-C$_6$ alkyl, halo(C$_1$-C$_6$ alkyl), —OR$^6$, —NR$^6_2$, —CO$_2$R$^6$ and —CONR$^6_2$. In yet another embodiment, R$^1$ and R$^2$ are independently unsubstituted C$_1$-C$_{12}$ alkyl. In yet another embodiment, R$^1$ and R$^2$ are independently unsubstituted C$_1$-C$_6$ alkyl.

In particular embodiments, the disclosure provides compounds as described above with any reference to formula (I) or (II), wherein R$^1$ and R$^2$ are both —CH(CH$_3$)$_2$.

In particular embodiments, the disclosure provides compounds as described above with any reference to formula (I) or (II), wherein X is —NH— or —O—. In other particular embodiments, X is —NH—. In yet other particular embodiments, X is —O—.

In particular embodiments, the disclosure provides compounds as described above with any reference to formula (I) or (II), wherein X is —N(R$^8$)CH$_2$—, —N(R$^8$)CHR$^8$—, or —N(R$^8$)(CHR$^8$)$_{2-5}$—.

In other particular embodiments, the disclosure provides compounds as described above with any reference to formula (I) or (II), wherein X is —N(R$^8$)CH$_2$—. In yet another embodiment, X is —NHCH$_2$—.

In particular embodiments, the disclosure provides compounds as described above with any reference to formula (I)

In certain embodiments, the disclosure provides compounds of formula (I) that have formula (II):

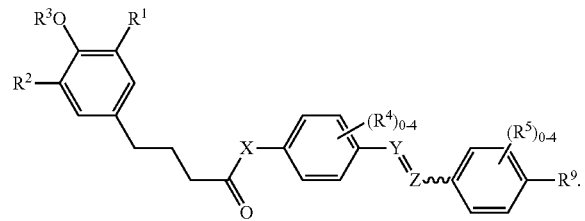

wherein the substituents (R$^1$, R$^2$, R$^3$, R$^4$, R$^5$, R$^6$, R$^7$, R$^8$, R$^9$, R$^{10}$, X, and Y=Z) are as defined above.

In particular embodiments, the compounds of formulae (I) and (II) as described herein, R$^1$ and R$^2$ are independently C$_1$-C$_{12}$ alkyl, halo(C$_1$-C$_{12}$ alkyl), C$_2$-C$_{12}$ alkenyl, or C$_2$-C$_{12}$ alkynyl, each optionally substituted with 1, 2, 3 or 4 substituents selected from halogen, —CN, —NO$_2$, —OR$^6$, —NR$^6_2$, —CO$_2$R$^6$ and —CONR$^6_2$;

R$^3$ is hydrogen, C$_1$-C$_6$ alkyl, or halo(C$_1$-C$_6$ alkyl);

or (II), wherein R⁴ and R⁵ are independently selected from the group consisting of halogen, —CN, —NO₂, C₁-C₆ alkyl, halo(C₁-C₆ alkyl), —OR⁶, and —NR⁶₂.

In other particular embodiments, the disclosure provides compounds as described above with any reference to formula (I) or (II), wherein R⁴ and R⁵ are absent. In such embodiment, the compounds are of formula:

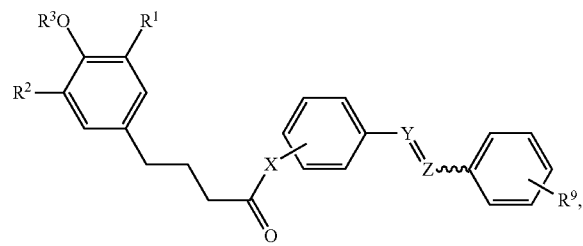

or of formula:

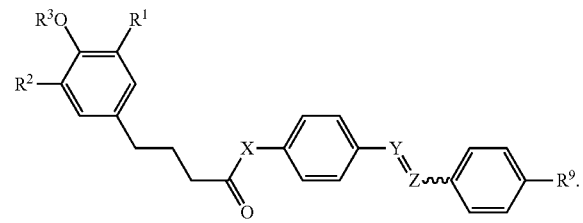

wherein the substituents (R¹, R², R³, R⁶, R⁷, R⁸, R⁹, R¹⁰, X, and Y═Z) are as defined above.

In particular embodiments, the disclosure provides compounds as described above with any reference to formula (I) or (II), wherein Y═Z is —N═N—. Such compounds can have cis or trans configuration. In further particular embodiments, Y═Z is —N═N— and is trans or (E) isomer.

In other particular embodiments, the disclosure provides compounds as described above with any reference to formula (I) or (II), wherein Y═Z is —CH═CH—. Such compounds can have cis or trans configuration. In further particular embodiments, Y═Z is —CH═CH— and is trans or (E) isomer.

In other particular embodiments, the disclosure provides compounds as described above with any reference to formula (I) or (II), wherein R⁹ is hydrogen, —CHR⁶ᵃ, —OR⁶ᵃ, —NR⁶ᵃ₂, —CO₂R⁶ᵃ, —CONR⁶ᵃ₂, —CON(R⁸)—(CH₂)₁₋₆—NR⁶ᵃ₂, —CON(R⁸)—(CH₂)₁₋₆—N(R⁸)COR⁶ᵃ, or —CON(R⁸)—(CH₂)₁₋₆—N(R⁸)COR¹⁰,
wherein R¹⁰ is —CH₂CH₂(OCH₂CH₂)₂₋₅₀—N(R⁸) COR⁶ᵃ.

In particular embodiments, the disclosure provides compounds as described above with any reference to formula (I) or (II), wherein R⁹ is hydrogen, —CO₂R⁶ᵃ, —CONR⁶ᵃ₂, —CON(R⁸)—(CH₂)₁₋₆—NR⁶ᵃ₂, —CON(R⁸)—(CH₂)₁₋₆—N(R⁸)COR⁶ᵃ, or —CON(R⁸)—(CH₂)₁₋₆—N(R⁸)COR¹⁰, wherein R¹⁰ is —CH₂CH₂(OCH₂CH₂)₂₋₅₀—N(R⁸)COR⁶ᵃ.

In other particular embodiments, the disclosure provides compounds as described above with any reference to formula (I) or (II), wherein R⁹ is hydrogen, —CO₂H, or —CONH—(CH₂)₂—NH₂.

In yet other particular embodiments, the disclosure provides compounds as described above with any reference to formula (I) or (II), wherein R⁹ is —CONH—(CH₂)₂—NH₂.

In yet further particular embodiments, the disclosure provides compounds as described above with any reference to formula (I) or (II), wherein R⁹ is —CONH—(CH₂)₂—NH-COR¹⁰, wherein R¹⁰ is —CH₂CH₂(OCH₂CH₂)₂₋₅₀—NHCOR⁶ᵃ, and R⁶ᵃ is heterocycle(C₁-C₆ alkyl) or heteroaryl (C₁-C₆ alkyl). In certain particular embodiments, R⁹ is

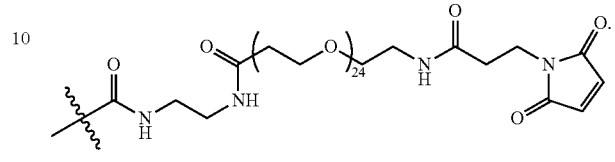

In particular embodiments, the disclosure provides compounds as described above with reference to formula (I) or (I), wherein each R⁶ is independently hydrogen, C₁-C₆ alkyl or halo(C₁-C₆ alkyl), wherein each alkyl is optionally substituted with 1, 2, 3 or 4 R⁷, or two R⁶ with the nitrogen to which they are attached form a heterocycle optionally substituted with 1, 2, 3 or 4 R⁷.

In another aspect, the disclosure provides compounds of formula (III)

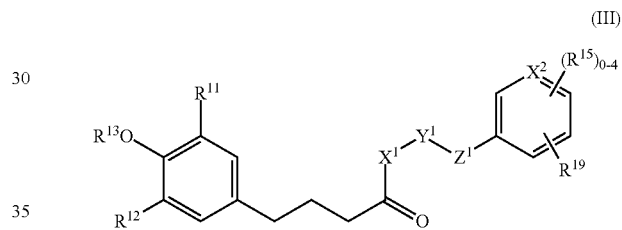

and pharmaceutically acceptable salts thereof, wherein
R¹¹ and R¹² are independently C₁-C₁₂ alkyl, halo(C₁-C₁₂ alkyl), C₂-C₁₂ alkenyl, or C₂-C₁₂ alkynyl, each optionally substituted with 1, 2, 3 or 4 substituents selected from halogen, —CN, —NO₂, C₁-C₆ alkyl, halo(C₁-C₆ alkyl), —OR¹⁶, —NR¹⁶₂, —CO₂R¹⁶, —CONR¹⁶₂, C₃-C₈ cycloalkyl, C₃-C₈cycloalkenyl, aryl, heteroaryl, and heterocycle, wherein each cycloalkyl, cycloalkenyl, aryl, heteroaryl, and heterocycle is optionally substituted with 1, 2, 3 or 4 R¹⁷;
R¹³ is hydrogen, C₁-C₆ alkyl, or halo(C₁-C₆ alkyl);
R¹⁵ is independently halogen, —CN, —NO₂, C₁-C₆ alkyl, halo(C₁-C₆ alkyl), —OR¹⁶, —NR¹⁶₂, —CO₂R¹⁶, or —CONR¹⁶₂;
X¹ is —N(R¹⁸)—, —N(R¹⁸)CHR¹⁸—, —N(R¹⁸) (CHR¹⁸)₂₋₈—, —O—, —OCHR¹⁸—, —O(CHR¹⁸)₂₋₈—, —CHR¹⁸—, or —(CHR¹⁸)₂₋₈—;
Y¹—Z¹ is -aryl-, -aryl-CO(NR¹⁸)—, -aryl-CO₂—, -aryl-OCO—, -heteroaryl-, -heteroaryl-CO(NR¹⁸)—, -heteroaryl-CO₂—, -heteroaryl-OCO—, -heterocyclyl-, -heterocyclyl-CO(NR¹⁸)—, -heterocyclyl-CO₂—, -heterocyclyl-OCO—, —C₃-C₈cycloalkyl-, —C₃-C₈cycloalkyl-CO(NR¹⁸)—, —C₃-C₈cycloalkyl-CO₂—, —C₃-C₈cycloalkyl-OCO—, —CO(NR¹⁸)—, —(NR¹⁸) CO—, —CO₂—, or —OCO—;
X² is CH, C bearing one of the R¹⁵, or N;
R¹⁹ is hydrogen, —CHR¹⁶ᵃ, —OR¹⁶ᵃ, —NR¹⁶ᵃ₂, —CO₂R¹⁶ᵃ, —CONR¹⁶ᵃ₂, —CON(R¹⁸)—(CH₂)₁₋₆—NR¹⁶ᵃ₂, —N(R¹⁸)CO—(CH₂)₁₋₆—NR¹⁶ᵃ₂, —CON (R¹⁸)—(CH₂)₁₋₆—N(R¹⁸)COR¹⁶ᵃ, —N(R¹⁸)CO—

$(CH_2)_{1-6}$—$N(R^{18})COR^{16a}$, —$CON(R^{18})$—$(CH_2)_{1-6}$—$N(R^{18})COR^{20}$, or —$N(R^{18})CO$—$(CH_2)_{1-6}$—$N(R^{18})COR^{20}$, wherein $R^{20}$ is —$CH_2CH_2(OCH_2CH_2)_{2-50}$—$N(R^{18})COR^{16a}$;

where each $R^{16}$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with $R^{17}$, or two $R^{16}$ with the nitrogen to which they are attached form a heterocycle optionally substituted with $R^{17}$;

where each $R^{16a}$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;

where each $R^{17}$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —$CO_2H$, —COH, —$CO_2R^{18}$, or —$CON(R^{18})_2$; and wherein each $R^{18}$ independently is hydrogen or $C_1$-$C_6$ alkyl.

In certain particular embodiments, the disclosure provides compounds as described above with reference to formula (III), wherein $R^{13}$ is hydrogen.

In other particular embodiments, the disclosure provides compounds as described above with any reference to formula (III), wherein $R^{11}$ and $R^{12}$ are independently $C_1$-$C_{12}$ alkyl, optionally substituted with one to four substituents selected from halogen, —CN, —$NO_2$, $C_1$-$C_6$ alkyl, halo($C_1$-$C_6$ alkyl), —$OR^{16}$, —$NR^{16}_2$, —$CO_2R^{16}$, —$CONR^{16}_2$, $C_3$-$C_8$ cycloalkyl, $C_3$-$C_8$cycloalkenyl, aryl, heteroaryl, and heterocycle. In another embodiment, $R^1$ and $R^2$ are independently $C_1$-$C_{12}$ alkyl, optionally substituted with one to four substituents selected from halogen, —CN, —$NO_2$, $C_1$-$C_6$ alkyl, halo($C_1$-$C_6$ alkyl), —$OR^{16}$, —$NR^{16}_2$, —$CO_2R^{16}$ and —$CONR^{16}_2$. In yet another embodiment, $R^{11}$ and $R^{12}$ are independently unsubstituted $C_1$-$C_{12}$ alkyl. In yet another embodiment, $R^{11}$ and $R^{12}$ are independently unsubstituted $C_1$-$C_6$ alkyl.

In certain particular embodiments, the disclosure provides compounds as described above with any reference to formula (III), wherein $R^{11}$ and $R^{12}$ are both —$CH(CH_3)_2$.

In particular embodiments, the disclosure provides compounds as described above with any reference to formula (III), wherein $X^2$ is CH. In certain particular embodiments, the disclosure provides compounds as described above with any reference to formula (III), wherein $X^2$ is N.

In particular embodiments, the disclosure provides compounds as described above with any reference to formula (III), wherein $R^{15}$ is independently selected from the group consisting of halogen, —CN, —$NO_2$, $C_1$-$C_6$ alkyl, halo($C_1$-$C_6$ alkyl), —$OR^{16}$, and —$NR^{16}_2$.

In certain particular embodiments, the disclosure provides compounds as described above with any reference to formula (III), wherein $R^{15}$ is absent.

In particular embodiments, the disclosure provides compounds as described above with any reference to formula (III), wherein $R^{19}$ is hydrogen, —$CHR^{16a}$, —$OR^{16a}$, —$NR^{16a}_2$, —$CO_2R^{16a}$, —$CONR^{16a}_2$, —$CON(R^{18})$—$(CH_2)_{1-6}$—$NR^{16a}_2$, —$CON(R^{18})$—$(CH_2)_{1-6}$—$N(R^{18})COR^{16a}$, or —$CON(R^{18})$—$(CH_2)_{1-6}$—$N(R^{18})COR^{20}$, wherein $R^{20}$ is —$CH_2CH_2(OCH_2CH_2)_{2-50}$—$N(R^{18})COR^{16a}$.

In particular embodiments, the disclosure provides compounds as described above with any reference to formula (III), wherein $R^{19}$ is hydrogen, —$CO_2R^{16a}$, —$CONR^{16a}_2$, —$CON(R^{18})$—$(CH_2)_{1-6}$—$NR^{16a}_2$, —$CON(R^{18})$—$(CH_2)_{1-6}$—$N(R^{18})COR^{16a}$, or —$CON(R^{18})$—$(CH_2)_{1-6}$—$N(R^{18})COR^{20}$, wherein $R^{20}$ is —$CH_2CH_2(OCH_2CH_2)_{2-50}$—$N(R^{18})COR^{16a}$.

In other particular embodiments, the disclosure provides compounds as described above with any reference to formula (III), wherein $R^{19}$ is hydrogen, —$CO_2H$, or —CONH—$(CH_2)_2$—$NH_2$.

In yet other particular embodiments, the disclosure provides compounds as described above with any reference to formula (III), wherein $R^{19}$ is —CONH—$(CH_2)_2$—$NH_2$.

In yet further particular embodiments, the disclosure provides compounds as described above with any reference to formula (III), wherein $R^{19}$ is —$CONR^{16a}_2$, and two $R^{16a}$ with the nitrogen to which they are attached form a heterocycle optionally substituted with $R^{17}$. In another embodiment, $R^{19}$ is morpholinylcarbonyl or piperazinylcarbonyl.

In particular embodiments, the disclosure provides compounds as described above with any reference to formula (III), wherein $X^1$ is —$N(R^{18})CHR^{18}$—, —$N(R^{18})(CHR^{18})_{2-8}$—, —$CHR^{18}$—, or —$(CHR^{18})_{2-8}$—.

In other particular embodiments, the disclosure provides compounds as described above with any reference to formula (III), wherein $X^1$ is —$N(R^{18})(CHR^{18})_{2-8}$—. In another embodiment, $X^1$ is —$NH(CH_2)_{2-8}$—. In yet another particular embodiment, $X^1$ is —$NH(CH_2)_{2-6}$—.

In yet other particular embodiments, the disclosure provides compounds as described above with any reference to formula (III), wherein $X^1$ is —$(CHR^{18})_{2-8}$—. In other particular embodiments, $X^1$ is —$(CH_2)_{2-8}$—. In yet other particular embodiments, $X^1$ is —$(CH_2)_{2-6}$—.

In other particular embodiments, the disclosure provides compounds as described above with any reference to formula (III), wherein $Y^1$—$Z^1$ is -heteroaryl-, -heterocyclyl-CO($NR^{18}$)—, —$C_3$-$C_8$cycloalkyl-CO($NR^{18}$)—, or —CO($NR^{18}$)—.

In other particular embodiments, the disclosure provides compounds as described above with any reference to formula (III), wherein $Y^1$—$Z^1$ is —CO(NH)—.

In other particular embodiments, the disclosure provides compounds as described above with any reference to formula (III), wherein $Y^1$—$Z^1$ is imidazolyl or triazolyl.

In other particular embodiments t, the disclosure provides compounds as described above with any reference to formula (III), wherein $Y^1$—$Z^1$ is -heterocyclyl-CO($NR^{18}$)—, or —$C_3$-$C_8$cycloalkyl-CO($NR^{18}$)—.

In another aspect, the invention provides methods of activating a GABA receptor comprising administering an effective amount of a compound or a pharmaceutically acceptable salt of the compounds of formula (I). In some embodiments the GABA receptor is a $GABA_A$ receptor.

In other aspects, the invention provides methods of treating a disease of hyperexcitability or retinal neurodegenerative disease comprising administering an effective amount of a compound or a pharmaceutically acceptable salt of the compounds of formula (I). In certain embodiments the hyperexcitability disease is epilepsy. In other embodiments, the retinal neurodegenerative disease is macular degeneration.

The essential role of rod and cone photoreceptors is to generate transient light-dependent molecular signals (reduced glutamate release) that modulate the activities of postsynaptic membrane receptors of retinal bipolar and horizontal cells. Thus, loss of retinal function resulting from photoreceptor degeneration could in principle be circumvented by introducing, at the postsynaptic membrane of proximal retinal neurons, molecular structures that bind to membrane receptors and modulate receptor activity in light-dependent fashion. The broad requirements of such a structure would include: accessibility to the receptor protein (i.e., dimensions on the order of microns to allow diffusion to the receptor when introduced into the retinal extracellular milieu); specificity of attachment to the extracellular face of the target receptor protein; high photic sensitivity (high absorptivity of light incident on the retina); ability to generate sufficiently large and long-lived changes in receptor activity upon photon absorption; spontaneous shut-off and recovery to the pre-illumination state following light absorption; biological compatibility (non-toxicity); and long-term physical/chemical stability, including resistance to native degradative enzymes.

FIG. 1 illustrates signal transmission at a normally functioning chemical synapse for which the postsynaptic membrane receptor is a hypothetical ligand-gated ion channel (LGIC) comprising two subunits and a single ligand-binding site. Neurotransmitter (filled circles) released from the presynaptic neuron in response to stimulation diffuses across the synaptic cleft and binds to the postsynaptic membrane receptors. The resulting activation of these receptor proteins opens transmembrane ion channels (inward-pointing arrow), thereby generating an electrical signal in the postsynaptic neuron.

FIG. 2 illustrates (not to scale) a "nanoscale neuromodulating platform (NNP)" of the present invention, wherein NNPs introduced as a suspension into the vicinity of the retina (intravitreal or subretinal injection into the eye) diffuses through extracellular clefts to target membrane receptors, where high-affinity binding to the receptor's extracellular face anchors the NNP. FIG. 2 further describes the function of a NNP under disease conditions where the pre-synaptic neuron has deteriorated. The NNP consists of derivatized native neurotransmitter or analog (small filled circle), here termed an effector, tethered to a structure (open circle labeled NNP) that incorporates a photoswitch, and an anchoring component (open triangle) that selectively and covalently attaches the NNP to the extracellular face of the receptor protein. Photon absorption by the NNP produces a transient conformational change in a linker arm that moves the effector to the receptor protein's ligand-binding site and thereby transiently activates the receptor, i.e., opens the receptor's ion channel. As a self-contained photosensor (i.e., not dependent on interfacing with a macroscopic structure) with localized stimulating activity, the envisioned NNP would achieve the critical feature of microspecific functionality.

Thus, in other aspects, the invention provides a nanoscale neuromodulator platform apparatus for activating membrane receptors of a postsynaptic neuron in response to light wherein the apparatus comprises an effector, a photoswitch wherein the photoswitch has a first and second configuration, an anchor and a linker between the effector and the photoswitch. Molecular structures (NNPs) selectively bind to GABA postsynaptic receptors, in particular GABAc postsynaptic receptors and render the receptor's channel gating activity controllable by light. End products of an iterative approach (illustrated in FIG. 3) are optimized separate/coupled platform components and configurations that can be maintained for incorporation within the ultimate, fully functional platform. A particular system under study can consist of a ligand/platform preparation (e.g., a ligand such as untethered candidate effector or phage-derived peptide anchor; test platform such as an effector-photoswitch-anchor conjugate) and a target protein preparation (e.g., GABAc-expressing oocyte or isolated GABAc extracellular domain). This system can involve determining the interactions between the ligand and target under defined conditions. In vitro reconstitution procedures can determine the strength and specificity with which the ligand or platform binds to the target. Cell-based binding assays involving incubation of GABAc-expressing cells with test ligand/platform can be used to quantify strength/specificity of binding to GABAc in situ. Model and native GABAc-expressing cells (oocytes, mammalian cell line, and isolated retinal bipolar cells) and, subsequently, intact retina (isolated retina and intact eye), can be used for electrophysiological determination of ligand/platform activity of the test preparation in GABAc-mediated ion channel gating.

In particular embodiments of the invention the receptor is a ligand-gated ion channel. In other embodiments the receptor is a metabotropic receptor. In yet other embodiments the receptor is a GABA receptor, particularly a GABAc receptor. In other embodiments the effector is a modulator of the receptor.

Development of NNPs can employ GABAc receptors as a model postsynaptic receptor protein. The GABAc receptor is a member of the ligand-gated ion channel superfamily, which includes nicotinic acetylcholine receptors as well as $GABA_A$, glycine and $5-HT_3$ receptors. Functional receptors of this family consist of five subunits, with each protein subunit consisting of a large extracellular N-terminal domain, four transmembrane segments connected by a small extracellular domain, and both a small and a large intracellular domain. The subunit's C-terminal domain is predicted to be extracellular and to contain only a few amino acids (Betz, 1990; Qian & Ripps, 2001), and shall henceforth the GABAc N-terminal extracellular domain is references as "the extracellular domain". GABA receptors are widely distributed in CNS tissue, including retina. GABAc receptors are present on all subtypes of bipolar cells in the retina, with locations including both proximal and distal regions of these cells (Qian & Dowling, 1994; Enz et al., 1996; Qian et al., 1997; Lukasiewicz & Shields, 1998; Euler & Wassle, 1998). GABAc receptors are, by comparison with $GABA_A$ receptors, non-desensitizing and exhibit slow response kinetics (Feigenspan et al., 1993; Qian & Dowling, 1993; Pan & Lipton, 1995). GABAc receptor activities are an integral part of retinal function, and GABAc-mediated activity is specifically detectable in electroretinographic (ERG) recordings obtained from the intact eye (McCall et al., 2002; Dong & Hare, 2002).

The art contains some references that metabotropic and ionotropic glutamate receptors (mGluR6 and AMPA glutamate receptors), the native postsynaptic membrane receptors at rod and cone synapses with ON and OFF bipolar cells, are the preferred targets for bypassing rod and cone photoreceptors. However, later studies indicated significant down-regulation of glutamate receptors on bipolar cells of degenerated retina (Varela et al., 2003; Strettoi et al., 2003; Cuenca et al., 2004). In addition, by contrast with the case of multiple glutamate receptors, ON and OFF bipolars possess the same types of GABA receptors (Euler & Wassle, 1998; Shields et al., 2000). Thus, tetherable effectors identified herein could ultimately have application in NNPs designed for both ON and OFF bipolar cells. A second advantage of GABAc receptors concerns the size of the receptor-mediated electrical response. By contrast with the relatively small size of desensitized responses mediated by mGluR6 and AMPA glutamate receptors, and despite the small single-channel conductance of GABAc receptors, overall (i.e., population-summed) GABAc-mediated responses of bipolar cells are relatively large, do not desensitize, and are readily measured in mechanically/enzymatically isolated retinal bipolars (Feigenspan et al., 1993; Gillette & Dacheux, 1995; Qian & Dowling, 1995; Qian et al., 1997). The known pharmacology of GABAc receptors is not as extensive as that for $GABA_A$ receptors (Johnston, 1996). However, a further advantage of the GABAc receptor, one especially relevant to the present project's use of receptor expression in model cells (oocytes and mammalian cell lines), is the relatively limited diversity of GABAc receptor subunits in retinal neurons. For example, only three GABAc subunits (p1, p2 and p3) are expressed in rat retina, and only two of these are expressed in bipolar cells (p1 and p2) (Enz et al., 1995, 1996; Ogurusu & Shingai, 1996) By contrast, 15 $GABA_A$ subunits have been cloned from CNS neurons (Whiting et al., 1995; Mehta & Ticku, 1999), and most of these are expressed in retina (Wassle et al., 1998). Moreover, there is abundant evidence that the GABAc p1 subunit readily associates to form functional homomeric receptors (Cutting et al., 1991; Zhang et al., 1995; Qian et al., 1998). The relative uniformity of native retinal GABAc receptors, the workability of recording GABAc-mediated responses in isolated bipolar cells, and the demonstrated functionality of GABAc subunits in the simplest (i.e., homomeric) model system are major advantages in developing molecular structures to interface with postsynaptic membrane receptors. Furthermore, GABAc receptors share high homology with other LGICs, providing a foundation for extension of the technology to be developed to other LGICs such as the $GABA_A$ receptor as set forth herein.

GABAc extracellular domain and full length sequences are expressed and isolated. NNP development involves in vitro testing of candidate components with a model target receptor, the expressed (N-terminal) GABAc extracellular domain. Many membrane proteins contain domains that, when expressed as isolated fragments, retain properties that mimic those of the native protein (e.g., Grauschopf et al., 2000). For example, Chen & Gouaux (1997) expressed linked extracellular domains of the native AMPA glutamate receptor and found that these domains exhibit glutamate-binding activity. Furthermore, an expressed portion of the $GABA_A$ extracellular domain exhibits a benzodiazepine-binding property resembling that of the native receptor (Shi et al., 2003). In addition, acetylcholine binding protein (AchBP), a soluble binding protein of snail glia that exhibits significant sequence homology with GABAc receptors and from which a crystal structure has recently been obtained (Breje et al., 2001; Srnit et al., 2001; Cromer et al., 2002), exists as a pentarneric complex. These findings suggest that expressed GABAc extracellular domain can exhibit folding, pentamer-forming and GABA-binding properties resembling those of native GABAc receptors.

Both bacterial and baculovirus (sf9 cells) expression systems are used for preparation of the GABAc extracellular domain. These two systems have complementary strengths. The bacterial system is a widely used system capable of yielding large amounts of expressed protein and has been used, in particular, to obtain a soluble N-terminal domain preparation of the AMPA glutamate receptor (Chen & Gouaux, 1997). The baculovirus system (baculovirus transfection of insect cells), which has been used to express both soluble and membrane proteins (e.g., Stauffer et al., 1991; Griffiths & Page, 1997; Hu & Kaplan, 2000; Gatto et al., 2001; Eisses & Kaplan, 2002; Massotte, 2003), also has distinct advantages. The insect cells are eukaryotic and can readily express mammalian proteins; the proteins are post-translationally processed appropriately (although there may be incomplete glycosylation); and cell culture of these cells is straightforward and relatively inexpensive. A specific advantage of the baculovirus system is its capacity to generate functional, multimeric membrane proteins. It is one of the most widely used systems for expressing these multimeric proteins because, unlike the bacterial system, the subunits of these proteins oligomerize well in this system (e.g., Eisses & Kaplan, 2002; Laughery et al., 2003). In addition, by contrast with mammalian cells, the baculovirus system is capable of high levels of expression of membrane proteins, a factor important for purified protein in multiple biophysical and biochemical assays. Experiments to obtain full-length GABAc advantageously employ the baculovirus system, while those to obtain GABAc extracellular domain advantageously employ the system (bacterial or baculovirus) that is found to be (overall) more efficient with respect to solubility, purity and functionality of the expressed protein.

Tetherable GABAc effectors are engineered. Receptor activation by the NNP is mediated by a tethered effector that in light-dependent fashion interacts with the GABAc ligand-binding site. Tetherable GABA analogs can serve this function in the fully assembled platform. The known pharmacology of GABAc receptors includes studies of muscimol (a potent agonist), and of phosphinic acid analogs that contain a (derivatizable) phosphorus atom in place of GABA's carboxyl carbon atom (Murata et al., 1996; Chebib et al., 1997a, b; Chebib & Johnston, 2000; Zhang et al., 2001; Johnston, 2002; Krehan et al., 2003). Of particular relevance are reports that indicate GABA receptor-binding activity by amide-linked GABA analogs, i.e., N-substituted forms that, unlike GABA, lack a protonatable nitrogen and are thus non-zwitterionic at neutral pH (Wang et al., 2000; Meissner & Haberlein, 2003). In addition, a GABA analog containing a similar N-amide linkage is recognized by GABA receptors of brain tissue (Carlier et al., 2002). As set forth herein, amide-linked, aminocaproyl-chain-containing derivatives of muscimol exhibit electrophysiological activity in GABAc-expressing *Xenopus* oocytes (Vu et al., 2005; section C.2). Derivatized forms of muscimol, and phosphinic acid GABA analogs are synthesized to determine the activities of these compounds in electrophysiological and in vitro/in situ binding experiments. Two strategies involve conjugation of the test effector with azobenzene, a molecular photoswitch that here is employed as a first-generation photoswitch moiety. In both strategies, effector/photoswitch couples are joined to a linear poly(ethylene glycol) (PEG) linker that in the fully assembled NNP connects the effector/photoswitch to an anchoring component, and both strategies involve biophysical/electrophysiological testing of effector/photoswitch/linker assemblies to identify effectors that meet projected, quantitative performance criteria. The main factor distinguishing the two strategies is the length of the PEG linker ("long" vs. "short" chain), a feature anticipated to be key in governing the ultimate physiological performance of the effector at the GABAc ligand-binding site.

Platforms at the GABAc extracellular face are selectively anchored. Microspecific functionality of the ultimately envisioned NNP depends on its covalent attachment to the GABAc extracellular face at a defined site distinct from the receptor's ligand-binding site. 12-mer peptides that exhibit high-affinity noncovalent binding to the GABAc extracellular domain, and that can be derivatized with a photoaffinity probe to afford covalent attachment are used as the anchoring component to be joined with the effector/photoswitch/linker in the fully assembled NNP. Phage display (Rodi et al., 2002) can be used to select the sequence(s) of the desired high-affinity peptide(s), a high-throughput, relatively low-cost technology (relative to generating monoclonal antibodies) that has been widely used to identify peptides with high affinity for specific molecular targets including transmembrane and soluble proteins (Sarrias et al., 1999; Whaley et al., 2000; Zurita et al., 2003). In the first of these, phage-displayed combinatorial peptide libraries are screened against both whole-cell-expressed target receptor (cf. Goodson et al., 1994; Fong et al., 1994; Waters et al., 1997; Brown, 2000; Popkov et al., 2004) and isolated, biotinylated (and immobilized) extracellular domain of the target (cf. Smith & Scott, 1993; Karatan et al., 2004; Scholle et al., 2004). Synthesized peptides of the sequences determined in this phage screening are tested for GABAc binding activity in biophysical and electrophysiological procedures, to identify "first-generation" peptide ligands for further investigation. The second phase can employ combined biochemical, receptor engineering (cysteine substitution) and computational modeling approaches, together with biophysical/electrophysiological testing of candidate peptide ligands, to guide modification of the first-generation ligands and yield peptides whose sequences are optimized for high-affinity $GABA_c$ binding; and to determine the GABAc sites of peptide binding through photoaffinity derivatization of the peptide and analysis of the products of this covalent attachment reaction. The third phase can also involve peptide derivatization with a photoaffinity probe with the more stringent (than the second-phase research) objective of identifying, for native GABAc, modes and sites of covalent attachment that preserve normal GADAc function ("silent" attachment) and thus are suitable for anchoring the fully assembled NNP.

In some embodiments of the invention, the anchor includes covalent attachment to the receptor that preserves normal receptor function. In other embodiments, the anchor incorporates peptides derived from phage display screening. In yet other embodiments, the anchor incorporates non-covalent binding of the apparatus to the receptor. In still yet other embodiments the anchor includes a photoaffinity probe.

In particular embodiments of the invention, the photoswitch has a first configuration being adapted to operatively approximate the effector with a postsynaptic receptor wherein the receptor is activated, and a second configuration maintaining the effector remote from the operative approximation with the postsynaptic receptor wherein the receptor remains unactivated, wherein the photoswitch is mediated between the first configuration and second configuration by exposure to a preconfigured range of electromagnetic radiation. In other embodiments the mediation of the photoswitch is transient. In yet other embodiments, the photoswitch spontaneously reverts to the second configuration after being put in the first configuration by exposure to a preconfigured range of electromagnetic radiation. The preconfigured ranged electromagnetic radiation can be visible light.

Photic control of GABAc receptor activity is achieved using azobenzenes. Azobenzenes have been widely used to light-regulate the properties of polymers and peptides, enzymes, and ionophores in vitro (Erlanger, 1976; Liu et al., 1997; Willner & Rubin, 1996; Pieroni et al., 1998; Borisenko et al., 2000; Dugave & Demange, 2003; Burns et al., 2004). The extensive use of azobenzenes as derivatizable photoswitches is based on their ease of synthesis as well as their physical and photochemical stability. The more stable trans isomer and the metastable cis isomer can be interconverted rapidly, efficiently and reversibly by light because they have distinct absorption maxima. Typically, irradiation in the near-UV (~370 nm) produces 80-90% cis, and irradiation in the visible (>450 nm) yields ~90% trans.

However, simple azobenzenes, the first-generation photoswitch, have the limitations of requiring UV light for activation and displaying slow thermal relaxation (time scale of hours or more). The latter property is extremely useful for prototype development and characterization. On the other hand, the compositions of the invention functionality requires the photoswitch's spontaneous relaxation with kinetics compatible with GABAc receptor physiology (time scale of seconds or less), as well as sensitivity to light in the visible range. Second-generation photoswitch compounds that address these limitations are synthesized and tested. One embodiment comprise derivatives of azobenzene possessing a red-shifted absorbance spectrum relative to simple azobenzenes (i.e., $\lambda_{max}$ in the visible range) and thermal relaxation on the desired (second- or sub-second-) time scale following photoisomerization. A prime justification for directing attention to azobenzene-based structures (push-pull azobenzenes and imines) is their successful application to the control of transmembrane ion channels. Of particular relevance to this embodiment is the demonstration, by Lester and colleagues, that both a freely diffusing azobenzene analog of acetylcholine (Ach), and a closely related, receptor-tethered analog, afford light-dependent activation of nicotinic Ach receptors (Bartels et al., 1971; Lester & Nerbonne, 1982; Lester et al., 1986; Gurney & Lester, 1987). Further encouragement for the development of azobenzene-based, receptor-anchored effectors comes from a ground-breaking study by Banghart et al. (2004), who demonstrated light-regulated control of hippocampal cell-expressed $K^+$ channels by a structure tethered to a cysteine (including in some embodiments a genetically engineered cysteine) on the protein, and linked via an azobenzene to a tetraethylammonium blocker of channel activity. However, both the system studied by Lester and co-workers, and that studied by Banghart et al. (2004) employed simple azobenzenes, and therefore required photic regeneration of the baseline (i.e., dark-adapted) state by light of a wavelength different from the activating wavelength. The use of the simple, slowly relaxing azobenzene structures (conjugation of an azobenzene-based photoswitch with an effector and linker), and the substantial body of literature describing the influence of substituents on the thermal and photochemical properties of azobenzene derivatives (e.g., Schanze et al., 1983; Asano & Okada, 1984; Kobayashi et al., 1987; Wachtveitl et al., 1997) is beneficial.

A prototype system consisting of a macroscopic surface (dimensions on the order of millimeters) coated with a redox-sensitive, chain-derivatized GABA analog and interfaced with a HgCdTe-based avalanche photodetector can be used, wherein this system is used to test the feasibility of light-dependent activation of GABAc receptors expressed in *Xenopus* oocytes. Certain aspects of the prototype, included completion of a study of immobilized GABA analog (Saifuddin et al., 2003) and of the synthesis/testing of muscimol-biotin, a candidate tetherable GABAc effectors (Nehilla et al., 2004; Vu et al., 2005) have been disclosed previously.

Synthesis, immobilization and biophysical characterization of chain-derivatized analogs of GABA and muscimol are determined. One embodiment can involve atomic force microscopy (AFM) testing of GABAc extracellular domain and prototype NNP components tethered to a solid support. Using commercially obtained anti-GABA antibody as a model, GABA-binding protein showed surface properties of a candidate chain-derivatized GABA analog. The analog consisted of a GABA moiety N-linked to biotin through an ethylene oxide chain. In AFM experiments employing surfaces coated with avidin-tethered biotinylated GABA analog and control surfaces lacking the analog, incubation with anti-GABA antibody (employed here as a model GABA-binding protein) produced changes in surface topology, indicating interaction of the antibody with the analog's GABA moiety.

The results obtained from this elementary model system provide evidence that tethering of a chain-derivatized GABA analog can preserve GABA-like biofunctionality. In another study (Nehilla et al., 2004), assembled and characterized silicon platforms containing a chainderivatized form of the GABAc receptor agonist muscimol that may be used in this embodiment.

In other embodiments of the invention, the effector can incorporate azobenzene. In yet other embodiments the effector can be an agonist including but not limited to a muscimol derivative. In other embodiments the effector is an antagonist. In other embodiments there can be a second effector. In yet other embodiments the effector is a neurotransmitter derivative. In other embodiments the effector is a neurotransmitter analogue.

Electrophysiological activity of chain-derivatized muscimol is used to identify tetherable analogs of GABA that exhibit agonist or antagonist activity at GABAc receptors expressed in *Xenopus* oocytes and mammalian cells. The biotinylated GABA compound exhibited little if any electrophysiological activity in GABAc-expressing oocyte. However, a biotinylated analog of the known GABA receptor agonist muscimol (termed muscimol-biotin herein, illustrated in FIG. 4), exhibits significant activity (Vu et al., 2005). Muscimol-biotin was synthesized wherein biotinamidoeaproic acid N-hydroxysuccinimide ester was reacted with muscimol in N-methylpyrrolidinone in the presence of diisopropylethylamine. The product was purified to homogeneity by reversed-phase HPLC. Peaks were detected by absorbance at 210 nm (FIG. 5), collected, and lyophilized to afford muscimol-biotin. The muscimol-biotin product was judged to be 97% pure by $^1$H NMR spectroscopy, with no detectable contamination of the HPLC-purified product peak by muscimol (limit of detection: ca. 1%). Muscimol-biotin was dissolved in DMSO, stored at 3° C., and diluted to desired concentrations in frog Ringer before testing on the oocyte. Electrophysiology procedures used for *Xenopus* oocyte preparation, including GABAc expression, followed those described previously (Qian et al., 1998). Membrane currents were recorded from GABAc-expressing oocytes by 2-electrode voltage clamp apparatus. FIGS. 6-7 show results obtained for muscimol-biotin in GABAc and $GABA_A$ expressing oocytes. At GABAc receptors (FIG. 6), muscimol-biotin exhibited agonist activity with an $EC_{50}$ of 20 μM and Hill coefficient of 4.4 (see legend), and this activity was suppressible by TPMPA, a known GABAc antagonist. Muscimol-biotin also exhibited agonist activity at $GABA_A$ receptors (FIG. 7), and this activity was suppressible by the known antagonist bicueulline. The finding of a Hill coefficient of 4.4 for GABAc receptors specifically suggests a high cooperativity in GABAc activation by muscimol-biotin; this cooperativity might reflect, for example, hydrophobic interactions among the alkyl chains of muscimol-biotin molecules at the GABAc receptor.

FIG. 4 depicts structures of GABA, muscimol and muscimol-biotin. FIG. 5 depicts HPLC isolation of muscimol-biotin from a preparative reaction mixture: Waters Delta-Pak C18 column (25×100 mm); elution with a linear gradient of 0-40% acetonitrile (0.08% TFA) in water (0.1% TFA) over 25 min. The three resolved peaks are N-hydroxysuccinimide and unreacted muscimol (it), N-methylpyrrolidinone (2) and muscimol-biotin (3).

FIGS. 6 and 7 show the effects of muscimol-biotin on GABAc- and $GABA_A$ expressing *Xenopus* oocytes. Left (FIG. 6: GABAc receptors. (A) Response to 10 μM muscimol and 500 μM muscimol-biotin recorded from a single oocyte. (B) Response of a single oocyte to 50 μM muscimol-biotin and to the co-application of 50 μM muscimol-biotin and 200 μM TPMPA. (C) Responses recorded from a single oocyte on the presentation of varying concentrations (in μM) of muscimol (upper) and muscimol-biotin (lower). (D) Normalized peak amplitudes (mean±SEM) of responses to muscimol and muscimol-biotin recorded from GABAc-expressing oocytes (n=5 for muscimol; n=6 for muscimol-biotin). Here and in the right-hand panel D, peak amplitudes of all responses obtained from a particular oocyte are normalized to the peak amplitude of the saturating response to muscimol; and fitted curves plot the Hill equation, $r/r_{max}=C^n/(C^n EC_{50}^n)$, where $r/r_{max}$ is the normalized response amplitude, c is the concentration of test substance, and n and $EC_{50}$ are fitted parameters. The fits yield $EC_{50}$=2.0 μM and n=1.2 for muscimol (open circles); and $EC_{50}$=20 μM and n=4.4 for muscimol-biotin (filled circles). Right (FIG. 7): $GABA_A$ receptors. (A) Responses of a single oocyte to 100 μM muscimot-biotin and 10 μM GABA. (B) Responses of another oocyte to 2.5 μM muscimol-biotin alone, and to co-application of 2.5 μM muscimol-biotin and 100 μM bicuculline. (C) Family of responses to varying concentrations of muscimol-biotin and to a single, saturating concentration of muscimol (200 μM thick trace) recorded from a single oocyte. (D) Normalized peak amplitudes (mean±SEM) of responses recorded from $GABA_A$-expressing oocytes upon the application of muscimol (open circles) and muscimol-biotin (filled circles) (n=9). The fitted Hill equation curves yield n=0.74 and $EC_{50}$=4.8 μM for muscimol; and n=1.4 and $EC_{50}$=385 μM for muscimol-biotin.

FIG. 8 graphs whole-cell patch recording of GABA-elicited response of a neuroblastoma cell expressing the human GABAc p1 subunit. Horizontal line: period of application of 10 μM GABA. FIG. 9 graphs ($^3$H)GABA competition binding data obtained from GABAc-expressing neuroblastoma cells. Data points are averages of duplicate samples. Result obtained in the absence of unlabeled GABA (B/Bo=100%) is arbitrarily positioned at log [GABA]=−9.3. The illustrated smooth curve was fitted to the data using Prism Graphpad software.

Electrophysiological and GABA-binding properties of GABAc-expressing mammalian cells involve cell-based and in vitro reconstitution of test ligand binding to GABAc receptors. In one embodiment, neuroblastoma cells stably are transfected with the human GABAc p1 subunit for their electrical response to GABA and for their binding of GABA. FIG. 7 shows a representative GABA-elicited response recorded from one of these cells. The response is robust and exhibits the slow kinetics typical of GABAc-mediated responses. GABAc-expressing neuroblastoma cells and control, non-GABAc-expressing neuroblastoma cells (ATCC) were analyzed for binding of ($^3$H)GABA in a competition binding assay (incubation with fixed amount of ($^3$H)GABA and varying amounts of non-radiolabeled GABA) using procedures similar to those described by Turek et al., 2002). Cells were seeded on 6-well plates and grown to 100% confluence, and then washed with 2 ml of binding buffer (50 mM Tris-HCl and 2.5 mM $CaCl_2$, pH 7.4) for 30 min. Fresh binding buffer (600 μL) containing 10 nM ($^3$H)GABA in the presence of varying concentrations of unlabeled GABA (0-400 μM) was added, and the solution was incubated on ice (to minimize cellular uptake of the ($^3$H)GABA) for 1 hr. After incubation, the plates were washed once with 2 mL ice-cold binding buffer, solubilized with 1 mL/well 0.3 N NaOH (shaking at room temperature for 10 min), and neutralized with 100 μL 3N HCl. The solubilized cells were then added to scintillation vials containing 10 mL Econo-Safe scintillation fluid and counted using a Beckman LS 6500M spectrometer. Nonspecific binding, defined as ($^3$H)GABA binding observed in the presence of 400 μM unlabeled GABA, represented about 50% of the maximal level of total ($^3$H)GABA binding observed in the absence of unlabeled GABA. FIG. 8 shows normalized levels (B/B$_0$, in percent) of specific ($^3$H)GABA binding, i.e., normalized values obtained after the subtraction of nonspecific binding The data yield a calculated IC$_{50}$ of 8.6×10$^{-8}$ M for the non-radiolabeled GABA, and indicate workability of the ($^3$H)GABA competition binding assay for determining binding properties of cell-expressed GABAc receptors. Assay of the control cells indicated the absence of specific ($^3$H)GABA binding.

Bacterial expression and ligand-binding of GABAc extracellular domain in vitro reconstitution can employ, as a model target, solubilized GABAc extracellular domain expressed using bacterial/baculovirus expression systems. The large extracellular N-terminal domains of GABA$_A$ and GABAc receptors are thought to contain the GABA-binding sites of the receptors. A primary objective is obtaining N-terminal extracellular domain of the human GABAc p1 subunit. As shown in FIG. 10, alignment of the amino acid sequences of human p1 subunit, GABA$_A$ receptor α1 subunit, acetylcholine binding protein (AchBP) and perch p1B predicts a GABAc N-terminal core fragment (~200 amino acids) structurally similar to AchBP and GABA$_A$ α1 (Cromer et al., 2002). To obtain a soluble form of this GABAc core fragment, His-tagged fusion proteins of N-terminal sequences of human p1 and perch p1B GABAc subunits (amino acid positions 68-273 for human p1; positions 64-269 for perch p1B) were expressed these constructs in bacterial strain SG13009. These segments of p1 subunits were amplified by PCR and subcloned in-frame into the BamHI-HindIII site of the pQE-His vector (Qiagen), which contains the phage T5 promoter and a synthetic ribosomal binding site, RBSII, for high translation rates. Strain SG13009 contains the pREP4 plasmid code for the lac repressor protein that binds to the operator sequences on pQE vector and tightly regulates recombinant protein expression. When IPTG is added, it binds the lac repressor protein and allows the host cell's RNA polymerase to transcribe the sequence of the recombinant protein.

FIG. 10 depicts alignments of amino acid sequences for AchBP, GABA$_A$ receptor α1 subunit, and human and perch GABAc receptor subunits (GABA p1 subunits).

Proteins synthesized in bacteria were analyzed by electrophoresis under denaturing conditions (SDS/PAGE). FIG. 11 shows results obtained with expression of the human p1 construct in bacteria. No recombinant protein was observed in the uninduced cells (lane 1). With IPTG induction (0.2 mM for 3 hr at 37° C.), a prominent band of about 27 kDa was present in the sample prepared from whole bacteria (lane 2). Further analysis indicated that a majority of the synthesized recombinant protein was present in an insoluble form in inclusion bodies (lane 4) rather than as soluble protein in the supernatant (lane 3). Recombinant proteins were purified from inclusion bodies using the following protocol. After 3-hr induction with IPTG, cells were collected by centrifugation at 8,000 g for 10 min. Cell pellets were lysed by sonication (5 min, full power) in buffer (300 mM NaCl, 10 mM imidazole and 50 mM phosphate buffer, pH 8.0). Inclusion bodies (i.e., the pellet) were collected by centrifugation at 14,000 g for 1 hr. Inclusion body proteins were solubilized by sonication (5 min, full power) in buffer containing 6 M guanidinium HCl (GuaHCl), 500 mM NaCl and 20 mM NaPO$_4$, pH 7.4; the resulting suspension was subjected to ultracentrifugation (100,000 g, 1 hr), and the supernatant was filtered through a 0.22 μm membrane. The His-tagged recombinant proteins present in the supernatant were purified on a HiTrap HP chelating column charged with Ni$^{2+}$ (Amersham Biosciences).

FIG. 11 shows SDS/PAGE analysis of recombinant His-human p1 protein synthesized in bacteria. Lane 1: uninduced cells. Lanes 2-4: induced cells; whole-cell lysate (2), supernatant (3) and pellet (4). Lane 5: protein standards.

To refold the His-p1B protein bound to the column, the following buffers were sequentially applied to the column: (1) 100 mM Tris (pH 7.5), 200 mM NaCl, 1M L-arginine, and glutathione as a redox system (3 mM GSH+0.3 mM GSSG); (2) same as buffer (1) but without the redox components; (3) 100 mM Tris (pH 8.0), 500 mM NaCl and 0.5 M Larginine; (4) 100 mM Tris (pH 8.0), 500 mM NaCl and 0.25 M L-arginine; (5) 100 mM Tris (pH 8.0), 500 mM NaCl and 0.1 M L-arginine; and (6) 100 mM Tris (pH 8.0), 500 mM NaCl. Elution from the column was performed using 100 mM Tris (pH 8.0), 500 mM NaCl, and 200 mM imidazole.

The eluted protein was subjected to dialysis against various buffers, as presented in the accompanying Table. Solubility was dependent on high pH (9.5-9.7), and the purified protein was finally dialyzed against buffers containing either Tris (50 mM), or CHES (15 mM) as buffering agents, pH 9.5, NaCl (20-200 mM) for subsequent analysis.

| Composition of dialysis buffer | pH | Protein Prep. | Composition of dialysis buffer | pH | Protein Prep. |
|---|---|---|---|---|---|
| 50 mM NaPO$_4$, 500 mM NaCl, 200 mM imidazole | 9.5 | Soluble | 50 mM NaPO4, 500 mM NaCl | 9.5 | Soluble |
| 50 mM NaPO$_4$, 500 mM NaCl, 200 mM imidazole | 8.0 | Precipitate | 50 mM Tris-HC1, 200 mM NaCl | 9.5 | Soluble |
| 50 mM NaPO$_4$, 500 mM NaCl, 200 mM imidazole | 7.8 | Precipitate | 50 mM Tris-HC1, 20 mM NaCl | 9.5 | Soluble |
| 50 mM NaPO$_4$, 500 mM NaCl, 0.5 mg/ml azolectin | | | 15 mM CHES, 200 mM NaCl | 9.5 | Soluble |
| | | | 15 mM CHES, 20 mM NaCl | 9.5 | Soluble |

Preliminary circular dichroism (CD) data obtained from the solubilized protein suggest an at least partially folded structure and argue against merely a randomly coiled state (FIG. 11; peak wavelength at λ=210-220 nm). This is consistent with the expected structure of the protein, based on comparison with the low-resolution structure of AchBP (Brejc et al., 2001), which predicts a helical region and several 13-sheet regions for the GABAc extracellular domain. In addition, preliminary data obtained in two experiments (results shown, in part, in FIG. 13) show that, by competition binding assay, the purified soluble protein exhibits specific GABA binding with an average calculated IC$_{50}$ of ~3.5×10$^{-8}$M and average specific binding of about 70%. This is consistent with data for GABA-activation of human p1 receptors expressed in a neuroblastoma cell line, as determined in a competition binding assay with ($^3$H)GABA (FIG. 8). These initial measurements of GABA binding by purified, soluble His-p1B protein suggest the feasibility of the in vitro reconstitution experiments discussed herein. A similar approach employing bacterial expression and isolation/solubilization of extracellular domain has been used successfully in studying both glutamate and glycine receptors (Chen & Gouaux, 1997; Breitinger et al., 2004). However, preliminary data, and variations seen in the radioligand binding results suggest that the bacterial protein expression/preparative procedures used here will require further optimization. The bacterial protein may improve the efficiency of protein re-folding by modifying the procedures according to published protocols (Chen & Gouaux, 1997; Breitinger et al., 2004; Oganesyan et al., 2004). In addition, experiments to determine biochemical/pharmacological properties of the soluble p 1B protein are discussed herein. The FIG. 13 data, which suggest a GABA-binding affinity of order similar to that of the GABA dissociation constant determined for cell-expressed GABAc, implies the capacity of the extracellular domain for proper folding. As GABA-binding sites of native GABAc receptors are thought to be located at junctions of the extracellular domains of adjacent subunits, as in acetylcholine receptors (Karlin, 2002; Cromer et al., 2002), significant GABA binding activity may be an indirect indication of subunit oligomerization to form a homopentamer.

FIG. 12 depicts a CD spectrum of a preparation of soluble extracellular domain of perch His p1B in 10 mM NaCl and 15 mM CHES, pH 9.5. FIG. 13. ($^3$H)GABA competition binding data obtained with a soluble His p1B preparation. Data points are averages of duplicate samples.

Screening of phage display peptides with GABA-expressing cells can employ phage display to identify 12-mer peptide sequences that can serve as an NNP anchoring element. GABAc-transfected neuroblastoma cells have yielded sequences of peptides that preferentially bind to GABAc-expressing cells. For phage selection, a screening method was used similar to that previously used to identify phages that bind to ErbB receptors (Stortelers et al., 2003). Briefly, $2 \times 10^{10}$ phage (Ph.D-12 library from New England Biolabs, MA) were incubated with control, non-transfected neuroblastoma cells in binding buffer (PBS containing 0.2% BSA, 0.05% Tween 20) for 2 hr. Non-bound phages were collected and then incubated with GABAc-transfected neuroblastoma cells for 2 hr. After rinsing several times with washing buffer (0.05% Tween 20 in PBS), bound phages were eluted using an acidic glycine buffer (50 mM glycine, 150 mM NaCl, pH 2.7) and neutralized with 1 M Tris, pH 8. After phage titration of the eluate, a second and then a third round of bio-panning was performed using the GABAc-transfected neuroblastoma cells. After the third round of panning, DNA isolated from individual phage plaques was sequenced. The Table below shows the peptide sequences of two distinct groups derived from multiple phages. A highly conserved sequence was observed for each group. The 7 illustrated sequences represent individual phage clones from a total of 36 sequenced clones.

| Phage ID | | | | | | | | | | | | |
|---|---|---|---|---|---|---|---|---|---|---|---|---|
| Group A | | | | | | | | | | | | |
| 9 | H | E | T | A | V | R | Q | T | S | P | P | M |
| 11 | H | E | T | A | C | R | Q | T | S | P | p | M |
| 20 | H | E | T | A | V | R | Q | T | S | p | p | M |
| 22 | H | E | T | A | V | R | Q | T | S | p | p | M |
| Group B | | | | | | | | | | | | |
| 6 | H | P | K | Q | S | L | H | F | P | D | L | S |
| 4 | H | P | Y | D | S | L | H | F | P | R | M | S |
| 6-1 | H | P | Y | D | S | L | H | F | P | R | M | S |

Visualization of receptor binding with nanocrystal-conjugated muscimol. A prototype system for testing candidate effectors may use prepared muscimol tethered via an aminocaproyl and PEG 3400 linker to AMP™ CdSe nanocrystals (coupling chemistry similar to that described by Rosenthal et al. (2002). The resulting muscimol-PEG-nanocrystal conjugate, which possesses an estimated 100-150 tethered muscimols per nanocrystal, is here abbreviated M-PEG-nc. By confocal microscopy the interaction of M-PEG-nc was analyzed with Xenopus oocytes expressing GABAc receptors. Images were obtained from oocytes positioned in a glass-bottom dish and immersed in Ringer solution containing the test agent. Oocytes were bathed in a surrounding drop (25 µl) of 34 nM M-PEG-nc (i.e., 34 nM in nanocrystals) in Ringer solution for defined periods and then imaged or, as controls, similarly incubated with unconjugated nanocrystals. Other preparations were pre-incubated for 15 min with 34 nM unconjugated nanocrystals, with 34 nM of PEG-conjugated nanocrystals (lacking muscimol), or with 500 µM GABA prior to 5-min incubation with 34 nM M-PEG-nc. Fluorescence was visualized using a Leica DM-IRE2 confocal microscope (20× objective) with excitation at 476 nm. Fluorescence emission was detected over a wavelength interval (580-620 nm) that included the nanocrystal emission peak ($\lambda$=605 nm). Microscope settings relevant to detection of fluorescence emission were established at the beginning of experiments on a particular day, and maintained without change for that set of measurements. The set of measurements (set 1 or set 2) performed on a particular day employed a single batch of oocytes and a single preparation of M-PEG-nc. FIG. 14 (upper row) shows results obtained from oocytes expressing perch p1B GABAc receptors (1) (set 1) and human p1 GABAc receptors (2) (set 2), and from a non-injected oocyte (3) (set 2), upon 5-min incubation with medium containing 34 nM M-PEG-nc. For (1) and (2), the fluorescence image (left-hand side) shows a thin halo of fluorescence at the oocyte surface, the intensity of which exceeds the surround fluorescence. By contrast, only diffuse surround fluorescence was observed with the non-injected (i.e., GABAc-lacking) oocyte (3). To illustrate the focus of the oocyte under investigation, panels 1-3 include (right-hand side) a bright-field image of the oocyte obtained simultaneously with the fluorescence image. The middle and lower rows of FIG. 14 (oocytes expressing, respectively, perch p 1B receptors (set 1) and human p1 GABAc receptors (set 2)) show results obtained on incubation with unconjugated nanocrystals alone (panel A); on pre-incubation with unconjugated nanocrystals followed by incubation with M-PEG-nc (B); on incubation with PEG-nanocrystals (lacking muscimol) alone (C); and on pre-incubation with GABA followed by incubation with M-PEG-nc (D). The data of A-B indicate the inability of unconjugated nanocrystals to bind to the oocyte membrane or to significantly inhibit M-PEG-nc binding; those of C indicate little if any binding by PEGnanocrystals lacking muscimol; and those of D indicate that GABA blocks M-PEG-nc binding. M-PEG-nc binding was similarly blocked by pre-incubation with 500 RM muscimol (data not shown).

The upper row of FIG. 14 depicts oocytes expressing perch p1B GABAc (1) or human p1 GABAc (2), and non-injected oocytes (3) were incubated with 34 nM of muscimol conjugated nanocrystals (M-PEG-nc) for 5 mm. To the right of fluorescence images 1, 2 and 3 are corresponding brightfield images. Middle and lower rows: fluorescence images obtained with perch p 1B (middle) and human p1 (lower) GABAc-expressing oocytes. A: incubation with 34 nM of unconjugated nanocrystals for 15 min. B: oocytes pre-incubated with 34 nM of unconjugated nanocrystals for 15 min, removed from the pre-incubation dish, and then incubated with 34 nM M-PEG-nc for 5 min. C: oocytes incubated with 34 nM of PEG-nanocrystals (i.e., no conjugated muscimol) for 15 min. D: oocytes pre-incubated with 500 µM of GABA for 15 min, removed from the pre-incubation dish, and then incubated with 34 nM M-PEG-nc for 5 min.

Postsynaptic membrane receptors of the ligand-gated ion channel (LGIC) family mediate signal transmission at numerous types of chemical synapses in the central nervous system (CNS). In neural diseases that at a particular synapse involve dysfunction/deterioration of the presynaptic neuron but preserve normal structure and function of the postsynaptic neuron, restoring signaling activity in the postsynaptic cell can be accomplished by derivatizing the postsynaptic receptor protein with a chemical structure that can regulate receptor activity in response to an external signal. Chemically modified LGICs with functional properties can restore or regulate neural signaling in neurodegenerative diseases. Receptors expressed in *Xenopus* oocytes and mammalian cell lines can be used as model systems. One such model system is the $GABA_A$ receptor, a heteromeric LGIC that is widely distributed in CNS tissue, a target of drug therapy in CNS disorders. Determination of specific sites on native $GABA_A$ subunits can accommodate covalent attachment, by photoaffinity labeling, of chemical structures whose distal components exhibit controllable reactivity at the receptor's GABA- or benzodiazepine binding sites.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 3 illustrates an iterative development process.

FIG. 10 illustrates the alignment of amino acid sequences for AchBP, $GABA_A$ receptor α1 subunit, and human and perch GABAc receptor subunits (GABA ρ1 subunits).

FIG. 27 depicts the N-terminal region of AchBP with predicted solvent accessible surface areas.

FIG. 42 illustrates a lack of agonist activity of MPC088 on PNs. a: Averages of 10 recordings from a PN exposed to multiple Blue/UV light flashes, in the presence of cis-dominant MPC088 before (black) and after (red) the addition of gabazine. b: Summary of results from 8 experiments (8 PNs) including that described in a.

FIG. 49 illustrates a lack of detectable effect of MPC088 on AMPAR/NMDAR-mediated EPSCs in hippocampal CA1 pyramidal neurons. a: Representative average recordings from a CA1 pyramidal cell held at +40 mV. b: Summary data including that shown in a.

FIG. 62 includes structures of Benzodiazepine derivatives 22 and 23 (left), and confocal microscopy of *Xenopus* oocytes with 23 (right).

FIG. 63 illustrates target regions A-E for refinement of the trans-MPC088 structure.

DETAILED DESCRIPTION OF THE PREFERRED EMBODIMENTS

Figure 2:
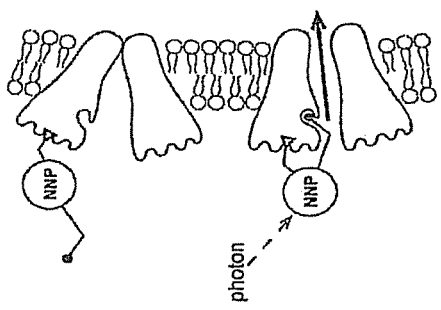
FIG. 2 illustrates a nanoscale neuromodulating platform (NNP).

The following description of the preferred embodiment(s) is merely exemplary in nature and is in no way intended to limit the invention, its application, or uses.

In one aspect, the disclosure provides compounds of formula (I)

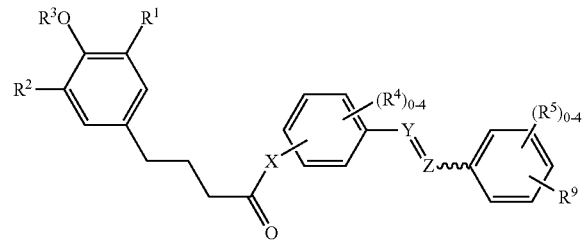

(I)

and pharmaceutically acceptable salts thereof, wherein $R^1$ and $R^2$ are independently $C_1$-$C_{12}$ alkyl, halo($C_1$-$C_{12}$ alkyl), $C_2$-$C_{12}$ alkenyl, or $C_2$-$C_{12}$ alkynyl, each optionally substituted with 1, 2, 3 or 4 substituents selected from halogen, —CN, —NO$_2$, —OR$^6$, —NR$^6_2$, —CO$_2$R$^6$, —CONR$^6_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle is optionally substituted with 1, 2, 3 or 4 $R^7$;

$R^3$ is hydrogen, $C_1$-$C_6$ alkyl, or halo($C_1$-$C_6$ alkyl);

$R^4$ and $R^5$ are independently halogen, —CN, —NO$_2$, $C_1$-$C_6$ alkyl, halo($C_1$-$C_6$ alkyl), —OR$^6$, —NR$^6_2$, —CO$_2$R$^6$, or —CONR$^6_2$;

X is —N(R$^8$)—, —N(R$^8$)CH$_2$—, —N(R$^8$)CHR$^8$—, —N(R$^8$)(CHR$^8$)$_{2-5}$—, or —O—;

Y=Z is —N=N— or —C(R$^8$)=C(R$^8$)—; and $R^9$ is hydrogen, —CHR$^{6a}$, —OR$^{6a}$, —NR$^{6a}_2$, —CO$_2$R$^{6a}$, —CONR$^{6a}_2$, —CON(R$^8$)—(CH$_2$)$_{1-6}$—NR$^{6a}_2$, —N(R$^8$)CO—(CH$_2$)$_{1-6}$—NR$^{6a}_2$, —CON(R$^8$)—(CH$_2$)$_{1-6}$—N(R$^8$)COR$^{6a}$, —N(R$^8$)CO—(CH$_2$)$_{1-6}$—N(R$^8$)COR$^{6a}$, —CON(R$^8$)—(CH$_2$)$_{1-6}$—N(R$^8$)COR$^{10}$, or —N(R$^8$)CO—(CH$_2$)$_{1-6}$—N(R$^8$)COR$^{10}$, wherein $R^{10}$ is —CH$_2$CH$_2$(OCH$_2$CH$_2$)$_{2-50}$—N(R$^8$)COR$^{6a}$;

where each $R^6$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;

where each $R^{6a}$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;

where each $R^7$ independently is halogen, —CN, —NO$_2$, —N$_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —CO$_2$H, —COH, —CO$_2$R$^8$, or —CON(R$^8$)$_2$; and where each $R^8$ is independently hydrogen or $C_1$-$C_6$ alkyl.

In one embodiment, the disclosure provides compounds of formula (I) that have formula (II):

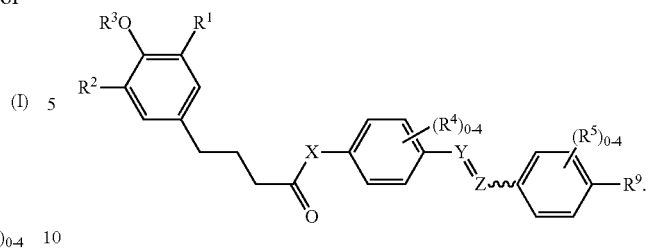

In particular embodiments, the compounds of formulae (I) and (II) as described herein, $R^1$ and $R^2$ are independently $C_1$-$C_{12}$ alkyl, halo($C_1$-$C_{12}$ alkyl), $C_2$-$C_{12}$ alkenyl, or $C_2$-$C_{12}$ alkynyl, each optionally substituted with 1, 2, 3 or 4 substituents selected from halogen, —CN, —NO$_2$, —OR$^6$, —NR$^6_2$, —CO$_2$R$^6$ and —CONR$^6_2$;

$R^3$ is hydrogen, $C_1$-$C_6$ alkyl, or halo($C_1$-$C_6$ alkyl);

$R^4$ and $R^5$ are independently halogen, —CN, —NO$_2$, $C_1$-$C_6$ alkyl, halo($C_1$-$C_6$ alkyl), —OR$^6$, —NR$^6_2$, —CO$_2$R$^6$, or —CONR$^6_2$;

X is —N(R$^8$)—, —N(R$^8$)CH$_2$—, —N(R$^8$)CHR$^8$—, —N(R$^8$)(CHR$^8$)$_{2-5}$—, or —O—;

Y=Z is —N=N— or —C(R$^8$)=C(R$^8$)—; and $R^9$ is hydrogen, —CHR$^{6a}$, —OR$^{6a}$, —NR$^{6a}_2$, —CO$_2$R$^{6a}$, —CONR$^{6a}_2$, —CON(R$^8$)—(CH$_2$)$_{1-6}$—NR$^{6a}_2$, —N(R$^8$)CO—(CH$_2$)$_{1-6}$—NR$^{6a}_2$, —CON(R$^8$)—(CH$_2$)$_{1-6}$—N(R$^8$)COR$^{6a}$, —N(R$^8$)CO—(CH$_2$)$_{1-6}$—N(R$^8$)COR$^{6a}$, —CON(R$^8$)—(CH$_2$)$_{1-6}$—N(R$^8$)COR$^{10}$, or —N(R$^8$)CO—(CH$_2$)$_{1-6}$—N(R$^8$)COR$^{10}$, wherein $R^{10}$ is —CH$_2$CH$_2$(OCH$_2$CH$_2$)$_{2-50}$—N(R$^8$)COR$^{6a}$;

where each $R^6$ independently is hydrogen, $C_1$-$C_6$ alkyl or halo($C_1$-$C_6$ alkyl), wherein each alkyl is optionally substituted with 1, 2, 3 or 4 $R^7$, or two $R^6$ with the nitrogen to which they are attached form a heterocycle optionally substituted with 1, 2, 3 or 4 $R^7$;

where each $R^{6a}$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;

where each $R^7$ independently is halogen, —CN, —NO$_2$, —N$_3$, $C_1$-$C_6$ alkyl, halo($C_1$-$C_6$ alkyl), $C_1$-$C_6$ alkoxy, amino, $C_1$-$C_6$ alkylamino, di$C_1$-$C_6$alkylamino, —CO$_2$H, —COH, —CO$_2$R$^8$, or —CON(R$^8$)$_2$; and wherein each $R^8$ is independently hydrogen or $C_1$-$C_6$ alkyl.

In one embodiment, the disclosure provides compounds as described above with reference to formula (I) or (II), wherein $R^3$ is hydrogen.

In another embodiment, the disclosure provides compounds as described above with any reference to formula (I) or (II), wherein $R^1$ and $R^2$ are independently $C_1$-$C_{12}$ alkyl, optionally substituted with one to four substituents selected from halogen, —CN, —NO$_2$, $C_1$-$C_6$ alkyl, halo($C_1$-$C_6$ alkyl), —OR$^6$, —NR$^6_2$, —CO$_2$R$^6$, —CONR$^6_2$, $C_3$-$C_8$ cycloalkyl, $C_3$-$C_8$cycloalkenyl, aryl, heteroaryl, and heterocycle. In another embodiment, $R^1$ and $R^2$ are independently $C_1$-$C_{12}$ alkyl, optionally substituted with one to four substituents selected from halogen, —CN, —NO$_2$, $C_1$-$C_6$ alkyl, halo($C_1$-$C_6$ alkyl), —OR$^6$, —NR$^6_2$, —CO$_2$R$^6$ and —CONR$^6_2$. In yet another embodiment, $R^1$ and $R^2$ are independently unsubstituted $C_1$-$C_{12}$ alkyl. In yet another embodiment, $R^1$ and $R^2$ are independently unsubstituted $C_1$-$C_6$ alkyl.

In one embodiment, the disclosure provides compounds as described above with any reference to formula (I) or (II), wherein $R^1$ and $R^2$ are both —CH(CH$_3$)$_2$.

In one embodiment, the disclosure provides compounds as described above with any reference to formula (I) or (II), wherein X is —NH— or —O—. In another embodiment, X is —NH—. In yet another embodiment, X is —O—.

In one embodiment, the disclosure provides compounds as described above with any reference to formula (I) or (II), wherein X is —N($R^8$)CH$_2$—, —N($R^8$)CHR$^8$—, or —N($R^8$)(CHR$^8$)$_{2-5}$—.

In another embodiment, the disclosure provides compounds as described above with any reference to formula (I) or (II), wherein X is —N($R^8$)CH$_2$—. In yet another embodiment, X is —NHCH$_2$—.

In one embodiment, the disclosure provides compounds as described above with any reference to formula (I) or (II), wherein $R^4$ and $R^5$ are independently selected from the group consisting of halogen, —CN, —NO$_2$, $C_1$-$C_6$ alkyl, halo($C_1$-$C_6$ alkyl), —OR$^6$, and —NR$^6$$_2$.

In one embodiment, the disclosure provides compounds as described above with any reference to formula (I) or (II), wherein $R^4$ and $R^5$ are absent. In such embodiment, the compounds are of formula:

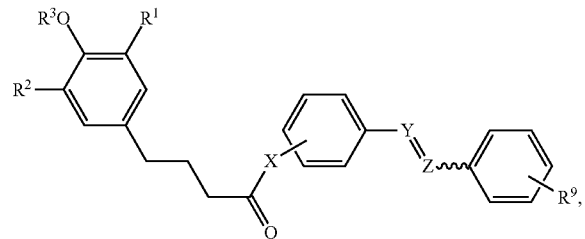

or of formula:

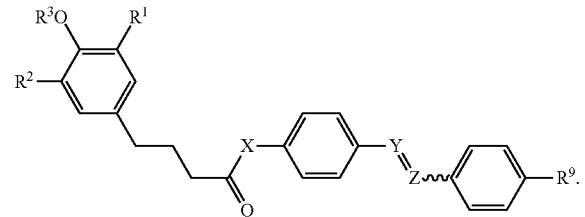

In one embodiment, the disclosure provides compounds as described above with any reference to formula (I) or (II), wherein Y=Z is —N=N—. Such compounds can have cis or trans configuration. In one embodiment, Y=Z is —N=N— and is trans or (E) isomer.

In another embodiment, the disclosure provides compounds as described above with any reference to formula (I) or (II), wherein Y=Z is —CH=CH—. Such compounds can have cis or trans configuration. In one embodiment, Y=Z is —CH=CH— and is trans or (E) isomer.

In one embodiment, the disclosure provides compounds as described above with any reference to formula (I) or (II), wherein $R^9$ is hydrogen, —CHR$^{6a}$, —OR$^{6a}$, —NR$^{6a}$$_2$, —CO$_2$R$^{6a}$, —CONR$^{6a}$$_2$, —CON(R$^8$)—(CH$_2$)$_{1-6}$—NR$^{6a}$$_2$, —CON(R$^8$)—(CH$_2$)$_{1-6}$—N(R$^8$)COR$^{6a}$, or —CON(R$^8$)—(CH$_2$)$_{1-6}$—N(R$^8$)COR$^{10}$, wherein $R^{10}$ is —CH$_2$CH$_2$(OCH$_2$CH$_2$)$_{2-50}$—N(R$^8$)COR$^{6a}$.

In one embodiment, the disclosure provides compounds as described above with any reference to formula (I) or (II), wherein $R^9$ is hydrogen, —CO$_2$R$^{6a}$, —CONR$^{6a}$$_2$, —CON(R$^8$)—(CH$_2$)$_{1-6}$—NR$^{6a}$$_2$, —CON(R$^8$)—(CH$_2$)$_{1-6}$—N(R$^8$)COR$^{6a}$, or —CON(R$^8$)—(CH$_2$)$_{1-6}$—N(R$^8$)COR$^{10}$, wherein $R^{10}$ is —CH$_2$CH$_2$(OCH$_2$CH$_2$)$_{2-50}$—N(R$^8$)COR$^{6a}$.

In another embodiment, the disclosure provides compounds as described above with any reference to formula (I) or (II), wherein $R^9$ is hydrogen, —CO$_2$H, or —CONH—(CH$_2$)$_2$—NH$_2$.

In yet another embodiment, the disclosure provides compounds as described above with any reference to formula (I) or (II), wherein $R^9$ is —CONH—(CH$_2$)$_2$—NH$_2$.

In yet another embodiment, the disclosure provides compounds as described above with any reference to formula (I) or (II), wherein $R^9$ is —CONH—(CH$_2$)$_2$—NHCOR$^{10}$, wherein $R^{10}$ is —CH$_2$CH$_2$(OCH$_2$CH$_2$)$_{2-50}$—NHCOR$^{6a}$, and $R^{6a}$ is heterocycle($C_1$-$C_6$ alkyl) or heteroaryl($C_1$-$C_6$ alkyl). In one embodiment, $R^9$ is

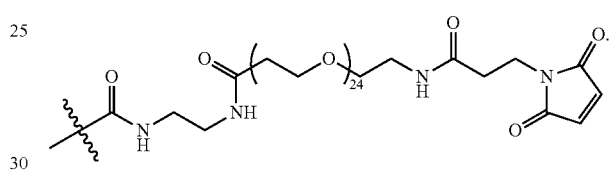

In particular embodiments, the disclosure provides compounds as described above with reference to formula (I) or (I), wherein each $R^6$ is independently hydrogen, $C_1$-$C_6$ alkyl or halo($C_1$-$C_6$ alkyl), wherein each alkyl is optionally substituted with 1, 2, 3 or 4 $R^7$, or two $R^6$ with the nitrogen to which they are attached form a heterocycle optionally substituted with 1, 2, 3 or 4 $R^7$.

In another aspect, the disclosure provides compounds of formula (III)

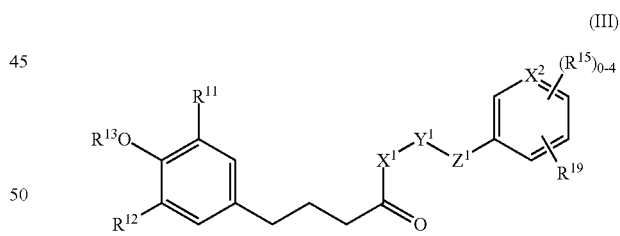

and pharmaceutically acceptable salts thereof, wherein $R^{11}$ and $R^{12}$ are independently $C_1$-$C_{12}$ alkyl, halo($C_1$-$C_{12}$ alkyl), $C_2$-$C_{12}$ alkenyl, or $C_2$-$C_{12}$ alkynyl, each optionally substituted with 1, 2, 3 or 4 substituents selected from halogen, —CN, —NO$_2$, $C_1$-$C_6$ alkyl, halo($C_1$-$C_6$ alkyl), —OR$^{16}$, —NR$^{16}$$_2$, —CO$_2$R$^{16}$, —CONR$^{16}$$_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle is optionally substituted with 1, 2, 3 or 4 $R^{17}$;

$R^{13}$ is hydrogen, $C_1$-$C_6$ alkyl, or halo($C_1$-$C_6$ alkyl);

$R^{15}$ is independently selected from the group consisting of halogen, —CN, —NO$_2$, $C_1$-$C_6$ alkyl, halo($C_1$-$C_6$ alkyl), —OR$^{16}$, —NR$^{16}$$_2$, —CO$_2$R$^{16}$, and —CONR$^{16}$$_2$;

$X^1$ is —N($R^{18}$)—, —N($R^{18}$)CHR$^{18}$—, —N($R^{18}$)(CHR$^{18}$)$_{2-8}$—, —O—, —OCHR$^{18}$—, —O(CHR$^{18}$)$_{2-8}$—, —CHR$^{18}$—, or —(CHR$^{18}$)$_{2-8}$—;

$Y^1$—$Z^1$ is -aryl-, -aryl-CO(NR$^{18}$)—, -aryl-CO$_2$—, -aryl-OCO—, -heteroaryl-, -heteroaryl-CO(NR$^{18}$)—, -heteroaryl-CO$_2$—, -heteroaryl-OCO—, -heterocyclyl-, -heterocyclyl-CO(NR$^{18}$)—, -heterocyclyl-CO$_2$—, -heterocyclyl-OCO—, —C$_3$-C$_8$ cycloalkyl-, —C$_3$-C$_8$ cycloalkyl-CO(NR$^{18}$)—, —C$_3$-C$_8$ cycloalkyl-CO$_2$—, —C$_3$-C$_8$cycloalkyl-OCO—, —CO(NR$^{18}$)—, —(NR$^{18}$)CO—, —CO$_2$—, or —OCO—;

$X^2$ is CH, C bearing one of the $R^{15}$, or N;

$R^{19}$ is hydrogen, —CHR$^{16a}$, —OR$^{16a}$, —NR$^{16a}{}_2$, —CO$_2$R$^{16a}$, —CONR$^{16a}{}_2$, —CON(R$^{18}$)—(CH$_2$)$_{1-6}$—NR$^{16a}{}_2$, —N(R$^{18}$)CO—(CH$_2$)$_{1-6}$—NR$^{16a}{}_2$, —CON(R$^{18}$)—(CH$_2$)$_{1-6}$—N(R$^{18}$)COR$^{16a}$, —N(R$^{18}$)CO—(CH$_2$)$_{1-6}$—N(R$^{18}$)COR$^{16a}$, —CON(R$^{18}$)—(CH$_2$)$_{1-6}$—N(R$^{18}$)COR$^{20}$, or —N(R$^{18}$)CO—(CH$_2$)$_{1-6}$—N(R$^{18}$)COR$^{20}$, wherein $R^{20}$ is —CH$_2$CH$_2$(OCH$_2$CH$_2$)$_{2-50}$—N(R$^{18}$)COR$^{16a}$;

where each $R^{16}$ independently is hydrogen, C$_1$-C$_6$ alkyl, halo(C$_1$-C$_6$ alkyl), C$_3$-C$_8$ cycloalkyl, aryl, heteroaryl, heterocycle, aryl(C$_1$-C$_6$ alkyl)-, C$_3$-C$_8$ cycloalkyl(C$_1$-C$_6$ alkyl)-, aryl(C$_1$-C$_6$ alkyl)-, heteroaryl(C$_1$-C$_6$ alkyl)-, or heterocycle(C$_1$-C$_6$ alkyl)-, wherein each alkyl, cycloalkyl, aryl, heteroaryl, and heterocycle is optionally substituted with $R^{17}$, or two $R^{16}$ with the nitrogen to which they are attached form a heterocycle optionally substituted with $R^{17}$;

where each $R^{16a}$ independently is hydrogen, C$_1$-C$_6$ alkyl, halo(C$_1$-C$_6$ alkyl), C$_3$-C$_8$ cycloalkyl, aryl, heteroaryl, heterocycle, aryl(C$_1$-C$_6$ alkyl)-, C$_3$-C$_8$cycloalkyl(C$_1$-C$_6$ alkyl)-, aryl(C$_1$-C$_6$ alkyl)-, heteroaryl(C$_1$-C$_6$ alkyl)-, or heterocycle(C$_1$-C$_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;

where each $R^{17}$ independently is halogen, —CN, —NO$_2$, —N$_3$, C$_1$-C$_6$ alkyl, halo(C$_1$-C$_6$ alkyl), C$_1$-C$_6$ alkoxy, amino, C$_1$-C$_6$alkylamino, diC$_1$-C$_6$alkylamino, —CO$_2$H, —COH, —CO$_2$R$^{18}$, or —CON(R$^{18}$)$_2$; and wherein each $R^{18}$ independently is hydrogen or C$_1$-C$_6$ alkyl.

In one embodiment, the disclosure provides compounds as described above with reference to formula (III), wherein $R^{13}$ is hydrogen.

In another embodiment, the disclosure provides compounds as described above with any reference to formula (III), wherein $R^H$ and $R^{12}$ are independently C$_1$-C$_{12}$ alkyl, optionally substituted with one to four substituents selected from halogen, —CN, —NO$_2$, C$_1$-C$_6$ alkyl, halo(C$_1$-C$_6$ alkyl), —OR$^{16}$, —NR$^{16}{}_2$, —CO$_2$R$^{16}$, —CONR$^{16}{}_2$, C$_3$-C$_8$ cycloalkyl, C$_3$-C$_8$cycloalkenyl, aryl, heteroaryl, and heterocycle. In another embodiment, $R^1$ and $R^2$ are independently C$_1$-C$_{12}$ alkyl, optionally substituted with one to four substituents selected from halogen, —CN, —NO$_2$, C$_1$-C$_6$ alkyl, halo(C$_1$-C$_6$ alkyl), —OR$^{16}$, —NR$^{16}{}_2$, —CO$_2$R$^{16}$ and —CONR$^{16}{}_2$. In yet another embodiment, $R^{11}$ and $R^{12}$ are independently unsubstituted C$_1$-C$_{12}$ alkyl. In yet another embodiment, $R^{11}$ and $R^{12}$ are independently unsubstituted C$_1$-C$_6$ alkyl.

In one embodiment, the disclosure provides compounds as described above with any reference to formula (III), wherein $R^{11}$ and $R^{12}$ are both —CH(CH$_3$)$_2$.

In one embodiment, the disclosure provides compounds as described above with any reference to formula (III), wherein $X^2$ is CH. In one embodiment, the disclosure provides compounds as described above with any reference to formula (III), wherein $X^2$ is N.

In one embodiment, the disclosure provides compounds as described above with any reference to formula (III), wherein $R^{15}$ is independently selected from the group consisting of halogen, —CN, —NO$_2$, C$_1$-C$_6$ alkyl, halo(C$_1$-C$_6$ alkyl), —OR$^{16}$, and —NR$^{16}{}_2$.

In one embodiment, the disclosure provides compounds as described above with any reference to formula (III), wherein $R^{15}$ is absent.

In one embodiment, the disclosure provides compounds as described above with any reference to formula (III), wherein $R^{19}$ is hydrogen, —CHR$^{16a}$, —OR$^{16a}$, —NR$^{16a}{}_2$, —CO$_2$R$^{16a}$, —CONR$^{16a}{}_2$, —CON(R$^{18}$)—(CH$_2$)$_{1-6}$—NR$^{16a}{}_2$, —CON(R$^{18}$)—(CH$_2$)$_{1-6}$—N(R$^{18}$)COR$^{16a}$, or —CON(R$^{18}$)—(CH$_2$)$_{1-6}$—N(R$^{18}$)COR$^{20}$, wherein $R^{20}$ is —CH$_2$CH$_2$(OCH$_2$CH$_2$)$_{2-50}$—N(R$^{18}$)COR$^{16a}$.

In one embodiment, the disclosure provides compounds as described above with any reference to formula (III), wherein $R^{19}$ is hydrogen, —CO$_2$R$^{16a}$, —CONR$^{16a}{}_2$, —CON(R$^{18}$)—(CH$_2$)$_{1-6}$—NR$^{16a}{}_2$, —CON(R$^{18}$)—(CH$_2$)$_{1-6}$—N(R$^{18}$)COR$^{16a}$, or —CON(R$^{18}$)—(CH$_2$)$_{1-6}$—N(R$^{18}$)COR$^{20}$, wherein $R^{20}$ is —CH$_2$CH$_2$(OCH$_2$CH$_2$)$_{2-50}$—N(R$^{18}$)COR$^{16a}$.

In another embodiment, the disclosure provides compounds as described above with any reference to formula (III), wherein $R^{19}$ is hydrogen, —CO$_2$H, or —CONH—(CH$_2$)$_2$—NH$_2$.

In yet another embodiment, the disclosure provides compounds as described above with any reference to formula (III), wherein $R^{19}$ is —CONH—(CH$_2$)$_2$—NH$_2$.

In yet another embodiment, the disclosure provides compounds as described above with any reference to formula (III), wherein $R^{19}$ is —CONR$^{16a}{}_2$, and two $R^{16a}$ with the nitrogen to which they are attached form a heterocycle optionally substituted with 1, 2, 3 or 4 $R^{17}$. In another embodiment, $R^{19}$ is morpholinylcarbonyl or piperazinylcarbonyl.

In one embodiment, the disclosure provides compounds as described above with any reference to formula (III), wherein $X^1$ is —N(R$^{18}$)CHR$^{18}$—, —N(R$^{18}$)(CHR$^{18}$)$_{2-8}$—, —CHR$^{18}$—, or —(CHR$^{18}$)$_{2-8}$—.

In another embodiment, the disclosure provides compounds as described above with any reference to formula (III), wherein $X^1$ is —N(R$^{18}$)(CHR$^{18}$)$_{2-8}$—. In another embodiment, $X^1$ is —NH(CH$_2$)$_{2-8}$—. In yet another embodiment, $X^1$ is —NH(CH$_2$)$_{2-6}$—.

In another embodiment, the disclosure provides compounds as described above with any reference to formula (III), wherein $X^1$ is —(CHR$^{18}$)$_{2-8}$—. In another embodiment, $X^1$ is —(CH$_2$)$_{2-8}$—. In yet another embodiment, $X^1$ is —(CH$_2$)$_{2-6}$—.

In another embodiment, the disclosure provides compounds as described above with any reference to formula (III), wherein $Y^1$—$Z^1$ is -heteroaryl-, -heterocyclyl-CO(NR$^{18}$)—, —C$_3$-C$_8$cycloalkyl-CO(NR$^{18}$)—, or —CO(NR$^{18}$)—.

In another embodiment, the disclosure provides compounds as described above with any reference to formula (III), wherein $Y^1$—$Z^1$ is —CO(NH)—.

In another embodiment, the disclosure provides compounds as described above with any reference to formula (III), wherein $Y^1$—$Z^1$ is imidazolyl or triazolyl.

In another embodiment, the disclosure provides compounds as described above with any reference to formula (III), wherein $Y^1$—$Z^1$ is -heterocyclyl-CO(NR$^{18}$)—, or —C$_3$-C$_8$cycloalkyl-CO(NR$^{18}$)—.

In providing the ability to control circuit excitability with spatial and temporal precision, switchable modulators of neural activity provide potential treatment possibilities for exploring the links between neuronal activity and behavior. This approach can be used to explore which brain regions are most important for anesthesia and sedation. Clinical contexts in which a photo-switchable GABA modulator can be useful include diseases of hyperexcitability, such as epilepsy. (Baulac et al., 2001; Palma et al., 2005; Goodkin et al., 2008; McDonald et al., 2010). Propofol is known to be an effective therapeutic for intractable epilepsy, although side effects are a concern. (Power et al., 2011; Iyer et al., 2009; Rossetti et al., 2011). Photo-switchable propofol analogs, in combination with localized optical stimulation (Yizhar et al., 2011) and appropriate electrical monitoring, provide a potential treatment for the reduction of side effects in treating epilepsies, by employing spatially precise, optically-regulated receptor modulation specifically during bouts of hyperexcitability. Furthermore, even with a diffusible modulator, focally directed illumination can allow spatially restricted actions of the anti-epileptic drug around seizure foci. In particular aspects of the invention, the postsynaptic receptor is a GABA receptor such as a $GABA_A$ receptor ($GABA_AR$). $GABA_ARs$ are pentameric ligand-gated ion channels that function as postsynaptic and extrasynaptic receptors for the inhibitory neurotransmitter γ-aminobutyric acid (GABA) in the brain and retina. (Farrent, et al., 2005; Olsen et al., 2009; Mortensen et al., 2010). The $\alpha_1\beta_2\gamma_2$ $GABA_AR$, which consists of two $\alpha_1$ subunits, two $\beta_2$ subunits and a single $\gamma_2$ subunit, is among the most abundant and widely distributed of this receptor type. A number of naturally occurring and synthetic low-molecular weight compounds are known to modulate the $\alpha_1\beta_2\gamma_2$ $GABA_AR$ response to GABA. (Farrant, M. et al., 2005). In other aspects of the invention the receptor is a $GABA_AR$.

In vitro reconstitution of NNP components may employ isolated (i.e., purified) target GABAc in the form of solubilized or membrane-associated full-length protein, and soluble extracellular domain. Such in vitro experiments complement electrophysiological and cell-based binding experiments, provide information on the key issue of whether an activity of the test component determined in the whole-cell experiments reflects the test component's direct interaction with GABAc. Isolated GABAc can be obtained in the extracellular domain because monomers of isolated GABAc, like those of acetylcholine binding protein (AchBP) and of homologous extracellular domains of related membrane proteins, spontaneously associate to form a pentameric complex whose extracellular topology and GABA-binding properties resemble those of homomeric GABAc receptors in situ. A primary construct used to obtain GABAc extracellular domain is a core extracellular segment of human GABAc p1 subunit as identified below. Bacterially expressed perch p1B construct can be solubilized, and the perch sequence provides an alternative to the preparation/characterization of human p1 protein. As perch and human GABAc receptors exhibit similar pharmacology (Qian et al., 1998; Qian & Ripps, 2001), the expressed/solubilized perch sequence are expected to be adequate for use in testing platform components. The N-terminal positions of both the human and perch constructs correspond with the beginning of a predicted GABAc helical domain associated with a known helical domain of AchBP. In addition, these two expressed GABAc sequences include a region inferred from mutation studies to contain the GABA-binding site for both $GABA_A$ and GABAc receptors (Chang & Weiss, 2000, 2002; Newell & Czajkowski, 2003; Sedelnikova et al., 2005). The C-terminal of both constructs corresponds with the C-terminal of AchBP and is the start of a putative transmembrane segment of native GABAc.

His-tagged fusion proteins have been generated from bacterial expression with the extracellular domain of the human and perch p1 subunits. Both constructs are actively synthesized in bacteria in insoluble form, and can be purified in their denatured condition. For perch p1B protein, a refolding condition that yields a soluble protein with potentially high GABA-binding capacity is provided herein. To further characterize the purified protein, size exclusion and sucrose density centrifugation experiments can determine the molecular mass of the protein complex, which serves as an index of oligomerization. The functional integrity of the purified protein is determined by GABA-binding assays as set forth below. Multiple parameters, including ionic strength, pH, the presence of redox agents, polar/nonpolar agents, poly(ethylene glycol) (PEG) and detergents are known to alter the refolding process (Chen & Gouaux, 1997; Breitinger et al., 2004), wherein refolding efficiency using such agents can be and the amount of soluble protein determined by SDS/PAGE, with functional integrity assayed by GABA binding.

Radiolabeled GABA is used to determine the protein's GABA-binding activity in saturation binding assays (dependence of bound $^3H$ on the molar concentration of ($^3H$)GABA of fixed specific radioactivity) and in competition binding assays (dependence of bound $^3H$ on the molar concentration of unlabeled GABA combined with a fixed amount of ($^3H$) GABA). Methods used to analyze ($^3H$)GABA binding by the soluble protein can follow those described by Kim et al. (1992). Briefly, for saturation binding assays the protein is incubated with varying concentrations of ($^3H$)GABA at room temperature for 40 min, then vacuum-filtered through GF/B glass fiber filters (pre-treated with 0.5% polyethylenimine for 1 hr) to trap the protein. The filters are rapidly washed once with 3 mL ice-cold binding buffer; bound protein is solubilized with 0.3N NaOH and then neutralized with HCl; and bound ($^3H$)GABA measured by liquid scintillation counting. Procedures for determining nonspecific ($^3H$)GABA binding in these assays are similar to those described below. Data is interpreted as follows. In competition binding assays, a GABA $IC_{50}$ for GABAc extracellular domain similar to that of cell-expressed GABAc is interpreted as an indication of proper folding of the extracellular domain and used as the main performance criterion for this preparation. Furthermore, as the GABA-binding sites of native GABAc receptors are thought to be located at the junctions of (the extracellular domains of) adjacent subunits, as in acetylcholine receptors (Karlin, 2002; Cromer et al., 2002), significant GABA binding activity would be an indirect indication of subunit oligomerization to form a homopentamer. However, even correctly folded and oligomerized extracellular domain exhibits GABA-binding affinity well below that of native receptor due to differences from native orientation/conformation of the associating subunits. GABA binding activity is used to track appearance of the protein in chromatographic column fractions and to optimize protein preparative procedures (e.g., determining the effects of detergent treatment on protein recovery). Conventional methods of size-exclusion chromatography, native gel electrophoresis and dynamic light scattering are used specifically to determine whether the expressed extracellular domain forms a pentamer. Atomic force microscopy (AFM) can be used to investigate the expressed extracellular domain's state of oligomerization. Resolving monomer (predicted particle size: ~40 A) from pentamer (predicted outer diameter of the putative doughnut-shaped structure: ~80 A) is well within the capabilities of this method. AFM in tapping mode may be used to quantitatively analyze the sizes of GABAc extracellular domain particles tethered to a supporting surface under defined conditions of GABAc concentration (areal density of the protein), presence of added control protein of known size, and presence of surface-tethered organic compounds that modify the surface microenvironment, e.g., its hydrophilicity (e.g., Sharma et al., 2002, 2003). The method used to tether the GABAc extracellular domain to the supporting surface can in certain embodiments use a commercially available chip with epoxide activation or amine-reactive species (e.g., EDC technology similar to that used to cross-react proteins). However, these cross-linking approaches (or, e.g., terminal biotinylation of the protein and immobilization on an avidin-coated support) may yield heterogeneous orientation of the tethered protein (in the case of surface avidin coating, due to heterogeneous orientation of the avidin) that could confound determinations of the state of oligomerization. Alternatively, GABAc can be tethered using a more site-selective procedure (C-terminal histidine-tagging of the protein and tethering to a $Ni^{2+}$ support, or cysteine-tagging and tethering to a gold surface) to achieve greater uniformity in protein orientation. In summary, GABA-binding activity similar to that of the native receptor, and the occurrence of pentameric structure as determined by chromatographic behavior and AFM, together with CD and SDS-PAGE behavior, together represent performance criteria for extracellular domain preparation.

Expression of full length and extracellular domain GABAc in baculovirus system: Baculovirus (i.e., insect cell) expression of full-length GABAc can yield enriched protein that is folded and associates to form a pentameric structure. Relative to bacterial expression, there is a greater likelihood of correct folding in the insect cell line even if the protein being expressed is extracellular domain rather than full-length. Preparative procedures are based on experience with use of the baculovirus system for membrane protein expression (e.g., Stauffer et al., 1991; Gatto et al., 2001). In particular, expression of mammalian membrane proteins has been successfully achieved by the infection of sf9 or High Five cells with recombinant baculovirus particles; membrane proteins that have been expressed and whose molecular characterization continues includes Na, K-ATPase, a heterodimeric active transport protein, Wilson Disease protein (i.e., ATP7B, a human Cu-activated transporter), and hCTR1 (the major human membrane protein responsible for Cu entry into cells; Hu & Kaplan, 2000; Eisses & Kaplan, 2002; Tsivkovskii et al., 2000; Laughery et al., 2003). In the case of the Na,K-ATPase, baculovirus-mediated expression produces the protein at levels representing 3-5% of total membrane protein, a level significantly higher than obtainable in mammalian cells. Moreover, the expressed protein exhibits catalytic activity similar to that of the protein expressed in mammalian cells, i.e., this two-subunit protein properly assembles and exhibits full functionality when expressed in the insect cells. Strategies that have proven successful for other membrane proteins to express GABAc receptor in sf9 membranes may be used. Overexpression can supply a source of intact full-length receptor, and functionality of the receptor is confirmed by electrophysiological (patch-clamp) recording. sf9 insect cells can be used with baculovirus constructs to stably express the GABAc receptor. The baculovirus system can be used to produce GABAc extracellular domain under circumstances where bacterial expression of the protein does not yield refolded functional protein in sufficient quantities. Engineering, preparation and isolation of recombinant baculovirus; infection of insect cells and their fractionation; and techniques associated with isolation of the expressed receptor molecules are used in these alternatives. More specifically, donor plasmids are constructed by subcloning wild-type GABAc receptor into one of the cloning sites of the pFAST-BACDUAL vector (Life Technologies, Inc). Recombinant baculovirus are then produced following the Bac-to-Bac baculovirus expression system provided by the manufacturer. The best MOI values and periods of infection prior to cell harvesting are determined for GABA receptor expression. Full-length receptor appears in membrane fractions and its distribution among the plasma membrane, ER and Golgi pools determined through assays of GABA-binding. Ligand binding experiments can be used to detect functional differences in the receptor in each fraction. If no such differences are detected, unfractionated membrane preparations can be used. Mutant GABAc receptors (for example, prepared with site-directed modification) can also be generated using these protocols. Isolation of the extracellular domain can be accomplished using an epitope-tagged version bearing the His6-epitope at the C-terminus, to facilitate purification with metal-ion columns (as was done with the recent successful expression/isolation/purification of the ATP-binding domain of the Na, K-ATPase in the Kaplan laboratory; Gatto et al., 1998; Costa et al., 2003). For use in the reconstitution assays, preparation of both membrane-associated and solubilized (by e.g., CHAPS) full-length protein (e.g., Stauffer et al., 1991) can be used and the more readily obtained preparation adopted for routine use. In the event of difficulties with expression of the extracellular domain sequence in the baculovirus system, an available alternative strategy is to express, in this system, a mutated full-length sequence containing an engineered protease site. The needed size of the introduced cleavage site is likely to be about 10-15 amino acids (including, e.g., glycines and prolines as well as the specific amino acids needed for recognition by the protease) to displace the desired extracellular domain from the surface of the plasma membrane, i.e., to make it accessible to the protease. In addition, for protein purification, the cleavage site can be engineered to incorporate adjacent histidines (for attachment of the protein to a nickel-coated substrate) or cysteines (for attachment to a gold substrate) (e.g., Gatto et al., 1998). More generally, a further alternative strategy for obtaining purified membranes containing full-length GABAc is to use an already available neuroblastoma cell line stably transfected with GABAc human p1 subunit.

Obtaining structural information on the GABAc extracellular domain is advantageous for interacting molecular structures with this domain. In light of the importance of such information (e.g., Sabini et al. 2003), the putative pentameric complex of GABAc extracellular domain prepared from bacterial and/or baculovirus expression systems is crystallized. Crystallization methods are well established. As GABAc p1 subunits are predicted to form a homopentamer, purified GABAc extracellular domain can afford crystallization of pentameric complexes. To increase the likelihood of obtaining diffraction-quality crystals, GABAc fragments of different lengths and from different species are tested. Crystallization procedures can employ pre-formulated solutions (Hampton Research) and use of differing protein concentrations and temperatures (4, 12 and 20° C.). An available rotating-anode x-ray generator and image plate detector, can be used to screen any crystals that attain a suitable size (~100-200 μm). This procedure solves the structure by molecular replacement using the available model of AchBP (Brejc et al., 2001; Cromer et al., 2002). Alternatively, the Multiwavelength Anomalous Dispersion technique can be applied.

Figure 1:
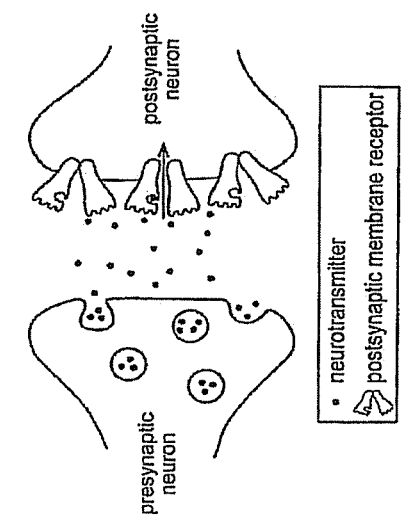
FIG. 1 depicts signal transmission in a normally functioning synapse.

Tetherable, i.e., chain-derivatized, compounds that have activity at the GABAc receptor, can, upon coupling with photoswitch/anchor components, afford light-regulated control of receptor activation (cf. FIG. 1). In two alternatives, a photoisomerizable organic structure is positioned in close proximity to the effector moiety. Involved in these alternatives are: use azobenzene as a prototype photoswitch; syntheses of candidate compounds that incorporate an effector, neighboring photoswitch, and poly(ethylene glycol) (PEG) linkers; and approaches for biophysical/electrophysiological testing of the synthesized structures.

Figure 15:
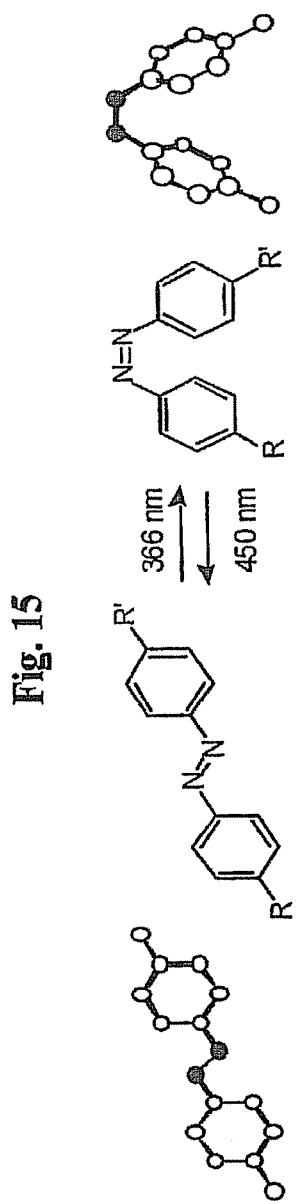
FIG. 15 depicts photoisomerization of azobenzene.

Rationale for use of azobenzene-based photoswitches: Azobenzenes, which have been used widely as photochemical switches, undergo cis/trans isomerization of the N═N bond in response to light. At thermodynamic equilibrium in darkness, azobenzenes exist almost exclusively in the trans form. Isomerization to the cis form is induced by near-UV light (366 nm), and back-isomerization to trans is induced by visible light. The photoisomerization event is rapid (~1 ps), and population changes are readily accomplished on a submillisecond time scale with a flashgun or laser apparatus (Lester & Nerbonne, 1982; Gurney & Lester, 1987; also cf. Denk, 1997). The trans and cis isomers of azobenzene differ in two important respects. The first is geometric: the trans configuration is planar and provides a large, flat hydrophobic surface, whereas the cis configuration is forced out of planarity by steric clashes between the rings, giving it a bulky, irregular shape (FIG. 15). The second difference is electrostatic: the trans configuration has no net dipole moment due to the cancellation of internal dipoles through symmetry, while the cis configuration has a large dipole moment that makes it more polar and less hydrophobic. FIG. 15 depicts photoisomerization of azobenzene. The trans to cis isomerization decreases the distance between the 4- and 4'-substituents (R and R') from 12 Å to 6 Å.

Azobenzenes have several additional advantages. Chief among these are small size, predictable geometry, ease of synthesis, chemical robustness, tolerance for a wide array of substituents, and relative absence of photochemical side reactions. Moreover, Lester et al. (1980) linked an azobenzene-based analog of acetylcholine directly to the acetylcholine receptor and demonstrated light-regulated receptor activation, and Banghart et al. (2004) employed azobenzene as a switch to photo-regulate the activity of a mutant $K^+$ channel. In the parent azobenzene molecule itself, and in most simple derivatives, the cis isomer is produced by irradiation in the near-UV (370 nm), and back-isomerization to trans is effected by blue light (450 nm), and the dark isomerization is extremely slow (days). Importantly, the isomerization wavelengths can be red-shifted such that both are in the visible range, and the thermal isomerization greatly accelerated through the use of special substituents, notably electron donor groups on one ring coupled with electron acceptor groups on the other, so-called "push-pull" azobenzenes. The slow thermal isomerization of typical (not push-pull) azobenzenes is a great advantage in characterizing the behavior of the individual photoisomers, whereas the rapid thermal isomerization will be necessary in a working device.

Synthesized chain-derivatized effector compounds found in free (i.e., untethered) form to have activity at GABAc receptors are candidates for anchoring and photoswitch incorporation, for further testing as workable NNPs. Identification of an effector as a candidate for use in the ultimately desired NNP is based on the GABAc-binding properties of the effector (free effector, or part of an effector/photoswitch/linker assembly): specifically, the dissociation constant ($K_D$) determined in cell-based and in vitro binding assays; the $EC_{50}$ (or $IC_{50}$) determined by measurement of the dose-response curve in electrophysiological experiments; and, for effector/photoswitch/linker assemblies, length of the linker chain and photoisomerization induced change in end-to-end photoswitch length. FIG. 15 illustrates two models through which the suitability of an agonist effector is estimated from the interrelationship of these four parameters. In a specific example provided herein is an agonist effector (e.g., muscimol), a linker consisting of a linear PEG chain, and azobenzene as the photo switch.

In particular embodiments the linker maintains the effector within a range of the receptor sufficient for the effector to operatively approximate with the receptor when the photoswitch is in the first configuration. In other particular embodiments, the linker is a PEG chain.

Figure 16:
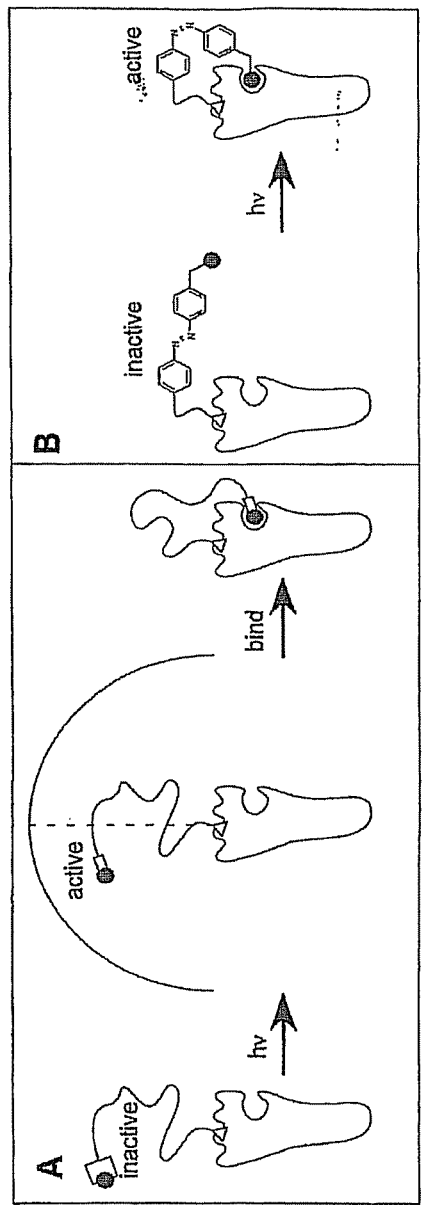
FIG. 16 illustrates photoregulated presentation of an agonist effector to the GABA receptor.

In a first, or "long linker" embodiment, the effector (filled circle), close-coupled to an azobenzene photoswitch (open rectangle), is anchored (open triangle) to the receptor via a long, highly flexible PEG linker. FIG. 16. The "inactive" isomer of the photoswitch (denoted by the large size of open rectangle) conformationally blocks effector binding. Light, by isomerizing the photoswitch (transition to small open rectangle), relieves the conformational block and allows effector binding at the receptor's ligand-binding site. At all times the close-coupled effector-photoswitch is confined to an approximate hemisphere by the PEG linker, which has a random conformation. The size of the hemisphere is controlled through the length of the PEG chain, which is chosen to establish a local molarity of the effector-photoswitch greater than the $EC_{50}$ for the active state (active isomer of the photoswitch) and below the $EC_{50}$ for the inactive (i.e., non-binding or weakly binding) state.

In a second, or "short linker" embodiment, a constitutively active effector is prevented from reaching the receptor's ligand-binding site by the conformational constraint of the azobenzene photoswitch, which is anchored to the receptor by a minimal length of tethering chain (e.g., a few ethylene oxide units). Photoisomerization of the switch re-orients the effector, allowing its binding to the receptor's ligand-binding site. Molecular structures are not drawn to scale.

Tethering the effector to the receptor causes an increase in the local concentration (molarity) of the effector. Herein are illustrated the effects of polyethylene glycol (PEG) comprising chains of different lengths. PEG is a highly flexible polymer, and a fully extended PEG chain has a length of 3.5 Å per EG unit. However, Bedrov & Smith (2003) showed that this fully extended configuration is energetically disfavored, and that the interval representing 0-80% of full extension is essentially isoenergetic. Thus, it can be assumed that the free terminus of a PEG chain, when the other end is attached to a membrane receptor, moves randomly about an isoenergetic, hemispheric volume with a radius equal to $(n)(0.8)(3.5 \text{ Å})$, where n is the number of EG units (FIG. 16). PEG 3400 (n=77) provides an attractive starting length because a wide variety of functional derivatives of it are commercially available and moderately priced, and the size of the hemisphere (radius=216 Å) is larger than the GABAc receptor subunit, so that a molecule tethered at any point on the receptor should have free access to the ligand binding site. In the simplest possible model, wherein the anchored effector is viewed as a freely diffusing element, the effective volume available to the effector is $2.1 \times 10^{-20}$ L, and its effective molarity is 79 µM. This simplest scenario ignores several potentially complicating factors, including: the volume excluded by the chain itself; a geometric factor influencing the effector's local concentration (i.e., proportionality to $(\text{radius})^{-2}$ in non-excluded volume elements); the non-planarity of the receptor's extracellular surface and surrounding membrane; possible attractive/repulsive interactions of the effector, photoswitch or PEG chain with the receptor or surrounding membrane; and the need for (and possible interactions among)>2 tethered effectors per pentameric receptor to achieve activation (Amin & Weiss, 1996; Karlin, 2002). The aggregate effect of these factors are resolved through variation of the PEG chain length. This specifically predicts that an effector with an $EC_{50}$ substantially above about 80 µM cannot achieve significant occupancy, whereas an effector with an $EC_{50}$ significantly below 80 µM is expected to have significant occupancy.

In certain embodiments, comprising "long" PEG chain length, successful operation of the device requires a high differential in the binding affinity of the effector upon isomerization of the photoswitch. In this regard the effect of the photoswitch on the effective volume calculation is a relevant consideration. A p,p'-disubstituted azobenzene moiety is approximately 12 Å long in the trans form and 6 Å long in the cis form (FIG. 15), and other conceivable photoswitches undergo changes of the same order of magnitude. Clearly, a 6 Å change in radius is negligible in relation to the 216 Å effective length of a PEG 3400 chain. Workability in the long-chain strategy requires that the photoswitch moiety be proximally coupled to the effector, so that it acts through local, specific effects such as steric hindrance (FIG. 16A). Specific performance criteria are dictated by the effective molarity of 80 µM enforced by the PEG 3400 chain. For the device to function well, the $EC_{50}$ of the permissive (active) photoisomer must be substantially lower than 80 µM, and that of the non-permissive (inactive) photoisomer must be significantly higher. These criteria define a target range of affinity for the permissive and non-permissive forms of the effector/photoswitch combination. That is, the permissive form should have an $EC_{50}$<25 µM, the non-permissive form should have an $EC_{50}$>250 µM, and the dynamic range of the effector-photoswitch combination needs to be at least one order of magnitude. It is important to note that it is entirely reasonable to expect such a dynamic range from an azobenzene-based system. For example, Westmark et al. (1993) prepared a simple, azobenzene-based inhibitor of the protease papain which displayed $K_i$'s of ~2 µM and ~80 µM for the trans and cis forms, respectively (dynamic range of 40). In addition, the target affinity of $EC_{50}$<25 µM in the permissive form is also reasonable in that the amount of material required is not excessive, and a saturating response can be achieved at 100 µM (untethered ligand), which is below the point where water-solubility of the ligand is expected to be a problem. Importantly, it has already been shown that muscimol-biotin has an adequate $EC_{50}$ (20 µM at GABAc).

Certain alternative embodiments, comprising short PEG chain length, utilize expansion, contraction or bending of the photoswitch, coupled to both receptor and ligand with tethers of minimal length, to re-orient the effector moiety. FIG. 16B depicts the case in which the dark-state trans isomer precludes full entry of the effector into the ligand binding site. Photoisomerization to the cis form relieves the block and allows activation. It is useful to compare the short PEG length to the long PEG length discussed above, which have the following differences. First, the net length of the PEG chains employed is required to be short (n<6). In this "short" regime, the effective molarity of the effector is in principle very high (over 10 mM), but its movement will be highly constrained by the short tether, and displacements of a few Å within the photoswitch moiety are relied upon to move the effector into or out of the binding site. A specific (though hypothetical) implementation of the FIG. 15B scheme can involve an anchoring at 10 Å from the opening to the binding site, an azobenzene photoswitch, and a linker of two EG units. The maximum extension of this linker is 7 Å, and the minimum is about 3 Å (van der Waals contact of termini). As depicted in FIG. 15B, the range of extension of the short linker (3-7 Å), in combination with the rigid 12 Å trans azobenzene, precludes access of the effector to the binding site. By contrast, photoisomerization to a 6 Å cis azobenzene permits access.

In principle, a very weak effector, i.e., one with a high value of $EC_{50}$, could be employed in the short PEG chain length embodiments due to the high effective molarity envisioned. However, in these embodiments an $EC_{50}$ for the untethered effector of 100 µM or lower is desired. One reason is that the effector could ultimately be responsible for targeting the NNP to the $GABA_A$ receptor, and molecules of lower affinity might lack adequate specificity. Another reason is practicality, in that compounds with significantly higher $EC_{50}$'s must be made in greater quantities for characterization and might present solubility problems. With regard to photoisomerization directionality, both embodiments are intended to operate with trans-to-cis photoisomerization as the activating event, i.e., the cis form is permissive. Although a device functioning in the opposite way (trans form permissive) in vitro, is within the scope of the invention the trans-to-cis activation is preferable. The thermodynamic preference for the trans form is large, $\Delta G \approx \Delta H = 49$ kJ/mol in azobenzene itself (Dias et al., 1992), leading to negligible thermal population of the cis state (molar ratio cis/trans=$K_{eq}$=3×10$^{-9}$ at 25° C., derived from the relation $K_{eq}$=exp(−ΔG°/RT). Thus, a device with a non-permissive trans form will return spontaneously to the baseline dark state, whereas a device in which the trans form is permissive will spontaneously move toward full activation through thermal cis-to-trans isomerization. With the cis form permissive, binding affinity by the ligand will favor the cis configuration. However, for this effector-binding energy to overcome the intrinsic thermodynamic preference for trans, the cis form must have a binding energy of >49 kJ/mol, and hence a $K_D$<3 nM. As known GABAc effectors have $K_D$'s well above this value, there should be no constraint on prototype system design by an upper-limit binding affinity in a trans-nonpermissive configuration.

The NNP employs an agonist as effector. Use of an antagonist effector is expected to be difficult in vivo, as a background of GABA would be required. However, identification of tetherable GABAc antagonists can provide insights into advantageous or optimum NNP designs and, in particular, can be used for developing a "scaffold" strategy for platform anchoring. Both agonists and antagonists as potential effectors are within one scope of the invention. For the agonist, a particular embodiment is muscimol, that has been prepared as a tetherable derivative through simple modification chemistry having has sufficient potency (Vu et al., 2005). To prepare a tetherable antagonist, phosphinic acids are exemplary, which are the only known specific GABAc antagonists.

Figure 17:
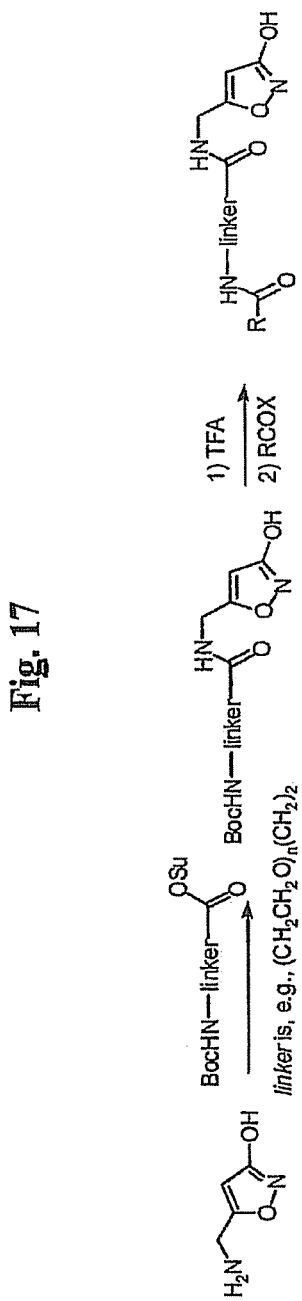
FIG. 17 depicts preparation of chain-derivatized muscimol.
Figure 20:
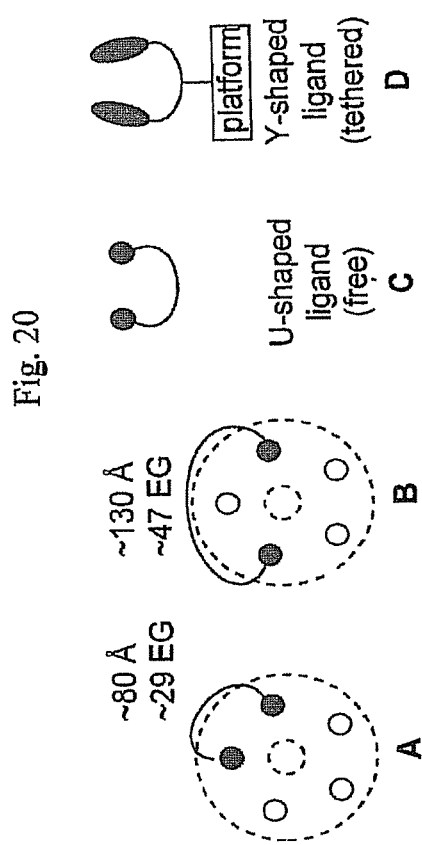
FIG. 20 depicts design of PEG-linked bivalent effectors.
Figure 21:
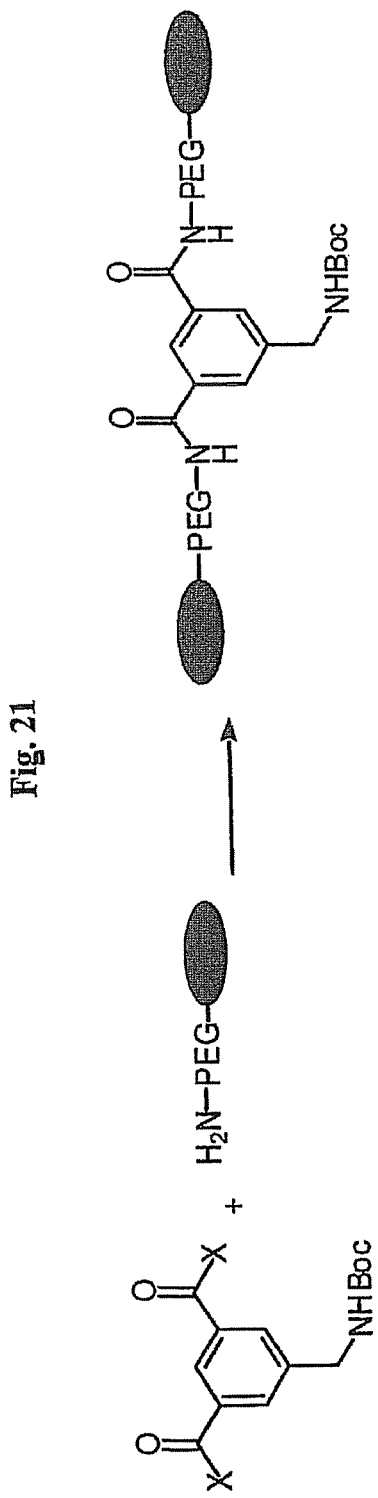
FIG. 21 depicts a synthetic route to Y-shaped PEG-length effectors.

The rationale for investigating muscimol derivatives is based on results obtained with muscimol-biotin and muscimol-BODIPY, two chain derivatized forms of muscimol that exhibit agonist activity at both GABAc and $GABA_A$ receptors expressed in Xenopus oocytes (Vu et al., 2005). The activities of these compounds show that muscimol conjugated to structurally different molecules through a linear (aminocaproyl) linker can activate these receptors. As pointed out in the Discussion section of Vu et al. (2005), it is not yet clear to what extent the biotin in muscimol-biotin, with its relatively short aminocaproyl linker, extends to the extracellular space beyond the receptor's ligand-binding site. However, preliminary fluorescence data indicate that muscimol conjugated to a (sterically bulky) CdSe nanocrystal via a PEG 3400-aminocaproyl combination linker displays marked affinity for GABAc. For accessibility of the distal end of the chain, a series of compounds biotin-(PEG)-muscimol are prepared to assess the impact of soluble streptavidin on the biochemical and physiological properties of the compound. Where co-incubation with streptavidin lacks an effect, it is inferred that the distal end of the chain is both beyond the immediate vicinity of the binding site and is accessible to the bulky streptavidin protein; such linkers are ideal. Where streptavidin has an effect, it is inferred that the distal terminus is not free of the receptor; here, the corresponding chain lengths will potentially be useful positioning of the photoswitch. In addition to PEG 3400 (n=77 EG units), initially n=4, 8, 16 and 32 are tested, relying, where possible, on commercially available bifunctional PEG derivatives and preparing unavailable reagents from appropriate base polymers (FIG. 17). These compounds can be purified by reversed-phase HPLC or (for PEG derivatives) crystallization or sizeexclusion/ion-exchange chromatography. For muscimol-based effector/photoswitch/linker assemblies identified in tests of GABA-binding and electrophysiological activity, variants are prepared that contain acyl-linked GABA rather than muscimol. Although a previously synthesized, biotinylated GABA-based compound exhibited little or no electrophysiological activity, these GABA-based variants may be useful in combination with anti-GABA antibody (Saifuddin et al., 2003) as a check on AFM surface characterization procedures to be used to study the interaction of GABAc extracellular domain with muscimol-containing test components. An alternative can be trans-aminocrotonic acid (TACA) as an effector moiety (Kusama et al., 1993).

Cd Se nanocrystals (diameter ~4-10 nm), either as uncoated cores or coated with a shell that passivates the core material and can itself be functionalized using conventional bioconjugate chemistry, exhibit the ability to present ligands to membrane surface receptors under physiological conditions (Rosenthal et al., 2002), and have several properties of particular value. The first of these is the ability to support a large and adjustable number of tethered ligands; that is, the maximum number of tethered test ligands (~160 for a 60 Å CdSe nanocrystal) can be reduced by diluting the test ligand with a suitably functionalized inert ligand during conjugation. In addition, CdSe nanocrystals have high fluorescence yield (product of quantum yield and extinction coefficient) with excitation near 480 nm, and resistance to photobleaching. These properties, together with preliminary data indicating the feasibility of targeting cell-expressed GABAc with PEG-linked, muscimol-conjugated nanocrystals, encourage their use as a prototype system for addressing two issues of importance to the proposed research. First, these nanocrystal preparations afford an alternative test of "receptor clearance" by the linker component of a particular derivatized ligand. That is, despite the presence of many copies of a particular effector/linker conjugate on the nanocrystal, a linker whose ligand-distal (i.e., nanocrystal-linked) terminus is too short to extend beyond the receptor's extracellular surface is expected not to bind to the receptor. Second, these preparations afford the ability to examine the effect of a wide range of valencies of a test effector. Due to the multivalency of the GABAc receptor, effector valency is expected to important. The synthesis of chemically defined divalent effectors may be used. Nanocrystal-conjugated effector preparations can allow a survey of the effect of valency through appropriate dilution of the effector by the co-conjugation of inert ligand to the nanocrystal. In this way, a wide range of average valencies can be prepared rapidly. While any particular preparation will be heterogeneous (i.e., will contain a distribution of valencies with known average), correlation of the average valency with data obtained in fluorescence visualization and other in vitro and electrophysiological experiments will guide the choice of synthetic structures of defined valency.

Incorporation of a photoswitch into effector-PEG preparation involves positioning the photoswitch in close proximity to the effector (FIG. 16). A series of molecules were constructed in which muscimol is connected through a short linker (0-6 EG units, linker 1 in FIG. 18) to a photoswitch element (e.g., azobenzene-based amino acid), an optional second linker (linker 2) of varying length, and a variable distal group. FIG. 18 depicts a synthetic route to muscimol-azobenzene-PEG assemblies. Linker 1 is 0-6 EG units, linker 2 is 0-77 EG units, and Aza (Ulysse & Chmielewski, 1994) is a representative azobenzene-based amino acid. A first objective is to identify a functional photoswitch/linker combination. Initially linkers of 0-6 EG units are examined using and a series of azobenzene-based amino acids. In nine of these, including several based on azobiphenyl, the change in end-to-end distance produced by trans-to-cis photoisomerization (18 to 5 Å) is amplified relative to the corresponding change in azobenzene (12 to 6 Å) (Park & Standaert, 2001). For prototype investigation of other, distally attached NNP components, a group of biotin-terminated PEG linkers can be prepared. Electrophysiological and/or other testing of these molecules in the presence vs. absence of streptavidin allows the lower limit on the length of the linker 2 chain that allows biotin to move clear of the ligand binding site to be determined. The occurrence, in the streptavidin experiments, of a differential result between cis and trans azobenzene isomers can be interpreted to suggest that the linker length under investigation is at the threshold of streptavidin accessibility to the biotin moiety, a finding that would facilitate determination of the clearance length of the linker/photoswitch assembly.

The following points describe alternative approaches to be pursued to identify GABAc-reactive effector/photoswitch/linker assemblies. (1) Antagonist (phosphinic acid) approach: An alternative strategy within the scope of one invention is the use of phosphinic acids, a known prominent class of GABAc antagonists. Phosphinic acid analogs of GABA; upper left: reduced-pyridine derivatives (TPMPA and TPEPA). Middle: 3-aminopropyl n-butyl phosphinic acid. Right: proposed new 3-aminopropyl phosphinic acids. Lower: General synthetic route to 3-aminopropyl phosphinic acids (Froestl et al., 1995), where 3-aminopropyl n-butyl phosphinic acid (CGP36742) (Chebib et al., 1997b) is advantageous because it has an $IC_{50}$ of 60 μM (suggesting that KD<60 μM), which is below the 80 μM criterion, and because it demonstrates that a long alkyl side chain is tolerated in this series. By analogy with the derivatization of muscimol described above, phosphinic acid analogs are assessed to identify PEG-chain-derivatized (i.e., tetherable) compounds that incorporate an antagonist effector and neighboring photoswitch, and that in binding and electrophysiological tests exhibit GABAc reactivity. Thus, phosphinic acid analogs are by synthesized, via Froestl's method (Froestl et al., 1995), comprising a series of arylalkyl groups (starting with 2-phenylethyl) coupled with the 3-aminopropylphosphinic moiety to determine how long a chain is tolerated, and whether a sterically bulky group (initially, phenyl; subsequently, photoswitch candidates) is tolerated at the end of the chain, where the chain of interest is derived from the corresponding bromide or tosylate. Most of the requisite alkyl and arylalkyl bromides are commercially available, while the PEG tosylates are straightforward to prepare. Upon identification of a GABAc-reactive phenyl derivative, compounds are synthesized with additional substituents on the benzene (e.g., alkyl group or amide) as potential tethering moieties.

(2) Multivalent ligands: Native GABA receptors and other ligand-gated ion channels exist as heteromeric pentamers with two ligand-binding sites, and full channel opening requires simultaneous binding of two ligands (Woodward et al., 1993; Ortells & Lunt, 1995; Karlin, 2002). Moreover, homomeric GABAc receptors are believed to exist as pentamers with five GABA-binding sites (one at the interface of each pair of subunits) and to require the simultaneous binding of at least two ligands for receptor activation (Amin & Weiss, 1996; Karlin, 2002). The high Hill coefficient observed for homomeric GABAc receptors in experiments with muscimol-biotin (Vu et al., 2005) is consistent with such a possibility. Linking two (or more) effectors into a single, multivalent molecule can provide more potent ligands due to a linkage-induced entropic advantage, and satisfy the requirement of multiple ligand binding. Multivalent ligands thus represent particular and advantageous embodiments of the invention. AchBP is known to form a symmetric pentamer with the overall shape of a barrel having an outer diameter of about 80 Å, an inner diameter of about 16 Å, and a height of about 60 Å. The ligand-binding sites are approximately equatorial and are about 25 Å from the barrel's center (Brejc et al., 2001). Assuming a similar structure for the GABAc receptor, there can be two modes of binding for a pair of effectors (adjacent sites vs. nonadjacent sites) and two ways of connecting them (through the center of the protein or around its circumference) (as illustrated in FIGS. 20 and 21). However, as access to the ligand-binding sites of AchBP is thought to be from the outside (Brejc et al., 2001), it is likely that a linker would go around the outside of the GABAc receptor. These considerations suggest that the linker must minimally be 80 Å long and could need to be as long as 130 Å. Distances this long cannot readily be spanned by a hydrocarbon linker in water because the requisite chain length would make the molecules insoluble. The primary choice of linker is PEG, which is highly flexible and water-soluble. PEG has an effective length of 0.7-2.8 Å per EG unit, and thus the length of PEG linkers that can advantageously be used is about 30-50 EG units (molecular weights: 1300-2200). Monodisperse PEG of n=28 is commercially available (Polypure; Oslo, Norway); the monomer and dimer of this product, together with the commercial availability of a wide variety of PEGylating reagents, thus afford reasonable coverage of the desired =30-50 EG unit range. Dimers are prepared of azobenzene photoswitches conjugated with suitable muscimol- and phosphinate-based compounds identified as described above, and the PEG length requirement tested systematically. FIG. 20 depicts the design of PEG-linked bivalent effectors. Dotted lines in A-B depict boundaries of the pentameric GABAc; open circles are effector binding sites; closed circles are effectors; and curved lines are PEG chains. Possible binding modes employ adjacent (A) or non-adjacent (B) sites. Linker length estimates assume 15 A from the binding site to the receptor circumference and 2.8 A per EG unit. C-D show free (C) and tethered (D) forms of the bivalent ligand. Filled circles in C represent effectors; filled ovals in D represent effectors or effector/photoswitch assemblies. FIG. 21 depicts a synthetic route to Y-shaped PEG-linked effectors (filled circles in FIG. 20) or effector/photoswitch assemblies (filled ovals). U-shaped molecules (not shown) containing, e.g., muscimol as effector can be prepared by reaction of muscimol with bifunctional PEG-bis(NHS ester) reagents.

(3) Photoaffinity attachment of effector/photoswitch/linker: The above approaches 1-2 emphasize the importance of determining the distance between the GABAc ligand-binding site and the receptor site at which the distal end of the linker ultimately is anchored. Photoaffinity labeling is used to covalently attach a suitable peptide anchor at a specific GARAc site. However, an effector/photoswitch/linker assembly incorporating a distal photoaffinity probe (i.e., lacking a peptide anchor) can exhibit covalent, photoisomerization-dependent attachment at a specific GABAc site upon photoaffinity linking illumination, with the site specificity conferred by the combination of (i) effector binding at the ligand site, (ii) the isomeric state of the photoswitch moiety, and (ii) the length of the linker. Such alternatives bypass the need for an inherently site-selective anchor but can be less advantageous in large part because if features (i-iii) in themselves do not establish the desired anchoring specificity. However, such alternatives can provide alternatives in certain embodiments. For example, said embodiments can serve as a molecular "yardstick" for mapping the attachment site(s) of an assembly with particular linker length.

Figure 22:
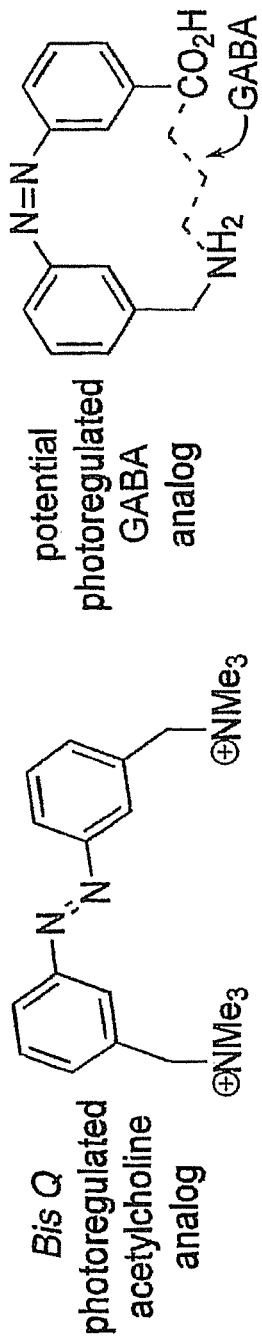
FIG. 22 depicts known photoregulated nAchR agonist.

(4) Photoswitch analog of GABA: In these embodiments, the azobenzene nucleus is inserted into the GABA backbone. A azobenzene can position amino and carboxyl substituents on neighboring rings at distances comparable with that of the respective groups in GABA (as illustrated in FIG. 22). FIG. 22 shows left: BisQ, a known photoregulated nAchR agonist in its active, trans form. Right: Proposed azobenzene-based GABA analog in cis form with GABA backbone (dashed bonds) superimposed. Regarding whether the GABAc ligand-binding site can accommodate such a large template, Lester et al. (1986) found that an analogous compound ("BisQ") containing two choline-like side chains exhibits agonist activity at nicotinic Ach receptors. Synthesis procedures for the new GABA analog are analogous to those described for azobenzene-based amino acids synthesized by Ulysse & Chmielewski (1994) and by Park & Standaert (1999, 2001).

Biophysical and electrophysiological testing of GABAc effector interaction: Determining the activity of a particular test effector or effector/photoswitch/linker assembly (FIG. 16) is based on results obtained in electrophysiological experiments (see below), and in cell-based and in vitro experiments measuring binding of the test effector to GABAc expressing cells and to isolated GABAc protein. Cell-based assays and in vitro reconstitution experiments are used to determine the strength and specificity of the effector GABAc interaction. The in vitro reconstitution assays employ soluble GABAc extracellular domain, and solubilized or membrane-associated full-length protein. The primary preparation used for the cell-based binding assays is GABAc-expressing neuroblastoma cells. The multiple proposed binding assays described below provide characterizations on which are based conclusions about the effectiveness of a particular test effector. The availability of multiple assays permits meaningful characterization even in the event that any particular assay is unworkable or inconclusive.

Binding affinity and photoaffinity labeling: GABAc-binding activity of a particular test component (free effector or effector/photoswitch/linker) can be determined using ($^3$H) GABA competition binding assays performed on intact GABAc-expressing cells of the neuroblastoma cell line Concentration of test ligand required for criterion (e.g., 50%) displacement of bound ($^3$H)GABA from the cells is determined. Candidate ligands identified in this initial test are further investigated in competition binding assays with isolated GABAc (full-length or extracellular domain). These binding tests using isolated GABAc specifically address the possibility that in whole-cell assays, that ($^3$H)GABA uptake or ligand binding at nonGABAc sites (beyond that routinely compensated for through the use of non-GABAc expressing cells as controls) rather than actual GABAc-specific binding, contributes significantly to the measured level of binding. Candidate ligands identified in competition binding assays can be used in saturation binding assays with GABAc-expressing cells and isolated GABAc wherein the candidate ligand is prepared to contain a $^3$H radiolabel. Saturation binding data are evaluated (by Scatchard analysis; e.g., Kim et al., 1992) to yield values for binding affinity and number of binding sites. Evaluation of the binding parameters determined for different test ligands thus yields a ranking of their potential suitability in ultimately assembled platform structures. However, the ranking established by these tests of free ligand will need to be assessed when using ligand anchored to the receptor.

AFM analysis: Upon identification of a candidate ligand in the GABAc-binding experiments, AFM processes are conducted similar in general design to those of Saifuddin et al. (2003), to examine the interaction of the ligand with isolated GABAc extracellular domain. The results of these experiments are used to whether GABAc exhibits specific binding affinity for the ligand. To determine specificity, the test agent or, as control, an inactive analog, is immobilized on a solid support either through a biotin-avidin interaction (Saifuddin et al., 2003) or by chemical cross-linking to the substrate, and surface changes correlated with the introduction of the GABAc protein quantitatively analyzed. As a further control, the test ligand is examined for its interaction with putatively inactive proteins. In particular, AFM provides information on integrity of the presumed pentameric structure of the GABAc protein.

Surface-force measurements: In similar preparations, AFM is used to obtain surface-force data for the interaction of GABAc extracellular domain with test effectors and effector/photoswitch/linker assemblies. Procedures for AFM tip preparation and data collection follow those described by Schmitt et al. (2000). Such measurements can provide information on, e.g., relative strengths of GABAc binding of monovalent vs. multivalent ligands (FIG. 20), and on structural correlates of the test component/GABAc interaction (e.g., the range of tolerated PEG linker lengths, a consideration important for linker optimization).

It will be recognized by one of ordinary skill in the art that evaluation of the activity of a particular test component is based on combined results obtained from the reconstitution/cell-based binding procedures described above, and from electrophysiological procedures (see below). Compounds found to be electrophysiologically active exhibit binding activity. However, data from reconstitution and cell-based binding procedures can indicate in the alternative activity of a particular test ligand at GABAc receptors even under circumstances where the compound lacks electrophysiological activity. While this outcome precludes use of the candidate ligand in the final NNP, such a result provides additional information on the structural features of advantageous NNP anchors. For example, in some embodiments observed binding of a test compound can reflect interaction with a site on the protein not accessible in vivo to the extracellularly located compound when performing in vitro tests of isolated GABAc (full-length or extracellular domain).

Micelle-incorporated test ligand: A aqueous solubilities of muscimol and phosphinic acid compounds provided herein can influence how particular embodiments of the invention disclosed herein, for example, by limiting the effectiveness of assessing these embodiments using particular GABAc binding or electrophysiological experiments. In such instances T a candidate compound (i.e., one with possibly high intrinsic activity when incorporated in an anchored platform but not amenable to aqueous delivery as a free compound at the concentrations needed for characterization) is further assessed using sterically stabilized mixed micelles as a solubilizing medium. Compositions of the micelles employed and procedures for their preparation follow those routinely used for solubilizing hydrophobic drugs such as the potent antitumor agent paclitaxel (e.g., Krishnadas et al., 2003). If needed, a similar approach can be undertaken for the delivery of anchors or complete NNP assemblies.

Electrophysiological testing: As primary systems for electrophysiological testing of candidate effectors and other platform components, GABAc-expressing *Xenopus* oocytes and neuroblastoma cells are used, and native GABAc-expressing bipolar cells isolated from the rat retina. In these experiments, a particular test component is injected into intact mouse eye (see below). Whole-cell patch recording from both isolated bipolar cells (Qian & Dowling, 1995; Qian et al., 1997) and mammalian cells (see below), is used in these preparations using a requested patch-clamp recording system. Oocyte recording (e.g., Vu et al., 2005), is done on *Xenopus* oocytes. The multiple preparations are used as primary systems and have complementary advantages. *Xenopus* oocytes_expressing GABAc (and other) receptors are a robust system with several important advantages. These include cell size (~1 mm diameter) and their relative ease of handling. The large size establishes a large surface area, affording expression of a large population of receptors. Furthermore, oocytes are routinely suitable for recording over periods of several hours. Typically, initial investigation of a particular test ligand utilize the oocyte system. For these and the other electrophysiological experiments involving tests of components that contain isomerizable photoswitches, the isomeric state of the photoswitch is measured both shortly before and shortly after the experiment.

GABAc-expressing mammalian cell lines serve as an intermediate system for testing. While mammalian cells are much smaller than oocytes and ordinarily permit recording for only shorter periods (~15-30 min), procedures for expression of defined receptors, as well as overall cell preparation and maintenance methods, are well established. These experiments are focused on using a GABAc human p1-expressing neuroblastoma cell line described above. Isolated rat retinal bipolar cells serve as a model system for testing the action of ligands on native GABAc receptors of retinal neurons. Although there is evidence to suggest that native GABAc receptors of rat retinal bipolar cells are heteromeric (composed of p1 and p2 subunits; Zhang et al., 1995), pharmacological properties of native GABAc receptor activation are very similar to those of the homomeric p1 receptor formed in expression systems (Feigenspan et al., 1993; Pan et al., 1995; Zhang et al., 2001).

Figure 23:
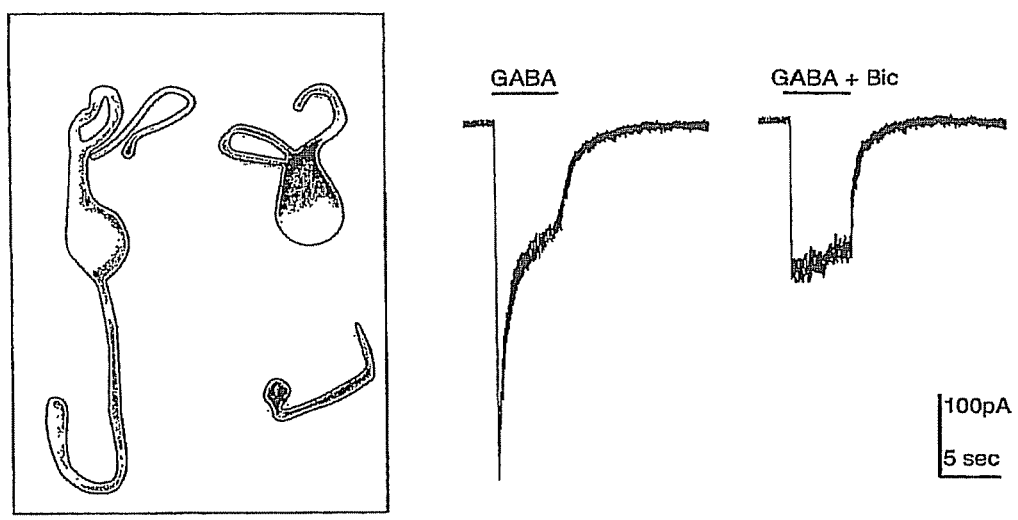
FIG. 23 depicts solitary bipolar cells isolated from baboon retina.

Preparative procedures: Single, isolated bipolar cells of the rat retina are prepared using procedures similar to those described for bipolar cells of white perch retina (Qian & Dowling, 1995). These procedures have been successfully used to prepare mammalian (baboon) retinal bipolar cells in culture and to record GABAc-mediated responses (as shown in FIG. 23). These cells maintain their native morphology in culture, and three major regions are easily identified: dendrites, which receive inputs from retinal photoreceptors; the cell body; and the axon terminal, which sends output to retinal amacrine/ganglion cells. GABAc receptor-mediated responses have been reported for both dendrite and axon terminal regions of retinal bipolar cells (Qian & Dowling, 1995; Kaneda et al., 2000); GABA receptors present in these distinct cellular regions can separately be activated by local puff (picospritzer) delivery of solutions containing GABA agonist (Qian & Dowling, 1995). As both $GABA_A$ and GABAc receptors are present on retinal bipolar cells, pharmacological approaches are used to separate responses mediated by each receptor type. For example, bicuculline is used specifically to block $GABA_A$ activity, and TPMPA will be applied to inhibit GABAc-mediated responses. A particular test component (effector alone, or effector/photoswitch/linker) is examined for both GABAc agonist and antagonist activity, and the potency of observed actions quantified by determination of the dose-response relation. Evaluation of the effector's activity and conclusions about its mechanism of action are based also on analysis of the kinetics of effector-elicited responses, and kinetic comparison of these responses with those produced by control compounds including potential contaminants. Performance criteria relevant to the evaluation of a component are: (1) whether the maximum elicited GABAc mediated response exceeds 50% of that elicited by GABA; (2) whether the affinity of the component (from dose-response determinations) is compatible with $EC_{50}$ ranges for workability; and (3) whether the time scale of the response to the (untethered) test component is sufficiently fast (seconds or faster) to afford potential, at least prototype modulation of neuronal activity in the retina.

In FIG. 23, Left, Solitary bipolar cells isolated from baboon retina are shown. In the Middle are GABA (100 μM) elicits a large transient inward current in a baboon bipolar cell held at −60 mV. Right: The transient GABA response is blocked in the presence of bicuculline (200 μM), leaving a more sustained, GABAc receptor-mediated response.

Pilot electroretinographic (ERG) candidate effectors identified in the binding and electrophysiological processes described above are further examined in pilot ERG procedures involving in vivo intravitreal injection of the test agent into eyes of anesthetized mice. (Hetling & Pepperberg, 1999; Saszik et al., 2002). The effects of defined quantities of test effector on components of the full-field, dark-adapted ERG including the rod photoreceptor-mediated a-wave and inner retinal components (b-wave and oscillatory potentials) can be confirmed in wild type mice (e.g., C57BL/65). These procedures determine whether the test agent is toxic for, or acts nonspecifically on, ERG components such as the leading edge of the rod-mediated a-wave (a component believed not to depend on the activity of GABAc or other postsynaptic receptors; Pattnaik et al., 2000; Picaud et al., 1998). For test agents found to be non-toxic in acute experiments (up to several hr), subsequently experiments are conducted to determine whether the test agent alters ERG components for which GABAc receptor activity is thought to play a role. For comparison with responses recorded from wildtype mice, these later procedures can employ a recently described mutant mouse strain that lacks GABAc receptors (McCall et al., 2002).

Figure 24:
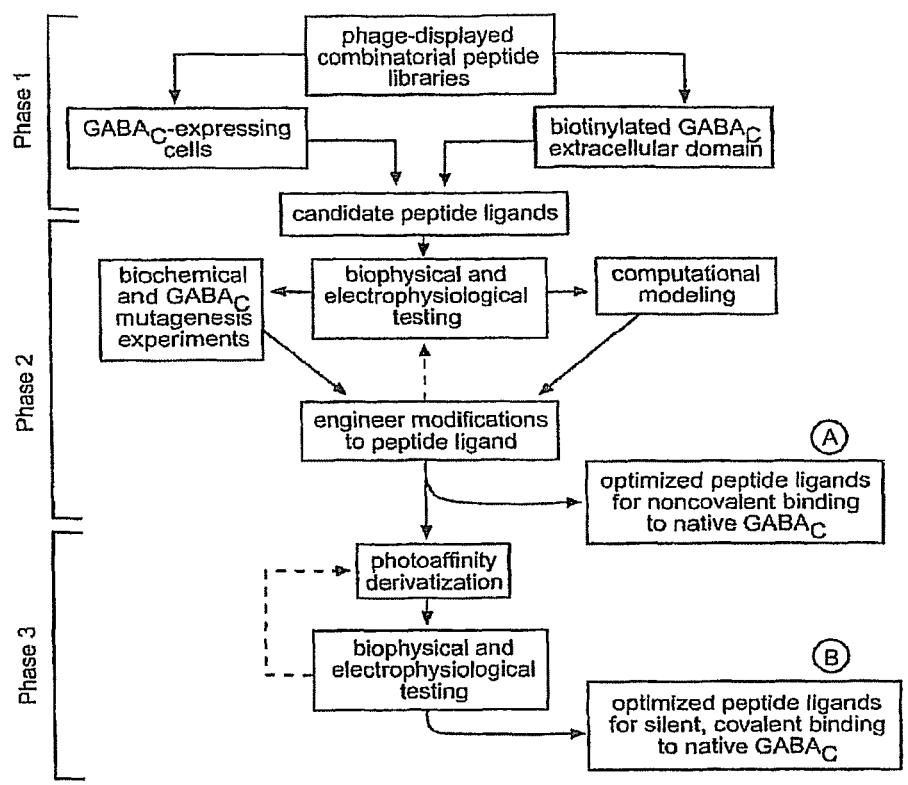
FIG. 24 diagrams development approaches for achieving "silent" covalent attachment of the NNP to a native receptor.

Overall organization of Platform localization/anchoring: NNP operation requires anchoring of the effector-photoswitch complex to the extracellular domain of the GABAc receptor (as shown in FIGS. 1 and 16). Advantageously, covalent attachment of the NNP to the native, i.e., non-mutated, receptor is accomplished "silently," i.e. in a non-perturbing manner as described below. FIG. 24 diagrams these embodiments of the invention, based on the use of phage display technology to identify 12-mer peptide ligands that display high affinity for the GABAc extracellular domain. There are three phases in the development of these embodiments. Phase 1 uses two complementary strategies to select peptides with high GABAc binding affinity: cell-based screening, (i.e., screening against intact GABAc expressing sf9 and neuroblastoma cell lines); and screening in vitro against isolated GABAc extracellular domain(s). Synthesized peptides with sequences determined through these screening approaches are tested in biophysical/electrophysiological assays to identify "first-generation" peptide anchors. In Phase 2, the peptide's noncovalent binding to the native receptor are optimized. Engineering of modifications to the peptide ligand are based on results obtained from mutagenesis/biochemical experiments and from computational modeling. Recursive engineering and biophysical/electrophysiological testing (cf. upward dashed arrow within Phase 2) yield a determination of the sequences, binding affinities, and sites of noncovalent binding to the native receptor (i.e., GABAc amino acid position) of these optimized "second-generation" peptides (box "A"). In Phase 3, the Phase 2 optimized peptides are checked for photoaffinity derivatization, covalent (photoaffinity) attachment to native GABAc, and biophysical/electrophysiological testing of the peptide-receptor conjugate. In this way the peptides whose covalent attachment to native GABAc preserves normal receptor function ("silent attachment") and, for each of these peptides, the GABAc amino acid position of photoaffinity attachment (potentially, a single site determined by the noncovalent interaction of the parent peptide with the receptor) (box "B") are identified. The scheme set forth in FIG. 24 is analogous to paradigms used in pharmaceutical drug design. That is, an economical approach (here, phage display) is used with the known target (GABAc) to obtain as many initial "hits" (candidate peptide sequences) as possible. Based on optimization, the number of candidate sequences is reduced, or "filtered", so that labor-intensive further investigation (Phase 3 photoaffinity tagging and analysis) is carried out only on the most promising candidates. In FIG. 24 dashed arrows denote the "feedback" of results obtained, which will guide the optimization experiments of Phases 2-3.

Turning to a fuller explication of the experiments comprising Phase 1, phage display technology is well suited for the present goal of obtaining peptide ligands that interact selectively and tightly with the target receptor's extracellular domain. In phage-display, combinatorial peptides are expressed at the amino-terminus of protein III on the surface of bacteriophage M13, encoded by degenerate oligonucleotides of fixed length. Phage display offers the advantages that: (1) the peptides expressed on the surface of the viral particles are accessible for interactions with their targets; (2) the recombinant viral particles are stable (i.e., can be frozen, exposed to pH extremes); (3) the viruses can be amplified; and (4) each viral particle contains the DNA encoding the recombinant genome (Kay et al., 1996). Consequently, these libraries can be screened by isolating viral particles that bind to targets, plaque-purifying the recovered phage, and sequencing the phage DNA. Phage-displayed combinatorial peptide libraries have proven useful in identifying novel ligands for membrane receptors and other proteins (e.g., Johnson et al., 1998; Paige et al., 1999; Kay et al., 2000; Sidhu et al., 2003).

Figure 25:
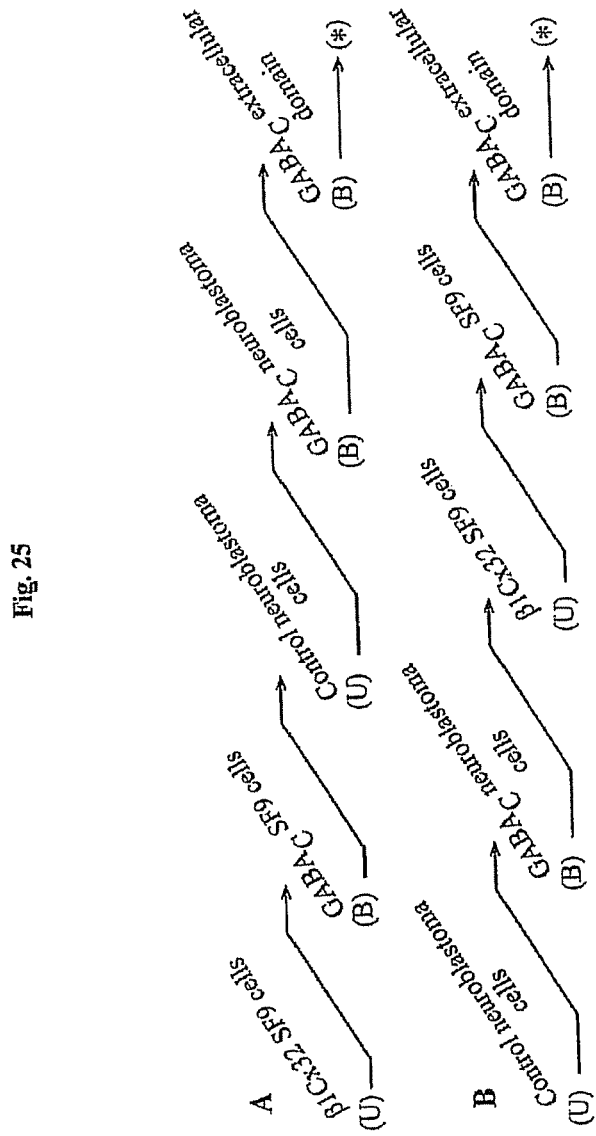
FIG. 25 depicts phage screening to isolate GABAc-binding phage.

FIG. 25 shows strategies A and B for phage screening. Symbols B and U denote, respectively, the selective recovery of bound and unbound phage particles. Asterisks denote populations of phage in the final output.

For cell-based phage screening, a large collection of phage-displayed combinatorial peptide libraries are used for cell panning procedure to select phage that specifically bind to GABAc-expressing cells. As the cells will express many proteins in addition to the expressed GABAc that can bind phage, a "ping-ponging" approach with two different cell types is used (neuroblastoma cells and baculovirus transfected insect cells) to isolate GABAc-binding phage (as shown in FIG. 25). This strategy, which assumes that the only common cell surface protein will be GABAc, has been used successfully in previous studies (Goodson et al., 1994). This screening procedure, following multiple rounds of biopanning, can (upon sequencing of the phage's inserts encoding the 12-mer expressed peptide) yield candidate 12-mer peptides with specific GABAc-binding activity. Immunofluorescence tests on GABAc-expressing cells serve as a further assay for binding activity. If the number of differing phage sequences resulting from the above-described screening procedure is very large, a whole-phage binding assay can be used (Heitner et al., 2001) to confirm binding of the phage to intact cell surfaces. Phage particles from individual clones expressing the putative peptide ligand are incubated with GABAc-expressing neuroblastoma cells and with control, non-GABAc-expressing neuroblastoma cells. Following washing steps to remove unbound phage, cells are incubated with a mouse monoclonal antibody to the M13 phage (Amersham Pharmacia) (Maruta et al., 2002) and then with FITC-conjugated secondary antibody. When phage expressing the candidate peptide specifically bind to GABAc receptors, the fluorescence signal measured for the GABAc-expressing cells treated with test phage exceeds the fluorescence signal of the controls. For phage that have been confirmed to bind to cells expressing GABAc, biotinylated forms of the peptides are synthesized and used for co-localization studies using fluorescently labeled streptavidin (Molecular Probes) to detect the bound peptide. A rabbit polyclonal antibody to the intracellular loop of GABAc receptor (Santa Cruz Biotechnology) can be generated by conventional methods (Hanley et al., 1999), affinity purified and used, together with a different, fluorescently labeled secondary antibody, for detection of the receptor. Co-localization is determined by confocal microscopy (Leica DM-IRE2 microscope). Initially, GABAc transfected neuroblastoma cells are used with non-transfected cells as controls. Cells are fixed with 4% formaldehyde and permeabilized, and varying concentrations of primary antibody, peptides and secondary reagents are used to optimize the signal/background ratio. To determine if the peptide remains attached to the cells during the fixation and subsequent steps, the signal obtained from unfixed cells is compared following sequential incubation with the peptide and labeled streptavidin with the signal obtained from cells fixed, permeabilized and similarly treated.

In vitro screening against isolated extracellular domain is achieved using biotinylated protein targets for in vitro screening of phage-displayed combinatorial peptide libraries. Purified GABAc extracellular domain obtained using bacterial or baculovirus expression systems as set forth herein are chemically biotinylated (using, for example, a Pierce Biotinylation kit) to attach biotin to the sidechain epsilon amino group of lysine residues within the target protein. Since there are multiple lysines in the GABAc extracellular domain (10 for human p1; 9 for perch p1 B), and one or more may be important for functional binding of GABA, partial biotinylation conditions are used so that only 1-2 lysines are modified on average. To test for functionality of the modified form, binding assays are performed on the biotinylated material before and after immobilization with streptavidin-coated surfaces, to determine whether the target protein remains active. Approximately 200 μg of biotinylated protein are needed to select phage and confirm binders. For selection, the biotinylated proteins are incubated with super-paramagnetic, polystyrene beads that have streptavidin covalently attached to their surface. 23 different libraries for peptide ligands to the GABAc target are screened. These libraries consist of 12-mer combinatorial peptides, with fixed amino acids such as cysteine at various positions within the peptide. It is noteworthy that since bacteriophage M13 is secreted from bacteria, peptides with multiple cysteines form intramolecular disulfide bonds, often yielding strong binding ligands (Yamabhai et al., 1998). Phage ligands from most of these libraries (Scholle et al., 2005) and other similar libraries have been isolated. After three rounds of affinity selection, a phage-based ELISA is used to quantify phage binding to the biotinylated target compared to negative control proteins such as bovine serum albumin, SH3 domains, streptavidin, and other biotinylated proteins. Liquid handling robotic workstations (Beckman FX robot, plate washers, etc.) can be used for the high-throughput processing of libraries.

Figure 26:
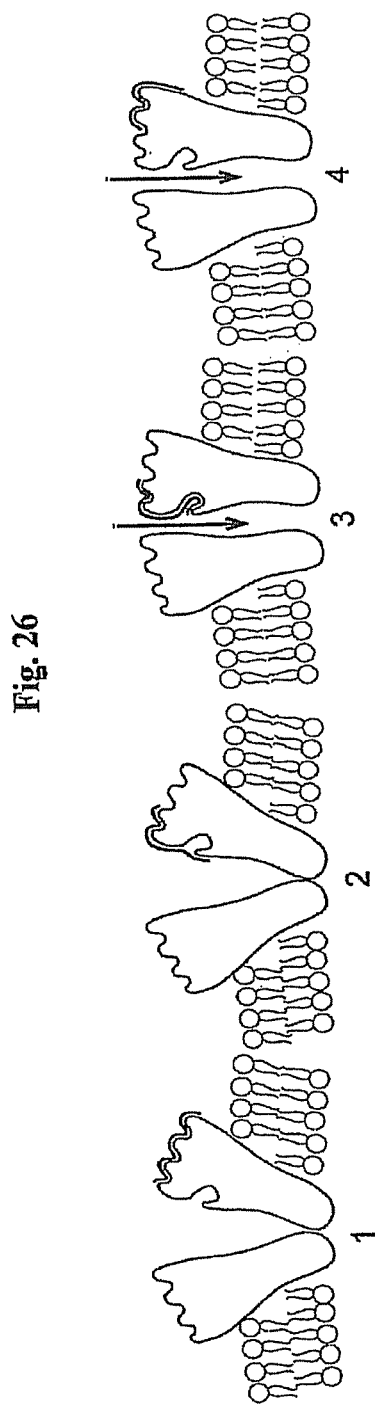
FIG. 26 depicts interactions of phage-derived peptide with GABA receptor.
Figure 28:
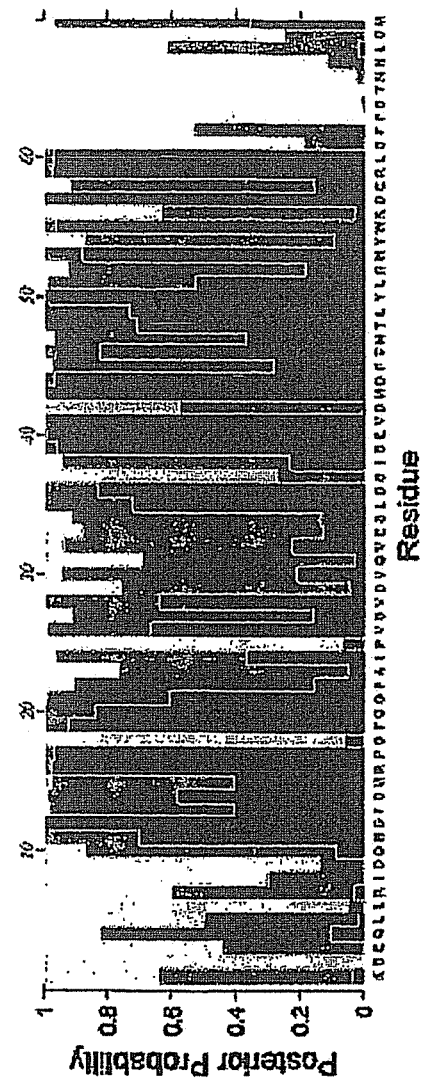
FIG. 28 illustrates posterior probability analysis of amino acid substitution rates.

Biophysical/electrophysiological testing: Peptides determined from screening with whole cells and isolated extracellular domain, henceforth termed "phage-derived peptides", are synthesized. Following initial optimization of the peptide sequence through systematic residue replacement and analysis of in vitro binding affinities (see below), candidate peptides are tested for of binding activity assays. In particularly advantageous embodiments, the desired activity of the peptide(s) is a physiologically "silent" (i.e., non-agonist, non-antagonist) attachment at a site on the GABAc extracellular domain distinct from the GABA-binding site (as shown in FIG. 16 and FIG. 26, panel 1). However, alternative activities are possible (FIG. 26, panels 2-4). As silent peptides themselves lack electrophysiological activity, characterization of GABAc binding of candidate peptides requires a "toolbox" of assays. Set forth below are procedures that available for initial optimization and characterization of particular candidate peptides. In particular, FIG. 26 depicts interactions of phage-derived peptide (thick wavy line) with the GABAc receptor (for simplicity, shown here as a two-subunit receptor as in FIG. 1). 1: "Silent" binding at a site distinct from the receptor's ligand-binding site (nominally desired interaction). 2: Inhibitory interaction (blockage of ligand-binding by the receptor). 3 and 4: Activating interactions in which the peptide mimics GABA (3) or acts allosterically (4).

Initial optimization of critical residues in peptide ligands is achieved using results obtained from the two phage screening approaches and initial biophysical/electrophysiological testing to determine ligand preferences with chemically synthesized peptides. Peptide synthesis methods are used because certain peptide sequences may be absent from the library, for example, if they interfere with viral morphogenesis or secretion. It has been observed that peptides with runs of arginines (Peters et al., 1994) or odd numbers of cysteines (Kay et al., 1993) are not displayed efficiently on bacteriophage M13. Also, sometimes only a small number of binding isolates are recovered from phage-display experiments, making it difficult to recognize a consensus. Because peptides are displayed on viral protein III, which is pentavalent on M13, it is difficult to discriminate between weak and strong binding interactions due to avidity effects, i.e., multivalent interactions between phage and the immobilized target. Thus, it is hard to know how to weight the contributions of residues that vary between phage-displayed peptides toward binding. Initially, using small-scale syntheses, peptides that have been truncated at the N or C-terminus are prepared to determine the boundaries of the peptide's binding element, and in which residues have been systematically replaced with alanine (Yamabhai & Kay, 2001) to determine which residues that contribute to binding. An Advanced ChemTech Apex 396 robot is used to synthesize via standard Fmoc chemistry (Merrifield, 1965) up to 96 peptides at a time, in small scale (<1 mg). The N-termini thereof are chemically biotinylated, and binding of the resulting peptides is determined in vitro by an enzyme-linked assay (binding to immobilized target monitored using streptavidin conjugated to alkaline phosphatase). Once critical positions are defined, they are replaced with other amino acids to see if replacement improves binding. Often, the binding of phage-derived peptide ligands to their targets can be improved 3-5 fold by systematic residue replacement/optimization (DeLano et al., 2000).

Binding affinities and binding kinetics of peptide ligands: The selected peptide ligands are synthesized on a larger scale (~10 mg or greater), and their GABAc-binding properties determined by isothermal titration calorimetry (ITC) and by in vitro/whole-cell assays (see below). These larger-scale syntheses also employ the Advanced ChemTech Apex 396 instrument. Peptides are HPLC-purified and their quality evaluated by MALDI-TOF mass spectrometry. The dissociation constant for the binding of a particular peptide to the GABAe extracellular domain can be measured by ITC, which affords determination of the separate contributions of changes in enthalpy ($\Delta H$; typically indicating changes in electrostatic, van der Waals and hydrogen-bond interactions) and entropy (AS; typically reflecting changes in solvation entropy and conformational entropy) to equilibrium binding, as well as the value of the equilibrium binding constant (e.g., Leavitt & Freire, 2001). This methodology thus can provide important insights into the molecular mechanism of the binding reaction. For example, ITC measurements for a particular candidate peptide's binding to GABAc can indicate the change in $\Delta S$ to be the dominant factor driving the binding reaction; under such circumstances, a hydrophobicity-increasing modification of the peptide's sequence would produce even tighter binding to the receptor. Dissociation constants ($K_D$'s) of peptides recovered by phage display, when synthesized and tested in solution, typically range from 10 µM to 300 nM (Hyde-DeRuscher et al., 2001), and occurrence of a $K_D \sim 10^{-6}$ or lower identifies such a peptide as a particularly advantageous species. From the dissociation constant $K_D$, the $k_{dissoc}$, the dissociation rate constant (in s$^{-1}$), can be estimated through the relations:

$$K_D = (k_{dissoc})(k_{assoc})^{-1}$$

and $$(k_{dissoc})[peptide-GABAc] = (k_{assoc})[peptide][GABAc],$$

that describe the association of peptide and GABAc to form a complex, where $k_{assoc}$ (in M$^{-1}$ s$^{-1}$) is the association rate constant. Assuming $k_{assoc} \sim 10^8$ M$^{-1}$ s$^{-1}$ as a diffusional association rate, setting (for illustration) $K_D = 1$ µM yields $k_{dissoc} \sim 10^2$ S$^{-1}$, i.e., ~10 ms for the dwell time of the noncovalently bound peptide. Peptide synthesis on the large scale permits driving the association reaction, by sufficiently high concentrations of peptide, to render useful measurements of (instantaneous, equilibrium) noncovalently associated peptide GABAc. Furthermore, the stability of the peptide GABAc interaction can be increased, thus reducing $k_{dissoc}$. In one exemplary and advantageous example thereof, divalent or multivalent forms of the peptides can be created which, through the phenomenon of avidity, exhibit greatly enhanced binding to the pentameric receptor (Mourez et al., 2001). Alternatively, human single-chain fragments of variable regions (scFv's) for GABAc binding can be selected from a phage library; scFv's tend to bind to targets with low nanomolar $K_D$'s due to their stable three-dimensional structure (Sheets et al., 1998).

GABAc-binding assays and AFM experiments: The strength of binding of candidate peptides to GABAc-expressing cells is determined using cell-expressed (e.g., neuroblastoma cells) and isolated extracellular domain/full-length GABAc. In these binding experiments, which involve the synthesis of radiolabeled peptide ligand, the possibility that the state of the GABAc receptor (open or closed) influences peptide binding is considered, as has been observed for certain ligands in other receptor systems (e.g., Djellas et al., 1998). (One method for testing is by determining whether added GABA (and thus, occupation of the receptor's ligand sites) alters binding of the radio labeled peptide. AFM processes test the specificity of GABAc's binding of a particular test peptide. The GABAc-peptide interaction using surface tethering of the candidate peptide vs. (as a control in separate preparations) a known nonreactive peptide, and with use of isolated GABAc extracellular domain, can be characterized. This interaction can be influenced by the peptide site (amino acid position) used for tethering, and on the surface density of the tethered peptide. AFM data provides insight into the mode of peptide conjugation to NNP effector, photoswitch and linker components that will preserve the peptide's GABAc-binding activity.

Peptide sequences may be tested for GABAc activity electrophysiologically. Electrophysiology is not be a stringent test of peptide activity, i.e., peptide binding to the $GABA_C$ extracellular domain may be silent. A peptide can have agonist activity (as illustrated in FIG. 26, panel 3), and that peptide may be an effector moiety.

Figure 18:
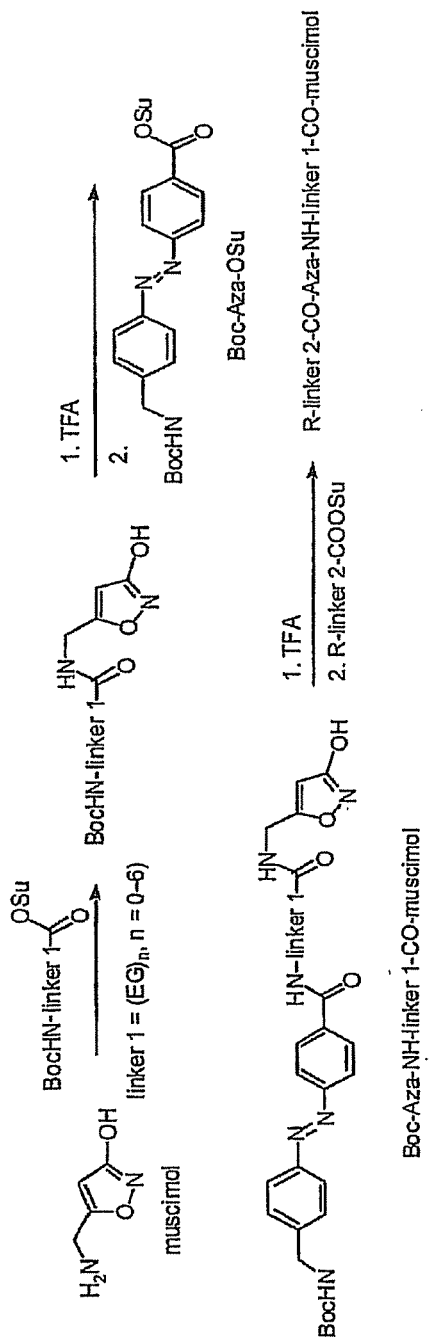
FIG. 18 depicts a synthetic route to muscimol-azobenzene-PEG assemblies.
Figure 19:
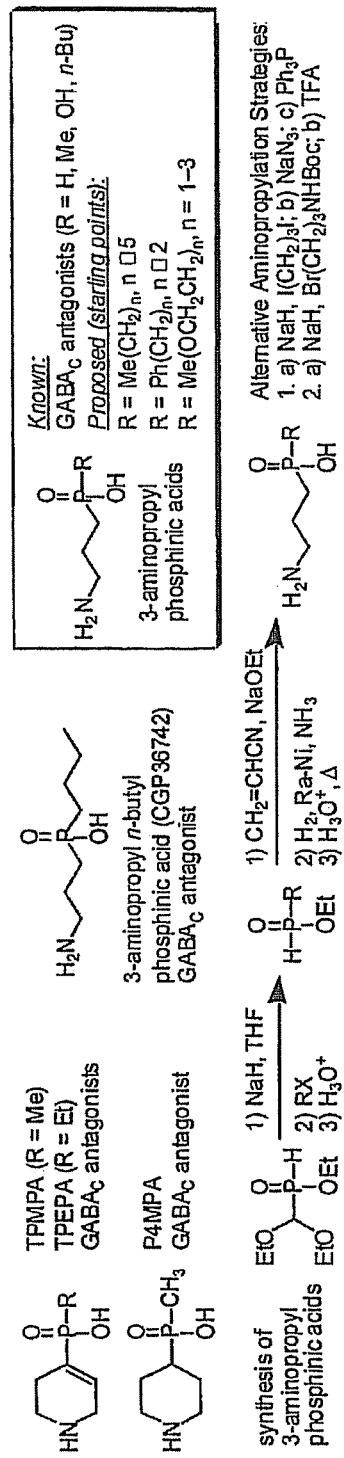
FIG. 19 depicts a phosphinic acid analog of GABA.

The binding of candidate peptides to GABA receptors of retinal bipolar cells is be analyzed in immunofluorescence experiments. Frozen cryosections (16 µm thick) from mouse retina are mounted on polylysine coated slides and incubated with biotin-labeled peptide and antibodies to GABAc receptor. A biotin-labeled control peptide that does not bind to retina is used to assess binding specificity. Bound peptide and primary antibody are detected by fluorescently labeled streptavidin and secondary antibody, respectively. Receptor specificity of a particular peptide anchor can be determined by comparing the GABAc co-localization signal with that obtained for a differing expressed receptor, e.g., $GABA_A$ $\alpha_1\beta_2\gamma_2$ receptors. Such specificity of receptor binding is related to functionality of the ultimately envisioned NNP (FIG. 1), and the screening procedure used in the present experiments (FIG. 18) is intended to yield GABAc specificity. However, cross-reactivity of a particular peptide with, e.g., the $GABA_A$ receptor need not preclude platform anchoring in GABAc-expressing model cells.

Optimization of noncovalent peptide binding: By recursive biophysical/electrophysiological testing and peptide modification (FIG. 24), peptide ligand sequence can be optimized and functional/structural information on the nature of the peptide-GABAc interaction obtained. The precise atomic details of the peptide-GABAc interaction can be used to determine, e.g., directions in which the peptide chain could be extended/shortened to yield tighter binding to the receptor. NMR spectroscopy and X-ray crystallography of the complex formed by the peptide's noncovalent binding to the GABAc extracellular domain can provide such information. However, NMR analysis requires relatively high concentrations of the target receptor (~10-20 mg/ml) that can remain properly folded and in solution over the extended period of data collection. Similarly, crystallization requires large amounts of receptor, and the success of crystallization of the complex cannot be presumed. Photoaffinity labeling and GABAc mutagenesis are two analytical-scale approaches that require orders of magnitude less material than NMR or crystal studies of the peptide-GABAc complex. Facilitating these two experimental approaches is computational modeling of GABAc.

Procedures with engineered GABAc: Site-directed mutagenesis techniques can be used to introduce a cysteine residue within the extracellular domain to afford covalent anchoring of a particular test system (e.g., azobenzene-derivatized effector; through a thiol-reactive moiety such as maleimide that can readily be introduced into the test system. Cysteine substitution has been widely used to probe structure-function relationships of proteins including, for example, the GABA-binding pocket and channel lining domain of GABA receptors (Xu & Akabas, 1993; Chang & Weiss, 2002; Newell & Czajkowski, 2003). The method is commonly used as a substituted-cysteine accessibility assay, where the accessibility of a native amino acid residue participating in a particular function of the protein is inferred from accessibility of the introduced cysteine to sulfhydryl group modification (Karlin & Akabas, 1998). By contrast, use of cysteine substitution involves selection of an amino acid position on the GABAc extracellular face that is not essential for receptor function, analogous to the approach employed by Banghart et al. (2004) Thus, linkage of an NNP to the introduced cysteine residue preserves the native GABAc receptor's functionality (ligand-gating of the chloride channel). Selection of initial GABAc amino acid sites for substitution is based on previous indications that for $GABA_A$ receptor subunits, introducing a foreign tag between the fourth and fifth amino acid after the signal peptide yields expression of the tag sequence at the receptor surface with preservation of receptor function (Connolly et al., 1996). Introduction of a cysteine at this location in GABAc thus will likely yield an exposed sulfhydryl group on the receptor surface. Selection of candidate receptor sites for further investigation by cysteine substitution can be based on photoaffinity labeling data and computational modeling results (see below), as well as on results from the initial cysteine substitution procedures. For a particular site of mutagenesis, the effect of cysteine substitution at the selected position is first tested in electrophysiological/binding experiments on unconjugated receptor, vs. receptor incubated with a sulfhydryl-specific florescent reagent such as TEXAS RED™-MTSEA (Toronto Research Chemicals). When these initial procedures indicate both preserved function of the receptor and accessibility of the cysteine, peptide ligands that have been modified to contain a thiol-reactive moiety can be prepared and tested.

Photoaffinity labeling for covalent anchoring to native receptor: Peptide ligands modified through conventional methods to incorporate a photoaffinity probe can be used on isolated GABAc extracellular domains and on GABAc-expressing cells, to map the amino acid positions of native GABAc at which candidate peptide ligands bind (FIG. 24). In vitro experiments on photoaffinity mapping traditionally have employed a radiolabel photoaffinity probe, digestion of the tagged protein target with proteases, and purification/identification of the modified (radiolabeled) amino acids of the target. However, current mass spectrometric (MS) methods suitable for protein analysis now often permit a non-radiolabel approach; modified regions of the protein are identified by changes in HPLC retention times of tryptic fragments, and specific labeled residues are identified by MS and microsequencing of the tryptic fragments. There are four major classes of photoaffinity probes: aryl azides, benzophenones, diazirines, and a-diazocarbonyl compounds, each of which has advantages and disadvantages. Based on past experience (e.g., Turek et al., 2002) and the commercial availability of a wide spectrum of reagents, waryl azide, a probe that is activated by light of ~260 nm wavelength, is used. (However, fully assembled NNPs containing muscimol as an effector moiety will require use of a photoaffinity probe that absorbs at longer wavelengths, as muscimol is photolabile at wavelengths near this value.) The incorporation position of the photoaffinity probe is at the N- or C-terminus of the peptide. The core of the 12-mer peptide largely mediates the interaction with the receptor, and that the termini are not within a surface groove and thus of relatively little importance to binding. The peptide can be modified through its N-terminal amino group using an appropriate linker reagent. Alternatively, the peptide can be re-synthesized to incorporate an Fmoc benzophenone photoaffinity probe at any position (also cf. Bosse et al., 1993; Tian et al., 2004). For example, successful crosslinking of azidophenylalanine modified insulin to the insulin receptor has been reported (Kurose et al., 1994). Alanine scanning is used to identify candidate sites for incorporation of the photoaffinity probe. Peptide positions for which alanine preserves receptor binding affinity can be interpreted as positions that do not contribute directly to binding and thus are candidates for benzophenone incorporation. For GABAc-expressing cells, the primary photoaffinity approach involves in vitro testing, i.e., the use of isolated GABAc extracellular domain. However, to test the validity of the in vitro results obtained, the site of target protein tagging on GABAc-expressing cells is also mapped according to the following four-step procedure, and is performed only for peptides that appear promising based on the in vitro results. (1) Preparation of photoaffinity-tagged and biotinylated peptide (here termed peptide PB): The test peptide is derivatized to incorporate a biotin moiety (e.g., at the peptide's N-terminal) and a photoaffinity agent. Competition binding and electrophysiological assays of peptide PB's activity, as well as pull-down assays similar to those previously used (Nielsen & Kumar, 2003), are conducted to determine if PB retains the activity of the parent underivatized peptide. The biotinylated peptide is further derivatized to contain an aryl azide probe at a suitable site. Alternatively, a commercially available bifunctional probe such as Sulfo-SBED (Pierce) that incorporates both biotin and an aryl azide and can be attached to (cysteine-free) peptide at the N-terminus is employed. (2) Linking illumination: The candidate peptide PB is incubated with GABAc expressing cells in the presence (or, as control, absence) of UV (i.e., photoaffinity linking) illumination. This illumination covalently couples (some of) the GABAc/PB complexes present, and can covalently link PB with other, unwanted target proteins. (3) Recovery of GABAc-PB conjugate: The treated cells are extensively washed to remove unreacted peptide and the cell membranes are solubilized with CHAPS. The solubilized membranes containing GABAc-PB (and other PB-containing) conjugates are subjected to one of two procedures designed to isolate GABAc-containing material (GABAc-PB conjugate and free GABAc): either immunoaffinity chromatography using anti-GABAc antibody as the immobilizing agent, or ligand affinity chromatography using tethered muscimol as the immobilizing agent. Using streptavidin-coated beads, the GABAc-PB conjugate is selectively immunoprecipitated and its purity determined by SDS-PAGE and Western blotting. (4) Generation/analysis of PB-tagged GABAc fragment: To determine the site (i.e., local GABAc sequence) at which the peptide PB is bound, limited proteolysis of the GABAc-PB conjugate is performed, wherein limited proteolysis involves incubation with trypsin or another protease under conditions designed to avoid hydrolysis of the peptide PB moiety of the conjugate. As the PB sequence is known, PB's preservation during this step can readily be checked. Following purification of the GABAc-PB conjugate by streptavidin-coated beads, the conjugate is analyzed by MS and microsequencing. As the GABAc amino acid sequence is known and peptide PB's sequence is then known, identification of the GABAc amino acid position photoaffinity-tagged by peptide PB is achieved.

While the multi-step procedure just described is likely to have a relatively low overall yield, it should be possible with sufficient scale-up of the starting preparations (including, e.g., a population of GABAc-expressing neuroblastoma cells) to achieve an absolute yield sufficient for MS/microsequencing. Alternatively, photoaffinity experiments can instead employ radiolabeled (rather than biotinylated) affinity-tagged peptide, with corresponding procedures to recover/analyze the radiolabeled conjugate of peptide and OABAc fragment. This approach, however, requires HPLC separation of the digested receptor fragments using a radiochemical detector.

FIG. 27 shows the N-terminal region of AchBP, which will serve as a template for the modeling of the corresponding region of GABAc. The model obtained from Protein Data Bank. The C-terminus of this region is at the bottom. On the right are predicted solvent-accessible surface areas (in square Angstroms; $A^2$) for the N-terminal domain of the human p1 GABikc sequence. Peaks indicate amino acid positions predicted to be relatively exposed to the extracellular medium.

Figure 29:
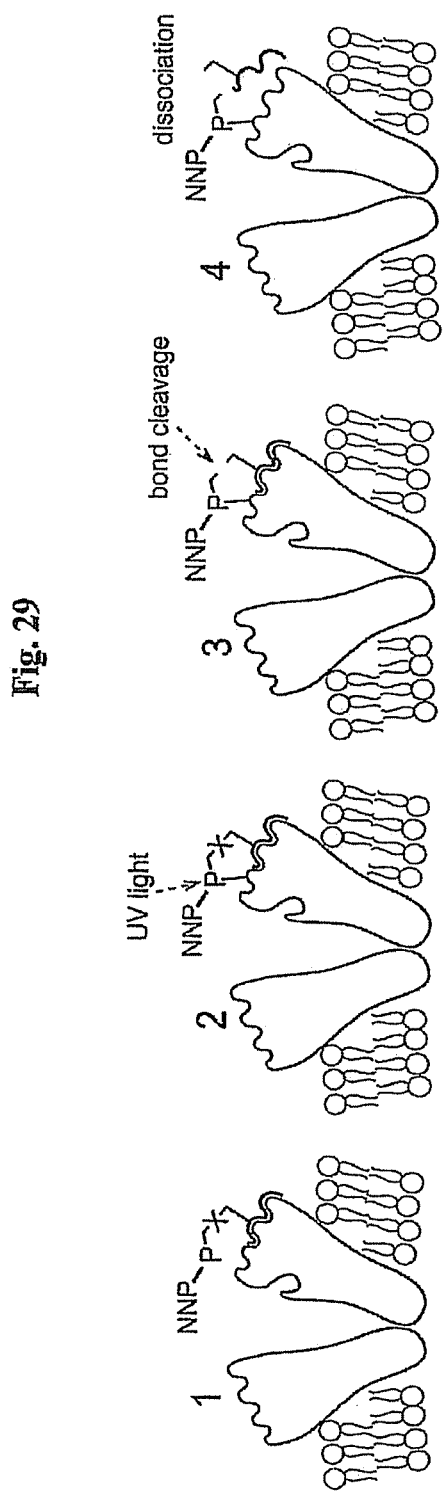
FIG. 29 depicts a scaffold approach using a noncovalently bound peptide as scaffold.

Computational modeling: To facilitate the interpretation of data obtained in the photoaffinity and cysteine mutagenesis experiments of Phase 2, and to guide the design of subsequent experiments aimed at optimizing the sites of peptide anchoring, we carry out a two-pronged approach to model both the molecular structure of the GABAc extracellular domain and its evolutionary history. Structural model of the GABAc extracellular domain: We first construct explicitly a homology model structure of the extracellular domain of GABAc. This is based on an AchBP template structure (FIG. 27) and a high quality multiple sequence alignment obtained using psi-blast and culstalW (Altschul et al., 1997; Chenna et al., 2003). We use the MODELLER package to build the three dimensional structure (Fiser & SalI, 2003), an approach similar that described by Ernst et al. (2003), and calculate surface-accessible regions on this model structure. To improve our confidence in predicted surface residues, we further predict solvent-accessible surface residues from the GABAc primary sequence using neural network and profile-based techniques (Ahmad & Gromiha, 2003; Gianese et al., 2003) (FIG. 27). Results from the two approaches are compared and consensus regions identified. Because our goal is to locate residue sites that are accessible for cysteine substitution and peptide attachment that will not perturb receptor physiology, the most relevant information sought from this model is identification of the set of surface exposed residues, which will be combined with information obtained from evolutionary analysis. Predictions regarding the spatial conformations of side chains of buried residues will be less important. Amino acid sites predicted to be favorable for, e.g., cysteine substitution, will be chosen from surface residues that are distant from the effector site but are within or adjacent to solvent-exposed patches. To identify energetically most favorable sites, we will generate and analyze an exhaustive set of candidate surface patches using a geometrically confined breadth-first search method (Cormen et al., 2001). Identification of candidate sites of receptor modification: To select candidate GABAc surface sites, we extract information from the evolutionary history of the GABAc receptor. Specifically, we carry out an extensive maximum likelihood analysis using a continuous-time Markov model to estimate the mutation rates at different residues, based on the phylogenetic tree for a set of orthologs and paralogs of the extracellular domain. Through this analysis we will identify amino acid residues that are relatively variable (i.e., not highly conserved) and thus are potential sites of peptide attachment. The continuous-time Markov model and maximum likelihood approach clarifies a controversy in the field of protein folding: namely, whether folding nuclei residues are conserved by evolution (Tseng & Liang, 2004). We have carried out a preliminary study of human p1 GABAc and have identified 25 DNA sequences for detailed phylogeny analysis. FIG. 28 shows a preliminary posterior probability analysis of amino acid residues 1-70 of the 25 investigated sequences (data obtained from GeneBank) in which the occurrence among species of synonymous vs. nonsynonymous codon substitutions (Tseng & Liang, 2004) yields a predicted index of mutation rates. Here, darkly shaded, medium shaded and lightly shaded vertical segments at a particular amino acid position (whose amplitudes sum to unity) represent, respectively, predictions of relatively high, medium and low conservation. For example, a relatively large amplitude of light shading indicates relatively little amino acid conservation (i.e., high variability) and thus relative likelihood of solvent exposure and accessibility to modification. The illustrated (aligned) sequence is that of human p1 GABAc. In addition to predictions of positions for modification, this and related computational analyses (Li et al., 2004; Li & Liang, 2005) will yield predictions for amino acids at subunit interfaces of the pentameric GABAc receptor, a property important to understanding receptor subunit assembly and physiology (Qian & Ripps, 1999). Importantly, the computational modeling approaches just described are necessary even if a crystal structure of the GABAc receptor is achieved. For example, the crystal structure of AchBP is available (Brejc et al., 2001), but does not afford specific predictions for the binding of peptide ligands to be examined. Determination of the GABAc crystal structure is of course desirable and would place the modeling on a firmer foundation, e.g., would allow more accurate determinations of parameters such as solvent accessibility, but would not replace the need for modeling.

Phase 3: Silent, covalent peptide binding to native receptor: We identify from the "filtered" set of candidates (FIG. 24), photoaffinity-derivatized peptides that bind to GABAc in a manner that does not perturb receptor physiology. While this objective of nonperturbative binding is clearly more stringent than the Phase 2 goal of using photoaffinity tagging to map the GABAc position of ligand attachment, we these silent ligands may be a sub-set of, or closely related to, those investigated in the course of Phase 2. Importantly, the identification of silently binding peptides and their sites of photoaffinity attachment is likely to facilitate later-generation structures employing chemical mechanisms of attachment, e.g., peptide derivatization with an amine-reactive, activated ester group rather than a photoaffinity probe. As with the photoaffinity probe, the specificity of this chemically-based covalent attachment would be governed by the binding specificity of the peptide and the proximity of suitable functional groups on the native receptor.

Alternative approaches: (1) If the ultimately isolated peptide ligands lack the desired specificity or binding strength needed for NNP functionality, an antibody substitute may be used. It is possible to display single-chain fragments (scFv's) of antibodies on the surface of phage (Sheets et al. 1998). Advantages of scFv's are that they have a stable three-dimensional structure, often exhibit very high affinity (low nanomolar dissociation constants) for their targets, and can adopt a concave or convex surface to bind target proteins. Antibody fragments to a wide variety of targets have been generated (Han et al., 2004). (2) In the event of difficulties with use of the GABAc extracellular domain for in vitro phage screening, e.g., if the proper folding of GABAc requires membrane insertion, detergent-solubilized full-length GABAc prepared using the baculovirus system may be used. Importantly, the presence of solubilizing detergent such as CHAPS is not expected to interfere with the capacity of phage binding. Here a possible pitfall is the selection of peptide ligands (or scFv's) that are reactive with the cytoplasmic or trans-membrane domains of the receptor rather than the extracellular domain. Results obtained by testing peptide binding on whole GABAc-expressing cells (see section above) allow the exclusion of such peptides as candidates and the focus, in further investigation, on those peptides that exhibit high affinity for cell-expressed GABAc as well as GABAc extracellular domain. (3) A further alternative strategy for achieving (ultimately silent) photoaffinity-mediated anchoring is the use of a scaffold, i.e., a temporary molecular structure, e.g., a phage-derived peptide or chainderivatized agonist or antagonist that ultimately dissociates from the receptor, to localize the site of binding of a photoaffinity probe that will serve as a covalent anchor (FIG. 29). Here, a cleavable bond (e.g., the phosphate of a hemiacetal that in the presence of endogenous/added phosphatase yields a spontaneously hydrolyzing hemiacetal) initially links the test NNP structure and a photoaffinity probe to the scaffold. Subsequent photoaffinity labeling and scaffold dissociation would establish covalent NNP binding at a site determined by the scaffold's binding. Synthetic peptides related to a-conotoxins (antagonists at neuronal nicotinic Ach receptors; e.g., Azam et al., 2005) may be used as a GABAc scaffold. FIG. 29 depicts the scaffold approach using, as illustration, a noncovalently bound peptide (thick wavy line) as scaffold. The peptide, previously derivatized to incorporate a cleavable bond (X), a photoaffinity probe (P), and other platform components (NNP), attaches to the receptor (panel 1). UV photoaffinity linking illumination (2), chemically induced bond cleavage (3) and peptide dissociation (4) yield the site-directed, covalently bound NNP.

Upon the identification of peptides with high GABAc-binding affinity, it will become important, for refinement of the approaches used, to explore additional measures of the peptide-GABAc interaction. Surface plasmon resonance (SPR): Using SPR, an optical technique that affords time-resolved determinations of binding kinetics, we analyze the interaction of GABAc extracellular domain with a particular candidate peptide or, alternatively, with a population of whole phages expressing the peptide. Such SPR determinations for defined peptide sequences, by affording a ranking of these candidate peptide anchors based on kinetic binding parameters, may complement the primary proposed approaches in identifying peptides with high affinity for GABAc. Surface force measurements are taken. These procedures test the interactions of candidate peptides with tethered isolated GABAc and cell-expressed GABAc.

To achieve light-dependent control of GABAc channel gating, we (1) identify a second-generation organic photoswitch whose spectral properties and relaxation kinetics (relative to the unmodified azobenzene photoswitch of effector/photoswitch/linker assemblies) to be tuned to meeting physiological requirements of the ultimate device; and (2) interface effector/photoswitch/linker assemblies with the peptide-based anchors, and biophysical/electrophysiological testing optimizes this interfacing for GABAc control.

Second-generation photoswitches. Modified azobenzenes: The photoconversion of trans to cis azobenzene requires near-UV (366 nm) rather than visible light, and the thermal relaxation of cis to the (favored) trans occurs on a time scale of hours to weeks. Thus, while the slow thermal isomerization of azobenzenes is workable and indeed desirable for the azobenzene-based prototype photoswitches, (as it allows an ample time window for experimental investigation of simple, one-way light-induced changes), meaningful physiological activity of the envisioned structure will require far faster relaxation. In addition, a light-sensitivity of the ultimate, clinically used NNP in the visible rather than near-UV wavelength range is critical, in significant part because the intensity of UV light in conventional environments, and of UV light transmitted by the (native) lens of the eye, is considerably lower than light intensity in the visible (400-700 nm) range. The immediately following paragraphs address these two points.

Figure 30:
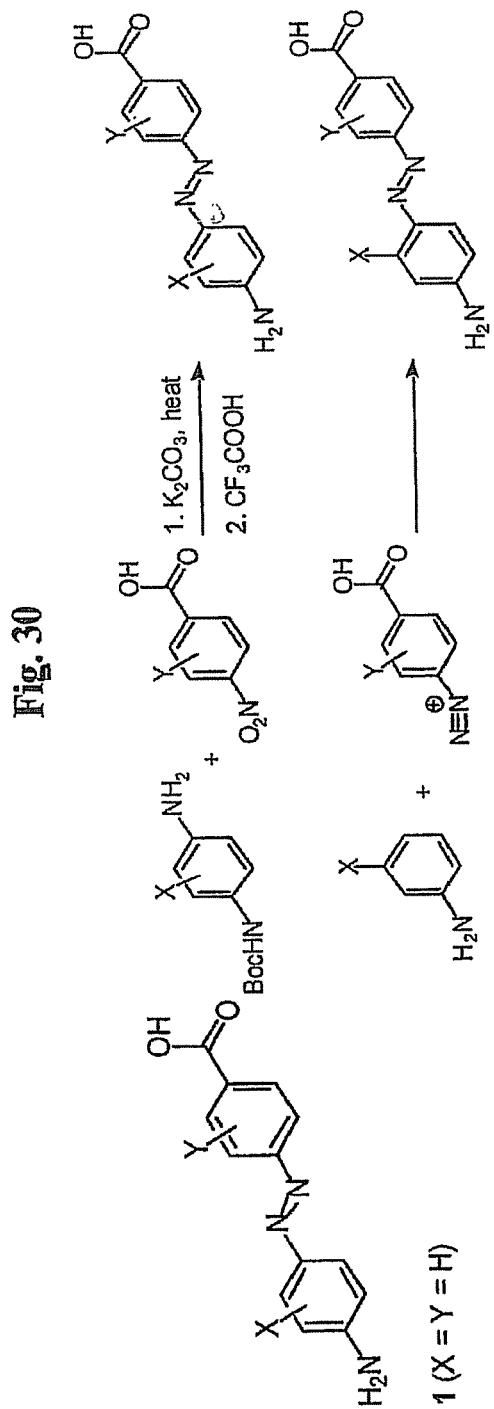
FIG. 30 depicts synthetic routes to target push-pull azobenzene and derivatives through nitro-anilino coupling and diazonium coupling.

Photoswitch relaxation time is a critical design parameter for the NNP, as it governs not just how long the GABA receptor remains activated but how fast the device can cycle, i.e., recover sensitivity to an activating photon. The general model of LGIC function includes the concept of an essential locking of bound ligand by the receptor in its channel-open state (Colquhoun, 1999; Bianchi & Macdonald, 2001). In the case of a tethered ligand, the behavior at the binding site is yet to be determined, but for the present discussion it shall be assumed that the effector moiety of the test system under study behaves as a diffusible ligand. Chang & Weiss (1999) have developed a model of GABAc receptor activation based on a combination of electrophysiology and ligand binding studies on GABAc p1 receptors expressed in *Xenopus* oocytes. This model provides two initial performance criteria for relaxation of the NNP photoswitch. First, the evident transition time to the channel-open state (280 ms; r in Table 1 of Chang & Weiss, 1999) suggests a lower limit of ~30 ms ($0.1\beta^{-1}$) for the photoswitch relaxation time, to provide a significant (assumed 10%) probability of channel opening during the lifetime of the photogenerated isomer. (Cis and trans azobenzenes have distinct absorbance spectra, and their interconversion on this time scale can be monitoring using a UV-visible spectrophotometer for flash photolysis.) The second criterion is provided by the model's mean channel open time (~3 s; $\alpha^{-1}$), i.e., the period during which the agonist remains locked. This period of ~3 s provides a target upper limit of the photoswitch relaxation time. It is important to emphasize that these criteria derive from the assumption that the photoswitch cannot relax when the ligand is locked at the binding site. However, this assumption may not be correct. A highly exothermic cis-trans photoswitch isomerization may cause the receptor channel to close on a time scale faster than the intrinsic ~3 s. Reciprocally, it is possible that the receptor might perturb the photoswitch relaxation kinetics. The occurrence of this latter possibility would likely be manifest as a reduced thermal isomerization rate of the photoswitch. In the event of such a distortion of receptor or photoswitch relaxation kinetics, we would retune the intrinsic photoswitch lifetime to compensate. The above considerations are based on the Chang & Weiss (1999) analysis of oocyte-expressed GABAc receptors, the relaxation times of which are ~5-10 times longer than those of native retinal GABAc receptors (Qian & Ripps, 1999). The oocyte system will be a focus of initial electrophysiological testing (see Aim 2), however the performance of 1\INP assemblies with native retinal receptors may be re-assessed. Importantly, a fast-relaxing, "retinal GABAc-tuned" device will likely be capable of eliciting measurable responses in slowly-relaxing oocyte-expressed GABAc receptors, as bright light flashes can be used to drive the photoisomerization, and membrane current as little as 1% of the GABA-elicited maximum can be distinguished from baseline noise. In addition, it is likely that the performance criterion for a particular receptor preparation may undergo changes for several reasons. One of these relates to the fact that GABAc activation requires ligand binding at >2 of the receptor's five binding sites (Amin & Weiss, 1996; Karlin, 2002). If the NNP under investigation is monovalent, i.e., if a particular photoswitch molecule regulates a single effector moiety (see, however, FIGS. 20-21), and assuming a 1-s lifetime of the photoactivated state, the requirement for temporally well-overlapping occupation of multiple ligand-binding sites on a particular receptor translates to a requirement for photoactivating isomerizations of multiple NNPs on the receptor within a period short by comparison with 1 s. Assuming the objective of NNP function at bright but conventionally encountered levels of ambient light (at wavelengths absorbed by the photoswitch), it may become important to tune the photoswitch lifetime to significantly longer values, thereby sacrificing some temporal resolution of NNP function to assure multi-site ligand occupancy. Yet a further consideration is the relationship of photoswitch relaxation time to the period after photoisomerization that is required for diffusion of the effector to the receptor's ligand binding site. This consideration is most applicable to the length of the tethering chain which may range up to ~216 Å. The mean time T for diffusion of a molecule from the surface of a sphere of radius L to a target of radius b in the center is particular by $T=L^3/3 Db$ (Berg & von Hippel, 1985) For consideration of this relation, we shall take L=216 Å as the chain length, b=10 Å as the radius of the ligand-binding site, and $D=1\times10^{-6}$ cm$^2$ s$^{-1}$ as the diffusion coefficient. The chosen value of the diffusion coefficient is appropriate for a small protein like lysozyme (MW 14,000) in water. Although a small molecule like sucrose ($D=5\times10^{-6}$ cm$^2$ s$^{-1}$ in water) might be viewed as a more appropriate reference due to its near-identity in molecular weight with the anticipate photoswitch effector couples, the value of $1\times10^{-6}$ cm$^2$ s$^{-1}$ seems appropriate because of the expected tortuosity/viscosity of the extracellular space at the cell surface membrane, which typically reduces diffusion coefficients by 1.5-2.5 fold from their value in water (Nicholson & Sykova, 1998). With these values of L, D and b, the diffusion time T is equal to 34 µs, a period tiny by comparison with the targeted 30-ms lower limit of photoswitch relaxation time. As the diffusion coefficient grows approximately with the cube root of molecular weight, one would predict that the diffusion coefficient for PEG 3400 would have only an ~2-fold effect on the above value of T. Primary Targets: Push-pull azobenzenes. Both relaxation time and isomerization wavelength in azobenzenes can be tuned through appropriate choice of substituents. Notable are "push-pull" azobenzenes, where an electron donor substituent on one ring is paired with an electron acceptor substituent on the other (Ross & Blanc, 1971; Kobayashi et al., 1987). Tuning is accomplished by varying the strength of the donor [e.g., $CH_3<OCH_3<N(CH_3)_2$], the strength of the acceptor (e.g., $COOH<SO_2OH<NO_2$), and their positions on the rings (FIG. 30). Importantly, substituent combinations that lead to cis-trans relaxation rates in the target range typically shift the trans-cis excitation wavelength into the visible region due to the extended n-conjugation. Push-pull azobenzenes can be prepared by one of three routes: condensation of a nitroso compound with an aniline (cf. Ulysse & Chmielewski, 1994; Park & Standaert, 1999), condensation of a nitro compound with an aniline (FIG. 30, upper route), or coupling of a diazonium salt with an aniline or phenol (FIG. 30, lower route). Published spectral data and isomerization rates provide examples of compounds with visible-light absorbances and isomerization rates that bracket the target range. For example, 4-amino-4'-carboxyazobenzene (FIG. 30, compound 1), $\lambda_{max}$ (trans) is 420 nm, and the time constant for cis-trans isomerization is 3 min in DMSO (Wachtveitl et al., 1997). For 4-dimethylamino-4'-sulfoazobenzene, which has a more powerful donor-acceptor pair, $\lambda_{max}$ is ~480 nm (Oakes & Grafton, 1998), and the lifetime in water is 6.6 s at 25° C. (Asano & Okada, 1984). Use of an even more powerful 4-diethylamino-4'-nitro pair affords $\lambda_{max}$ of 512 nm and a lifetime of 2.2 ms in DMSO. The same compound has a $\lambda_{max}$ of 493 nm and a lifetime of 1.0 s in chloroform (Schanze et al., 1983). As this last example illustrates, thermal isomerization rates are highly sensitive to solvent, with polar solvents accelerating the process, and it is not yet clear which solvent will best model the micro-environment of the NNP photoswitch. Thus, we anticipate that identification of the appropriate donor/acceptor combination will require considerable effort in synthesis and empirical testing.

Alternative targets: While azobenzenes are the primary choice for the second-generation photoswitch, brief mention of other alternatives is appropriate. One potential class of targets are the imine (Schiff base) analogs of azobenzene, in which one N of the azo linkage is replaced with a CH. These are photoisomerizable, isosteric with azobenzene, and can exhibit thermal cis-trans relaxation times of about 1 s, even without push-pull substituents (Wettermark & Dogliotti, 1964; Anderson & Wettermark, 1965; Wettermark et al., 1965; Gorner & Fisher, 1991). Several other photoisomerizable organic structures have been closely investigated as switch nuclei. However, none are likely to be suitable because they have either or both of two problems: the need for UV photoactivation [spiropyrans (Hobley et al., 2003); spirooxazines (Metelitsa et al., 2002); naphthopyrans (Jockush et al., 2002; Gabbutt et al., 2005)] or thermal relaxation times well outside the target range [spiropyrans (Gorner, 2001); diarylethylenes and fulgides (Kobatake & Inc.i 2003); thioindigos (Rosengaus & Willner, 1995; Fyles & Zeng, 1998); and hemithioindigos (Steinle & Rueck-Braun, 2003; Lougheed et al., 2004)]. Extended-lifetime core/shell nanocrystals. CdSe nanocrystals possess a large dipole moment (up to ~60 Debye) that is believed to reflect the electrical polarization of interatomic bonds in the CdSe wurtzite crystal structure (Shim & Guyot-Sionnest, 1999). Photogeneration of an electron-hole pair significantly reduces this dipole moment, and in CdSe core and core/shell nanocrystals of ordinary composition, recombination of the electron-hole pair returns the nanocrystal's electronic structure to the pre-illumination state on a time scale of ~10 ns (Javier et al., 2003). By analogy with a concept considered by Schmidt & Leach (2003) in which nanocrystals positioned at the membrane of nerve axons could be used to initiate action potentials, extension of the electron-hole lifetime to the ps range or greater could permit use of the photo-induced dipole perturbation as a photoswitch. If the above strategies to obtain an organic photoswitch that absorbs efficiently at visible wavelengths and spontaneously relaxes on the needed time scale are not acceptable using core/shell nanocrystals as the photoswitch component may be. This specifically involves engineering the core and shell bandgaps of CdSe/ZnSe nanocrystals to achieve a type-II offset of the valence and conduction bands, and (at Vanderbilt Univ.) pilot opto-electronic testing of the preparations to evaluate their potential suitability as a photoswitch component.

Figure 14:
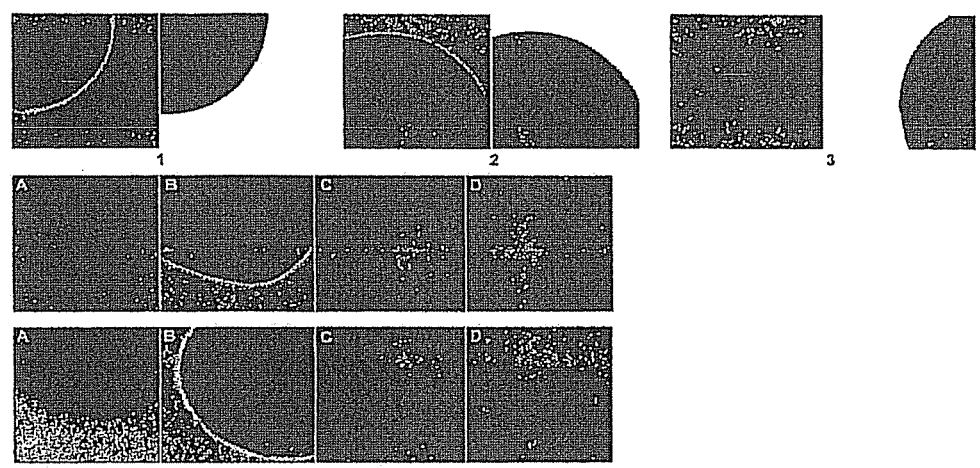
FIG. 14 (upper row) shows results obtained from oocytes expressing perch ρ1B GABAc receptors (1) (set 1) and human ρ1 GABAc receptors (2) (set 2), and from a non-injected oocyte (3) (set 2), upon 5-min incubation with medium containing 34 nM M-PEG-nc.

Preparation/testing of platform assemblies: The modular design of the NNP will allow assembly using conventional peptide coupling chemistry to join the effector/photoswitch/linker to a defined position on a photoaffinity-probe-derivatized anchor. Fully assembled candidate NNPs (i.e., structures in which the effector/photoswitch and PEG linker of a particular test length joined to a defined amino acid position of the peptide anchor) may be used with isolated GABA extracellular domain and with GABAc-expressing cells in biophysical/electrophysiological experiments (FIG. 14) to achieve transient, visible-lightstimulated GABAc channel gating. The following considerations will be important to optimizing the assembly with respect to physiological performance. Short-wavelength photolability of muscimol: Muscimol is photolabile at wavelengths near 254 nm and in fact can act as a photoaffinity label at this wavelength (Cavalla & Neff, 1985). Many of the photoaffinity probes noted above, while anticipated to be workable for mapping the site of GABAc attachment of a particular peptide ligand and for determining silent modes of the peptide attachment, require activation with similar wavelengths and are likely to be unworkable for use as the covalent binding component in full NNP structures that employ muscimol as the effector moiety. For use in such muscimol-based, fully assembled structures, the use of photoaffinity probes such as benzophenones (Dorman & Prestwich, 1994) are activatable with light of 350-360 nm, where muscimol has negligible absorbance. Energetics of photoswitch cis vs. trans states: One of the design criteria discussed above is the use of cis-permissive azobenzenes, a choice dictated by the much larger thermodynamic stability of the trans isomer. Where the exponential lifetime of the thermal relaxation from cis to trans is on the order of 1 s, as is anticipated with push-pull azobenzenes, complete relaxation will occur in a few seconds in darkness, and a trans-permissive device would remain perpetually activated. It is of interest to consider how push-pull substitution affects this equilibrium, in conjunction with the binding of the NNP effector at the ligand-binding site. In azobenzene itself, the trans form is more stable by 49 kJ/mol (Dias et al., 1992). While corresponding data are not available for the fast-relaxing push-pull azobenzenes, the energy difference between the cis and trans forms of these compounds should be even greater due to the highly favorable conjugation of the push-pull groups in the trans isomer, which is disrupted in the cis isomer. We can conservatively retain the value of 49 kJ/mol as the energy difference between the cis and trans states. Even with a high-affinity effector like GABA ($K_D$~1 µM, corresponding with a 34 kJ/mol binding energy; $\Delta G° = -RT$ [in ($K_D/(1\ M)$)]}, the ligandbinding energy is still far lower than the cis-trans energy difference for the push-pull azobenzene. Thus, the thermodynamic preference for trans is expected to be 15 kJ/mol (49 kJ/mol-34 kJ/mol); the trans form is still favored by a factor of 400, and the thermal occupancy of the permissive, cis form is only 1/400.

Signal transmission at chemical synapses in the nervous system involves the action of receptor proteins at the postsynaptic membrane that respond to neurotransmitter released by the presynaptic neuron. Ligand-gated ion channels (LGICs) represent a major group of postsynaptic membrane receptors. LGIC receptors, which include $GABA_A$, $GABA_D$, glycine, serotonin and nicotinic acetylcholine receptors, exhibit a common overall structure consisting of five noncovalently assembled subunits. The ligand-binding sites of LGICs are located at junctions of the extracellular domains of adjacent subunits, and the subunits exhibit significant amino acid sequence homology. Although crystal structures are not yet available for any LGIC, the recent determination of the crystal structure of acetylcholine binding protein (a glial protein of the snail) (Brejc et al., 2001, Sixma & Smit, 2003) has afforded relatively detailed homology-based modeling of LGIC structure (Ernst et al., 2003). GABA is the major inhibitory neurotransmitter in the brain, and $GABA_A$ receptors are widely distributed in the CNS. In addition to GABA binding sites, the $GABA_A$ receptor exhibits modulatory sites sensitive to benzodiazepines, barbiturates and neurosteroids (Johnston, 1996), and the regulation of $GABA_A$ activity by drugs targeting these sites is a major focus of psychiatric therapies.

Figure 31:
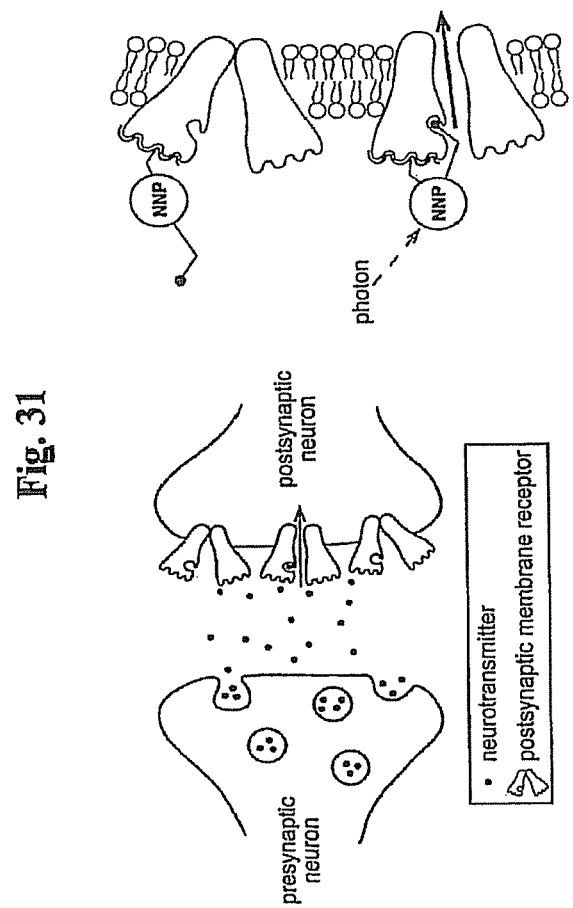
FIG. 31 depicts schematically the operation of the NNP.
Figure 32:
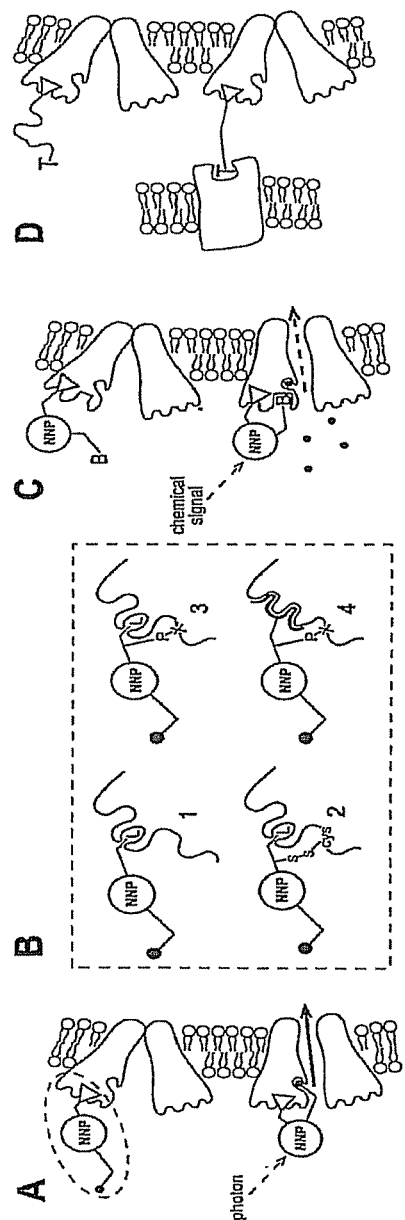
FIG. 32 depicts GABAa functionalization.

The objective of the procedures relating to the $GABA_A$ receptor referred to above is further described by FIGS. 31 and 32. FIG. 31 considers a molecular device ("nanoscale neuromodulating platform", or NNP) proposed in that application as a therapy in retinal degenerative disease. The left-hand diagram of FIG. 31 describes signal transmission at a normally functioning chemical synapse. Here the postsynaptic membrane receptor is a (hypothetical) LGIC consisting of two subunits and a single ligand-binding site. Neurotransmitter (filled circles) released from the presynaptic neuron in response to stimulation diffuses across the synaptic cleft and binds to the postsynaptic receptors. The resulting activation of these receptor proteins opens transmembrane ion channels (inward-pointing arrow), thereby generating an electrical signal in the postsynaptic neuron. The right-hand diagram describes operation of the NNP envisioned for development. The diagram specifically considers the case of photoreceptor degenerative disease (e.g., age-related macular degeneration, in which retinal neurons postsynaptic to the degenerated rod and cone photoreceptors are believed in certain cases to remain potentially capable of function), and envisions the restoration of light-stimulated signaling in post-photoreceptor neurons by NNPs introduced into the diseased retina. The illustrated NNP consists of a neurotransmitter or analog (small filled circle; "effector" component) tethered to a chemical structure (circle labeled NNP) that incorporates a molecular photoswitch, and an anchoring moiety (thick wavy line) that attaches the introduced NNP at the extracellular face of postsynaptic receptors of specific post-photoreceptor neurons remaining healthy in the diseased retina. Photon absorption produces a transient conformational change in a linker arm that moves the effector to the receptor's ligand-binding site and thereby transiently activates the receptor, i.e., opens the receptor's ion channel. The NNP's anchoring moiety is a phage-display-derived peptide that noncovalently attaches the NNP to the postsynaptic receptor. As a self-contained photosensor with localized stimulating activity, the NNP would achieve the microspecific functionality required for meaningful visual signal initiation.

In FIG. 32A the anchoring portion of a representative functionalizing structure (here, the photosensitive NNP of FIG. 31) and the site of its covalent attachment to the $GABA_A$ subunit are together symbolized by the open triangle. The FIG. 32B diagrams show in expanded view the region enclosed by the dashed oval in A and illustrate several attachment strategies. In strategy 1, a prototype approach not involving covalent attachment to the receptor, a genetically engineered amino acid sequence contains, as a recognition element, the inserted sequence of a binding protein with high affinity for its ligand, and (ii) a tethered form of this ligand (L) as part of the functionalizing structure. Immediate candidates for testing this strategy are FKBP (Standaert et al., 1990), a 107-amino acid binding protein that binds its FK506 ligand with known nanomolar affinity; and dihydrofolate reductase, a protein that has similarly high affinity for its inhibitory ligand, methotrexate (Kopytek et al., 2000). Additional strategies for insertion of a recognition element within a target protein have been described (e.g., Adams et al., 2002). Strategy 2 combines binding protein insertion with covalent anchoring of the functionalizing structure at a cysteine residue introduced by site-directed mutagenesis at a position neighboring the inserted binding protein. Here the functionalizing structure is designed to incorporate a thiol-reactive moiety whose steric properties (e.g., length of an alkyl chain linking this moiety to the remainder of the structure) will favor bond formation specifically with the thiol group of the introduced cysteine. The rationale for this approach is that the high specificity of the functionalizing structure for the receptor's inserted binding protein will diminish nonspecific attachment to undesired cysteines and other thiol-containing molecules expected to be present on the surface of the cell expressing the target receptor. Strategies 3 and 4, conceptually similar to strategy 2, combine photoaffinity labeling with noncovalent attachment via either ligand-binding protein (3) or a phage-derived binding peptide (4; cf. FIG. 31). Here the functionalizing structure incorporates a tethered photoaffinity reagent P (aryl azide; e.g., Turek et al., 2002) whose steric position favors covalent linkage to a desired amino acid X of the receptor subunit upon UV illumination. A specific advantage of strategy 4 is its use of the native receptor subunit, a factor facilitating applications to LGICs of native CNS tissue. Critical to strategies 1-3 will be the identification of sites within the subunit's extracellular domain that afford expression/function of the desired sequence insertion/substitution while preserving physiological function of the receptor. Determining these permissive attachment sites involves homology-based and computational modeling using available sequence, structural and biochemical data (e.g., Brejc et al., 2001; Teissere & Czajkowski, 2001; Bera et al., 2002; Chang & Weiss, 2002; Ernst et al., 2003; Binkowski et al., 2003), and the testing of constructed receptors and anchoring moieties in biophysical, pharmacological and electrophysiological experiments.

Illustrated in FIG. 32C functionalization of the $GABA_A$ receptor with a structure that contains a tethered benzodiazepine derivative (B) as effector, and in controlled fashion interacts with the receptor's benzodiazepine modulatory site. By contrast with conventional therapies involving administration of a freely diffusing drug, the covalent attachment of this structure would afford specific and localized action by the effector. Furthermore, regulation of the presentation of this effector by an external signal acting on the structure's signal-responsive element (in FIG. 32C, an administered synthetic chemical designed to have activity only at the signal-responsive component) would render this benzodiazepine-based therapy externally controllable by a highly specific, i.e., otherwise innocuous, drug. Moreover, the binding affinity of a particular effector B could be tuned for a particular disease or receptor type by the length/hydrophobicity of the chain tethering B, affording a new dimension of efficacy to the design of $GABA_A$-targeted therapies. FIG. 32D shows another potential application of receptor functionalization, that of interfacing the receptor with an introduced biological target or prosthetic device (e.g., a transplanted differentiated neuron or stem cell, or a neurotransmitter-releasing microfluidic system; Peterman et al., 2003) whose function requires an intimate association with the receptor. Here, the receptor would be functionalized with a (non-regulated) structure terminated by a molecular component (T) designed to have high affinity for a molecular component of the partner cell/device (cf. Movileanu et al., 2000). Upon introduction of the partner (in FIG. 32D, a transplanted cell with a known surface binding protein) to the LGIC receptor-containing tissue, T's binding to its target would tether the partner, thereby promoting its intended physiological interaction with the postsynaptic receptor.

Figure 33:
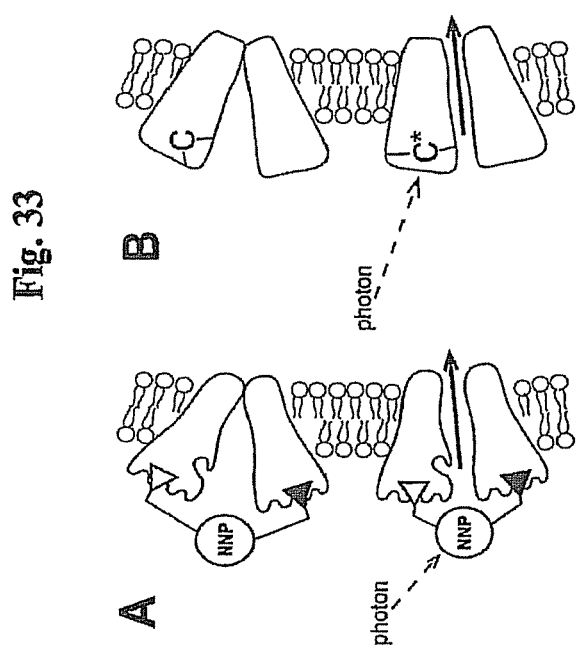
FIG. 33 depicts two LGIC receptor based therapies.
Figure 34:
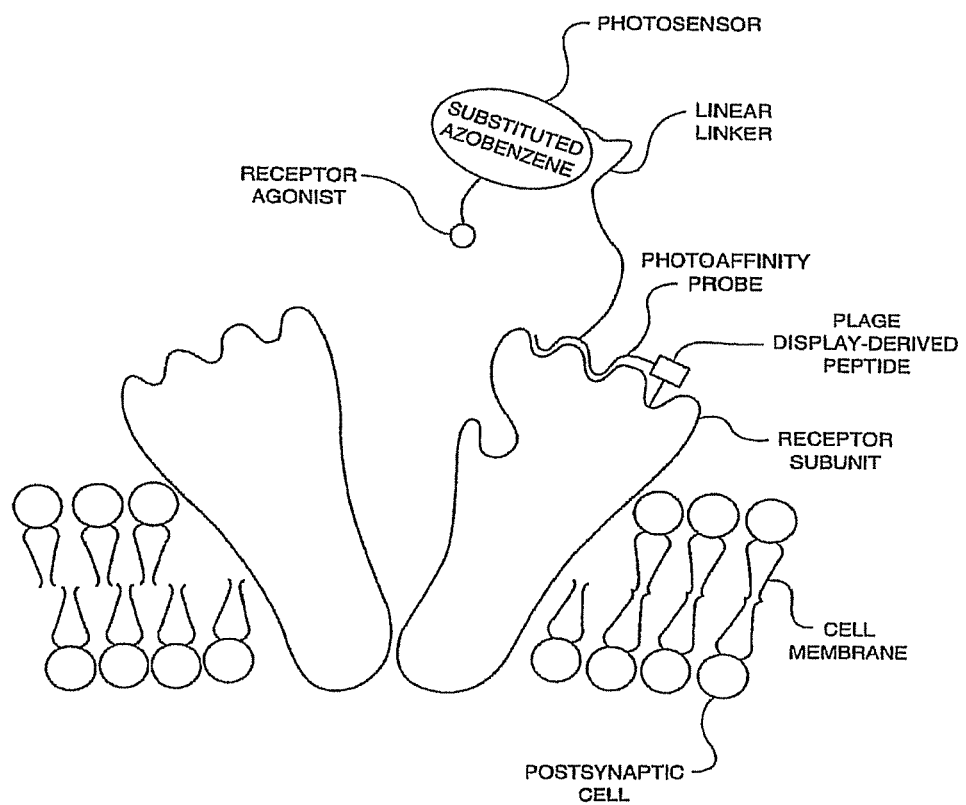
FIG. 34 depicts an NNP of the invention with an effector (open circle), a photoswtich (oval) a linker and an anchor peptide (rectangle).

In FIG. 33A a native LGIC functionalized with an introduced light-responsive structure (NNP) whose regulation of the receptor is mediated entirely through its covalent interactions with specific amino acid residues (open and filled triangles), i.e., whose operation does not require tethered forms of an activating receptor ligand or modulator. Panel 33B shows a fully synthetic light-sensitive protein whose synthesis within the neuron would be achieved by targeted gene therapy, and which responds to light (photic activation of chromophore C akin to those of naturally occurring photoproteins) with a conformational change that opens an ion channel. Initial constructs in model cells (*Xenopus* oocytes and HEK cells) are used to synthesize initial FK506-derivatized and aryl azide-(photoaffinity label-) containing compounds as test structures for subunit functionalization; and, through pharmacological/electrophysiological testing (e.g., Vu et al., 2004), to determine GABAA activity in the transfected cells in the absence vs. presence of the functionalizing structure. Site-directed cysteine substitution in $GABA_A$ subunits can determination intermolecular distances by fluorescence resonance energy transfer (FRET), computational molecular dynamics, and high-throughput assays for drug-receptor interactions.

In particular aspects of the invention, the composition can be used for treating neuronal hyperexcitable disease states, such as epilepsy. Other disease states or conditions affected by neuronal hyperexcitability include for example episodic ataxia, myokymia, neonatalconvulsions, cerebral ischemia, cerebral palsy, stroke, traumatic brain injury, traumatic spinal cord injury, asphyxia, anoxia or prolonged cardiac surgery. In other aspects of the invention the composition can be used in method s of treatment for retinal degenerative diseases such as macular degeneration. Examples of the "retinal diseases" include retinal vessel disorders and retinal inflammatory and degeneration lesions derived from systemic diseases such as diabetes, hypertension, arterial sclerosis, anemia, leukemia, systemic lupus erythematosus, and connective tissue diseases such as scleroderma; and inborn error of metabolism such as Tay-Sacks disease and Vogt-Spielmeyer disease, as well as local retinal diseases including retinal vessel disorders such as retinopathy of prematurity, retinal vein occlusion, retinal artery occlusion and retinal periphlebitis; retinal inflammation and degeneration derived from retinal detachment and trauma; age-related retinal degenerative diseases such as senile disciform macular degeneration; and congenital retinal degenerative disease. In particular, an agent for preventing, treating or suppressing progression of retinal diseases of the present invention can be particularly effectively used in congenital retinal degenerative disease, retinitis pigmentosa, macular degeneration, diabetic retinopathy, retinal detachment, glaucoma or retinal vessel occlusion.

Pharmaceutical Compositions

In another aspect, the present disclosure provides compositions comprising one or more of compounds as described above with respect to any of formula (I) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

DEFINITIONS

The following terms and expressions used herein have the indicated meanings.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "saturated" as used herein means the referenced chemical structure does not contain any multiple carbon-carbon bonds. For example, a saturated cycloalkyl group as defined herein includes cyclohexyl, cyclopropyl, and the like.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment of a disease or disorder described herein, in a subject, preferably a human, and includes:

i. inhibiting a disease or disorder, i.e., arresting its development;
  ii. relieving a disease or disorder, i.e., causing regression of the disorder;
  iii. slowing progression of the disorder; and/or
  iv. inhibiting, relieving, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Chemical synthesis and purifications were conducted in room light. All reactions were conducted under an atmosphere of dry nitrogen. All solvents used were anhydrous grade available commercially or were dried before use with appropriate dessicants. Thin layer chromatography was visualized by UV light or/and phosphomolybdic acid stain. $^1$H NMR spectra were recorded at 300, 360 and 400 MHz and $^{13}$C NMR spectra were recorded at 90.55, 100.62 MHz using sample solutions in the specific solvents listed. Chemical shifts are particular in ppm and referenced to external tetramethylsilane, and coupling constants are in Hz. Multiplicities of the signals were abbreviated as follows: s, singlet; d, doublet; t, triplet; q, quartet; m, multiplet; br, broad. High-resolution mass spectra (HRMS) were obtained with a LCMSIT-TOF spectrometer.

Representative synthetic procedures for the preparation of compounds of the invention are outlined below. Substituents $R^1$, $R^2$, $R^3$, $R^4$, $R^5$, $R^9$, X, Y, and Z carry the same meaning as defined above, unless otherwise noted.

Scheme 1
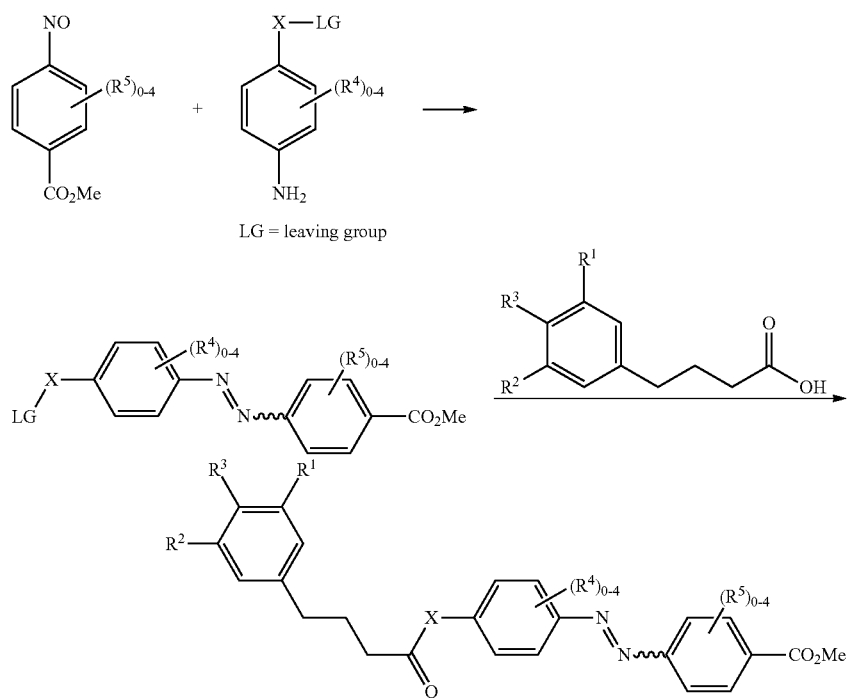
Scheme 2
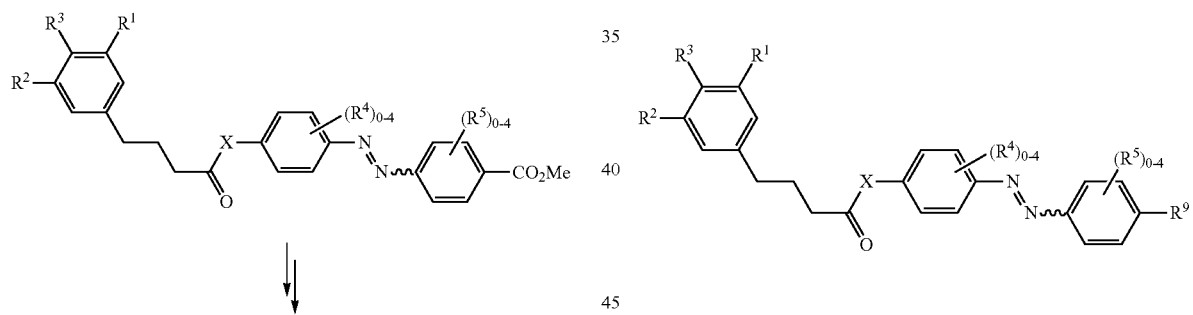

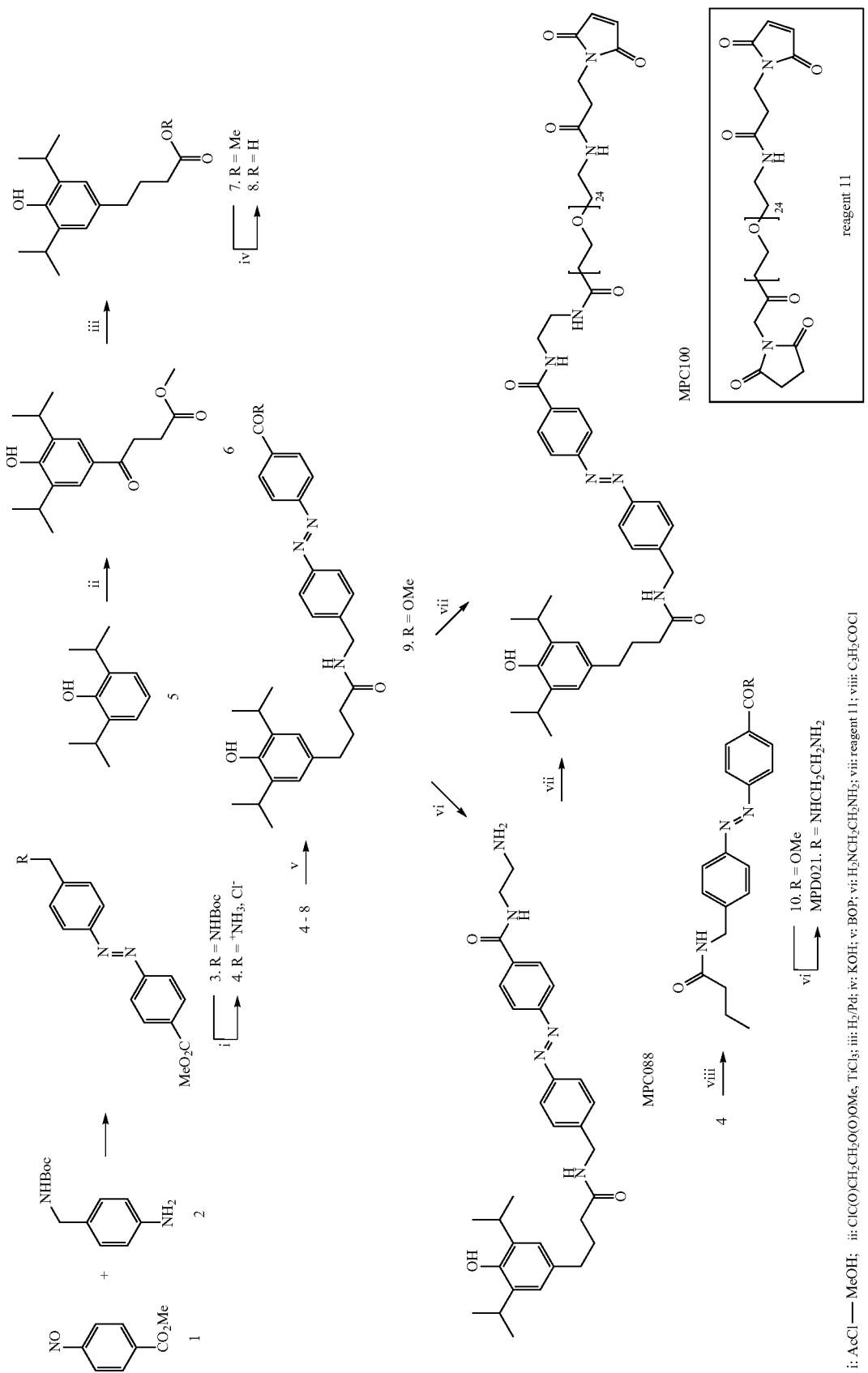

EXAMPLES

The compounds and methods of the disclosure are illustrated further by the following examples, which are provided for illustrative purposes and are not intended to be construed as limiting the disclosure in scope or spirit to the specific compounds and methods described in them.

Example 1

Preparation of MPC088

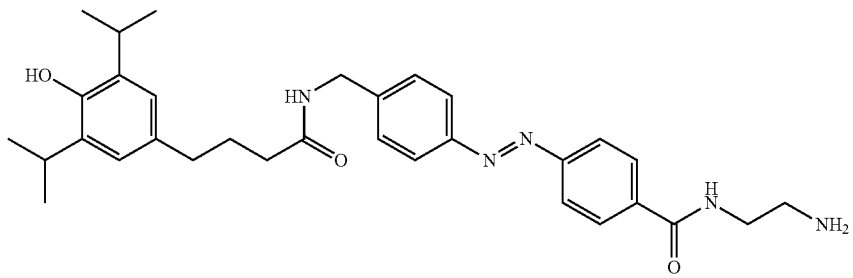 [SMILES: CC(C)c1cc(CCCC(=O)NCc2ccc(/N=N/c3ccc(C(=O)NCCN)cc3)cc2)cc(C(C)C)c1O]

(E)-N-(2-Aminoethyl)-4-((4-((4-(4-hydroxy-3,5-diisopropylphenyl)butanamido)methyl)phenyl)diazenyl)benzamide (MPC088)

(4-((4-(Methoxycarbonyl)phenyl)diazenyl)phenyl)methanaminium chloride (4)

Methyl 4-nitrosobenzoate 1 (1.16 g, 7.0 mmol) was dissolved in acetic acid (50 mL). tert-Butyl 4-aminobenzylcarbamate 2 (1.31 g, 5.9 mmol) was added, the mixture stirred for 3 h at room temperature, and the reaction was quenched by adding water (200 mL). The precipitated product was filtered, washed with water and dried on air yielding 3 (1.77 g, 81%) as orange crystals. This product was used in the next step without further purification. Acetyl chloride (2.0 g, 26 mmol) was added dropwise into anhydrous methanol (30 mL) at 0° C. After 10 min, to this solution compound 3 (1.0 g, 2.7 mmol) was added, the solution was allowed to warm up to room temperature, and solvents were evaporated to produce 4 (775 mg, 94%) as orange crystals. $^1$H NMR (300 MHz, DMSO-$d_6$): δ 8.48 (brs, 3H), 8.18 (d, J=8.4 Hz, 2H), 8.00 (d, J=8.1 Hz, 2H), 7.98 (d, J=8.1 Hz, 2H), 7.73 (d, J=8.1 Hz, 2H), 4.15 (s, 2H), 3.91 (s, 3H). $^{13}$C NMR (90.55 MHz, DMSO-$d_6$): δ 166.40, 155.13, 152.48, 139.07, 132.54, 131.42, 130.93, 123.76, 123.60, 53.30, 42.59. HRMS (m/z): [M+H]$^+$ calcd. for $C_{15}H_{15}N_3O_2$ 270.1237. found 270.1228.

Methyl 4-(4-hydroxy-3,5-diisopropylphenyl)-4-oxobutanoate (6)

Propofol 5 (1.78 g, 10.0 mmol) and methyl 4-chloro-4-oxobutyrate (4.5 g, 25 mmol) were dissolved in methylene chloride (350 mL), the reaction mixture was cooled to −78° C. and titanium (IV) chloride (5.7 g, 30 mmol) was added dropwise. The reaction mixture was stirred for 2 h at −78° C., allowed to warm up to room temperature and stirred overnight. The reaction mixture was then poured into water (300 mL), the organic phase was washed sequentially with saturated sodium bicarbonate solution, water and brine, and the solution dried over anhydrous magnesium sulfate. The product was purified by column chromatography on silica gel using hexane and hexane-ethyl acetate (4:1) step-gradient as an eluent to produce pure 6 (1.14 g, 39%) as a slightly yellow oil. $^1$H NMR (300 MHz, CDCl$_3$): δ 7.75 (s, 2H), 5.84 (s, 1H), 3.72 (s, 3H), 3.32 (t, J=6.8 Hz, 2H), 3.20 (septet, J=6.9 Hz, 2H), 2.76 (t, J=6.8 Hz, 2H), 1.28 (d, J=6.9 Hz, 12H). $^{13}$C NMR (100.61 MHz, CDCl$_3$): δ 196.81, 173.35, 154.40, 133.27, 129.05, 123.97, 51.41, 32.59, 27.82, 26.79, 22.18. HRMS (m/z): [M+H]$^+$ calcd. for $C_{17}H_{24}O_5$ 293.1747. found 293.1759.

4-(4-Hydroxy-3,5-diisopropylphenyl)butanoic acid (8)

Keto-ester 6 (1.0 g, 3.4 mmol) was dissolved in ethanol (50 mL) and palladium catalyst on charcoal (10%, 50 mg) was added. Hydrogenation was performed with 45 psi of hydrogen gas for 20 h. The catalyst was then filtered off and potassium hydroxide (909 mg, 16.2 mmol) was added, and the reaction mixture was refluxed for 1 h. The solvents were evaporated, and aqueous HCl (50 mL, 4.0 M) was added. The acidic aqueous phase was extracted with methylene chloride (3×30 mL), the combined organic extracts were dried over anhydrous magnesium sulfate and evaporated, giving 8 as white crystals (824 mg, 91%). $^1$H NMR (300 MHz, CDCl$_3$): δ 6.89 (s, 2H), 3.18 (septet, J=6.9 Hz, 2H), 2.64 (t, J=7.7 Hz, 2H), 2.43 (t, J=7.4 Hz, 2H), 1.98 (q, J=7.7 Hz, 2H), 1.29 (d, J=6.9 Hz, 12H). $^{13}$C NMR (90.55 MHz, CDCl$_3$): δ 180.51, 149.56, 134.07, 133.52, 123.83, 35.28, 33.98, 27.60, 27.09, 23.21. HRMS (m/z): [M+H]$^+$ calcd. for $C_{16}H_{24}O_3$ 263.1653. found 263.1664.

(E)-Methyl 4-((4-((4-(4-hydroxy-3,5-diisopropylphenyl)butanamido)methyl)phenyl)diazenyl)benzoate (9)

Acid 8 (164 mg, 1.00 mmol), benzotriazol-1-yloxy)tripyrrolidinophosphonium hexafluorophosphate (BOP, 884 mg, 2.00 mmol) and DMAP (12 mg, 0.10 mmol) were dissolved in methylene chloride (10 mL) and stirred at room temperature for 10 min. A solution of compound 4 (366 mg, 1.2 mmol) and triethylamine (505 mg, 5.0 mmol) in methylene chloride (15 mL) was added, and the reaction mixture was stirred at room temperature for 48 h. Aqueous work-up and chromatography on silica gel using chloroform and chloroform-methanol (3%) step-gradient as an eluent afforded pure 9 (296 mg, 57%) as orange crystals. $^1$H NMR (360 MHz, CDCl$_3$): δ 8.18 (d, J=8.6 Hz, 2H), 7.93 (d, J=8.7 Hz, 2H), 7.91 (d, J=8.6 Hz, 2H), 7.43 (d, J=8.3 Hz, 2H), 6.85 (s, 2H), 5.83 (t, J=9.1 Hz, 1H), 4.73 (s, 1H), 4.53 (d, J=5.9 Hz, 2H), 3.96 (s, 3H), 3.11 (septet, J=6.9 Hz, 2H), 2.60 (t, J=7.8 Hz, 2H), 2.29 (t, J=7.6 Hz, 2H), 1.99 (q, J=7.6 Hz, 2H), 1.24 (d, J=6.9 Hz, 12H). $^{13}$C NMR (90.55 MHz, CDCl$_3$): δ 173.23, 166.90, 155.42, 152.23, 148.52, 142.66, 133.99, 133.57, 132.17, 130.98, 128.85, 128.38, 123.87, 123.73, 123.01, 121.65, 120.13, 52.73, 43.56, 36.51, 35.45, 28.02, 27.51, 23.15. HRMS (m/z): [M+H]$^+$ calcd. for C$_{31}$H$_{37}$N$_3$O$_4$ 516.2857. found 516.2863.

(E)-N-(2-Aminoethyl)-4-((4-((4-(4-hydroxy-3,5-diisopropylphenyl)butanamido)methyl)phenyl)diazenyl)benzamide (MPC088)

The solution of the compound 9 (258 mg, 0.50 mmol) and ethylenediamine (600 mg, 10 mmol) in methanol (10 mL), water (5 mL) and chloroform (2.5 mL) was refluxed for 24 h. The solvents were then evaporated, the residue was dissolved in 1N potassium hydroxide (15 mL), and the mixture extracted with methylene chloride (4×15 mL). The combined organic phases were washed with water and brine, dried over magnesium sulfate, concentrated under vacuum, and the residue chromatographed on silica gel using chloroform and chloroform-methanol (5%) step-gradient as an eluent to produce pure MCP088 (201 mg, 74%) as orange crystals. $^1$H NMR (360 MHz, CD$_3$OD): δ 8.04-7.91 (m, 6H), 7.50 (d, J=8.4 Hz, 2H), 6.83 (s, 2H), 4.47 (s, 2H), 3.49 (t, J=6.4 Hz, 2H), 3.26 (septet, J=6.8 Hz, 2H), 2.90 (t, J=6.4 Hz, 2H), 2.55 (t, J=7.6 Hz, 2H), 2.30 (t, J=7.4 Hz, 2H), 1.92 (q, J=7.4 Hz, 2H), 1.19 (d, J=6.8 Hz, 12H). $^{13}$C NMR (90.55 MHz, CD$_3$OD): δ 175.13, 168.66, 154.57, 152.02, 148.72, 143.39, 136.55, 135.84, 133.40, 128.42, 128.38, 128.20, 129.90, 123.21, 122.99, 122.65, 120.98, 120.02, 42.66, 42.48, 40.89, 35.54, 35.08, 28.21, 26.83, 22.48. HRMS (m/z): [M+H]$^+$ calcd. for C$_{32}$H$_{41}$N$_5$O$_3$ 544.3282. found 544.3308.

Example 2

Preparation of MPC100

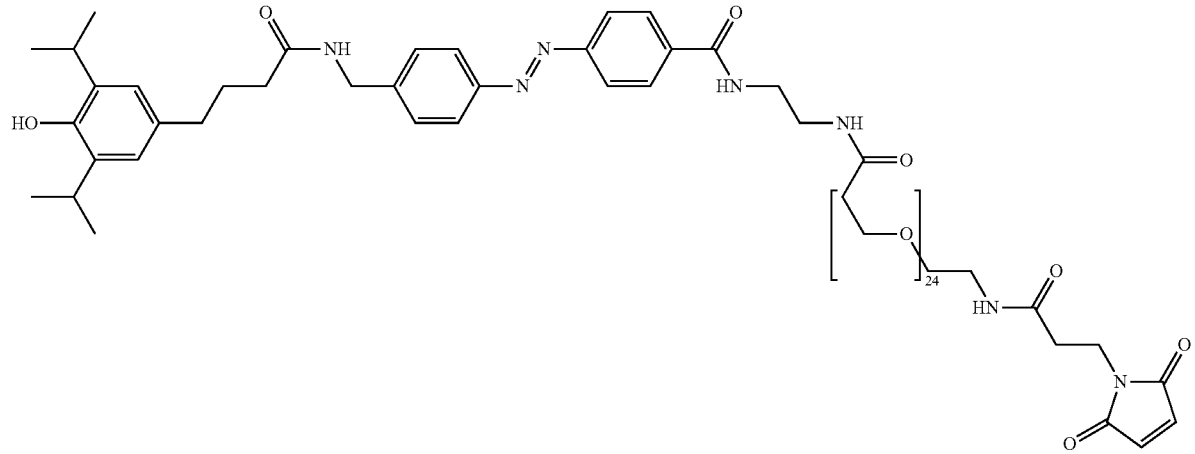

(E)-N-(82-(2,5-Dioxo-2,5-dihydro-1H-pyrrol-1-yl)-4,80-dioxo-7,10,13,16,19,22,25,28,31,34,37,40,43, 46,49,52,55,58,61,64,67,70,73,76-tetracosaoxa-3,79-diazadooctacontyl)-4-((4-((4-(4-hydroxy-3,5-diisopropylphenyl)butanamido)methyl)phenyl) diazenyl)benzamide (MPC100)

MPC088 (5.4 mg, 0.010 mmol) was dissolved in the mixture of methylene chloride (0.5 mL) and THF (0.2 mL). The solution of NHS-PEG$_{24}$-maleimide (13.9 mg, 0.010 mmol) in methylene chloride (0.5 mL) was added, and the reaction stirred at room temperature until TLC analysis indicated MPC088 was no longer present in the reaction mixture (8 h). The reaction mixture was washed with brine (2×0.5 mL) and concentrated. The product was purified by reverse phase chromatography on silica gel 60 RP-18 by elution first with water and slowly increasing methanol concentration until the colored fraction was eluted off. The colored fraction was concentrated under vacuum to give pure MPC100 (7.8 mg, 43%) as a yellowish oil. $^1$H NMR (400 MHz, CDCl$_3$): δ 8.05 (d, J=8.4 Hz, 2H), 7.96-7.90 (m, 4H), 7.44 (d, J=8.4 Hz, 2H), 6.86 (s, 2H), 6.71 (s, 2H), 6.42 (brt, 1H), 5.86 (brt, 1H), 4.74 (brs, 1H), 4.54 (d, J=5.6 Hz, 2H), 3.85 (t, J=7.2 Hz, 2H), 3.74 (t, J=5.6 Hz, 2H), 3.66-3.53 (m, 102H), 3.44-3.41 (m, 2H), 3.14 (q, J=6.8 Hz, 2H), 2.61 (d, J=7.6 Hz, 2H), 2.53 (t, J=6.8 Hz, 2H), 2.30 (d, J=7.6 Hz, 2H), 2.04-1.97 (m, 2H), 1.25 (d, J=6.8 Hz, 12H). HRMS (m/z): [M+H]$^{2+}$ calcd. for C$_{90}$H$_{147}$N$_7$O$_{31}$ 912.0144. found 912.0148; [M+H]$^{3+}$ calcd. for C$_{90}$H$_{147}$N$_7$O$_{31}$ 608.3453. found 608.3449.

Example 3

Preparation of MPD021

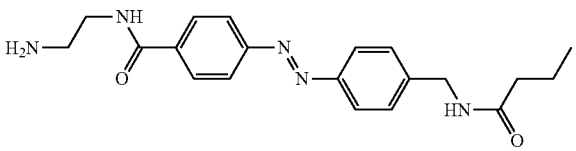 [SMILES: CCCC(=O)NCc1ccc(/N=N/c2ccc(C(=O)NCCN)cc2)cc1]

(E)-N-(2-Aminoethyl)-4-((4-(butyramidomethyl)phenyl)diazenyl)benzamide (MPD021)

(E)-Methyl 4-((4-(butyramidomethyl)phenyl)diazenyl)benzoate (10)

Into the solution of the amine 4 (915 mg, 3.0 mmol) in pyridine (15 mL) was added dropwise butyryl chloride (477 mg, 4.5 mmol), and the reaction was stirred overnight at room temperature. The solvent was evaporated, the residue dissolved in chloroform, washed with hydrochloric acid (1.0 M), water and brine, and dried with magnesium sulfate. Silica gel chromatography with chloroform as eluent gave pure 10 (916 mg, 90%) as orange crystals. $^1$H NMR (360 MHz, CDCl$_3$): δ 8.19 (d, J=8.4 Hz, 2H), 7.96-7.91 (m, 4H), 7.44 (d, J=8.0 Hz, 2H), 5.86 (br s, 1H), 4.55 (d, J=6.0 Hz), 3.97 (s, 3H), 2.56 (t, J=7.6 Hz, 2H), 1.73 (q, J=7.6 Hz, 2H), 0.99 (t, J=7.6 Hz, 3H). $^{13}$C NMR (100.61 MHz, CDCl$_3$): δ 172.55, 166.14, 154.70, 151.49, 141.99, 131.44, 130.22, 128.06, 123.11, 122.26, 51.95, 42.77, 38.29, 18.78, 13.42. HRMS (m/z): [M+H]$^+$ calcd. for C$_{19}$H$_{21}$N$_3$O$_3$ 340.1656. found 340.1669.

(E)-N-(2-Aminoethyl)-4-((4-(butyramidomethyl)phenyl)diazenyl)benzamide (MPD021)

The solution of compound 10 (170 mg, 0.5 mmol) and ethylenediamine (601 mg, 10 mmol) in methanol (10 mL), water (5 mL) and chloroform (2.5 mL) was refluxed for 24 h. The solvents were evaporated, the residue dissolved in aqueous potassium hydroxide (15 mL, 1 M), and extracted with methylene chloride (4×15 mL). The combined organic phases were washed with water and brine, dried over magnesium sulfate, and the residue chromatographed on silica gel using chloroform—chloroform:methanol (10%) step-gradient as an eluent to give pure MPD021 (113 mg, 62%) as orange crystals. $^1$H NMR (400 MHz, DMSO-d$_6$): δ 8.15 (d, J=8.4 Hz, 2H), 7.93-7.86 (m, 4H), 7.46 (d, J=8.4 Hz, 2H), 4.35 (s, 2H), 3.98 (t, J=6.0 Hz, 2H), 3.13 (t, J=6.0 Hz, 2H), 2.06 (t, J=7.2 Hz, 2H), 1.54-1.58 (m, 2H), 0.83 (t, J=7.2 Hz, 3H). $^{13}$C NMR (100.61 MHz, DMSO-d$_6$): δ 174.22, 166.43, 155.51, 153.37, 139.21, 137.12, 127.14, 127.09, 122.89, 122.78, 61.11, 43.66, 42.69, 37.04, 19.14, 13.06. HRMS (m/z): [M+H]$^+$ calcd. for C$_{20}$H$_{25}$N$_5$O$_2$ 368.2081. found 368.2099.

Example 4

Preparation of Additional Compounds

The following compounds were prepared according to the methods of the disclosure:

| Compound | Chemical Name |
|---|---|
| | (E)-4-(phenyldiazenyl)phenyl 4-(4-hydroxy-3,5-diisopropylphenyl)butanoate |
| | (E)-4-((4-(4-(4-hydroxy-3,5-diisopropylphenyl)butanamido)phenyl)diazenyl)benzoic acid |
| | (E)-N-(4-((4-(3-aminopropanamido)phenyl)diazenyl)phenyl)-4-(4-hydroxy-3,5-diisopropyl phenyl)butanamide |
| | (E)-N-(2-aminoethyl)-4-((4-(4-(4-hydroxy-3,5-diisopropylphenyl)butanamido)phenyl)diazenyl)benzamide |

| Compound | Chemical Name |
|---|---|
| | (E)-4-amino-5-(2-(4-((4-(4-(4-hydroxy-3,5-diisopropylphenyl)butanamido)phenyl)diazenyl)benzamido)ethylamino)-5-oxopentanoic acid |
| | (E)-4-((4-((4-(4-hydroxy-3,5-diisopropylphenyl)butanamido)methyl)phenyl)diazenyl)benzoic acid |
| | (Z)-N-(2-aminoethyl)-4-(4-((4-(4-hydroxy-3,5-diisopropylphenyl)butanamido)methyl)styryl)benzamide |
| | (E)-N-(2-aminoethyl)-4-(4-((4-(4-hydroxy-3,5-diisopropylphenyl)butanamido)methyl)styryl)benzamide |

Example 5

Spectrophotometric and NMR Analysis of Photoisomerization

Figure 44:
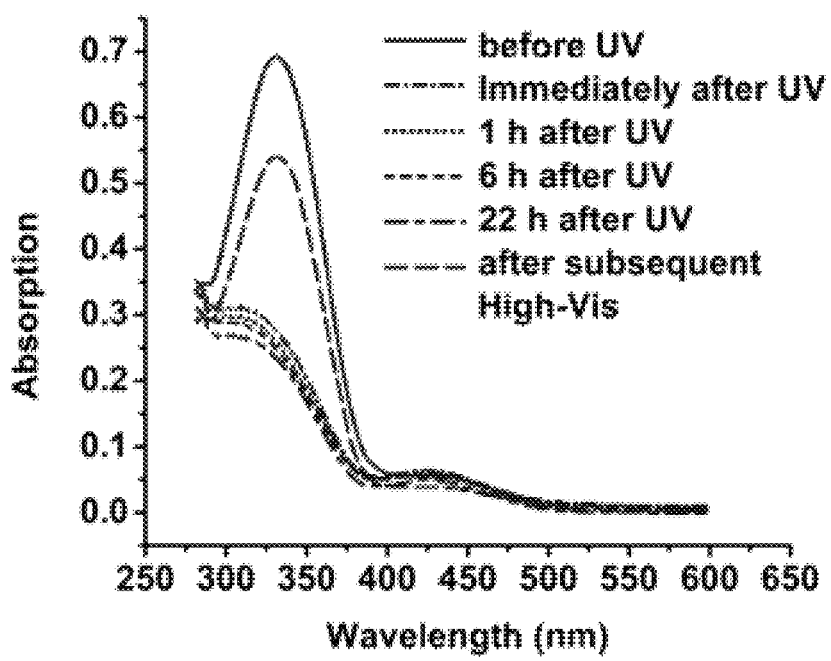
FIG. 44 illustrates stability of cis-MPC088 in darkness.
Figure 45:
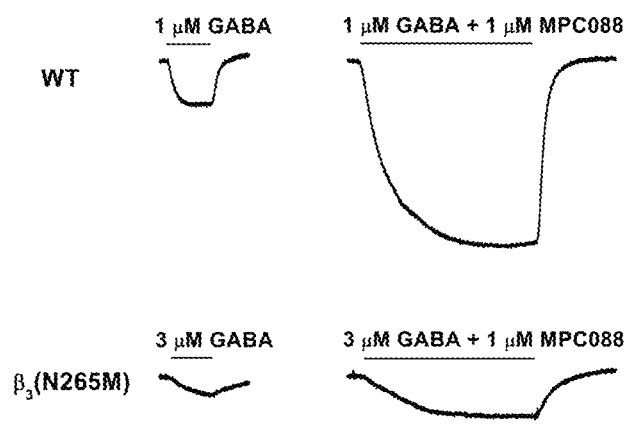
FIG. 45 illustrates the effect of 1 µM trans-dominant MPC088 on GABA-elicited responses of wildtype (WT) $\alpha_1\beta_3\gamma_2$ (upper) and $\alpha_1\beta_3$(N265M)$\gamma_2$ (lower) GABA$_A$Rs.

UV and visible light sources of the electrophysiological apparatus were used for the spectrophotometric and NMR experiments. MPC088 samples were analyzed as DMSO solutions in a quartz cuvette (spectrophotometry) and a DMSO-$d_6$ solution in a quartz NMR tube. When prepared and maintained in ambient light, trans-dominant MPC088 exhibited an absorbance peak at 338 nm (FIG. 44a; spectrum 1). UV illumination (wavelengths near 365 nm) for 5 min eliminated this peak and generated a minor peak at 438 nm (spectrum 2). Exposure (10 min) to high-intensity visible light largely reversed the UV-induced change (spectrum 3), and a second round of UV and visible illumination yielded spectra 4 and 5, which were virtually identical to 2 and 3, respectively. The spectra exhibiting the 338 and 438 nm peaks are analogous, respectively, to those exhibited by the trans and cis isomers of unmodified azobenzene (Standaert et al. (2006)). UV and visible light also produced opposing shifts in NMR peaks associated with the benzylic methylene resonances of MPC088 (FIG. 44b). In Fig. S1b, spectra i, depicting the solution of MPC088 (2.0 mM) in DMSO-$d_6$, displayed two peaks for the aminomethylene group: at 4.38 ppm (for the trans-isomer, 94%) and 4.20 ppm (cis-isomer, 6%). In spectra ii, the solution of MPC088 (2.0 mM) in DMSO-$d_6$ was placed in a quartz NMR tube and subjected to UV illumination for 5 min, yielding a mixture that contained 91% cis- and 9% trans-isomer. In spectra iii, the same solution was then exposed to visible light for 10 min, yielding a mixture of 81% trans- and 19% cis-isomer. Thus, the UV and visible light used in the electrophysiological experiments drove trans-to-cis and cis-to-trans isomerization, respectively.

Both the spectrophotometric data (FIG. 44a, spectra 1 and 3) and NMR data (FIG. 44b, spectra i and iii) indicated that exposure to visible light following UV illumination did not fully re-establish the initial spectrum. The second round of prolonged UV and the subsequent visible illumination yielded a spectrum (5) identical to spectrum 3. This suggested that the small difference between spectra 1 and 3 reflected a difference between the photostationary mixture of the two isomers produced by room light vs. the visible light source of the electrophysiological apparatus, rather than, e.g., decomposition of the trans-isomer due to UV illumination. Support for this conclusion came from the experiment of FIG. 44c, which showed that in the absence of UV pre-illumination, visible light exposure induced a time-dependent reduction in the 338 nm absorption peak similar to the difference between spectra 1 and 3 of FIG. 44a. A full cycle of spectral changes produced by UV and subsequent visible illumination indicated gradation of the changes with duration of the exposure (FIGS. 44d-f), consistent with the interconversion of only two species (trans- and cis-isomers) by these sources.

Although the trans-isomer of unmodified azobenzene is thermodynamically more stable than the cis isomer, reversion of the cis- to the trans-isomer at room temperature in darkness typically occurs on a time scale of hours or longer (Beharry et al. (2011); Sadovski et al. (2009)). To test the stability of cis-MPC088 in darkness, a preparation of 30 µM MPC088 in oocyte Ringer solution that had been converted to predominantly cis form by a 5-min UV illumination was spectrophotometrically analyzed. The sample was subsequently kept in darkness at room temperature. The absorption spectra of the sample were obtained before UV illumination (black), immediately after UV illumination (red), after 1 hr (blue), 6 hr (green) and 22 hr (magenta) incubation in darkness, and finally after a subsequent High-Vis illumination (dark yellow) (Fig. S2). Over the 22-hr incubation period (blue, green and magenta spectra), there was no evidence for a recovery of the absorbance peak (near 338 nm) characteristic of the trans-MPC088. The absence of trans-isomer formation was not due to degradation of the MPC088, since exposure to visible light at the end the incubation period largely restored the initial trans absorbance peak. The lifetime of cis MPC088 in darkness in physiological saline thus appears to be much longer than 22 hr.

Example 6

UV-Induced Response De-Potentiation

Figure 35:
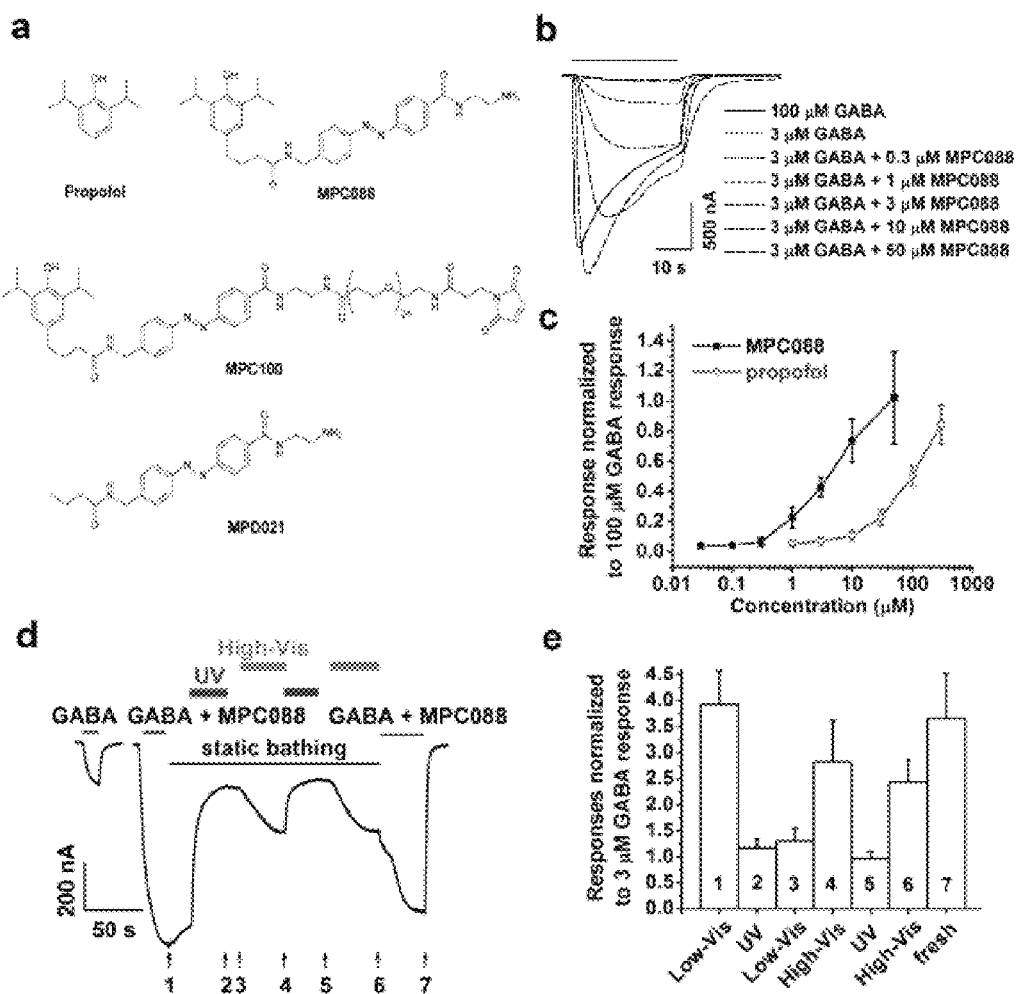
FIG. 35 illustrates the effect of MPC088 on the 3 μM GABA response of $\alpha_1\beta_2\gamma_2$ $GABA_AR$-expressing oocytes. a: Chemical structures. b: Responses of a single oocyte to co-applied 3 μM GABA and varying concentration of trans-dominant MPC088. c: Aggregate concentration-response data describing responses elicited by co-applied 3 μM GABA and trans-dominant MPC088 or propofol. d: Light-dependent alteration of the 3 μM GABA response by co-applied, initially trans-dominant, 1 μM MPC088. e: Results obtained in the experiment of d and 3 others of similar design.
Figure 36:
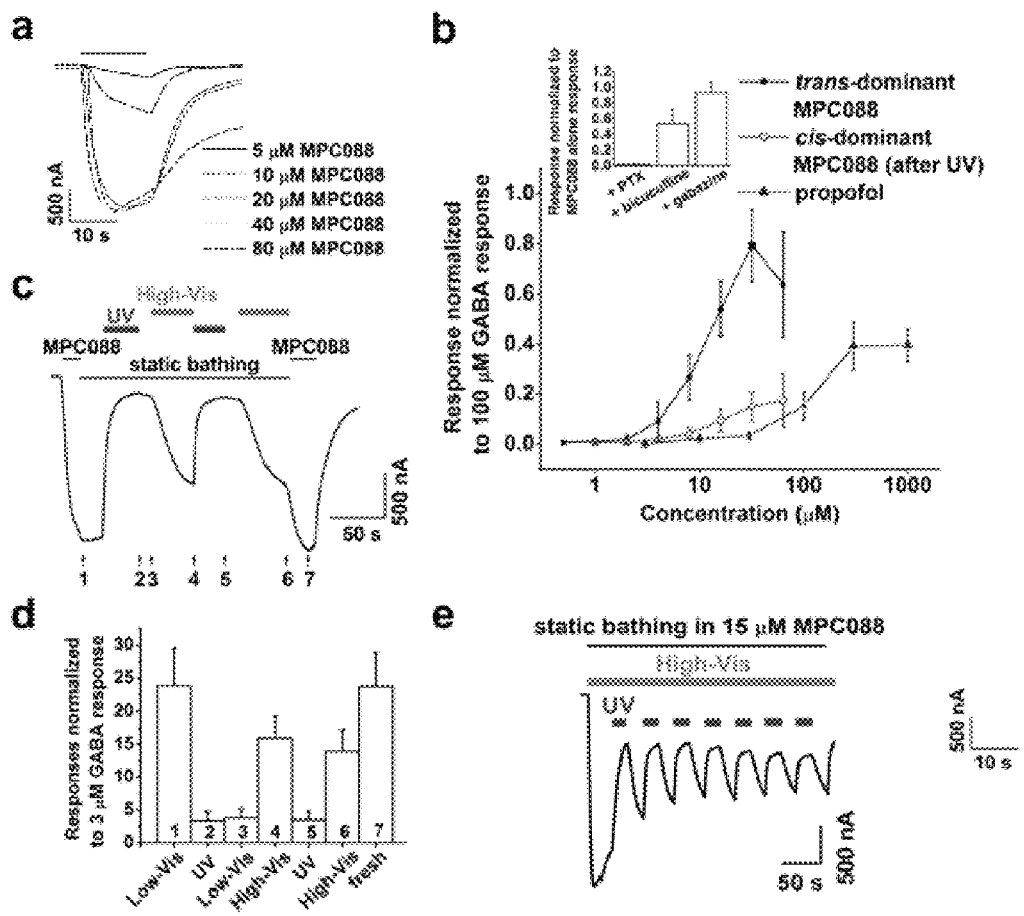
FIG. 36 illustrates MPC088 agonist activity in oocytes expressing $\alpha_1\beta_2\gamma_2$ $GABA_ARs$. a: Representative responses to MPC088 obtained in a single experiment. b: Concentration-response functions for trans- and cis-dominant MPC088 (n=6) and propofol (n=6). c: Photo-regulation of the response to 15 μM MPC088. d: Normalized current amplitudes determined in the experiment of c and in 3 others of similar design. e: Representative waveform obtained with repeated presentation of UV light during continuous High-Vis illumination (static bathing in MPC088-supplemented Ringer).
Figure 38:
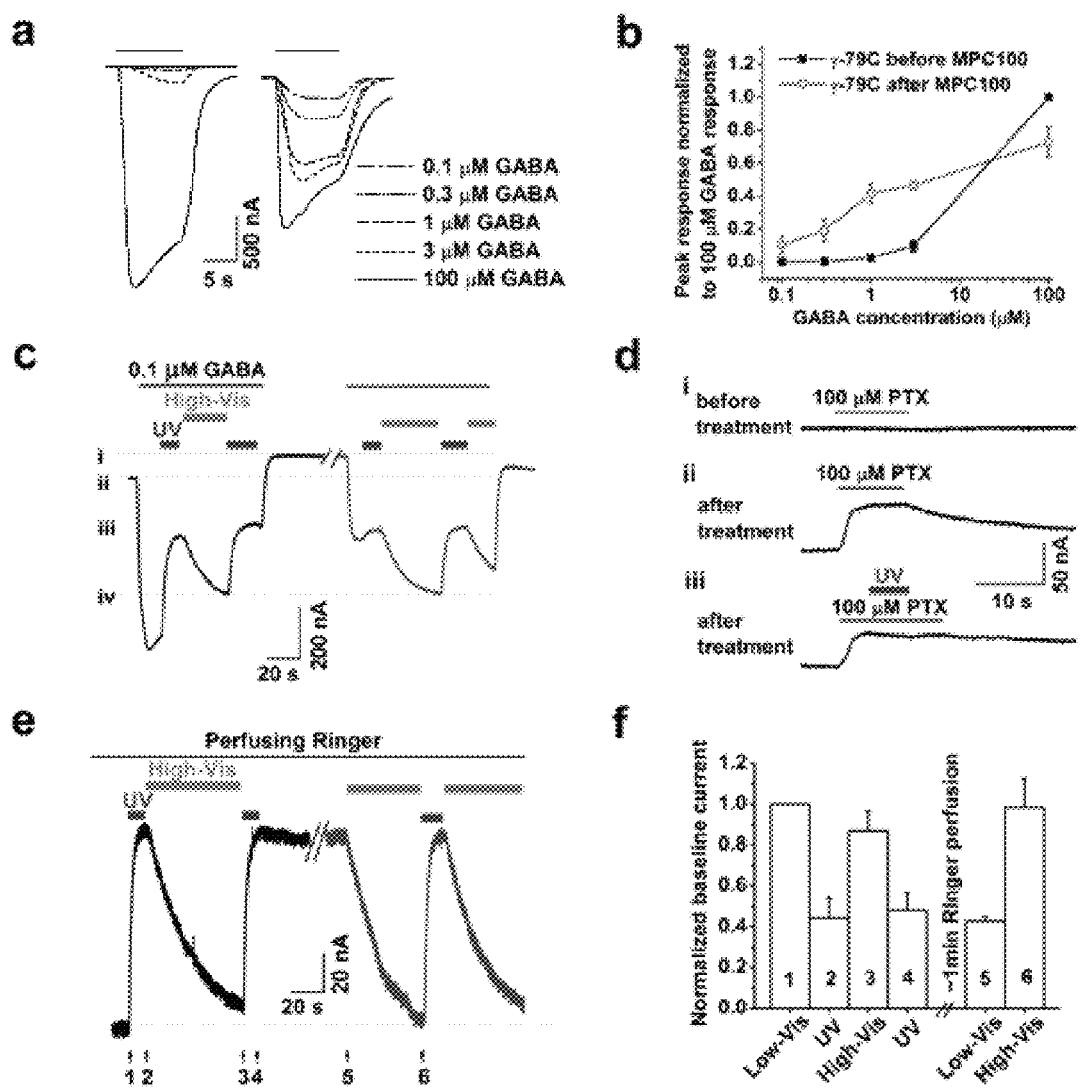
FIG. 38 illustrates persistent potentiation and activation by MPC100 in γ-79C-expressing oocytes. a: GABA responses of a single oocyte before and after MPC100 treatment. b: GABA response functions showing aggregate data before and after MPC100 treatment with and subsequent washout (~5 min). c: Light-dependence of persistent potentiation. d: Baseline currents obtained in a single experiment. e: Responses to UV and visible light following exposure to trans-dominant MPC100 and washout (~5 min) of free MPC100. f: Aggregate results from experiment e and 3 others, each involving amplitude determinations under 6 sequential experimental conditions.

Evidence for an effect of UV light intensity on the kinetics of de-potentiation (i.e., response decrease) came from further experiments on $\alpha_1\beta_2\gamma_2$ GABA$_A$R-expressing oocytes, in which the actions of two different UV intensities were compared: that routinely employed in the experiments of FIGS. 35, 36 and 38; and a 10-fold reduced UV intensity (same LED source). These experiments, like those of FIG. 35d, employed 3 µM GABA and 1 µM MPC088. The UV-induced decrease in membrane current was analyzed by fitting a simple exponential decay function to the waveforms obtained and determining the exponential time constant ($\tau$). This analysis yielded 0.43±0.09 s$^{-1}$ and 0.13±0.02 s$^{-1}$ (n=5), respectively, for the rate constants 1/$\tau$ associated with respectively, the nominal and the 10-fold reduced UV intensities. FIG. 44f also includes results of a separate spectrophotometric experiment that employed UV light of reduced intensity (10% of nominal). The fitting of simple exponential functions to the data obtained with UV, visible, and reduced-intensity UV light yielded time constants of 1.7±0.3, 36±2, and 22±3 s, respectively. The slowness of these time constants is not governed by the kinetics of the elemental photoisomerization event (Gorostiza et al. (2008)) but rather by the photon fluxes being used.

Example 7

Co-Application of MPC088 and GABA

Co-application of 3 µM GABA and 1 µM trans-dominant MPC088 markedly potentiated the GABA response, and brief UV illumination presented during static bathing of the oocyte decreased the membrane current to a level near that elicited by GABA alone (Yue et al. (2010)). This level of current was maintained in the ambient light after cessation of the UV illumination and, conversely, was increased by exposure to high-intensity visible light. The resumption of perfusion with co-applied GABA and trans-dominant MPC088 restored the membrane current to a level near that exhibited on initial presentation of the two compounds.

FIG. 35 illustrates the effect of MPC088 on the 3 µM GABA response of $\alpha_1\beta_2\gamma_2$ GABA$_A$R-expressing oocytes. GABA (3 µM) and varying concentrations (0.3 µM, 1 µM, 3 µM, 10 µM or 50 µM) of trans-dominant MPC088 were co-applied to a single oocyte (FIG. 35b). The horizontal bar indicates the period of superfusion with GABA- and MPC088-supplemented Ringer solution. Aggregate concentration-response data describes responses elicited by co-applied 3 µM GABA+trans-dominant MPC088, or 3 µM GABA+propofol was also determined (FIG. 35c). Response amplitudes obtained from each oocyte were normalized to that elicited by 100 µM GABA alone, which is a near-saturating condition that is essentially insensitive to propofol potentiation. MPC088 and propofol results, each obtained from 7 oocytes. Determination of whether exposure to UV or high-intensity visible light (High-Vis) alters the 3 µM GABA response by co-applied, initially trans-dominant, 1 µM MPC088 is shown in FIG. 35d. Black bars indicate periods of superfusion with co-applied 3 µM GABA and 1 µM MPC088. Purple and gray bars indicate periods of presentation of UV light (purple) and high-intensity visible light (High-Vis) (gray), respectively. FIG. 35e illustrates the results obtained in the experiment of FIG. 35d and 3 others of similar design. In this example, membrane current amplitudes, normalized to the peak amplitude of the 3 µM GABA response, were determined under 7 sequential conditions: (1) in low-intensity visible light (Low-Vis), at the conclusion of superfusion with (3 µM GABA+1 µM MPC088); (2) at the conclusion of UV illumination; (3) in low-intensity visible light; (4) at the conclusion of high-intensity visible illumination; (5) at the conclusion of a second UV illumination; (6) at the conclusion of a second high-intensity visible illumination; and (7) at the conclusion of resumed superfusion with fresh 3 µM GABA+1 µM trans-dominant MPC088. These amplitude determination conditions are denoted by numbers beneath the waveform in FIG. 35d. Repeated-measures ANOVA conducted on the aggregate data yielded $F(6,18)=41.975$, $p<0.001$. Post-hoc paired-sample t-tests corrected for multiple comparisons indicated significant differences produced by the initial UV, the initial High-Vis, the second UV, and the second High-Vis illuminations ($p\leq0.009$ for amplitude group 2 vs. group 1, for 4 vs. 3, for 5 vs. 4, and for 6 vs. 5, respectively); amplitude groups 7 and 1 did not differ significantly ($p=0.075$).

Example 8

Co-Application of MPD021 and GABA

In contrast with MPC088, MPD021 (FIG. 35a) that lacks the propofol moiety showed no potentiation of the GABA response and failed to inhibit potentiation by MPC088. MPD021 (FIG. 35a) lacked a potentiating effect on the GABA response on oocytes expressing $\alpha_1\beta_2\gamma_2$ GABA$_A$Rs. Specifically, co-application of 3 µM GABA with 10 or 100 µM MPD021 yielded respective response amplitudes, relative to the 3 µM GABA response, of 1.03±0.07 (p=0.3) and 1.03±0.11 (p=0.6; n=6). In addition, UV and visible light had no effect on currents induced by co-applied GABA and MPD021.

Example 9

Activity of Trans-Dominant MPC088 Preparation

In addition to potentiation, trans-dominant MPC088 exhibited robust activity as a direct activator of α1β2γ2 GABA$_A$Rs (FIG. 36; Yue et al. (2010)). The response elicited by trans-dominant MPC088, graded with concentration, was clearly evident at concentrations as low as 4 µM (FIGS. 36a-b), and considerably greater than the response to a matched concentration of cis-dominant MPC088. In each of the MPC088 experiments, the cis-dominant form was generated by UV light during static bathing. The maximum current generated by trans-dominant MPC088 was comparable with the peak current elicited by 100 µM GABA, while that generated by propofol represented only about 40% of the 100 µM GABA response. The potency of trans-dominant MPC088 exceeded that of propofol by ~25-fold, as determined by the concentrations of MPC088 vs. propofol required for a peak current equal to 40% of the 100 µM GABA-alone response (FIG. 36b). Amplitudes were normalized to the 100 µM GABA response. The MPC088-elicited response was eliminated by 100 µg of the GABA$_A$R channel blocker picrotoxin (PTX) (n=4) (Bali et al. (2007)), but was not sensitive to 30 µg gabazine (n=4) (SR-95531)—a competitive GABA antagonist (Ueno et al. (1997); Jones et al. (1998))—and was only partially antagonized by 100 µM bicuculline (n=4) (Adodra et al. (1995); Amin et al. (1993)) (FIG. 36b inset). These properties, which are shared by the known GABA$_A$R allosteric activators alphaxalone (Chang et al. (2003); Ueno et al. (1997)) and pentobarbital (Amin et al. (1993); Muroi et al. (2009)), suggested that MPC088 activates the receptors by binding at a site distinct from the GABA-binding site. UV illumination presented during static bathing reduced the MPC088-elicited current, and visible light reversed the effect of UV exposure (FIGS. 36c-d). Amplitudes in each experiment were normalized to that elicited by 3 µM GABA. Numbers beneath the waveform in FIG. 2(c) denote amplitude determination conditions for that experiment. Repeated-measures ANOVA conducted on the aggregate data yielded F(6, 18)=68.988, p<0.001. Post-hoc paired-sample t-tests corrected for multiple comparisons indicated significant differences produced by the initial UV, the initial High-Vis, the second UV, and the second High-Vis illuminations (p≤0.010 for amplitude group 2 vs. group 1, for 4 vs. 3, for 5 vs. 4, and for 6 vs. 5, respectively); amplitude groups 7 and 1 did not differ significantly (p=0.96). Furthermore, repeated pulses of UV light presented on a background of continuous visible light during MPC088 treatment yielded cyclic changes in response amplitude (FIG. 36e).

Figure 37:
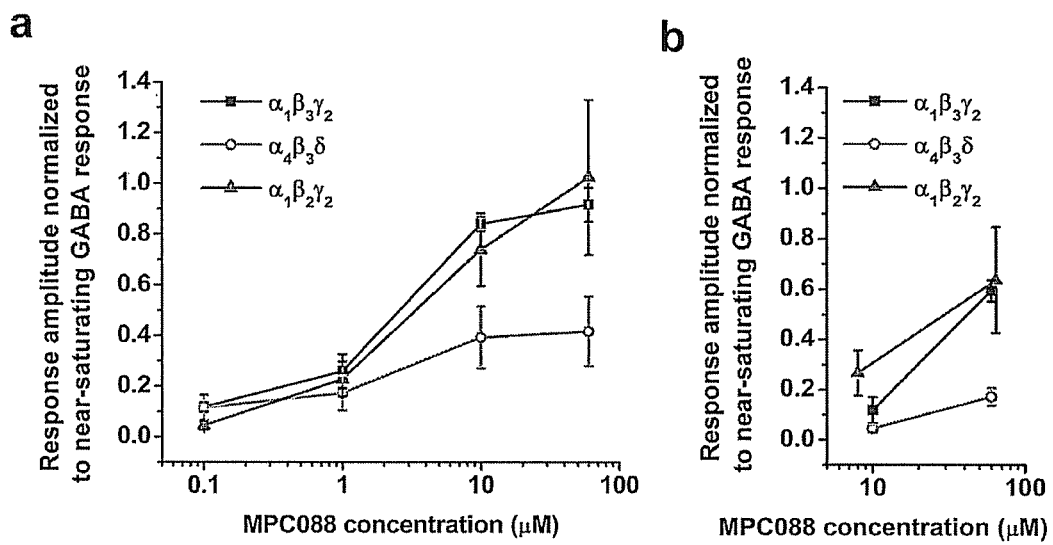
FIG. 37 illustrates the effect of MPC088 on $\alpha_1\beta_3\gamma_2$ and $\alpha_4\beta_3\delta$ $GABA_AR$-expressing oocytes. a: Aggregate concentration-response data obtained from $\alpha_1\beta_3\gamma_2$ and $\alpha_4\beta_3\delta$ receptors with co-applied GABA at similar $\sim EC_8$ dose and varying concentrations of trans-dominant MPC088. b: Aggregate concentration-response data obtained from $\alpha_1\beta_3\gamma_2$ and $\alpha_4\beta_3\delta$ receptors with trans-dominant MPC088 alone. Results for $\alpha_1\beta_2\gamma_2$ $GABA_ARs$ in a and b reproduced from those of FIGS. 35*c* and 36*b*, respectively.

Propofol is known to modulate GABA$_A$ receptors that contain a β subunit. To determine whether trans-MPC088 is active at other β-containing GABA$_A$ subtypes, the compound was tested at oocyte-expressed $\alpha_1\beta_3\gamma_2$, a GABA$_A$R that, like α1β2γ2, is widely expressed in CNS neurons (Farrant et al. (2005); Wisden et al. (1996); Fritschy et al. (2006); Wulff et al. (2007)); and at $\alpha_4\beta_3\delta$, a subtype that is typically expressed extrasynaptically and exhibits high sensitivity to GABA (Farrant et al. (2005); Mortensen et al. (2010); Meera et al. (2009)) (FIG. 37). Data in each group was obtained from 4 oocytes. Aggregate concentration-response data was obtained from $\alpha_1\beta_3\gamma_2$ (squares) and $\alpha_4\beta_3\delta$ (circles) receptors with co-applied GABA at similar ~EC$_8$ dose (i.e., 3 µM and 0.05 µM, respectively) and varying concentrations of trans-dominant MPC088 (FIG. 37a). Response amplitudes obtained from each oocyte were normalized to its saturating GABA response (i.e., responses obtained with 1,000 µM GABA for $\alpha_1\beta_3\gamma_2$ and 100 µM GABA for $\alpha_4\beta_3\delta$ GABA$_A$Rs). Aggregate concentration-response data was also obtained from $\alpha_1\beta_3\gamma_2$ (squares) and $\alpha_4\beta_3\delta$ (circles) receptors with trans-dominant MPC088 alone (FIG. 37b). Data was similarly normalized to the saturating GABA response obtained from each oocyte. Results for $\alpha_1\beta_2\gamma_2$ GABA$_A$Rs in a and b (triangles) were reproduced from those of FIGS. 35c and 36b, respectively.

Trans-dominant MPC088 showed potentiating activity on both receptor types (FIG. 37a), and this activity was reduced by UV illumination (not shown). With co-applied 3 µM GABA (representing ~EC$_8$), the $\alpha_1\beta_3\gamma_2$ GABA$_A$R response function obtained with trans-dominant MPC088 closely resembled that determined for the α1β2γ2 subtype. By contrast, the trans-MPC088 response function obtained for $\alpha_4\beta_3\delta$ with co-applied 50 nM GABA (~EC$_8$) approached a plateau representing ~42% of the response amplitude obtained with high GABA concentration. The low plateau level of the $\alpha_4\beta_3\delta$ response to trans-MPC088 did not reflect a general insensitivity to propofol-based compounds, since co-applied 200 µM propofol and 50 nM GABA yielded a response representing 1.2±0.1-fold (n=4) that of the saturating GABA-alone response. In addition, the direct agonist activity of trans-MPC088 at $\alpha_4\beta_3\delta$ was much lower than those at $\alpha_1\beta_3\gamma_2$ and $\alpha_1\beta_2\gamma_2$ (FIG. 37b). Thus, trans-MPC088, like propofol, modulates multiple types of β-containing GABA$_A$ receptors, albeit with different efficacy.

Figure 46:
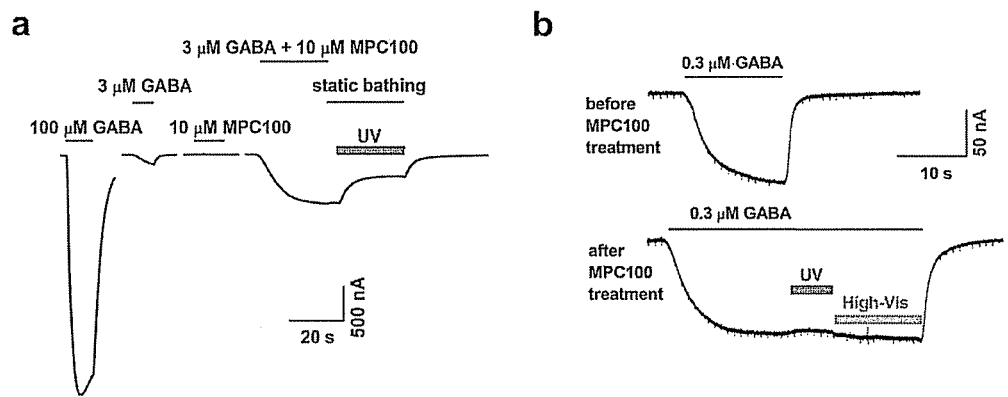
FIG. 46 illustrates treatment of wildtype $\alpha1\beta2\gamma2$ GABA$_A$Rs with MPC100. a: Membrane currents recorded from a single oocyte in response to applied MPC100. b: Responses of a single oocyte to GABA presented before and after MPC100 treatment, with subsequent Ringer perfusion.

The activity of trans-dominant MPC088 was also tested at receptors containing the β-subunit substitution N265M, a mutation that markedly reduces the action of propofol both in vitro and in vivo (Jurd et al. (2003); Siegwart et al. (2002)). These experiments specifically involved comparison of the normalized responses of $\alpha_1\beta_3\gamma_2$ (upper) and $\alpha_1\beta_3$(N265M)$\gamma_2$ (lower) GABA$_A$Rs to trans-MPC088 (1 µM) and co-applied GABA (Fig. S3). For each receptor type, illustrated responses are representative data obtained from a single oocyte. At $\alpha_1\beta_3\gamma_2$, 1 µM GABA represented ~EC$_3$; at $\alpha_1\beta_3$(N265M)$\gamma_2$, 3 µM GABA represented ~EC$_2$. Response enhancement by trans-MPC088 was substantial at both receptor types, but the response enhancement for $\alpha_1\beta_3$(N265M)$\gamma_2$ (2.9±0.8-fold, n=4) was significantly smaller than that for the wildtype $\alpha_1\beta_3\gamma_2$ (4.4±1.3-fold, n=5; p=0.03) (FIG. 46). Like propofol, trans-MPC088 lacked both potentiating and direct agonist activity on oocytes expressing the GABA$_A$R subtype that consists of a pentameric assembly of ρ1 subunits (Mihic et al. (1996)).

Example 10

Activity of Cis-Dominant MPC088 Preparations

While the rising portion of the response function for cis-dominant MPC088 occurred over a concentration range similar to that exhibited by trans-dominant preparations (FIG. 36b), the approximate plateau levels of the trans- and cis-dominant functions differed. In light of the indication (NMR data) that the cis-dominant preparations contained a small residual amount of the trans-isomer, the low plateau level exhibited by the cis response function suggests a possible inhibitory effect of cis on receptor activation by trans. That is, if the cis-isomer were completely inactive but the cis-dominant preparation contained a small amount of trans, the cis response function should resemble that of trans but simply be displaced to the right of the trans function. Together, the data of FIGS. 35-36 do not rule out an action of cis-MPC088 in receptor potentiation or direct activation, but indicate that any such activity is much weaker than that of the trans-isomer.

Example 11

Effects of Tethering of MPC100 to γ-79C GABA$_A$Rs

MPC088 is a freely diffusible compound and can be removed by superfusion of the oocyte with Ringer. Covalent tethering of a similar compound to a suitably modified receptor was tested to determine whether this produced persistent potentiation and/or activation. MPC100 (FIG. 35a), prepared by coupling a maleimide-terminated 24-mer poly(ethylene glycol) (PEG) linker to the free amino group of MPC088, was tested on oocytes expressing a cysteine substitution at position 79 of the single γ subunit of α1β2γ2 [α$_1$β$_2$γ$_2$(A79C)] (Kucken et al. (2000); Kucken et al. (2003)); henceforth abbreviated γ-79C. The thiol group of the cysteine residue, located near the known site for benzodiazepine binding (Kucken et al. (2000); Kucken et al. (2003)) covalently anchored MPC100 (Banghart et al. (2004); Volgraf et al. (2006); Janovjak et al. (2010)). Isomers of MPC100 containing cis and trans forms of the azobenzene moiety were generated by UV and visible (white) light, respectively. Oocytes expressing γ-79C GABA$_A$Rs, prior to (left) and following (right) incubation with trans-dominant MPC100 (100 μM, ~5-7 min) and then superfusion with unsupplemented Ringer to remove untethered compound, exhibited persistent potentiation of the GABA response (FIGS. 38a-b). FIG. 38b includes aggregate data from 5 oocytes, with amplitudes normalized to that elicited by 100 μM GABA before MPC100 treatment. This persistent enhancement of the response to GABA alone was sensitive to UV and visible light (FIG. 38c; Yue L, Pawlowski M, et al. (2011)). Specifically, the left trace depicts a response to UV and visible light in the presence of 0.1 μM GABA, following treatment with 100 μM trans-dominant MPC100. Dotted lines i and ii highlight the difference in baseline current before (ii) vs. after (i) UV illumination). The right trace depicts a later phase of the same experiment (responses obtained after a further ~1 min Ringer perfusion). These effects of illumination resembled those displayed by wildtype α1β2γ2 GABA$_A$R-expressing oocytes in the presence of co-applied GABA and MPC088 (compare FIGS. 35d and 38c), although the extent of UV-induced de-potentiation observed with the tethered MPC100 was less than that determined on similar treatment with (diffusible) MPC088. The smaller excursion of de-potentiation likely resulted from the inability of the UV stimulating light, which was delivered from above the (opaque) oocyte, to efficiently access MPC100 tethered to the lower, approximately hemispherical, surface of the cell. Furthermore, tethering of MPC100 at the γ-79C cysteine site eliminated the potentiating action of diazepam on the α1β2γ2 (A79C) receptor, consistent with proximity of this anchoring site to the benzodiazepine binding site (data not shown).

Figure 4:
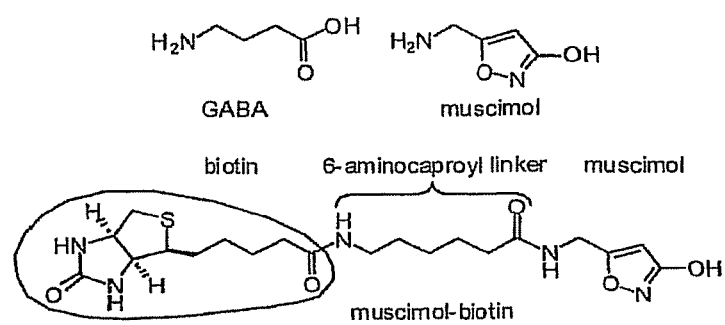
FIG. 4 depicts the structure of muscimol-biotin.
Figure 5:
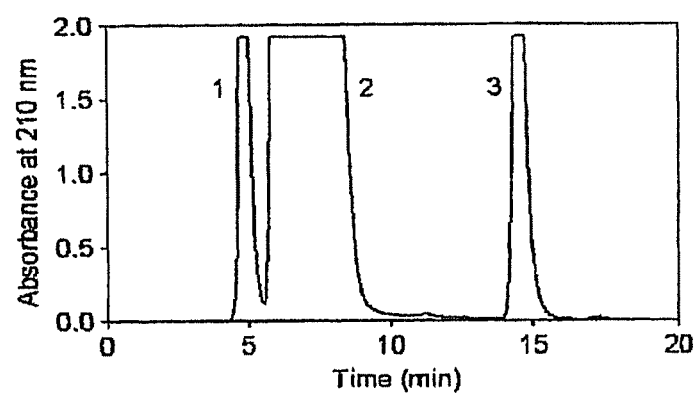
FIG. 5 illustrates muscimol-biotin high performance liquid chromatography.
Figure 6:
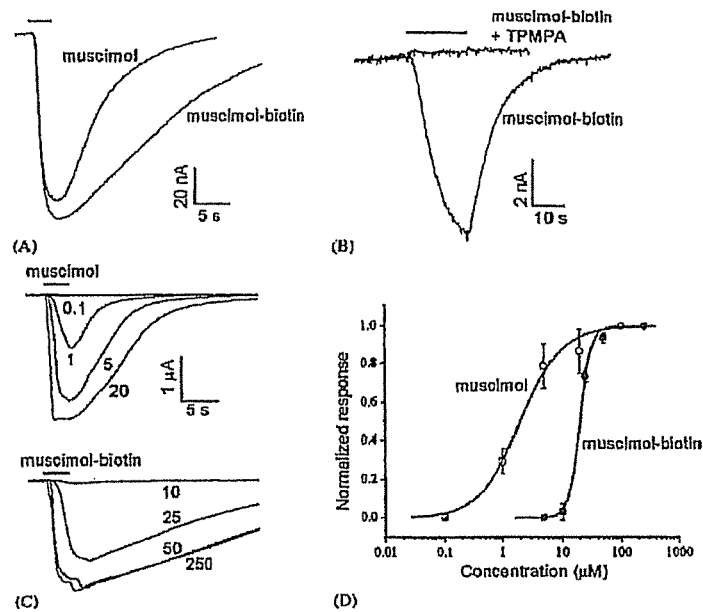
FIG. 6 depicts agonist activity at GABAc receptors.
Figure 7:
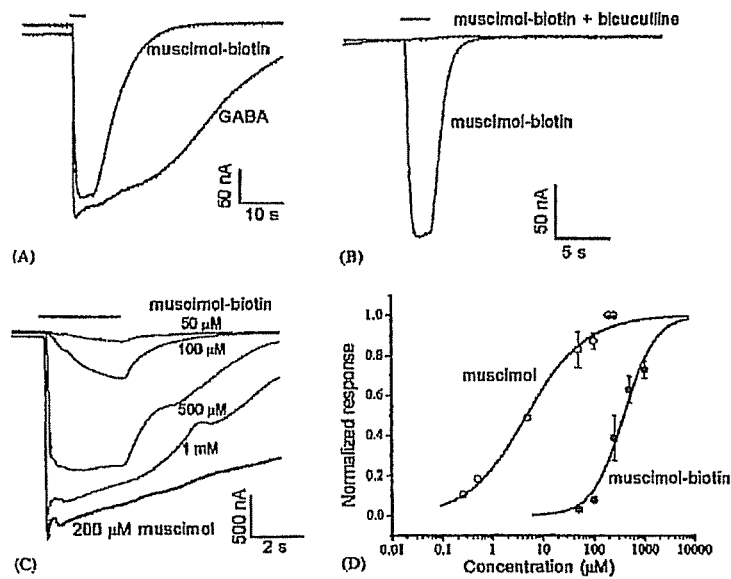
FIG. 7 illustrates agonist activity at GABAa receptors.
Figure 8:
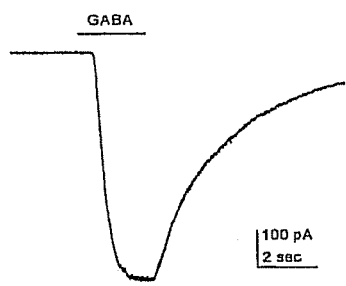
FIG. 8 graphs whole-cell patch recording of GABA elicited response.
Figure 9:
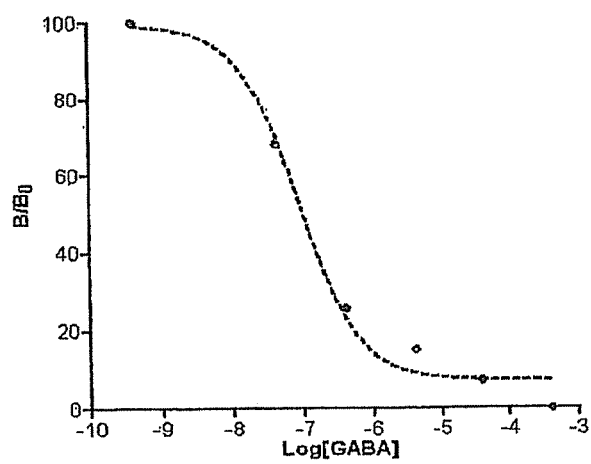
FIG. 9 graphs (3H) GABA competition binding.
Figure 11:
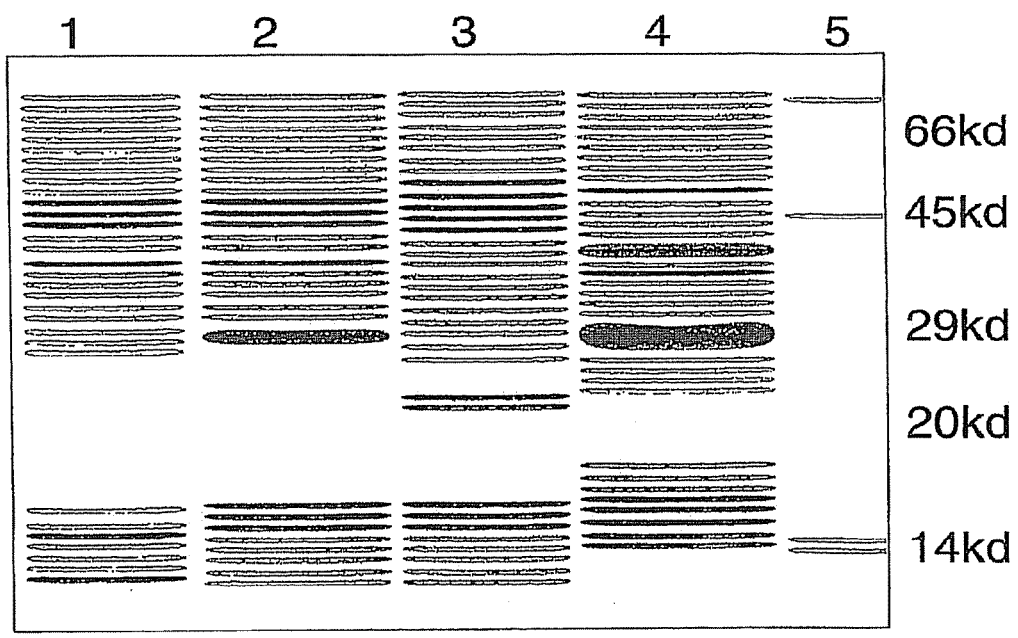
FIG. 11 illustrates expression of a human ρ1-expressing construct in bacteria.
Figure 12:
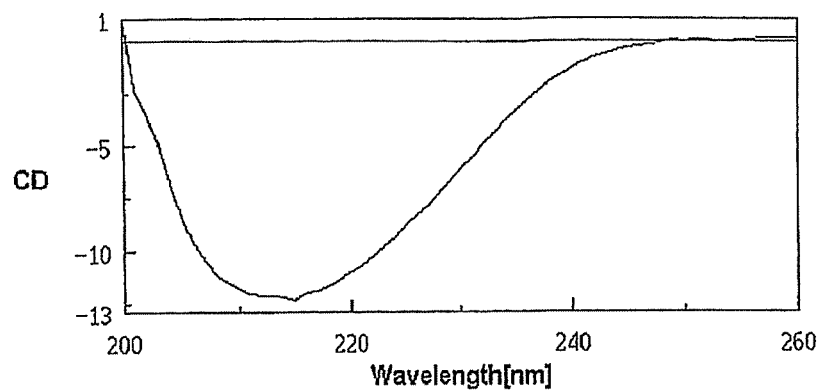
FIG. 12 depicts circular dichroism of a preparation of soluble extracellular domain of perch His ρ1B.
Figure 13:
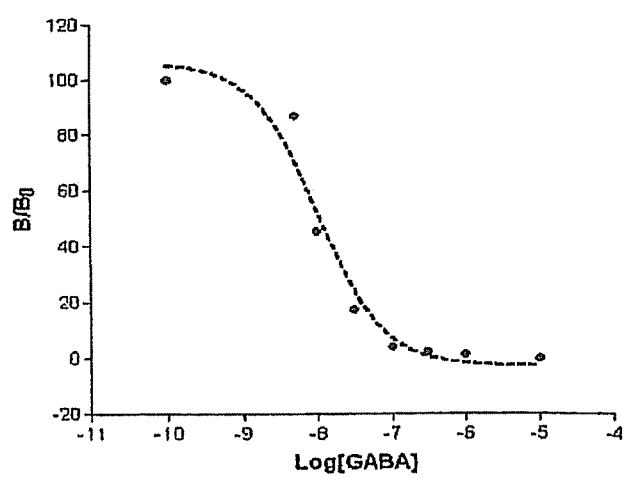
FIG. 13 graphs specific GABA binding of a soluble His ρ1B preparation.

Treatment of γ-79C-expressing oocytes with trans-dominant MPC100 led to a greater (i.e., more negative) baseline current, and UV illumination produced an opposite change (FIG. 38c; note the relationship of the dotted reference lines i and ii). To test whether the baseline change reflected continuing, direct activation by the tethered MPC100 in the absence of GABA, the effect of picrotoxin (PTX), a GABA$_A$ channel blocker, presented before and after 100 μM MPC100 treatment, was tested. PTX application to MPC100-treated and then washed cells reversibly reduced the baseline current by 85±7% (n=5) (FIG. 38d, traces i-ii). UV (i.e., cis-generating) illumination delivered during PTX treatment did not further reduce the baseline amplitude, but inhibited baseline recovery following PTX removal, consistent with a UV-induced reduction in the amount of trans-MPC100 present (FIG. 38d, trace iii). Furthermore, responses to UV and visible light following exposure to trans-dominant MPC100 were determined from a single oocyte (FIG. 38e). A period of Ringer perfusion (~1 min) separated the initial (left trace) and later (right trace) phases of the experiment. UV and visible light delivered to MPC100-treated γ-79C-expressing oocytes produced, respectively, decreases and increases in membrane current qualitatively similar to those exhibited by wildtype α1β2γ2 GABA$_A$Rs in the presence of trans-MPC088 alone (FIGS. 38e-f). FIG. 4f depicts aggregate results from FIG. 4e and three others. Data was normalized to the persisting shift in baseline produced by MPC100 treatment. Periods of treatment in each experiment were similar to those illustrated in e. Numbers beneath the waveforms in e denote amplitude determination conditions for the experiment shown in e. Repeated-measures ANOVA conducted on the aggregate data yielded $F(6,18)=65.290$, $p<0.001$. Post-hoc paired-sample t-tests corrected for multiple comparisons indicated significant differences produced by the initial UV, the initial High-Vis, the second UV, and the second High-Vis illuminations ($p \leq 0.007$ for amplitude group 2 vs. group 1, for 3 vs. 2, for 4 vs. 3, and for 6 vs. 5, respectively). Thus, the larger baseline current persisting after MPC100 treatment (FIG. 38c) reflected sustained, direct activation of the receptor by tethered trans-MPC100.

Figure 47:
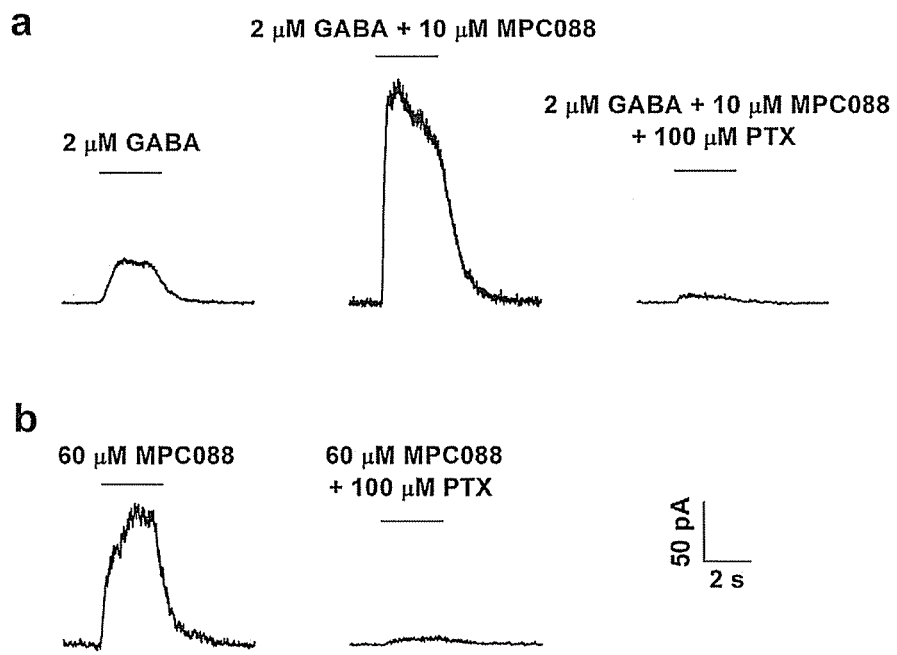
FIG. 47 illustrates the inhibitory effect of PTX on the action of trans-dominant MPC088 on retinal ganglion cells. a: Responses to GABA and to GABA+trans-dominant MPC088 without and with co-applied PTX. b: Responses to trans-dominant MPC088 without and with PTX.

These persistent effects of MPC100 required the γ-79C modification. While MPC100 exhibited potentiation on wildtype α1β2γ2 GABA$_A$Rs (albeit to an extent less than that exhibited by MPC088), this effect was eliminated by Ringer perfusion (FIG. 47). In addition, on γ-79C-expressing oocytes, pre-treatment with the thiol-reactive compound methyl-(PEG)$_{11}$-maleimide blocked the activity of subsequently applied MPC100. These findings indicate a dependence of MPC100's persistent activity on tethering specifically at the engineered cysteine site of the γ-79C receptor.

Example 12

Treatment of Wildtype GABA$_A$Rs with MPC088

Figure 39:
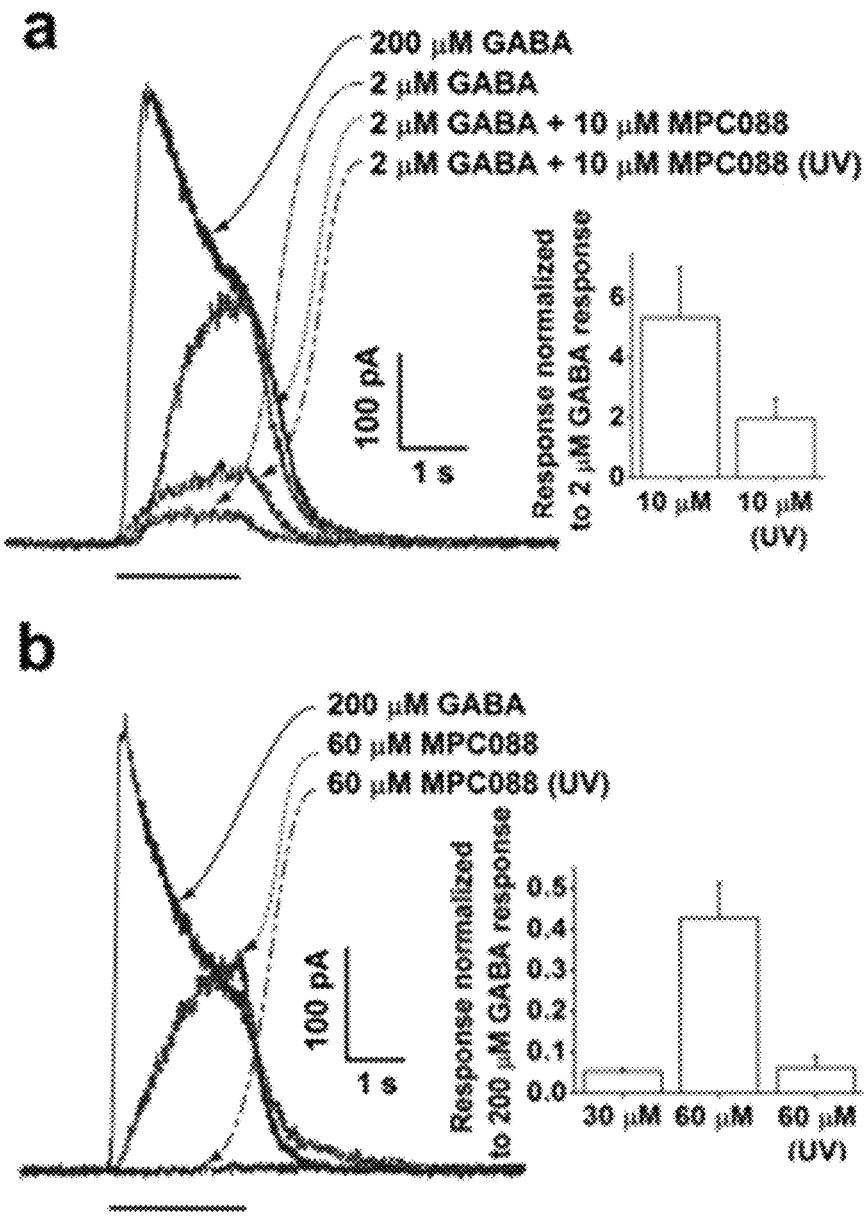
FIG. 39 illustrates action of MPC088 on retinal ganglion cells. a: Potentiation data obtained with trans- and cis-dominant MPC088 b: Direct activation data obtained with trans- and cis-dominant MPC088.

To test whether native neuronal GABA$_A$Rs respond to MPC088, retinal ganglion cells (RGCs), a cell type known to abundantly express GABA$_A$Rs (Ishida et al. (1988); Fischer et al. (1998); Wässle et al. (1998); Rotolo et al. (2003)), were examined. When presented to single dissociated RGCs of rat retina, 10 μM trans-dominant MPC088 produced, on average, an approximately 5-fold potentiation of the response elicited by 2 μM GABA, while cis-dominant MPC088 exhibited much less potentiation activity (FIG. 39a). The cis-dominant preparation was obtained by pre-treating trans-dominant MPC088 with UV light for 5 min. Representative responses obtained from a single cell treated with 200 μM GABA (black), 2 μM GABA (red), 2 μM GABA co-applied with 10 μM of trans-dominant (blue) or cis-dominant (magenta) MPC088. Inset: Aggregate data (mean±SD) for potentiation factor determined with trans- and cis-dominant MPC088 (left and right bars, respectively) (n=6, p=0.003) (FIG. 39a).

Figure 48:
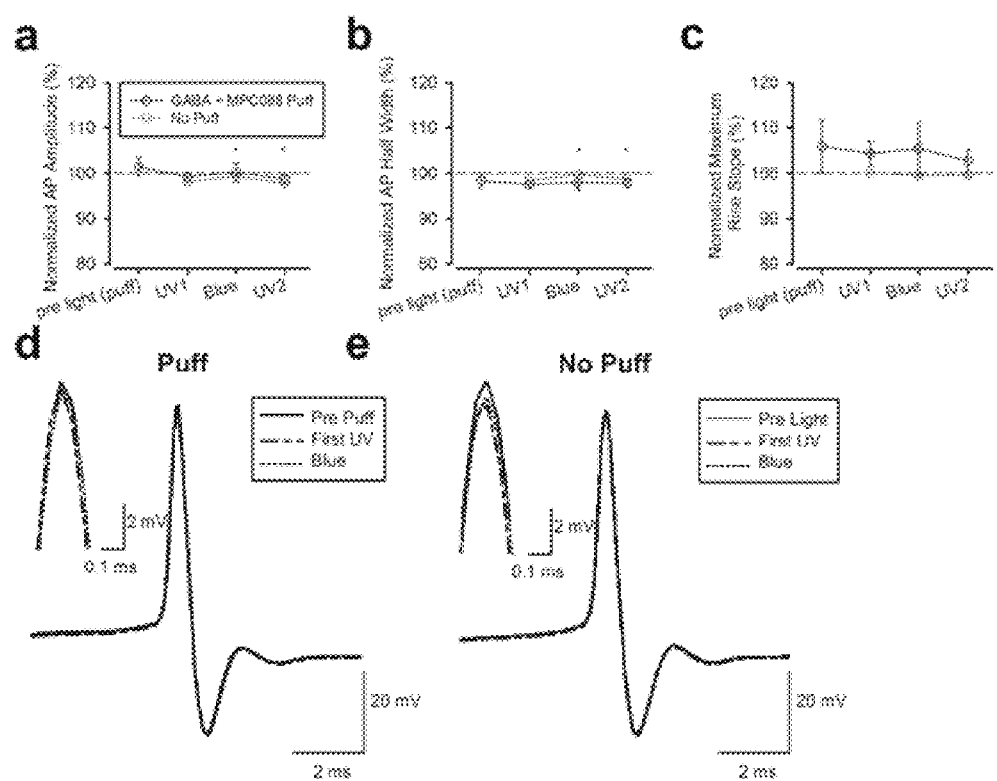
FIG. 48 illustrates a lack of detectable effects of MPC088 on AP waveform in cerebellar Purkinje neurons. a: Summary of AP amplitudes from the experiments described in FIG. 41. b: Same as a, but for the AP half width. c: Same as a-b but for the maximum rise slope for the AP. d: Representative AP waveform from a puff experiment. e: As in d, but from a no-puff experiment.
Figure 60:
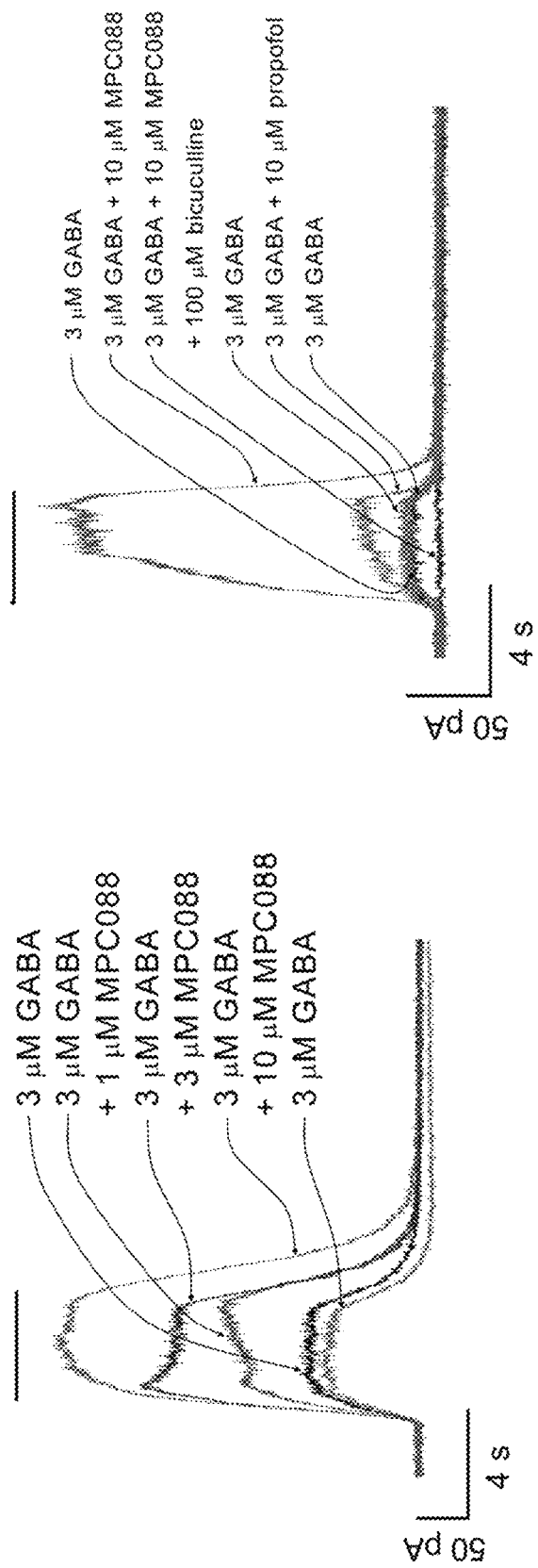
FIG. 60 illustrates the effect of trans-dominant MPC088 on retinal ganglion cells. Left: Potentiation data (with co-applied 3 µM GABA) obtained from a single cell. Right: Sensitivity of the trans-MPC088-potentiated response to bicuculline.

Direct activation data obtained with trans- and cis-dominant MPC088 is shown in FIG. 39b. Representative responses were obtained from a cell treated with 200 μM GABA (black), 60 μM of trans-dominant (blue) and 60 μM of cis-dominant (magenta) MPC088. Inset: Aggregate data for direct activation by MPC088. Left, middle and right bars show results obtained, respectively, with 30 μM trans-dominant (n=3), 60 μM trans-dominant (n=7), and 60 μM cis-dominant MPC088 (n=4). At 30 μM, trans-dominant MPC088 alone produced a membrane current response whose peak amplitude amounted, on average, to 5% of the cell's response to 200 μM GABA (FIG. 39b, inset). However, at 60 μM, the agonist effect increased to 43±9% of the response to 200 μM GABA (n=7), and pre-treatment of trans-dominant MPC088 with UV light reduced this agonist activity by 88±6% (n=4; p=0.002) (FIG. 39b). This activity is dependent on the compound's concentration and, consistent with its action at GABAAARs, is sensitive to the $GABA_A R$ antagonist bicuculline (FIG. 60a-b). Co-application of 100 μM of the GABA receptor channel blocker PTX virtually eliminated the ganglion cell response to 2 μM GABA+10 μM trans-dominant MPC088 by 94±1% (n=5), and reduced the response to 60 μM trans-dominant MPC088 alone by 95±2% (n=4) (FIG. 48), consistent with mediation of trans-MPC088's potentiation and direct activation by $GABA_A Rs$. FIG. 48 illustrates representative data obtained from a single cell for responses to 2 μM GABA, and to (2 μM GABA+10 μM trans-dominant MPC088) without (left) and with (right) co-applied 100 μM PTX (FIG. 48a), and to 60 μM trans-dominant MPC088 without (left) and with (right) 100 μM PTX (FIG. 48b).

Figure 61:
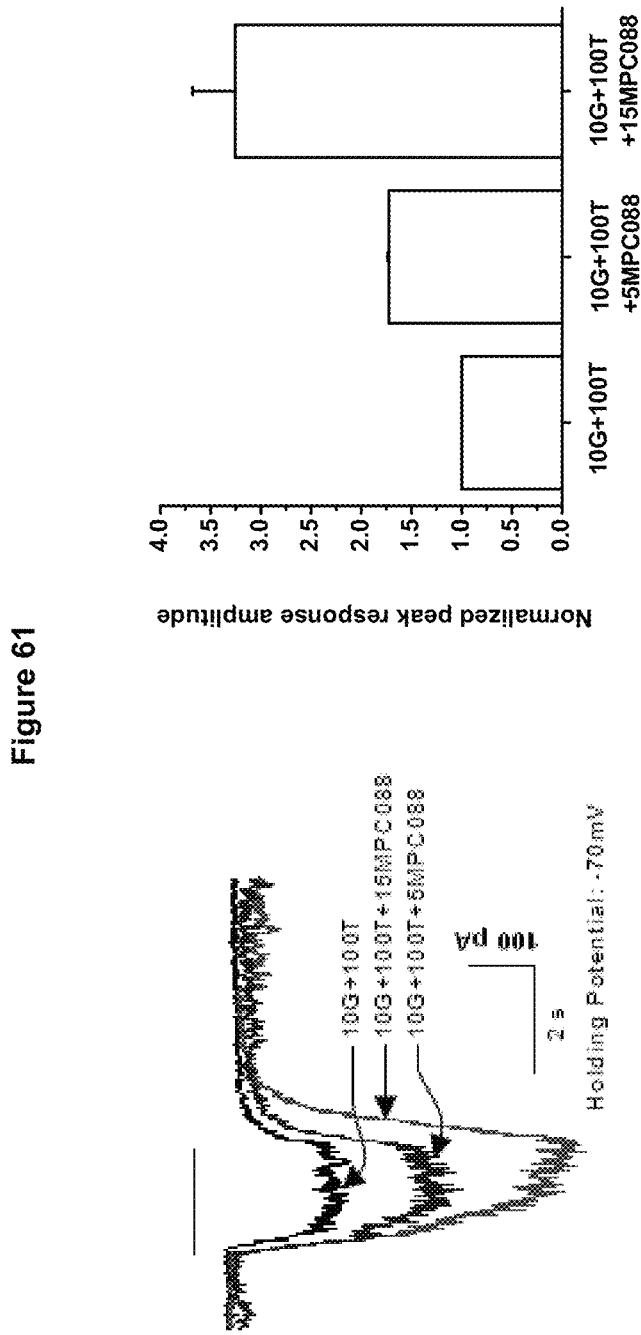
FIG. 61 illustrates the potentiating action of 5 µM and 15 µM trans-MPC088 on isolated, single bipolar cells of rat retina. Left: Responses obtained in a single representative experiment involving co-applied 10 µM GABA and 100 µM TPMPA. Right: Aggregate data for potentiation by trans-MPC088.

Testing was also performed on isolated bipolar cells of rat retina, following procedures used in a recent study of propofol's action on these cells (Yue L, Xie A, et al. (2011)), which are known to possess $GABA_C$ (also known as $GABA_A$-ρ) as well as $GABA_A$ receptors, which demonstrated a potentiating action of propofol specifically at the $GABA_A Rs$. Data obtained with trans-MPC088 indicated substantial $GABA_A R$ potentiating activity by trans-MPC088 (FIG. 61). When co-applied with 10 μM of GABA (10 G) and with 100 μM of the well-known $GABA_C$ antagonist TPMPA (100 T) (Yue L, Xie A, et al. (2011); Ragozzino et al. (1996)), potentiating factors (peak amplitudes relative to that of the 10 G response) are 1.73±0.01 (n=3) and 3.26±0.42 (n=6) for 5 μM and 15 μM trans-MPC088, respectively.

Figure 40:
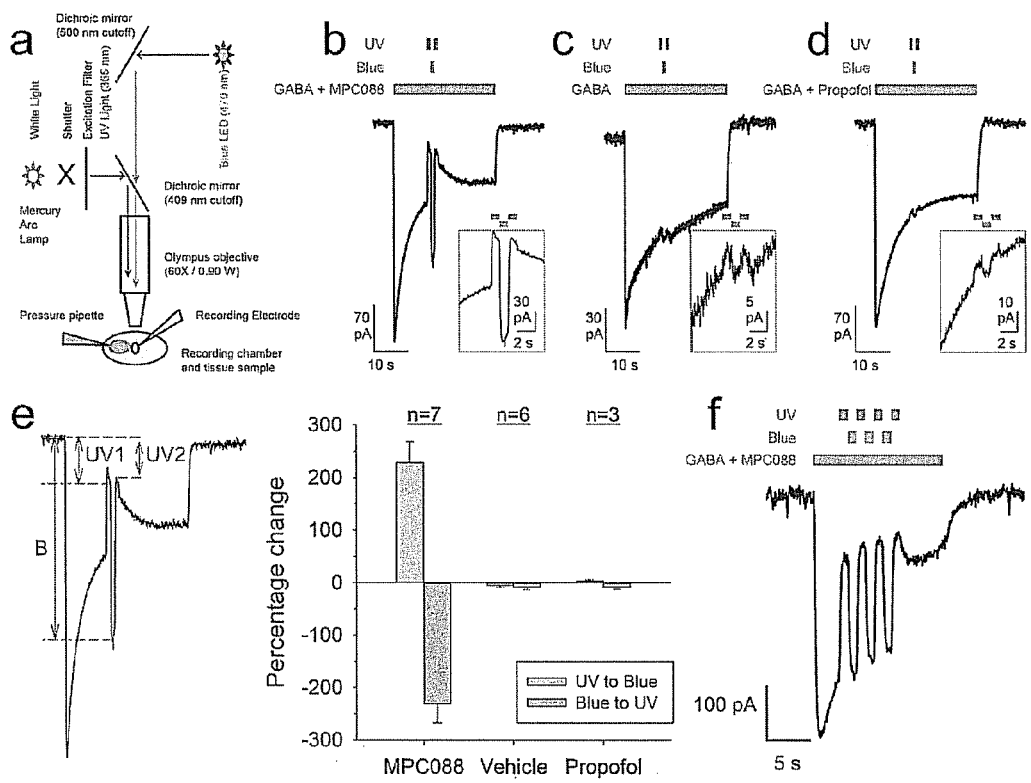
FIG. 40 illustrates the effect of MPC088 photoactivation on GABA-evoked currents in cerebellar PNs. a: Optical configuration. b: Representative trace from a whole-cell voltage-clamp recording from a PN. c: Trace from the same cell as in b, but with exposure to GABA alone. d: Trace from the same cell as in b-c, but with exposure to GABA+propofol. e: Summary of results described in b-d. f: Representative trace from a cell exposed to multiple UV/blue light flashes during application of GABA and MPC088.

To evaluate the efficacy of MPC088 in $GABA_A R$-expressing cells in situ, whole-cell voltage-clamp experiments were conducted on Purkinje neurons (PNs) in parasagittal slices from mouse cerebellum (Häusser et al. (1997); Smith et al. (2003)) (FIG. 40). PNs are known to express $GABA_A Rs$ of the $\alpha_1 \beta_{2/3} \gamma_2$ forms (Wisden et al. (1996); Fritschy et al. (2006); Wulff et al. (2007)). FIG. 40a shows the experimental setup, indicating how blue and UV light sources were combined in the epifluorescence pathway of an upright microscope. Currents were evoked in the PNs by applying 10 μM GABA from a local pressure pipette that also contained 30 μM trans-dominant MPC088. The cell was held at −70 mV, and 10 μM GABA+30 μM MPC088 were applied via pressure pipette for 30 s. The cell was flashed with UV light (1 s, shuttered from a mercury arc lamp), then blue light (1 s, from a 470 nm LED), and then again with UV light (1 s). Insets expand the segments of the trace recorded when the light pulses were delivered (FIG. 40b). UV illumination during the elicited response markedly decreased the membrane current; conversely, blue light enhanced the current (FIG. 40b). To determine whether these effects of light required the presence of MPC088, similar experiments were performed on the same cell by replacing the pressure pipette with one that contained only 10 μM GABA (FIG. 40c) or 10 μM GABA plus 300 μM propofol (FIG. 40d). By contrast with the FIG. 40b results, there was little or no light-induced current change under either condition. To quantify these results, the current change in response to transitions from UV to blue light and from blue to UV light were measured (FIG. 40e). The left-hand trace shows the method used to obtain the numerical data shown at the right. The magnitude of the UV-to-blue transition was calculated as (B-UV1)/UV1; that of the blue-to-UV transition was calculated as (UV2-B)/UV2. Here, UV1, B and UV2 are, respectively, the magnitude of the current evoked by the first UV flash, the blue flash and the second UV flash, as referenced to the pre-GABA current level. The number above each condition indicates the number of cells from which data were obtained. For the negative control experiments (i.e., those involving exposure to vehicle or propofol alone) in which no light-evoked current was detectable, current was measured for identical epochs at the terminations of the light pulses. Error bars represent the SEM. For both the blue-to-UV and the UV-to-blue transitions, the Kruskal-Wallis ANOVA on Ranks yielded p<0.005 (H>11, df=2). Post-hoc statistical tests showed that results obtained with MPC088 treatment differed significantly from those obtained under either negative control condition (Mann-Whitney Rank-Sum Test: MPC088 vs. vehicle (blue-to-UV and UV-to-blue), p=0.002; MPC088 vs. propofol (blue-to-UV and UV-to-blue), p=0.014; p values adjusted for multiple comparisons). The current changes produced by these transitions were opposite and, on average, equal in magnitude (mean ratio of absolute current magnitude in response to blue→UV/UV→blue was 1.00±0.01, a value that did not differ significantly from unity; p=0.86, n=7) (FIG. 40f). Together, these results demonstrate that MPC088 directly modulates $GABA_A Rs$ of cerebellar PNs in situ.

Example 13

Treatment of Wildtype $GABA_A Rs$ with MPC100

In the presence of 10 μM MPC100, wildtype $\alpha_1 \beta_2 \gamma_2$ receptors exhibited photo-regulatable potentiation of the GABA response (FIG. 47a), although this potentiation was smaller than that produced by equimolar trans-dominant MPC088. Waveforms show responses to, sequentially, (i) 100 μM GABA alone, (ii) 3 μM GABA alone, (iii) 10 μM MPC100 alone, and (iv) 10 μM MPC100 co-applied with 3 μM GABA. During phase (iv), introduction of the co-applied MPC100 and GABA was followed by a period of static bathing and UV illumination. Direct activation of wildtype receptors by 10 μM MPC100 was negligible (FIG. 47a). Responses of a single oocyte to 0.3 μM GABA presented before MPC100 treatment (upper), and after MPC100 treatment (100 μM, 7 min) with subsequent Ringer perfusion (lower) are shown in FIG. 47b. Following treatment with MPC100, the response to 3 μM GABA was not significantly enhanced (p=0.9; n=4), and neither UV nor high-intensity visible light delivered in the presence of 0.3 μM GABA substantially affected the membrane current (FIG. 47b).

Example 14

Sequential Treatment of γ-79C-Expressing Oocytes with Methyl-(PEG)$_{11}$-Maleimide and MPC100

To examine whether pre-treatment with a general cysteine-reactive compound blocks the tethering of MPC100 to the receptor, by comparison with the nominal response to 3 μM GABA determined initially in these experiments, γ-79C-expressing oocytes were treated for 10-min with 1 mM methyl-$(PEG)_{11}$-maleimide, which led to a persistent increase of 71±25% (p=0.01; n=4) in the GABA response. Compared with the effect of MPC100 treatment, this increase was relatively small and insensitive to UV illumination. The mutant cysteine residue of γ-79C neighbors the benzodiazepine binding site at the α/γ interface (Kucken et al. (2000); Kucken et al. (2003)). As benzodiazepines are potent $GABA_AR$ potentiators, the increase observed with methyl-$(PEG)_{11}$-maleimide may have resulted from occupation of the benzodiazepine binding site. Subsequent treatment (10 min) with 100 μM MPC100 had no significant effect on the 3 μM GABA response (ratio of response amplitudes post- vs. pre-MPC100 treatment: 1.1±0.1 (p=0.3; n=4).

Example 15

Effects of MPC088 on Action Potential Firing in PNs

The effects of MPC088 on action potential firing in PNs of the cerebellar slice were also examined. These experiments were similar to those, except that the cells were recorded under current-clamp in order to allow the cell to spike. To each of the PNs described in FIGS. 41*a-b*, GABA (10 μM) plus trans-dominant MPC088 (30 μM) was delivered by pressure application, and then the cell was exposed to sequences of UV-Blue-UV light. Representative data was obtained by whole-cell current-clamp recording from a PN which was injected with 468 pA to elicit a high-frequency train of action potentials. During this current step, 10 μM GABA+30 μM trans-dominant MPC088 were applied via pressure pipette for 10 s. The cell was then exposed for 1-s durations to UV light (UV1), then blue light, and then again with UV (UV2). The entire illustrated voltage vs. time trace occurs during application of GABA/MPC088. Below this trace is plotted the instantaneous firing frequency vs. time; the dashed line reflects the average firing frequency during the 1-s epoch that preceded the first UV exposure (FIG. 41*a*). FIG. 41*b* depicts a summary of results from experiments of the type shown in a. Average spike frequencies were obtained for each cell in each of five 1-s epochs, then normalized to the pre-GABA/MPC088 firing frequency (n=8 cells from 4 animals). Error bars here and in c represent the SEM. Repeated-measures ANOVA on the aggregate data yielded F(3,21)=10.213, p<0.001. Red asterisks above the purple and blue bars indicate significance of the average frequency in that epoch vs. the preceding epoch (e.g., the asterisk above the UV1 bar refers to significance of the average firing rate in the UV1 epoch vs. the GABA/MPC088 pre-UV epoch). Significance was determined from post-hoc paired-sample t-tests corrected for multiple comparisons, which yielded p<0.02. FIG. 41*c* depicts a summary of results from experiments similar to that described in a, but in which the cell was exposed only to the UV/Blue/UV flash sequence (i.e., no GABA/MPC088 applied). Data was normalized to the average firing frequency during the 1-s period preceding the first UV flash (n=7 cells from 3 animals). Repeated-measures ANOVA on the aggregate data yielded F(3,18)=3.057, p>0.05. Three post-hoc statistical tests were then performed as described in b; none of these yielded significance at the uncorrected 0.05 level Exposure to GABA+trans-dominant MPC088 decreased the firing rate by approximately 50%, on average (FIG. 41*b*). Furthermore, in all of the 8 investigated cells, the UV-Blue-UV flash sequence led, respectively, to an increase, decrease and increase in firing rate. Overall, the firing rate produced by blue light was 52±14% of that produced by UV light. In 3 of the 8 PNs, blue light decreased the firing rate to <20% of that exhibited during the UV illumination, and one PN exhibited a blue-light-induced complete cessation of spiking that was reversed by subsequent UV. As a negative control, cells were exposed to the UV-Blue-UV light sequence but in the absence of GABA/MPC088 application. In these cells, there was no significant change in firing rate with any of the light flashes (FIG. 41*c*). Together, these data indicate a reversible, light-dependent action of MPC088 on PN spike-firing rate.

Example 16

Direct Agonist Activity of MPC088 on PNs

Figure 42:
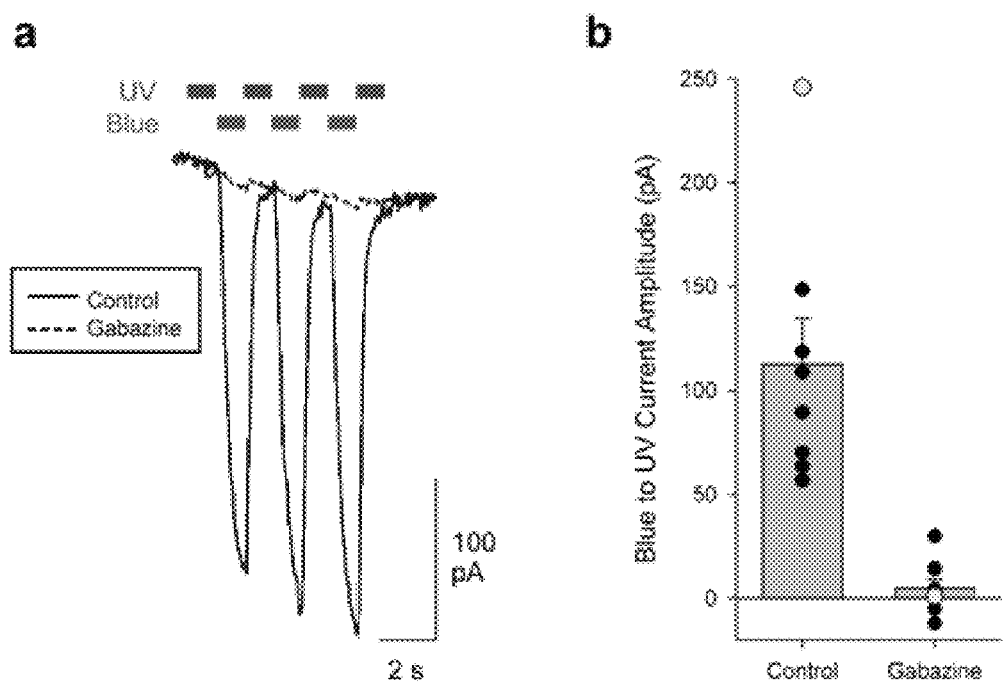
Figure 43:
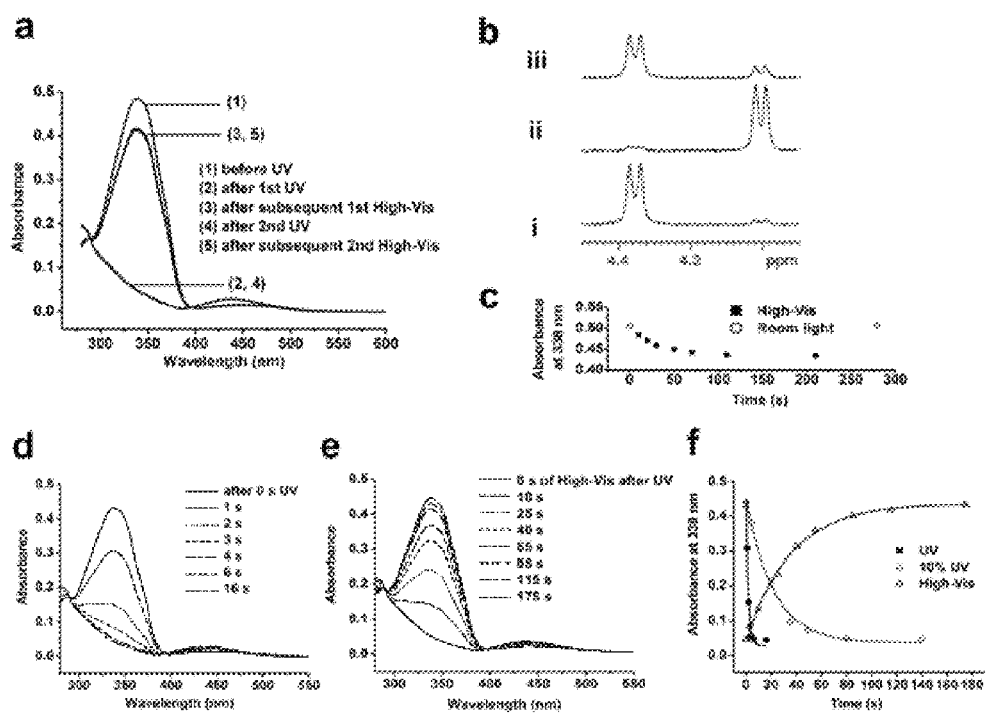
FIG. 43 illustrates the effect of UV and visible light on isomeric composition of MPC088. a: Absorbance spectra of 15 µM MPC088 in DMSO. b: Determination of trans/cis-isomer ratio in MPC088 by $^1$H NMR. c: Time course of MPC088 absorbance change at 338 nm produced by the visible light source of the electrophysiological apparatus. d and e: Absorbance spectra obtained from the sample described in c, with varying periods of UV illumination (d) and then varying periods of visible illumination (e). f: Time course of absorbance change at 338 nm produced by the UV exposures of d, by UV exposures at 10% of nominal, and by the visible light exposures of e.

To test for direct agonist activity of MPC088 on PNs, cerebellar slices were perfused with recirculating 30 μM MPC088 (the maximal MPC088 concentration that could be reliably maintained solubilized in bicarbonate-buffered solution). MPC088 was converted to cis-dominant form by a 2-min exposure to UV light (LED, 365 nm/160 mW, Mouser, Inc., Mansfield, Tex.; LED driver, 700 mA BuckPuck DC Driver, Quadica Developments, Inc., Brantford, Ontario, Canada), before its dilution into the recirculating external solution. The same LED was then used to continuously UV-illuminate the recirculating solution for the duration of the experiment. Whole-cell voltage clamp recordings were obtained from PNs and determined the change in membrane current produced by alternating blue and UV illumination of the slice, as in the FIG. 40 experiments. Of 44 cells examined, only 28 exhibited a current change >18 pA, which is the average amplitude of the Blue-to-UV light currents from the vehicle and propofol conditions described in FIG. 40. The average response from this subset of 28 cells was 80±13 pA. To test whether these currents were due to an agonist action of the drug, as opposed to a modulatory action occurring in concert with low levels of endogenous GABA present in the slice (Santhakumar et al. (2006), the modulation was discerned by analyzing the effect of added 30 μM gabazine (Ueno et al. (1997); Jones et al. (1998)), a condition expected to inhibit the potentiating action of MPC088 (i.e., to inhibit response enhancement dependent on endogenous GABA) but not to affect the direct agonist activity of MPC088 (FIG. 36). Averages of 10 recordings from a PN exposed to multiple Blue/UV light flashes, in the presence of cis-dominant MPC088 (30 μM) in the external solution, before (black) and after (red) the addition of gabazine (30 μM) are depicted in FIG. 42*a*. There was no exogenous GABA present in the tissue. FIG. 42*b* shows a summary of results from 8 experiments (8 PNs) including that described in a. The data indicate the magnitude of an outward current. The temporal sequence of illumination differed among the experiments (e.g., only the cell in a received multiple blue/UV exposures), but the data plotted are the amplitudes from the blue to UV transition (in the case of the cell in a, this is the blue/UV transition from the first of the three exposures). Yellow-filled data points indicate results from the experiment in a. Each data point is the average obtained from 4-10 consecutive recordings. The light-evoked membrane current was significantly reduced by gabazine (Wilcoxon Signed Rank Test, p=0.008). Error bars represent the SEM (FIG. 42*b*).

In all but one of eight cells that exhibited light-evoked responses of >50 pA to the Blue-to-UV switch, gabazine (30 μM) reduced the current to below the vehicle level of 18 pA (FIG. 42*a-b*). The average current remaining after gabazine treatment represented 11±3% of the pre-gabazine current (FIG. 42*b*). Even for the cell exhibiting the highest response of the 44 cells tested, gabazine completely abolished the response (FIG. 42a). Thus, at concentrations comparable to or lower than 30 µM, trans-MPC088 in cerebellar tissue is modulatory (endogenous GABA-dependent) rather than agonistic.

Example 17

Effects of MPC088 on Excitability

Figure 41:
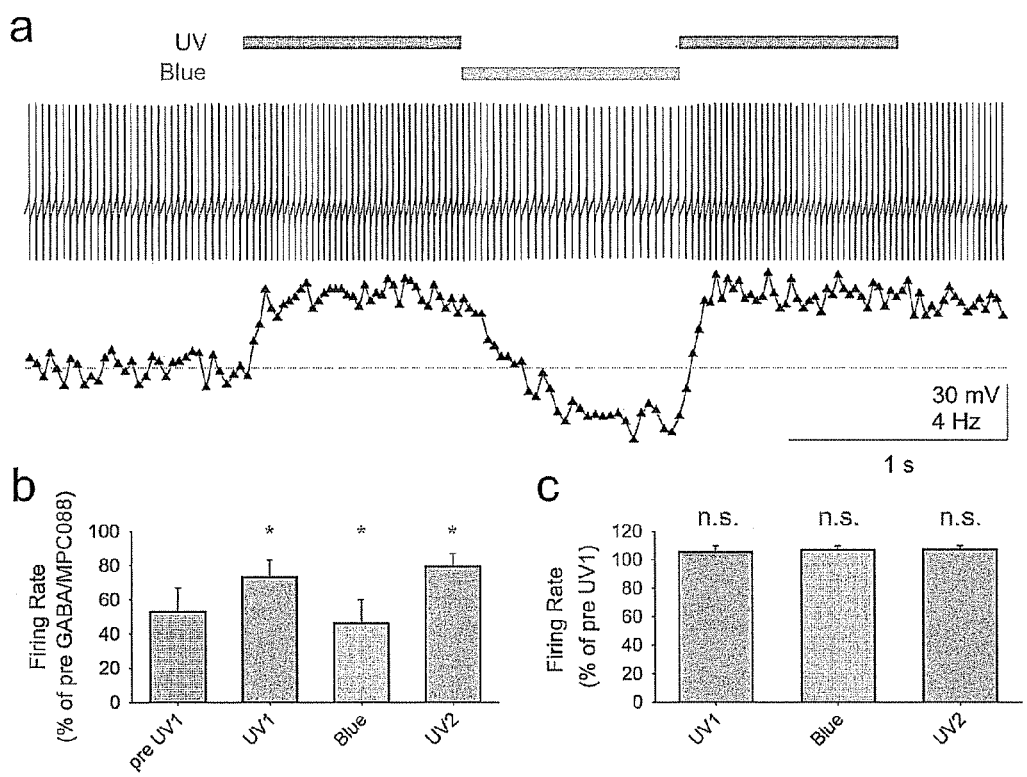
FIG. 41 illustrates the effect of MPC088 photoactivation on action potential firing frequency in PNs. a: Representative data obtained by whole-cell current-clamp recording from a PN injected with 468 pA to elicit a high-frequency train of action potentials. b: Summary of results from experiments of the type shown in a. c: Summary of results from experiments similar to a, but in which the cell was exposed only to the UV/Blue/UV flash sequence.
Figure 49:
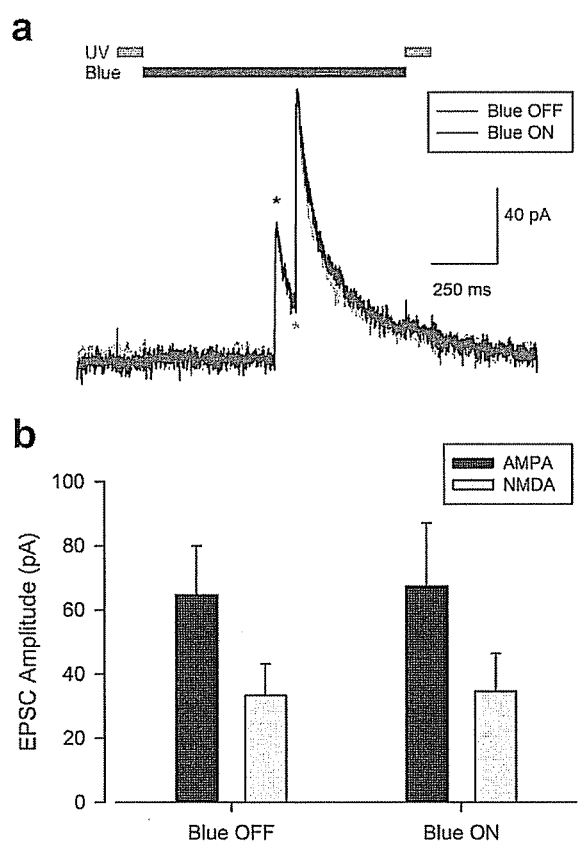

To further address whether MPC088 has non-specific effects on excitability, the spikes elicited in the experiment described in FIG. 41 were analyzed. Spikes recorded during exposure to GABA/MPC088 ("puff") and under conditions in which MPC088 was absent but in which the Purkinje cell received the UV/Blue/UV light sequence ("no-puff") were examined. Three action potential (AP) parameters were measured: peak amplitude, half width, and maximum rise slope. Parameters were obtained from spikes occurring in the same 1-s epochs in which average firing rate was significantly modulated by MPC088 (see FIG. 41b-c). AP waveform parameters were calculated for pre-puff, blue light, and UV epochs. Average values in the pre-treatment epochs for puff and no-puff did not significantly differ (Spike Amplitude (mV), 52±2 and 51±2; Half Width (ms), 0.61±0.03 and 0.57±0.03; Maximum Rise Slope (mV/ms), 150±10 and 161±13; p>0.4, unpaired t-test). In addition, for each parameter, the average values for each cell and for each epoch were normalized to the averages in the pre-treatment epochs (pre-puff, pre-light). This analysis of excitability showed first, that the only measurable effects on AP waveform are MPC088-independent and caused by light exposure, and second, that the effect size of light is extremely small (less than 2%; FIG. 49).

Example 18

Effects of MPC088 on Excitatory Synaptic Transmission

Figure 50:
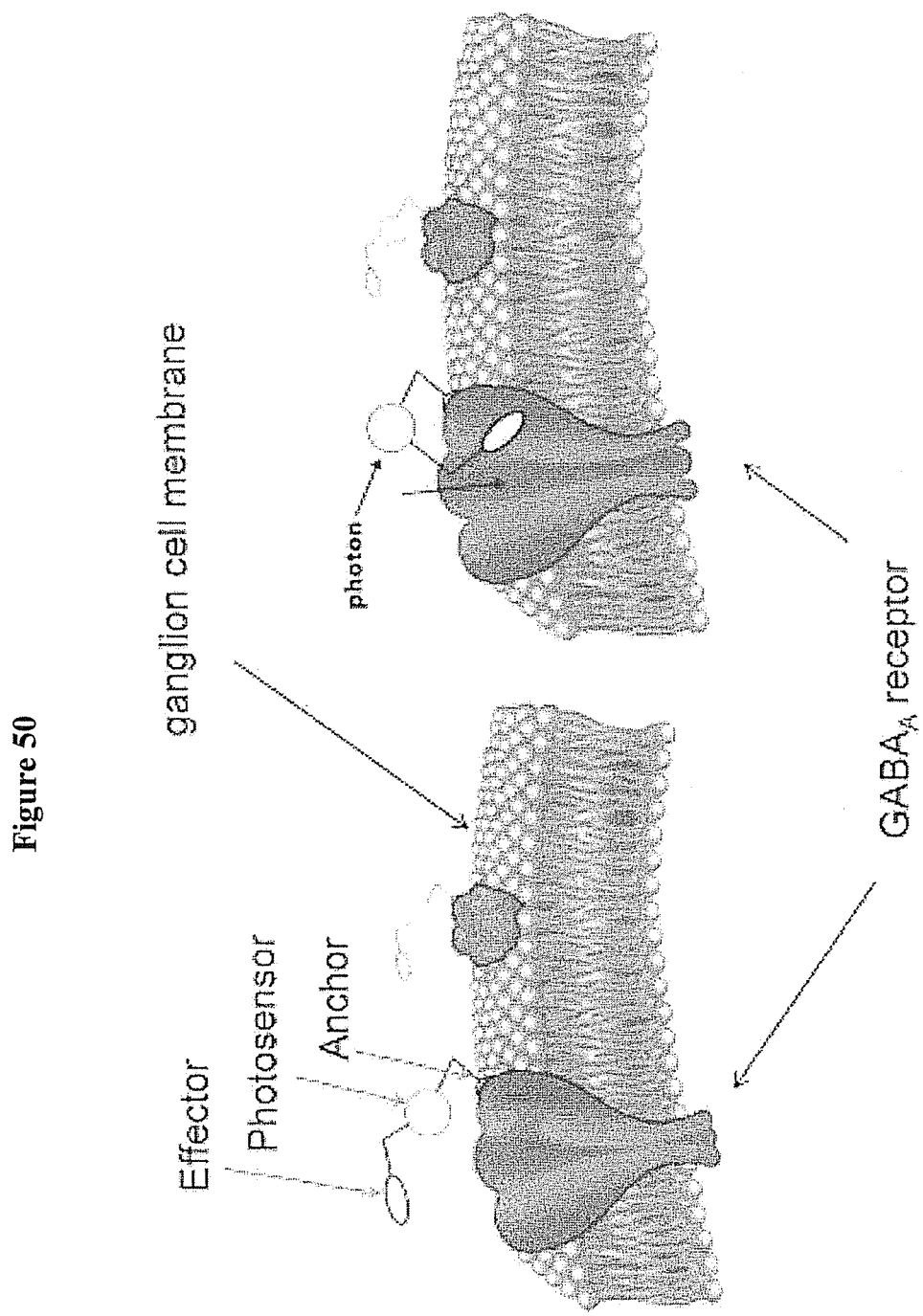
FIG. 50 depicts a GABA$_A$ receptor with an effector, photosensor, and anchor
Figure 51:
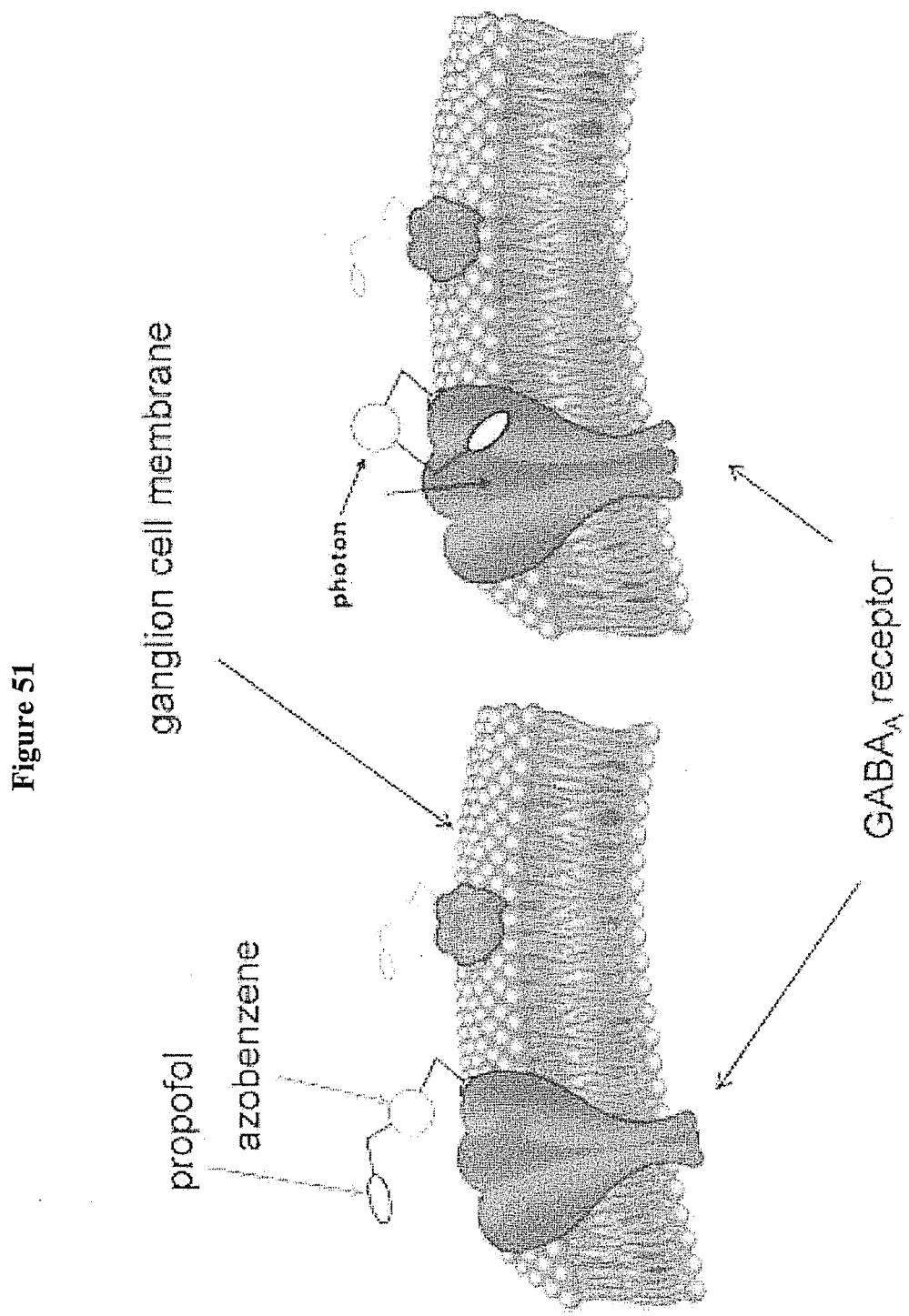
FIG. 51 depicts a GABA$_A$ receptor with propofol as effector and azobenzene as photosensor
Figure 52:
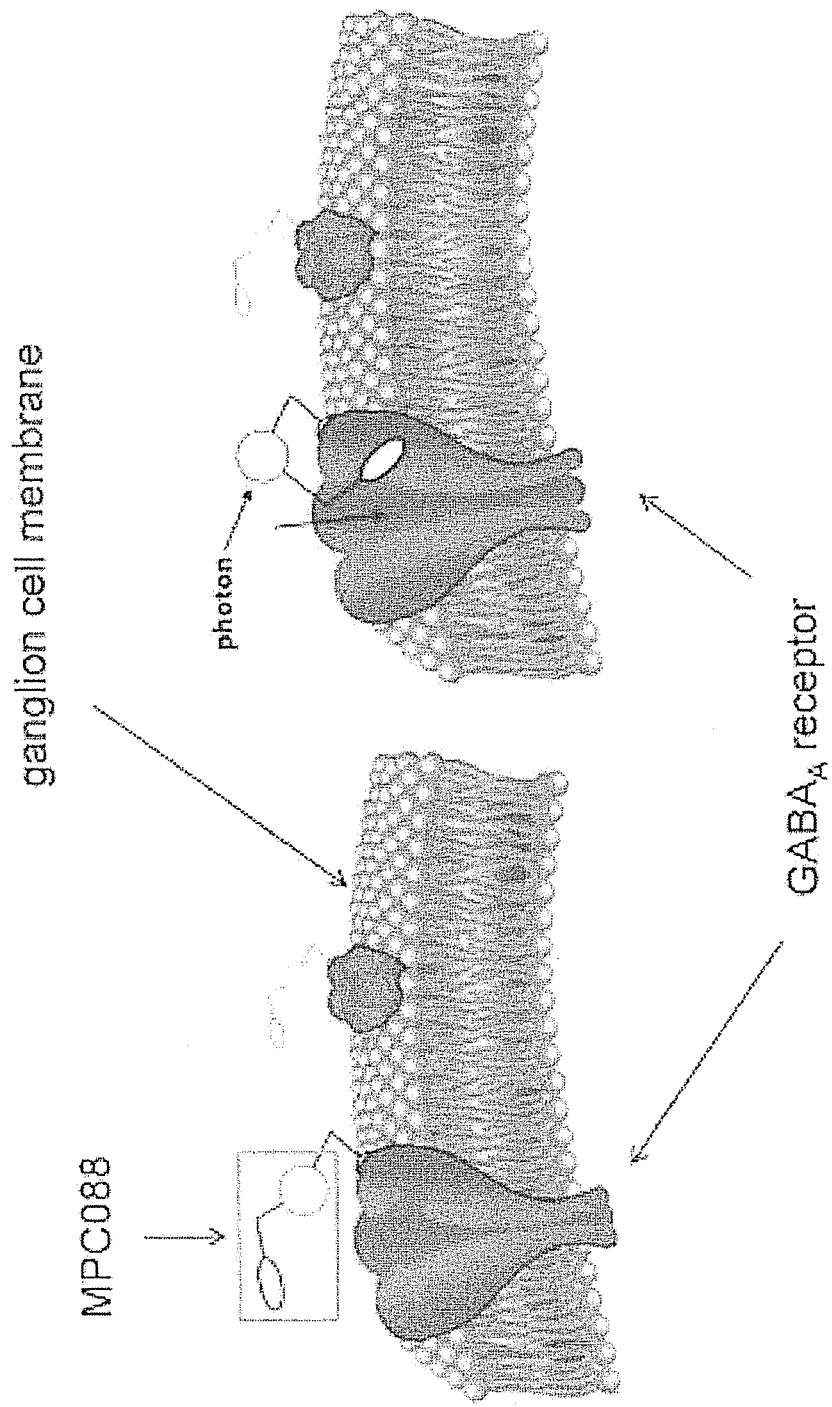
FIG. 52 depicts a GABA$_A$ receptor with MCP088 as effector and photosensor
Figure 53:
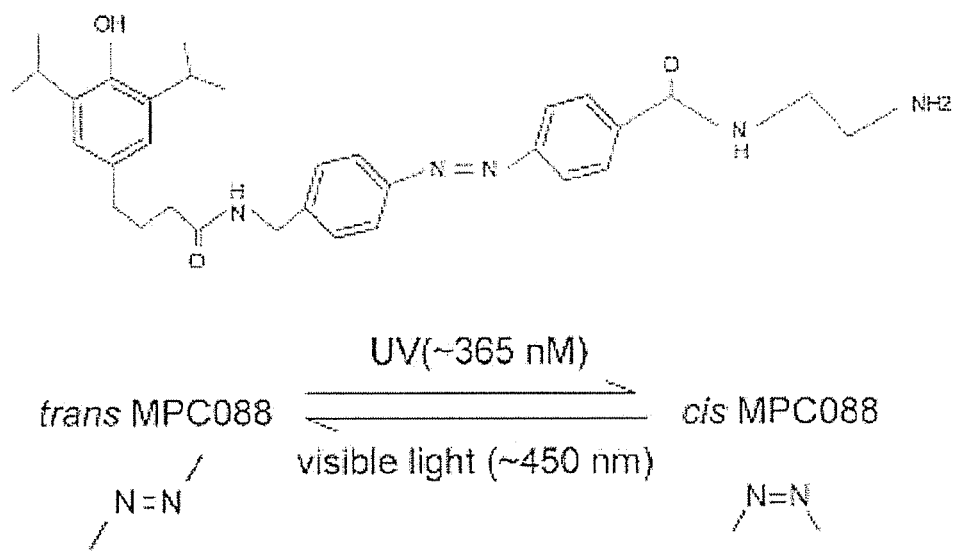
FIG. 53 shows the structure of MPC088 and reaction between cis and trans isomers
Figure 54:
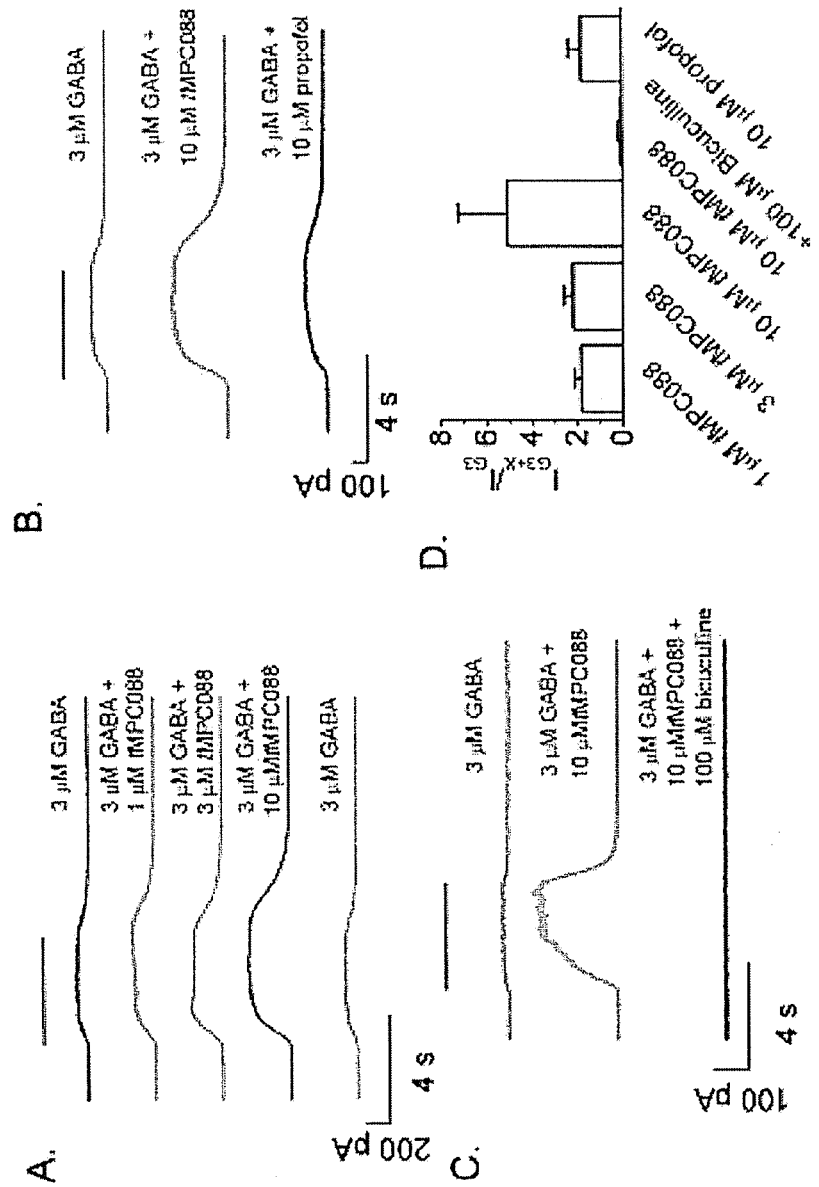
FIG. 54 illustrates trans-MPC088 enhancement of the 3 µM GABA response. Whole-cell voltage-clamp recordings of enzymatically dissociated rat retinal ganglion cells in the presence of: a. GABA alone and with various volume of trans-MPC088. b. GABA alone, GABA with trans-MPC088 and GABA with propofol. c. GABA alone, GABA with trans-MPC088, and GABA with trans-MPC088+bicuculline. d. Summary data including that shown in a-c.
Figure 55:
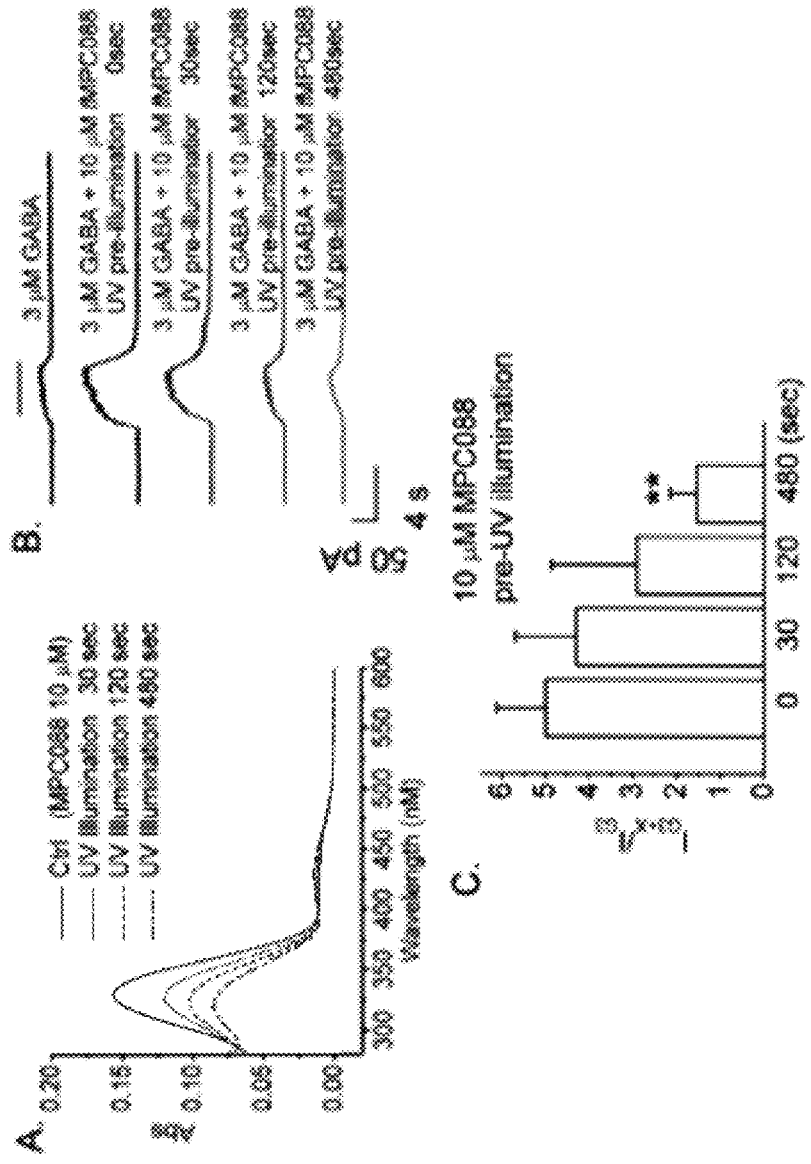
FIG. 55 illustrates the effect of trans- vs. cis-MPC088 on the 3 µM GABA response. a. Absorbance spectra of 10 µL MPC088 prior to and after various exposure times to UV illumination. b. Whole-cell voltage-clamp recordings of enzymatically dissociated rat retinal ganglion cells in the presence of GABA alone, and GABA+trans-MPC088 prior to and at various exposure times to UV illumination. c. Summary data including that shown in b.
Figure 56:
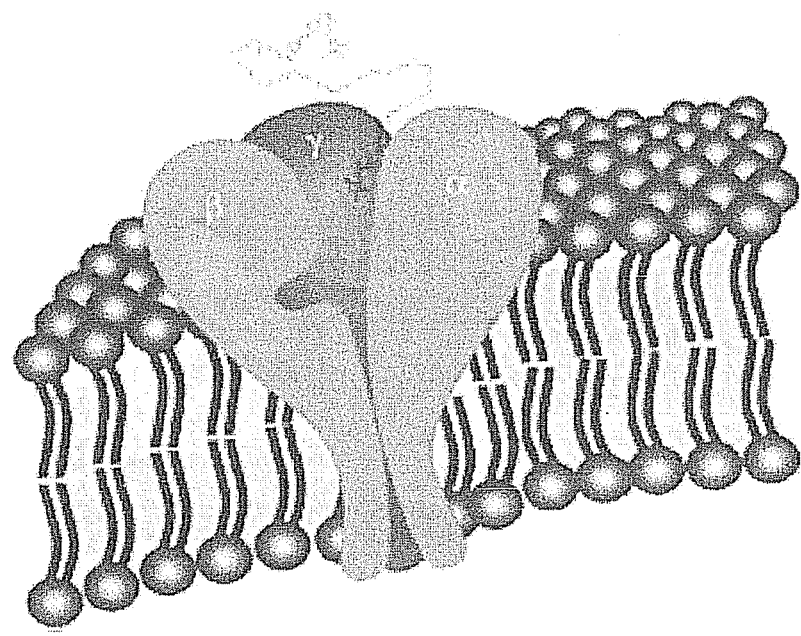
FIG. 56. Schematic diagram of MPC100 tethered to the $\alpha1\beta2\gamma2$ (A79C) receptor, $\alpha$, $\beta$ and $\gamma$ refer to subunits in this "sliced" view of the pentameric receptor; the $\beta$ subunit pocket represents a propofol binding site. MPC100 and receptor subunits shown roughly to scale. The thiol anchoring site ($\gamma$-79) lies within the benzodiazepine binding cavity.
Figure 57:
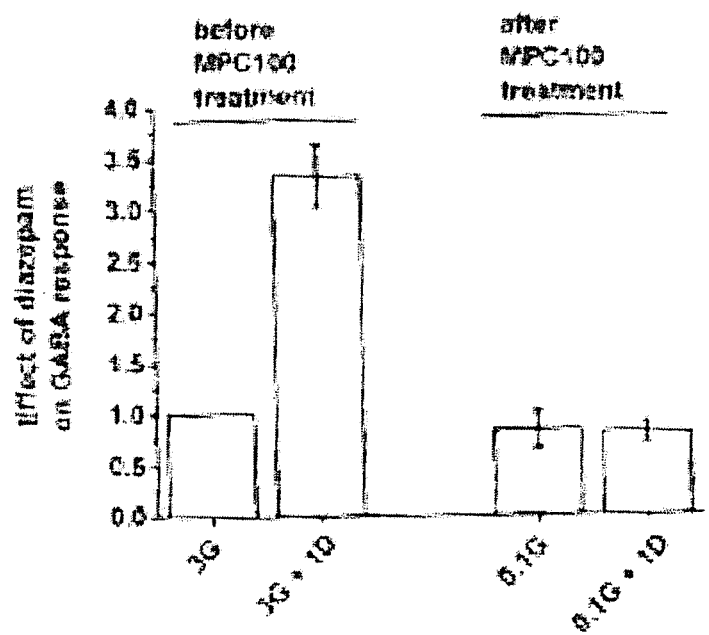
FIG. 57 Effects of anchoring MPC100 to $\alpha1\beta2\gamma2$ (A79C) GABAARs. Responses obtained following treatment with trans-dominant MPC100 and subsequent Ringer perfusion. B: Elimination, by MPC100, of the potentiating effect of diazepam on the GABA response. Amplitudes mornalized to that for 3 µM GABA determined before treatment (5 oocytes).
Figure 58:
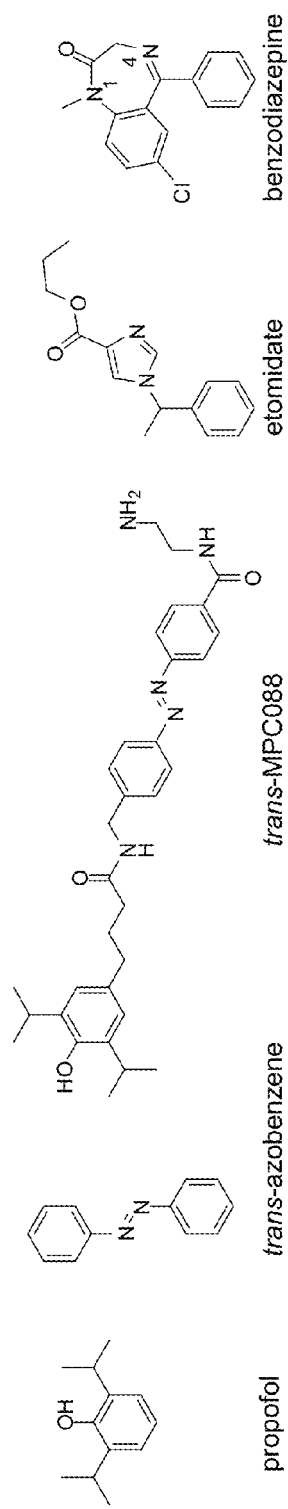
FIG. 58 depicts the structures of propofol trans-azobenzene, trans-MPC088, etomidate and a representative benzodiazepine.

To test whether MPC088 affects excitatory synaptic transmission, whole-cell voltage-clamp recordings were carried out in CA1 pyramidal neurons of mouse hippocampus. As in the experiments of FIG. 42, these recordings were obtained with perfusion of the slice with cis-dominant MPC088 (30 µM) under recirculation. PTX (10004) was also included in the external solution to block $GABA_A Rs$. EPSCs were evoked by stimulating the Schaffer collaterals with a bipolar matrix microelectrode (FHC, Inc., Bowdoin, Me.), and recorded at a holding potential of +40 mV to uncover the NMDA receptor (NMDAR) component of the EPSC. Paired electrical stimuli separated by 80 ms were also presented to assess possible effects of MPC088 on short-term plasticity. Each cell was particular 20 interleaved trials in which the cell was exposed to two 0.1-s UV pulses surrounding a 1-s period of either blue light or no light (FIG. 50). FIG. 50a shows representative average recordings from a CA1 pyramidal cell held at +40 mV. Each trace is the average of 10 traces with stimulus and shutter artifacts blanked for clarity. The black and grey asterisks indicate the time points, respectively, for the current measurements of the AMPAR- and NMDAR-mediated components. FIG. 50b depicts summary data including that shown in a. Plotted for the blue light and no blue light conditions are the average current amplitudes measured at the peak of the first EPSC (black bars), and just prior to the second stimulus (grey bars), as indicated by the asterisks in a. Neither current amplitudes were significantly altered by blue light (Paired t-tests, p>0.6, n=5 cells from 3 animals), and error bars represent the SEM.

The effectiveness of the 0.1-s UV and the 1-s blue stimuli in photoconverting MPC088 was confirmed in separate experiments using 30 µM MPC088 and 3 µM GABA on the same preparation. To quantify the effects of MPC088 on AMPA receptors (AMPARs) and NMDARs, for the first EPSC of the pair, the peak current and the current just prior to the second stimulus were measured, which reflect AMPAR and NMDAR components, respectively, of the EPSC[41]. Neither AMPAR-mediated nor NMDAR-mediated components of the EPSC were significantly altered by blue light (FIG. 50b). Additionally, blue light had no significant effect on the decay of the compound current (average τ from single-exponential fitting to the decay of the second EPSC: Blue off, 131±11 ms; Blue on, 131±11 ms; p=0.89). There was also no significant effect of blue light on the paired-pulse ratio (PPR, measured as Peak(2nd EPSC)/Peak(1st EPSC): Blue off, 1.72±0.07; Blue on, 1.85±0.14; p=0.34). Together, these results indicate that MPC088 does not significantly affect presynaptic function and that it has negligible actions on AMPAR-mediated and NMDAR-mediated EPSCs.

Example 19

Statistical Tests of the Effects of Light and MPC088 on AP Shape

FIG. 49 illustrates that there are no detectable effects of MPC088 on AP waveform in cerebellar Purkinje neurons. Representative average recordings from a CA1 pyramidal cell held at +40 mV are shown in FIG. 49a. For the puff experiments (black symbols/lines), the data are normalized to the average AP amplitudes in the 1-s epoch immediately preceding the puff. For the no-puff experiments (red symbols/lines), the data are normalized to the average AP amplitudes in the 1-s epoch immediately preceding the first UV light pulse. For the no-puff experiments, post-hoc paired-sample t-tests (or Wilcoxon Signed Rank Test when normality tests failed), corrected for multiple comparisons, were performed for each epoch versus the preceding epoch. These tests yielded significance for the Peak Amplitude and Half-Width (p<0.02; red asterisks in a-b). Data plotted here and in b-c are from n=8 cells for puff and n=7 cells for no-puff Error bars represent the SEM. FIG. 49b illustrates the same as a, but for the AP half width. FIG. 49c illustrates the same as a-b but for the maximum rise slope for the AP. FIG. 49d shows representative AP waveform from a puff experiment. The three superimposed APs are averages of all of the spikes in a single trial in the indicated epochs. The inset shows an expansion of the AP peak. Similarly, FIG. 49e shows the same as in d, but from a no-puff experiment. Notice the slight decrease in amplitude in UV and the slight increase in blue, as is seen in the summary data in a. These MPC088-independent effects are attributed to a small potentiating effect of UV light on voltage-gated K channels, an effect observed in prior experiments in cerebellar Purkinje neurons. As to why this effect is absent in the puff experiments; it is believed that UV absorption by MPC088 may reduce the effect on the K channels.

Further analyses of the results shown in FIG. 49 indicated effects of light but not MPC088 on AP shape. For the puff experiments, a repeated-measures ANOVA (or Friedman Repeated-Measures ANOVA on Ranks for the data set that failed normality tests) on the aggregate normalized data did not yield significance (Peak Amplitude: $F(3,21)=1.687$, p=0.2; Half Width: Chi-square=5.55, df=3, p=0.14; Maximum Rise Slope: $F(3,21)=0.298$, $p=0.83$). For the no-puff experiments, repeated-measures ANOVA did yield significance for the Peak Amplitude ($F(2,12)=28.103$, $p<0.001$) and Half Width ($F(2,12)=100.351$, $p<0.001$), but not for Maximum Rise Slope ($F(2,12)=3.660$, $p=0.057$). Post-hoc tests were then performed for Peak Amplitude and Half-Width in the no-puff data set, and these yielded significance (FIG. 49a-b).

Example 20

Developing New Propofol-Based Allosteric Modulators of GABA$_A$R

The approaches of chemical synthesis and electrophysiological testing will be combined to develop new propofol-based allosteric modulators of GABA$_A$R characterized by high-potency direct activation at $\alpha_1\beta_2\gamma_2$ GABA$_A$Rs (Aim 1) and GABA$_A$R subtype selectivity (Aim 2). Preliminary results indicate that molecular constructs based on propofol-azobenzene are potent positive allosteric modulators of GABA-induced ion currents, as well as strong direct activators of the GABA$_A$R. To develop new propofol-based allosteric modulators of GABA$_A$R characterized by high-potency direct activation at $\alpha 1\beta 2\gamma 2$ GABA$_A$Rs, structural modifications of the lead compound, trans-MPC088, will be performed to obtain molecules with low nanomolar potency at $\alpha 1\beta 2\gamma 2$ GABA$_A$Rs. The structure-activity relationship for this class of compounds will also be established, while testing for the necessity of the presence of azobenzene, the terminal ethylene diamine and primary amide groups, and the effects of aromatic ring substitution. In addition to increased potency, structure simplification, reduction in molecular size, and increased druggability will be sought, with the aim to develop potential CNS agents. To establish subtype selectivity for $\beta$(2,3)-containing (Aim 2a) or $\gamma$-containing (Aim 2b) GABA$_A$Rs, trans-MPC088-derived structures developed in Aim 1 will be combined with an analog of etomidate or benzodiazepine, respectively.

Trans-MPC088 exhibits GABA$_A$R potentiating and direct agonist activities that, in oocyte-expressing $\alpha 1\beta 2\gamma 2$ GABA$_A$Rs receptors, exceed the activity of the parent propofol by more than an order of magnitude. However, the compounds tested so far explore only a limited space of chemical diversity. To achieve single nanomolar binding affinity, it is believed that the potency of propofol-based ligands can be increased by inclusion of an appendix, bearing an aromatic residue equipped with hydrogen bonding functions, separated from the C-4 of propofol by ca. 15-20 Å, that interacts with the etomidate-binding cleft of the receptor. Using these expanded propofol analogs should enable additional interactions with the receptor, to explore structural differences between $\beta 1$ and $\beta$(2,3) receptors toward the design of a potent, subtype specific modulator and direct activator. The hypothesis underlying Aim 2b is that subtype selectivity for $\gamma$-containing GABA$_A$Rs can be achieved by bivalent interactions even at distant sites on the GABA$_A$R, through increased avidity resulting from interactions at the two sites.

Example 21

Refinement of Trans-MPC088 Structure

Refining the structure of the starting trans-MPC088 to achieve single nanomolar binding affinity, currently viewed as an upper limit of successful CNS drugs (Pajouhesh et al. (2005)), while additionally enhancing its direct activation property is possible due to the likely additivity of the binding energies supplied by the propofol and another (auxiliary) site. This is justified by the concept of multivalent ligands and inhibitors, where the overall binding enthalpy for such ligands is at least partially additive (Jencks (1981)), and binding of a single (multivalent) ligand vs. multiple (monovalent) ligands is favored entropically. Factors such as imperfect structure optimization to fit both binding sites, unfavorable orientation of ligand fragments and conformational effects of the bivalent ligand, as well as allosteric effects at one site on binding energy at another site, might contribute to only partial additivity that could reduce the overall binding energy. However, only a relatively small net gain of 2.5-3.5 kcal/mol would be necessary to obtain the low nanomolar ligand.

Figure 59:
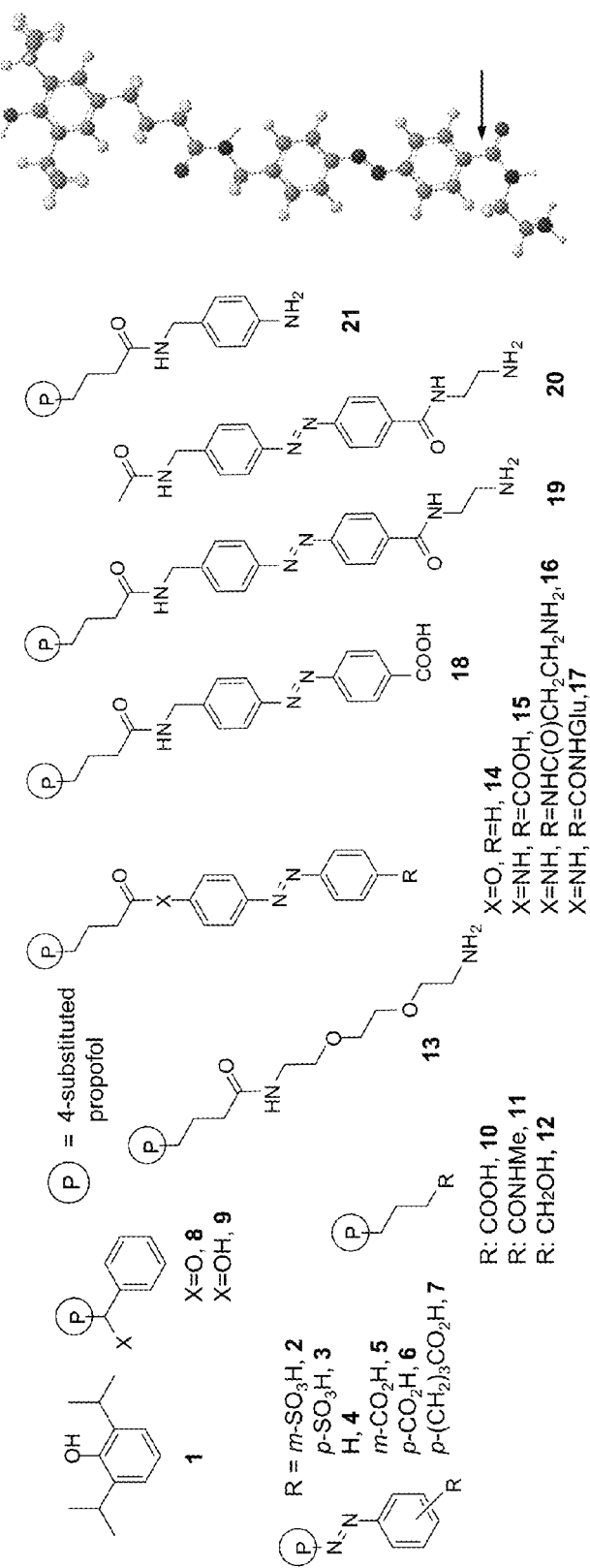
FIG. 59 illustrates structures of synthesized analogs of propofol.

FIG. 59 illustrates the structures of synthesized analogs of propofol. The structure of substituents joined to carbon-4 of propofol (FIG. 59, compound 1) were systematically varied and, using the *Xenopus* oocyte expression system, their electrophysiological activities at $\alpha 1\beta 2\gamma 2$ GABA$_A$Rs were examined. The first compounds (2-7 in FIG. 59), which incorporated a phenylazo residue directly linked to propofol, were inactive, leading to separation of the azobenzene moiety from the propofol ring. The separating spacer could not include a phenyl ring since, contrary to a literature report (Trapani et al. (1998)), compounds 8-9 displayed poor activity. By contrast, attachment of aliphatic chains was preferable, as compounds 10-12 showed significant activity, albeit lower than that of the parent propofol. The attachment of a PEG-like fragment (13) further diminished activity. However, incorporation of a hydrophobic azobenzene fragment yielded an active structure 14. Introduction of a metabolically more stable amide linkage produced less active compounds 15-17. Finally, increased separation by a single methylene group resulted in strong GABA$_A$R potentiation by 18 and 19. Amide 19, henceforth termed trans-MPC088, has proved to be the most active of the propofol-azobenzene conjugates yet tested. The distance between the phenol OH and distal ring C=O group (marked by arrows on the right) in compound 19 is 22.5. Of particular importance, the lower fragment of MPC088, compound 20, was devoid of any activity, and compound 21, missing the lower phenyl ring, had very low activity. Finally, variation of the length of the aliphatic linker between propofol and the first amide bond (using C3, C4 and C5 chains) indicated that the length of the initial four-carbon linker is optimal. These results indicate a fairly restrictive pharmacophore and suggest a unique allosteric binding site with preference for the distal phenyl moiety separated by ca. 15-20 Å from the propofol moiety. Based on these results, it is likely that the presence of the lower aromatic ring combined with hydrogen bonding residues is critical for activity. This is supported by the very low activity of the cis-isomer in which the distance between propofol and the lower ring is smaller. Thus, it is also likely that the lower ring of trans-MPC088 is reaching into the area that binds etomidate.

Figure 65:
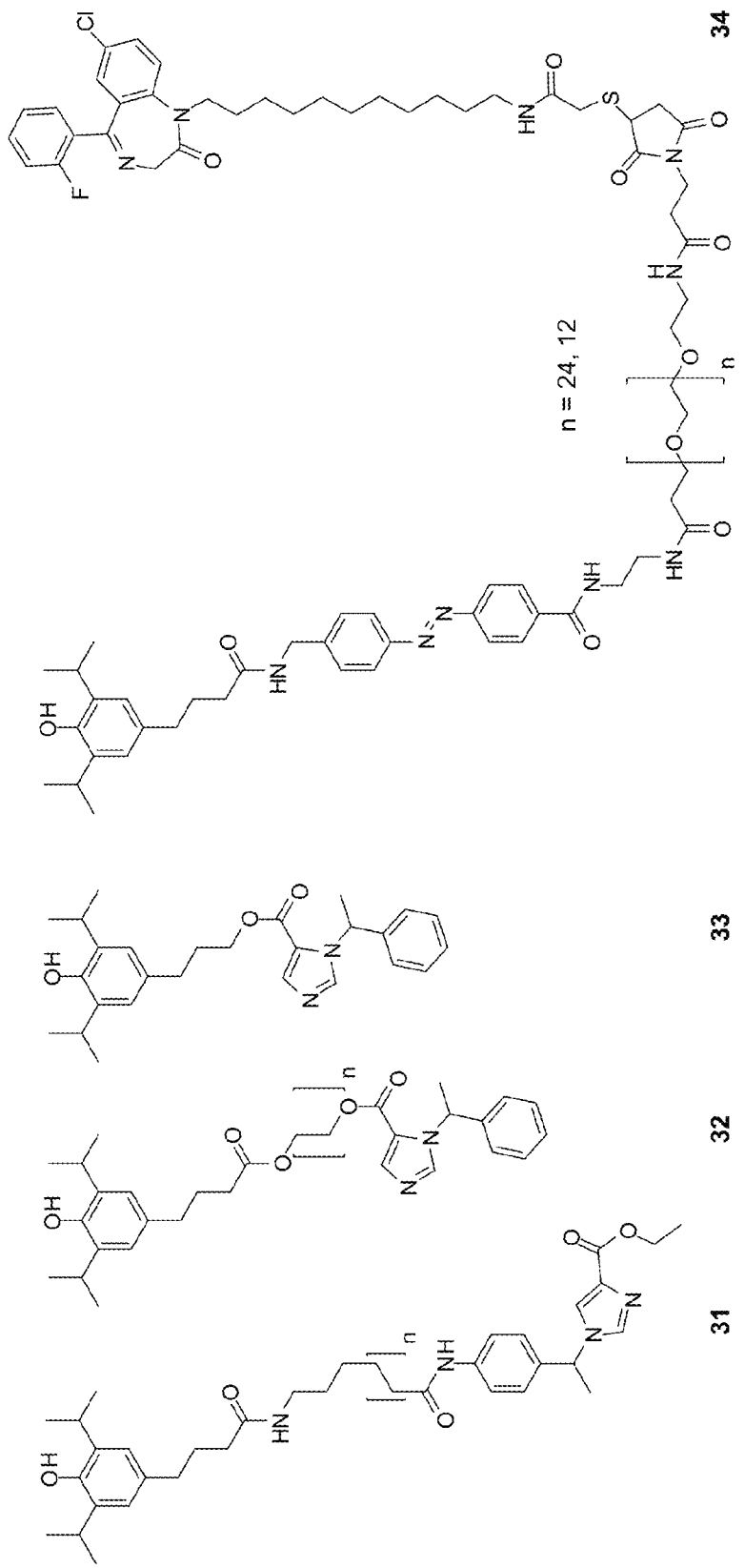
FIG. 65 depicts structures of bivalent ligands to be synthesized (propofol-etomidate and propofol-benzodiazepine conjugates).

As the activity of trans-MPC088 (19) far exceeds those of its precursors 10 and 11 (FIG. 59) and both truncated compounds 20 and 21 are inactive, the azobenzene residue (the part distal to the propofol moiety) is likely binding to another discrete site on the receptor; conceivably, the etomidate site thought to neighbor the propofol site (Forman (2011); Belelli et al. (1997); Drexler et al. (2009)). Thus, the activity of trans-MPC088 as compared to 10-12 might arise from ring stacking, hydrophobic and/or hydrogen bonding interactions of the lower part of the molecule with this other site. The hypothesis of specific site-binding is supported by the substantial difference in activities of the trans vs. cis isomers of MPC088. The initial limited SAR, based on structures synthesized so far, suggests that the activity of trans-MPC088 relies on the presence of the propofol moiety attached via its para-position to the distal phenyl ring (FIG. 65, fragment D), separated from propofol by about 15-20 Å in the extended conformation of trans-MPC088. In addition, the presence of specific residues on ring D is important since all of the compounds 14-17 were significantly less active than trans-MPC088; the distal phenyl ring D should most likely contain hydrogen-bonding residues. Because trans-MPC088 is more hydrophobic than propofol (log P>6 vs. ca. 4), the increased hydrophobicity due to the presence of aromatic residues must be offset by incorporating polar residues between the two constitutive fragments of the construct. Synthetic efforts will initially be aimed at determining the minimal pharmacophore still supporting direct activation of the receptor, by gradual simplification of the trans-MPC088 structure, and later at the enhancement of activity by modifying the propofol residue and exploring the chemical diversity of fragment E.

Example 22

Reduction of Structure Complexity, and Binding Enhancement of the Minimal Pharmacophore The aromatic ring proximal to propofol is likely not important for activity since the corresponding compound 21 (FIG. 59) is inactive, while compounds 10-12 retain some level of activity. Specific approaches to be pursued are as follows:

(a) Test for the Need for the Azo Group (Fragment C).

Synthesis of an analog in which the azo-group is replaced by a C—C bond (24; FIG. 66) has begun. By contrast with MPC088, preparations of which always contain inseparable mixtures of trans and cis isomers, this compound will be available as pure trans and cis isomeric forms. If the carbon analog(s) 24 prove(s) inactive, it will suggest a requirement for a hydrogen bond acceptor in this fragment of the molecule. In such an instance, the azo group function will be mimicked by incorporating other chemically and metabolically more stable basic residues such as triazole (25, X=N) or a corresponding imidazole (X=CH). However, if the carbon analog proves active, testing of whether the rigidity of fragment C is important will be performed by reducing the C=C bond.

(b) Test for the Need for Fragment B by Substituting a Flexible Alkylalkenyl Linker or Alicyclic Moiety.

The replacement of both fragments B and C with an aminohexanoyl residue will provide an analog 26 in which the lower phenyl ring (FIG. 66; fragment D) is at a similar distance from propofol as that in trans-MPC088. This compound also has a predicted log P in a range similar to that of propofol. The length of this linker will be optimized for maximum activity (26). Alternatively, the phenyl ring will be replaced by a saturated 6-membered ring (more flexible than phenyl but more rigid than alkyl) without or with heteroatoms (e.g., piperazine 27).

(c) Test for Necessity of the Para Geometry of Fragment D.

Meta- and ortho-analogs (28) will first be introduced, and then the phenyl ring will be replaced with either substituted pyridine or pyrimidine (FIG. 66).

(d) Test the Effect of Alternative Distal Ring Appendices (Fragment E).

In a simple synthetic scheme, a range of aliphatic diamines with different separation between nitrogens (30) will be explored, including cyclic (e.g., piperazine and morpholine 29) and aromatic (e.g., imidazole 31) aliphatic diamines (FIG. 66).

(e) Change Propofol Moiety to a Sec-Butyl Analog (Fragment A).

Previous work examining anesthetic activity indicated that mono- and di-sec-butyl analogs of propofol have a receptor affinity 10-fold greater than that of propofol (Maciagiewicz et al. (2007)). Therefore, mono- and di-sec-butyl analogs of the best ligands optimized above will be synthesized using methods that have already been developed. Since the increased potency of trans-MPC088 (as compared to propofol) is most likely due to interactions outside of the propofol core, it is entirely possible that the binding energy contributions from the propofol head and the bottom part of the molecule could be additive. If these analogs have substantially increased affinity, the effect of the chirality of the sec-butyl substituent will be further tested by separating enantiomers via chiral chromatography. Enantiomers of a barbiturate analog have recently been separated for testing at $GABA_A Rs$.

Each of the tasks described above will necessitate synthesis of a series of related structures, leading overall to a fairly large number of compounds to be made in this specific aim. Where possible, current approaches to generating chemical diversity can be adopted, such as parallel synthesis, and enabling preparation of multiple compounds in a single step.

Example 23

Whole-Cell Electrophysiology

Structures prepared above will be tested for effects on the electrophysiological properties of oocyte-expressed α1β2γ2 receptors, α1β2γ2 $GABA_A$R-expressing HEK 293 cells, and isolated single bipolar and ganglion cells of rat retina. Results obtained in these in vitro experiments will provide performance measures and thus guide the chemical syntheses.

(a) $GABA_A$-Expressing Oocytes:

Using known procedures (Vu et al. (2005); Muni et al. (2006); Adamian et al. (2009)), Xenopus oocytes expressing α1β2γ2 $GABA_A$ receptors will be prepared and examined to determine the potentiating and direct agonist activities of the new compounds. Of particular importance will be to compare the activities of these structures with trans-MPC088, the current lead compound. Primary evaluation criteria will be the absolute potency of the test compound in direct receptor activation, and in potentiating the response to a fixed, low concentration of GABA (e.g., 3 μM; see FIGS. 35, 36, 38). Additional key criteria will be considerations of polar vs. hydrophobic character and minimal molecular size (for ultimate potential in vivo applications). As further characterization, the action of pharmacological agents (e.g., $GABA_A$R antagonists such as bicuculline and picrotoxin) (e.g., Yue et al. (2001); Muni et al. (2006)) will be examined on the compound's activity. Aim 2b will also include tests of the propofol-benzodiazepine bivalent compound at mutant α1β2γ2 $GABA_A$Rs where the binding of either parent propofol or benzodiazepine is blocked by amino acid substitution at one of the respective receptor sites (Krasowski et al. (2001); Bali et al. (2009); Tan et al. (2011)). The rationale here is that, by comparison with the wild-type receptor that permits bivalent binding by the compound at the relatively distant propofol and benzodiazepine sites, investigation of the mutant receptor with mutationally blocked binding at one of these two sites (also see Amin et al. (1997); Moraga-Cid et al. (2011)) may afford a useful test of the potency enhancement enabled (in the wildtype) by bivalency.

(b) HEK Cells:

Design of the whole-cell voltage-clamp experiments to test the new compounds in HEK 293 cells will follow that to be used in the initial screening in the oocyte expression system (Gussin et al. (2011); Xie et al. *Malec. Pharmacol* (2011)).

(c) Isolated Retinal Ganglion Cells and Bipolar Cells:

Single, isolated bipolar and ganglion cells will be prepared from rat retina and studied by patch-clamp recording, using known procedures (Yue et al. (2011); Xie et al. (2010); Xie et al. *Invest Ophthalmol. Vis. Sci.* (2011); and FIGS. 60-61). In these experiments, the potency and efficacy of the new compounds will be determined in tests of both direct agonist and potentiation activity. As noted above, the new compounds to be examined in the retinal cell preparations will be those judged in the oocyte and HEK 293 screens to be most promising with respect to high potency, minimal molecular size, and suitable hydrophobic vs. polar character. Investigation of these compounds will include pharmacological tests to verify activity of the compound at $GABA_ARs$, and experimental designs to test for post-treatment effects of the compounds on $GABA_AR$ activity (e.g., Yue et al. (2011)).

Example 24

Consideration of Binding Analysis

As described above, all of the new compounds to be prepared will be screened for electrophysiological activity in $\alpha1\beta2\gamma2$ $GABA_AR$-expressing oocytes. Compounds judged to be promising based on this initial screen will be further evaluated by study of their electrophysiological activity in the technically more demanding preparations (transiently transfected, $\alpha1\beta2\gamma2$ $GABA_AR$-expressing HEK cells; native $GABA_ARs$ of retinal ganglion and bipolar cells); and (due to technical difficulty, only for exceptionally promising compounds) single-channel analysis. A logical and important complementary further analysis for these most promising compounds would be to test the hypothesized receptor-binding mode of the compound, by functionalizing the compound with radiolabel and photoaffinity tags, and determining the site(s) of binding to the receptor.

Example 25

Propofol-Etomidate Construct

As suggested above, due to the proximity of the binding sites of propofol and etomidate, it should be possible to design chimeric ligands that could target both sites and hence have very high affinity. Certain analogs shown in the preceding section already bear resemblance to etomidate structure. The simplest approach, although associated with significant risk, is to synthesize molecules in which propofol is directly linked to etomidate. While it may be difficult (or even impossible) to scan the whole space of relative orientations of the two fragments and their distances, this approach is worthwhile due to its potentially high significance and the utility of such a chimeric ligand. The design is based on recent findings that modifications of the ethyl ester and phenyl ring of etomidate are possible with retention of anesthetic activity, and that modifications of etomidate at the p-position of the phenyl ring and of its ester group are permissible (Husain et al. (2010)). Two methods of "hybrid" creation are envisioned. First, propofol will be linked to etomidate via the phenyl ring (e.g., 31; FIG. 67). This will necessitate synthesis of the 4-aminophenyl analog of etomidate, starting from the corresponding commercially available 4-nitroacetophenone. Synthesis of etomidate has previously been carried out using known methodology via a Mitsunobu reaction. The second mode of "hybridization" will involve linking etomidate via its ester function (e.g., 32; FIG. 67). In each case the effect of the distance between propofol and etomidate on ligand's activity will be explored by varying the length of the linkers. Another version (33; FIG. 67) of the second hybrid, which is expected to be unable to bind to both sites simultaneously due to its shorter linker, is currently being synthesized and will be used as a reference compound. All of the ligands 31-33 are expected to show significant activity. However, it is anticipated that there will be large enhancements of both affinity, potentiation and direct activation as compared to each of the agents individually. Development of the bivalent ligand will be enhanced by molecular modeling techniques based on homology models (Campagna-Slater et al. *Neurosci. Lett.* (2007); Campagna-Slater et al. *J Mol. Graph. Model* (2007)) using MOE and Sybil molecular modeling software. The fidelity of homology models is presently insufficient for structure-based ligand design. Rather, the generated structures will be used to broadly examine certain parameters of the ligands, such as receptor surface polarity, approximate distances between the putative receptor-interacting groups, and conformational fit of the ligand to receptor interfaces. If successful, the new ligands would be very significant in pharmacological research, and as candidates toward development of new clinical CNS agents.

Example 26

Propofol-Benzodiazepine Construct

Results obtained with MPC100 indicate that this compound can exert modulation of $\alpha1\beta2\gamma2$ $GABA_AR$ at a propofol site when covalently anchored to the receptor at a position close to the benzodiazepine site ($\gamma2$ position 79; FIG. 38 and accompanying text). In addition, the 1'-aminoundecylsubstituted benzodiazepine 22 exhibits potentiation of $\alpha1\beta2\gamma2$ $GABA_ARs$ in oocytes at concentrations as low as 30 nM. Benzodiazepine 22 and, initially, trans-MPC088 (later, a more potent optimized analog of trans-MPC088 will be used) will be joined via a $PEG_{24}$ chain to yield the dual-site ligand 34 in FIG. 67. In terms of expected activity, this design has a high probability of success because (i) the PEG chain will be linked at a position remote from the benzodiazepine core, and hence should have minimal effect on benzodiazepine binding, and (ii) the activity of trans-MPC100 was not significantly compromised (as compared to transMPC088) by the acylation of its terminal amino group. A ligand with $PEG_{12}$ will also be synthesized as a standard for comparison; the $PEG_{12}$-containing ligand is expected not to be capable of binding simultaneously at both the propofol and benzodiazepine sites due to the shortness of the $PEG_{12}$ chain.

Example 27

Activity of Linear-Chain-Derivatized Benzodiazepine

Figure 64:
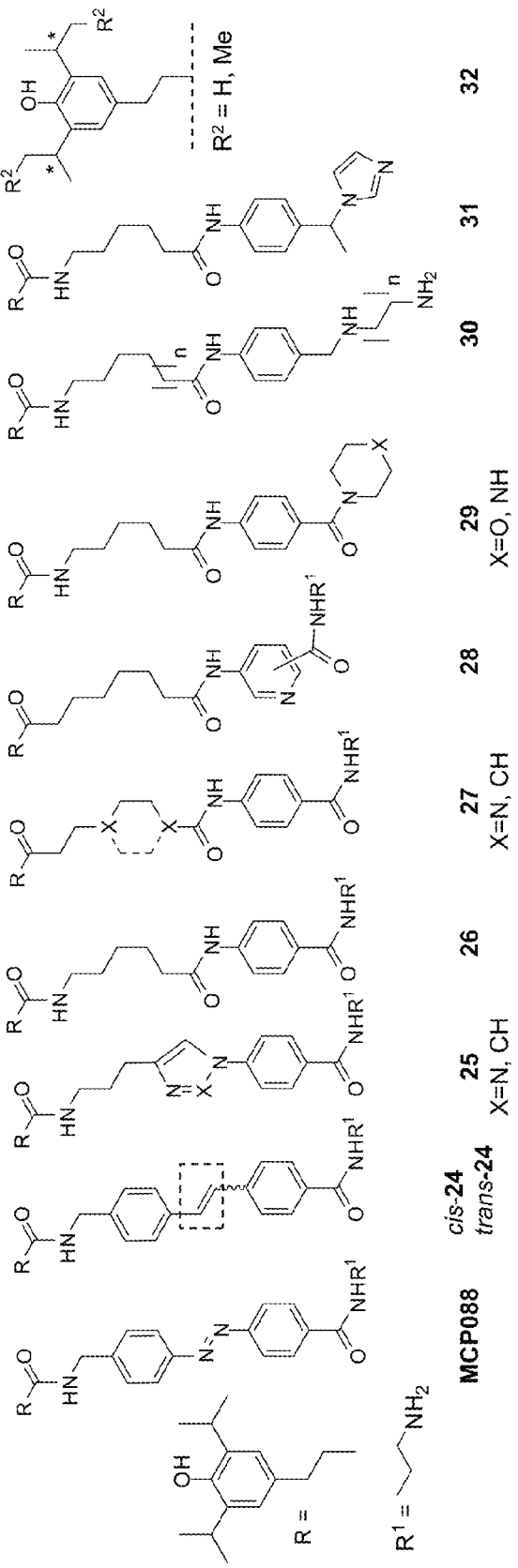
FIG. 64 depicts structures of analogs of propofol to be studied for minimal pharmacophore determination.

To develop a propofol- and benzodiazepine-based linear conjugate that reacts preferentially with $\gamma$-containing $GABA_ARs$, benzodiazepine was derivatized with a linear chain (for linkage to a propofol-containing, trans-MPC088-like structure), which preserves significant activity of the benzodiazepine. Results obtained in two types of experiment support this notion. First, benzodiazepine analog 22 (FIG. 64), which contains an amino-terminated alkyl chain attached at nitrogen-1 of the benzodiazepine, was prepared and supplied by Dr. Ian Tomlinson and Dr. Sandra Rosenthal (Vanderbilt Univ.). The synthetic route for this compound followed procedures similar to those reported by Velasquez et al. (1989). At $\alpha 1\beta 2\gamma 2$ GABA$_A$R-expressing Xenopus oocytes, (22 in FIG. 64) exhibits substantial potentiating activity. Specifically, at 30 nM concentration, 22 potentiates the 3 µM GABA response by a factor of 2.76±0.47 (n=3), a factor similar to (t-test p=0.051) the potentiation factor of 1.92±0.36 (n=3) produced by 30 nM diazepam (data not shown). Second, using procedures similar to those previously described (Gussin et al. (2006); Gussin et al. (2009); Gussin et al. (2010)), binding of a further functionalized benzodiazepine derivative to $\alpha 1\beta 2\gamma 2$ GABA$_A$R-expressing oocytes was examined. In this latter analog (23 in FIG. 64), also prepared by Drs. Tomlinson and Rosenthal, the linear chain of 22 is further extended by an amide-linked PEG5000 that is terminated by biotin. FIG. 64 shows representative fluorescence data obtained when an oocyte expressing $\alpha 1\beta 2\gamma 2$ GABA$_A$Rs was incubated with co-applied 10 µM 23 and 3 µM GABA, then with streptavidin-conjugated fluorophore (DyLight 488). Fluorescence (top row) and bright-field (bottom row) images of an oocyte expressing $\alpha 1\beta 2\gamma 2$ GABA$_A$Rs (left) and a nonexpressing oocyte (right), following, sequentially: 10-min incubation in Ringer supplemented with 3 µM GABA and 10 µM 23; washing with Ringer; 5-min incubation in Ringer supplemented with 10 µg/ml of streptavidin-conjugated DyLight 488 (Thermo Scientific); and further washing in Ringer. Bright-field images of the (opaque) oocytes illustrate the focus of the oocyte border during fluorescence microscopy. Treatment of the GABA$_A$R-expressing oocyte produced a fluorescent border, indicating the binding of 23 to the oocyte surface membrane, and this signal was absent in control, non-GABA$_A$R-expressing oocytes. In addition, the fluorescent border in $\alpha 1\beta 2\gamma 2$-expressing oocytes was virtually eliminated when the incubation medium containing 10 µM 23 and 3 µM GABA was further supplemented with either 1 µM diazepam, 1 µM of 22, or 1 µM of a benzodiazepine lacking the N1-substituted linear chain of 22 (not shown), indicating that these other compounds competed with the binding of 23 at the benzodiazepine site. Together, these electrophysiological and fluorescence results suggest that the presence of the N1-conjugated linear chains in 22 and 23 preserves significant activity of the benzodiazepine moiety, Example 28

Animal Experiments

Electrophysiological experiments were conducted on Xenopus laevis oocytes expressing $\alpha_1\beta_2\gamma_2$ GABA$_A$Rs (rat $\alpha_1$, rat $\beta_2$ and human $\gamma_{2S}$); on single, isolated ganglion cells of rat retina; on Purkinje neurons (PNs) in acute slice preparations of mouse cerebellum; and on CA1 neurons in acute slice preparations of mouse hippocampus. Animal care and all procedures involving the use of animals were conducted in accordance with institutional policies of the University of Illinois at Chicago (for Xenopus laevis and rats), and with the approval of the Chancellor's Animal Research Committee (Institutional Animal Care and Use Committee) at the University of California, Los Angeles (for mice).

(a) Xenopus laevis Oocytes

Oocytes expressing $\alpha_1\beta_2\gamma_2$ receptors (rat $\alpha_1$, rat $\beta_2$ and human $\gamma_{2S}$) were prepared and studied by two-electrode voltage-clamp recording[58] (holding potential: −70 mV; amplifier: GeneClamp500B; Axon Instruments, Foster City, Calif.). Unless otherwise indicated, oocytes were superfused with Ringer solution (physiological saline) at a rate of ~1 mL/min. The experiments of FIGS. 35d-e, 36c-e and 47 involved periods of static bathing, i.e., halted superfusion. The $\gamma_2$(A79C) subunit was prepared by site-directed mutagenesis. Oocyte electrophysiological experiments were carried out in room light. A UV light-emitting diode (peak wavelength: 365 nm; Hamamatsu Photonics, Japan) and a microscope illuminator (white light; Schott Fostec, Auburn, N.Y.) provided UV and visible stimulating light. As measured at the position of the oocyte, the intensity of the UV light at 365 nm was 220 µW/mm$^2$. At 440 nm, the nominal strength of the visible (white) light (referred to as high-intensity visible light) was 28 µW/mm$^2$, and that of the ambient room illumination was 0.045 µW/mm$^2$. In all experiments, low-intensity visible light from the microscope illuminator (3 µW/mm$^2$ at 440 nm) was present at all times except those involving high-intensity visible illumination. Electrophysiological data were obtained using Clampex 8.2 (Axon Instruments), analyzed using Clampfit 10.0 (Axon Instruments) and OriginPro7.5 (OriginLab, Northampton, Mass.). All statistical analysis employed a two-sample t-test.

(b) Retinal Ganglion Cells of Rat

Experiments were conducted on enzymatically dissociated ganglion cells obtained from adult Sprague-Dawley rats (male and female, 6-16 weeks of age) (Charles River Laboratories, Wilmington, Mass.). Procedures for euthanasia, isolation of the retina, and the dissociation of retinal cells were as described previously (Ramsey et al. (2007) except that the period of retinal cell dissociation was shortened from 40 min to 20 min. Isolated ganglion cells were identified on the basis of their morphological appearance and the presence of a large voltage-gated sodium current. Whole-cell patch-clamp techniques similar to those described (Ramsey et al. (2007)) were used to record membrane current responses to test agents. The patch pipette with a resistance of 8-12 MΩ was pulled in two stages using a micro-electrode puller (Model PP830, Narishige Group, Tokyo, Japan). The pipette was filled with an intracellular solution containing 95 mM CsCH$_3$SO$_3$, 20 mM TEA-Cl, 10 mM glutamic acid, 1 mM BAPTA, 10 mM HEPES, 8 mM phosphocreatine di(tris), 1 mM MgATP and 0.2 mM Na$_2$GTP; pH adjusted to 7.2 with CsOH. Cells were clamped at 0 mV (Axopatch 200B amplifier; Axon Instruments), and experimental runs were controlled by pCLAMP system software (Axon Instruments). Electrophysiological data were obtained in response to test compounds dissolved in physiological saline (Ringer solution) that consisted of 135 mM NaCl, 5 mM KCl, 2 mM CaCl$_2$, 2 mM MgCl$_2$, 10 mM glucose, and 5 mM HEPES, pH 7.4. Supplementation of aqueous test solutions with MPC088 was carried out by adding an aliquot of a stock solution containing the compound dissolved in dimethyl sulfoxide (DMSO). In all experiments, the amount of carrier DMSO present in the applied test solution was <1% (v/v). Test solutions were delivered from separate reservoirs by a multi-channel perfusion system. The same UV-LED used in the oocyte experiments was used for UV illumination of MPC088-supplemented test solutions. For preparation of cis-dominant MPC088, the test solution of initially trans-dominant compound underwent a 5-min UV illumination prior to its placement in the perfusion reservoir. All preparative procedures were performed in the dark, and the reservoirs and perfusion lines were light-protected with aluminum foil. As in the oocyte experiments, data were analyzed with Clampfit and plotted with Origin. Unless otherwise stated, numerical data from replicate experiments are presented as mean±SD, and all statistical analyses of data obtained from oocytes and from retinal ganglion cells employed a two-sample t-test.

(c) Cerebellar Purkinje Neurons (PNs) of Mouse

Experiments on cerebellar PNs employed acute slices obtained from cerebella of 16-30 day-old C57/BL6 mice (Charles River Laboratories). After induction of deep anesthesia with isoflurane, mice were decapitated, and the cerebellum vermis was removed and placed in an ice-cold cutting solution containing (in mM): 85 NaCl, 2.5 KCl, 0.5 $CaCl_2$, 4 $MgCl_2$, 1.25 $NaH_2PO_4$, 24 $NaHCO_3$, 25 glucose, and 75 sucrose. A Leica VT1000 vibratome was used to cut 250 µm thick, sagittal slices from the cerebellar vermis. Slices were then placed in an external recording solution containing (in mM): 119 NaCl, 2.5 KCl, 2 $CaCl_2$, 1 $MgCl_2$, 1 $NaH_2PO_4$, 26.2 $NaHCO_3$, and 25 glucose. The solution was warmed to 35° C. for 15-20 min and then allowed to reach room temperature. Both the cutting solution and the recording solution were continuously bubbled with 95% $O_2$/5% $CO_2$, and the recording solution was perfused at the rate of 2-4 mL/min.

Whole-cell voltage-clamp recordings were carried out at room temperature from PNs with an Axopatch 200A amplifier (Axon Instruments), and the neurons were held at −70 mV. Recording pipettes had bath resistances of 2-6 MΩ and were pulled using a horizontal micropipette puller (Model P-1000 Flaming/Brown Micropipette Puller, Sutter Instrument Company, Novato, Calif.). The internal solution for voltage clamp (FIGS. 40 and 42) contained (in mM): 140 CsCl, 3 NaCl, 10 HEPES, 2 $MgCl_2$, 4 ATP, 0.4 GTP, 1 EGTA, 10 TEA-Cl and 5 QX-314 Br (to block respectively, $K_v$ and $Na_v$ channels), and pH was adjusted to 7.4 with CsOH. Cs-based internal solutions prevented a small, UV light-elicited, transient outward current that was seen in the absence of GABA or MPC088. In some recordings $CdCl_2$ (100 µM) was included in the external solution to block synaptic transmission. Although we found no differences in the magnitudes of the MPC088-dependent currents, this had two benefits; it reduced spontaneous synaptic activity which would otherwise appear as high frequency noise on the traces, and it confirmed that MPC088 actions were cell-autonomous.

Whole-cell current-clamp recordings from PNs were carried out at room temperature with the same equipment as described above. Recording pipettes had bath resistances of 6-9 MΩ. The internal solution substituted 126-130 mM $KMeSO_3$ for CsCl/(TEA-Cl) and contained 5 mM EGTA. In some cases internal solutions for current clamp included 5 mM phosphocreatine and KCl substituted for NaCl to yield a final chloride concentration of 14 mM. Where appropriate, distilled water was added to adjust final osmolarity. In some cases positive current was injected into the PNs to elicit spiking. Local drug application to the PNs was achieved with a glass pipette (2-3 µm tip diameter) filled with the solution containing the indicated compounds dissolved in filtered external recording solution. Pressure pulses (0.5 to 2 psi) were provided by a Picospritzer II (Parker Hannifin Co., Cleveland, Ohio). Data from cells were excluded from analysis if there was no detectable decrease in firing rate with GABA+MPC088 application. They were also excluded if the average baseline (2-s epoch before drug application) firing rates fell outside the range 5 to 100 Hz, or if the cell stopped firing completely in the midst of the trial and did not recover by the end of the trial.

Pulses of UV light were presented to the tissue by shuttering a 100 W mercury arc lamp. Light from this source was collimated and focused through the objective lens of the recording apparatus. The broad-spectrum light from the arc lamp passed through an excitation filter (366 nm; full-width at half-maximum, 16.6 nm; Semrock, Inc., Rochester, N.Y.) to isolate the UV component, and reflected off a dichroic mirror (409 nm cutoff, Semrock, Inc.) (FIG. 40*a*). The blue light source was a 470 nm LED (Quadica Developments, Inc., Brantford, Ontario, Canada) that was connected to a beamsplitter cube (Siskiyou Designs, Grants Pass, Oreg.) located in the infinity space above the objective. The blue light was reflected by the dichroic mirror (500 nm cutoff, Chroma Technology Co., Bellows Falls, Vt.) positioned in the beamsplitter cube such that it passed through the 409 nm dichroic mirror in the UV filter cube to reach the slice. This configuration allowed UV and blue light to be combined in the epifluorescence path and independently controlled. To minimize exposure of the slice preparation and MPC088-containing solutions to ambient room light, the experimental apparatus housing the cerebellar slice, microscope, micromanipulators and perfusion lines was shielded by a dark curtain, and a photographic safe-light was used inside the area housing these components. Illumination from the microscope lamp used for visual inspection of the tissue passed through a Wratten 2 29 filter that attenuated wavelengths below 600 nm. All data from experiments on PNs are presented as mean±SEM.

(d) Cerebellar PNs

For the voltage-clamp experiments of FIG. 40, each cell was particular between 1-6 trials of the drug application+light flash protocol. All traces from a particular cell were then averaged, and magnitudes of the normalized current changes produced by the light flashes were obtained as described in Results. These data were then averaged across all cells to obtain the illustrated results. This analysis was done using ClampFit (Molecular Devices, Sunnyvale, Calif.), Excel, and SigmaPlot 11.0 (Systat Software, Inc., Chicago, Ill.). For the current-clamp experiments described in FIG. 41, each investigated cell underwent 1-6 trials of the drug application+light flash protocol (or in the case of the negative controls in FIG. 41*c*, the light flash only). A peri-stimulus time histogram (PSTH) was calculated for each trial using 250-ms time bins; these were averaged across trials to produce a PSTH for the experiment, using the software TaroTools (Dr. Taro Ishikawa, Jikei University School of Medicine, Tokyo, Japan) and Igor Pro 6.2 (WaveMetrics, Inc., Lake Oswego, Oreg.). Average spiking frequencies were computed for the 1-s epochs indicated in FIG. 41, and then normalized to the average spiking frequency for the 1-s epoch immediately preceding the GABA+MPC088 application (or, in the case of the negative controls, the 1-s epoch immediately preceding the first UV flash).

Example 29

Test of Effects of MPC088 on AMPAR/NMDAR-Mediated EPSCs

Recordings from hippocampal CA1 pyramidal neurons were obtained from 17-23 day old animals. Briefly, the hippocampus was completely removed from the brain and then sliced in 300-µm sections. Prior to recording, a cut was made with a scalpel blade between CA1 and CA3 in order to completely sever all connections between the two; this was done in order to abolish polysynaptic activity due to antidromic activation of CA3 pyramidal cells. Recordings were carried out under voltage clamp with an internal solution containing (in mM): 130 CsCl, 10 HEPES, 1 CaCl2, 2 ATP, 0.2 GTP, 10 EGTA, and 5 QX-314 Br, and pH was adjusted to 7.3 with CsOH. All data from these experiments are presented as mean±SEM.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting.

Thus, the breadth and scope of the present invention should not be limited by any of the above-described exemplary embodiments, but should be defined only in accordance with the following claims appended hereto and their equivalents.

REFERENCES

The following references, to the extent they provide exemplary procedural or other details supplementary to those set forth herein, are specifically incorporated herein by reference.

1. Baulac, S. et al. First genetic evidence of $GABA_A$ receptor dysfunction in epilepsy: a mutation in the $\gamma_2$-subunit gene. *Nature Genetics* 28, 46-48 (2001).
2. Palma, E. et al. Abnormal $GABA_A$ receptors from the human epileptic hippocampal subiculum microtransplanted to *Xenopus* oocytes. *Proc. Natl. Acad. Sci. USA* 102, 2514-2518 (2005).
3. Goodkin, H. P., Joshi, S., Mtchedlishvili, Z., Brar, J. & Kapur, J. Subunit-specific trafficking of $GABA_A$ receptors during status epilepticus. *J. Neurosci.* 28, 2527-2538 (2008).
4. Macdonald, R. L., Kang, J.-Q. & Gallagher, M. J. Mutations in $GABA_A$ receptor subunits associated with genetic epilepsies. *J. Physiol.* 588, 1861-1869 (2010).
5. Power, K. N., Flaatten, H., Gilhus, N. E. & Engelsen, B. A. Propofol treatment in adult refractory status epilepticus. Mortality risk and outcome. *Epilepsy Res.* 94, 53-60 (2011).
6. Iyer, V. N., Hoel, R. & Rabinstein, A. A. Propofol infusion syndrome in patients with refractory status epilepticus: an 11-year clinical experience. *Crit. Care Med.* 37, 3024-3030 (2009).
7. Rossetti, A. O. & Lowenstein, D. H. Management of refractory status epilepticus in adults: still more questions than answers. *Lancet Neurol.* 10, 922-930 (2011).
8. Yizhar, O., Fenno, L. E., Davidson, T. J., Mogri, M. & Deisseroth, K. Optogenetics in neural systems. *Neuron* 71, 9-34 (2011).
9. Farrant, M. & Nusser, Z. Variations on an inhibitory theme: phasic and tonic activation of $GABA_A$ receptors. *Nature. Rev. Neurosci.* 6, 215-229 (2005).
10. Olsen, R. W. & Sieghart, W. $GABA_A$ receptors: subtypes provide diversity of function and pharmacology. *Neuropharmacology* 56, 141-148 (2009).
11. Mortensen. M., Ebert, B., Wafford, K. & Smart, T. G. Distinct activities of GABA agonists at synaptic- and extrasynaptic-type $GABA_A$ receptors. *J. Physiol.* 588, 1251-1268 (2010).
12. Standaert, R. F. & Park, S. B. Abc amino acids: design, synthesis and properties of new photoelastic amino acids. *J. Org. Chem.* 71, 7952-7966 (2006).
13. Beharry, A. A. & Woolley, G. A. Azobenzene photoswitches for biomolecules. *Chem. Soc. Rev.* 40, 4422-4437 (2011).
14. Sadovski. O., Beharry, A. A. Zhang, F. & Woolley G. A. Spectral tuning of azobenzene photoswitches for biological applications. *Angew. Chem. Int. Ed.* 48, 1484-1486 (2009).
15. Gorostiza, P. & Isacoff, E. Y. Optical switches for remote and noninvasive control of cell signaling. *Science* 322, 395-399 (2008).
16. Bali, M. & Akabas, M. H. The location of a closed channel gate in the $GABA_A$ receptor channel. *J. GenPhysiol.* 129, 145-159 (2007).
17. Ueno, S., Bracamontes, J., Zorumski, C., Weiss, D. S. & Steinbach, J. H. Bicuculline and gabazine are allosteric inhibitors of channel opening of the $GABA_A$ receptor. *J. Neurosci.* 17, 625-634 (1997).
18. Amin, J. & Weiss, D. S. $GABA_A$ receptor needs two homologous domains of the $\beta$-subunit for activation by GABA but not by pentobarbital. *Nature* 366, 565-569 (1993).
19. Muroi, Y., Theusch, C. M., Czajkowski, C. & Jackson, M. B. Distinct structural changes in the $GABA_A$ receptor elicited by pentobarbital and GABA. *Biophys. J.* 96, 499-509 (2009).
20. Jones, M. V., Sahara, Y., Dzubay, J. A. & Westbrook, G. L. Defining affinity with the $GABA_A$ receptor. *J. Neurosci.* 18, 8590-8604 (1998).
21. Adodra, S. & Hales, T. G. Potentiation, activation and blockade of $GABA_A$ receptors of clonal murine hypothalamic GT1-7 neurones by propofol. *Br. J. Pharmacol.* 115, 953-960 (1995).
22. Chang, C. S., Olcese, R. & Olsen, R. W. A single M1 residue in the $\beta 2$ subunit alters channel gating of $GABA_A$ receptor in anesthetic modulation and direct activation. *J. Biol. Chem.* 278, 42821-42828 (2003).
23. Farrant, M. & Nusser, Z. Variations on an inhibitory theme: phasic and tonic activation of $GABA_A$ receptors. *Nature. Rev. Neurosci.* 6, 215-229 (2005).
24. Wisden, W., Korpi, E. R. & Bahn, S. The cerebellum: a model system for studying $GABA_A$ receptor diversity. *Neuropharmacol.* 35, 1139-1160 (1996).
25. Fritschy, J.-M., Panzanelli, P., Kralic, J. E., Vogt, K. E. & Sassoè-Pognetto, M. Differential dependence of axo-dendritic and axo-somatic GABAergic synapses on $GABA_A$ receptors containing the $\alpha 1$ subunit in Purkinje cells. *J. Neurosci.* 26, 3245-3255 (2006).
26. Wulff, P. et al. From synapse to behavior: rapid modulation of defined neuronal types with engineered $GABA_A$ receptors. *Nature Neurosci.* 10, 923-929 (2007).
27. Mortensen. M., Ebert, B., Wafford, K. & Smart, T. G. Distinct activities of GABA agonists at synaptic- and extrasynaptic-type $GABA_A$ receptors. *J. Physiol.* 588, 1251-1268 (2010).
28. Meera, P., Olsen, R. W., Otis, T. S. & Wallner, M. Etomidate, propofol and the neurosteroid THDOC increase the GABA efficacy of recombinant $\alpha 4\beta 3\delta$ and $\alpha 4\beta 3$ $GABA_A$ receptors expressed in HEK cells. *Neuropharmacology* 56, 155-160 (2009).
29. Jurd, R. et al. General anesthetic actions in vivo strongly attenuated by a point mutation in the $GABA_A$ receptor $\beta 3$ subunit. *FASEB J.* 17, 250-252. (2003).
30. Siegwart, R., Jurd, R. & Rudolph, U. Molecular determinants for the action of general anesthetics at recombinant $\alpha_2\beta_3\gamma_2$ $\gamma$-aminobutyric $acid_A$ receptors. *J. Neurochem.* 80, 140-148 (2002).
31. Mihic, S. J. & Harris, R. A. Inhibition of $\rho_1$ receptor GABAergic currents by alcohols and volatile anesthetics. *J. Pharmacol. Exp. Ther.* 277, 411-416 (1996).
32. Kucken, A. M. et al. Identification of benzodiazepine binding site residues in the $\gamma_2$ subunit of the $\gamma$-aminobutyric $acid_A$ receptor. *Molec. Pharmacol.* 57, 932-939 (2000).
33. Kucken, A. M., Teisséré, J. A., Seffinga-Clark, J., Wagner, D. A. & Czajkowski, C. Structural requirements for imidazobenzodiazepine binding to $GABA_A$ receptors. *Molec. Pharmacol.* 63, 289-296 (2003).
34. Banghart, M., Borges, K., Isacoff, E., Trauner, D. & Kramer, R. H. Light-activated ion channels for remote control of neuronal firing. *Nature Neurosci.* 7, 1381-1386 (2004).

35. Volgraf, M. et al. Allosteric control of an ionotropoic glutamate receptor with an optical switch. *Nature Chem. Biol.* 2, 47-52 (2006).

36. Janovjak, H., Szobota, S., Wyart, C., Trauner, D. & Isacoff, E. Y. A light-gated, potassium-selective glutamate receptor for the optical inhibition of neuronal firing. *Nature Neurosci.* 13, 1027-1032 (2010).

37. Ishida, A. T. & Cohen, B. N. GABA-activated whole-cell currents in isolated retinal ganglion cells. *J. Neurophysiol.* 60, 381-396 (1988).

38. Fischer, K. F., Lukasiewicz, P. D. & Wong, R. O. L. Age-dependent and cell class-specific modulation of retinal ganglion cell bursting activity by GABA. *J. Neurosci.* 18, 3767-3778 (1998).

39. Rotolo, T. C. & Dacheux, R. F. Evidence for glycine, $GABA_A$ and $GABA_B$ receptors on rabbit OFF-alpha ganglion cells. *Visual Neurosci.* 20, 285-296 (2003).

40. Wässle, H., Koulen, P., Brandstätter, J. H., Fletcher, E. L. & Becker, C.-M. Glycine and GABA receptors in the mammalian retina. *Vision Res.* 38, 1411-1430 (1998).

41. Yue L, Xie A, Bruzik K S, Frolund B, Qian H & Pepperberg D R. Potentiating action of propofol at $GABA_A$ receptors of retinal bipolar cells. *Invest. Ophthalmal. Vis. Sci.* 52:2497-2509 (2011).

42. Yue L, Pawlowski M, Feng F, Bruzik K S, Qian H & Pepperberg D R. Light-modulated activation of $GABA_A$ receptors by a propofol-azobenzene conjugate. 2010 Society for Neuroscience Meeting, Abstract 338.21 (2010).

43. Yue L, Pawlowski M, Bruzik K S, Qian H & Pepperberg D R. Photo-regulated activity of a tethered propofol derivative at $GABA_A$ receptors. *Invest. Ophthalmol. Vis. Sci.* 52: ARVO E-abstract 11166 (2011).

44. Ragozzino D, Woodward R M, Murata Y, Eusebi F, Overman L E & Miledi R. Design and in vitro pharmacology of a selective y-aminobutyric acidc receptor antagonist. *Malec. Pharmacal.* 50:1024-1030 (1996).

45. Häusser, M. & Clark, B. A. Tonic synaptic inhibition modulates neuronal output pattern and spatiotemporal synaptic integration. *Neuron* 19, 665-678 (1997).

46. Smith, S. L. & Otis, T. S. Persistent chances in spontaneous firing of Purkinje neurons triggered by the nitric oxide signaling cascade. *J. Neurosci.* 23, 367-372 (2003).

47. Santhakumar, V., Hanchar, H. J., Wallner, M., Olsen, R. W. & Otis, T. S. Contributions of the $GABA_A$ receptor α6 subunit to phasic and tonic inhibition revealed by a naturally occurring polymorphism in the α6 gene. *J. Neurosci.* 26, 3357-3364 (2006).

48. Jones, M. V., Sahara, Y., Dzubay, J. A. & Westbrook, G. L. Defining affinity with the $GABA_A$ receptor. *J. Neurosci.* 18, 8590-8604 (1998).

49. Pajouhesh H & Lenz G R. Medicinal chemical properties of successful central nervous system drugs. *NeuroRx* 6:541-553 (2005).

50. Jencks W R. On the attribution and additivity of binding energies. *Proc. Natl. Acad. Sci. USA* 78:4046-4050 (1981).

51. Trapani G, Latrofa A, Franco M, Altomare C, Sanna E, Usala M, Biggio G & Liso G. Propofol analogues. Synthesis, relationships between structure and affinity at $GABA_A$ receptor in rat brain, and differential electrophysiological profile at recombinant human $GABA_A$ receptors. *J. Med. Chem.* 41: 1846-1854 (1998).

52. Forman S. Clinical and molecular pharmacology of etomidate. *Anesthesiology* 114:695-707 (2011).

53. Belelli D, Lambert J J, Peters J A, Wafford K & Whiting P J. The interaction of the general anesthetic etomidate with the γ-aminobutyric acid type A receptor is influenced by a single amino acid. *Proc. Natl. Acad. Sci. USA* 94:11031-11036 (1997).

54. Drexler B, Jurd R, Rudolph U & Antkowiak B. Distinct actions of etomidate and propofol at β3-containing y-aminobutyric acid type A receptors. *Neuropharmacol.* 57:446-455 (2009).

55. Maciagiewicz I, Bruzik K S, Hopfinger A J, Jenkins A & Harrison N. Design and synthesis of propofol analogs as new anesthetic agents. ACS National Meeting, Chicago, Ill., Apr. 24-28, 2007 (2007).

56. Vu T Q, Chowdhury S, Muni N J, Qian H, Standaert R F & Pepperberg D R. Activation of membrane receptors by a neurotransmitter conjugate designed for surface attachment. *Biamaterials* 26: 1895-1903 (2005).

57. Muni N J, Qian H, Qtaishat N M, Gemeinhart R A & Pepperberg D R. Activation of membrane receptors by neurotransmitter released from temperature-sensitive hydrogels. *J. Neurosci. Meth.* 151:97-105 (2006).

58. Adamian L, Gussin H A, Tseng Y Y, Muni N J, Feng F, Qian H, Pepperberg D R & Liang J. Structural model of ρ1 GABAc receptor based on evolutionary analysis: Testing of predicted protein-protein interactions involved in receptor assembly and function. *Protein Sci.* 18:2371-2383 (2009).

59. Krasowski M D, Nishikawa K, Nikolaeva N, Lin A & Harrison N L. Methionine 286 in transmembrane domain 3 of the $GABA_A$ receptor β subunit controls a binding cavity for propofol and other alkylphenol general anesthetics. *Neuropharmacal.* 41:952-964 (2001).

60. Bali M, Jansen M & Akabas M H. GABA-induced intersubunit conformational movement in the $GABA_A$ receptor α1M1-β2M3 transmembrane subunit interface: experimental basis for homology modeling of an intravenous anesthetic binding site. *J. Neurasci.* 29:3083-3092 (2009).

61. Tan K R, Rudolph U & Lüscher C. Hooked on benzodiazepines: $GABA_A$ receptor subtypes and addiction. *Trends Neurosci.* 34:188-197 (2011).

62. Amin J, Brooks-Kayal B & Weiss D S. Two tyrosine residues on the α subunit are crucial for benzodiazepine binding and allosteric modulation of γ-aminobutyric acid$_A$ receptors. *Malec. Pharmacal.* 91:833-841 (1997).

63. Moraga-Cid G, Yevenes G E, Schrnalzing G, Peoples R W & Aguayo L G. A single phenylalanine residue in the main intracellular loop of α1 γ-aminobutyric acid type A and glycine receptors influences their sensitivity to propofol. *Anesthesial.* 115:464-473 (2011).

64. Gussin H A, Khasawneh F T, Xie A, Feng F, Memic A, Qian H, Le Breton G C & Pepperberg D R. Subunit-specific polyclonal antibody targeting human p1 GABAc receptor. *Exper. Eye Res.* 93:59-64 (2011).

65. Xie A, Van J, Vue L, Feng F, Mir F, Abdel-Halim H, Chebib M, Le Breton G C, Standaert R F, Qian H & Pepperberg D R. 2-Aminoethyl methylphosphonate (2-AEMP), a potent and rapidly acting antagonist of $GABA_A$-ρ1 receptors. *Malec. Pharmacal.* Epub ahead of print (2011).

66. Xie A, Vue L, Feng F, Pepperberg D R & Qian H. Propofol potentiates GABA-elicited responses of bipolar and ganglion cells in rat retina. *Invest. Ophtha/mal. Vis. Sci.* 51: ARVO E-abstract 1865 (2010).

67. Xie A, Pawlowski M, Feng F, Bruzik K S, Qian H & Pepperberg D R. Enhancement of GABA-elicited responses of retinal ganglion cells by a photo-isomerizable compound. *Invest. Ophthalmal. Vis. Sci.* 52:ARVO E-abstract 1610 (2011).

68. Krasowski M D, Koltchine W, Rick C E, Ye Q, Finn S E & Harrison N L. Propofol and other intravenous anesthetics have sites of action on the γ-aminobutyric acid type A receptor distinct from that for isoflurane. *Molec. Pharmacol.* 53:530-538 (1998).
69. Colquhoun D & Hawkes A G. The principles of the stochastic interpretation of ion-channel mechanisms. In Single Channel Recordings, 2nd Edition; Plenum Press, NY; pp. 397-482 (1995).
70. Lema G M & Auerbach A. Modes and models of $GABA_A$ receptor gating. *J. Physiol.* 572:183-200 (2006).
71. Purohit Y & Grosman C. Block of muscle nicotinic receptors by choline suggests that the activation and desensitization gates act as distinct molecular entities. *J. Gen. Physiol.* 127:703-717 (2006).
72. Purohit Y & Grosman C. Estimating binding affinities of the nicotinic receptor for low-efficacy ligands using mixture of agonists and two-dimensional concentration-response relationships. *J. Gen. Physiol.* 127:719-735 (2006).
73. Husain S S, Stewart D, Desai R, Hamouda A K, Li S G-D, Kelly E, Dostalova Z, Zhou X, Cotten J F, Raines D E, Olsen R W, Cohen J B, Forman S A & Miller K W p-Trifluoromethyldiazirinyl-etomidate: a potent photoreactive general anesthetic derivative of etomidate that is selective for ligand-gated cationic ion channels. *J. Med. Chem.* 53:6432-6444 (2010).
74. Campagna-Slater V & Weaver D F. Anaesthetic binding sites for etomidate and propofol on a $GABA_A$ receptor model. *Neurosci. Lett.* 418:28-33 (2007).
75. Campagna-Slater V & Weaver D F. Molecular modelling of the $GABA_A$ ion channel protein. *J. Mol. Graph. Model.* 25:721-730 (2007).
76. Velazquez J L, Thompson C L, Barnes E M Jr & Angelides K J. Distribution and lateral mobility of GABA/benzodiazepine receptors on nerve cells. *J. Neurosci.* 9:2163-2169 (1989).
77. Gussin H A, Tomlinson 10, Little O M, Warnement M R, Qian H, Rosenthal S J & Pepperberg D R. Binding of muscimol-conjugated quantum dots to GABAc receptors. *J. Amer. Chem. Soc.* 128:15701-15713 (2006).
78. Gussin H A, Tomlinson 10, Little O M, Qian H, Rosenthal S J & Pepperberg D R. Quantum dot conjugates of GABA and muscimol: binding to GABAA and GABAc receptors Annual Meeting, SOciety for Neuroscience. Abstract number 114.4 (2009).
79. Gussin H A, Tomlinson 10, Muni N J, Little O M, Qian H, Rosenthal & Pepperberg D R. GABAc receptor binding of quantum-dot conjugates of variable ligand valency. *Bioconjugate Chem.* 21:1455-1464 (2010).
80. Ramsey, D. J., Ripps, H. & Qian, H. Streptozotocin-induced diabetes modulates GABA receptor activity of rat retinal neurons. *Exper. Eye Res.* 85, 413-422 (2007).

---

We claim:

1. A compound of formula:

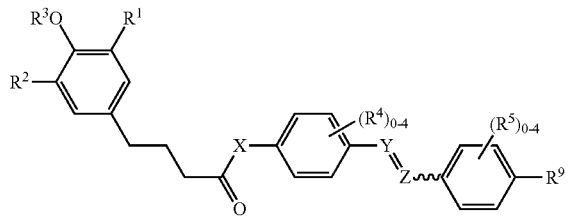

and pharmaceutically acceptable salts thereof, wherein
$R^1$ and $R^2$ are independently $C_1$-$C_{12}$ alkyl, halo($C_1$-$C_{12}$ alkyl), $C_2$-$C_{12}$ alkenyl, or $C_2$-$C_{12}$ alkynyl, each optionally substituted with 1, 2, 3 or 4 substituents selected from halogen, —CN, —NO$_2$, —OR$^6$, —NR$^6_2$, —CO$_2$R$^6$, —CONR$^6_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle is optionally substituted with 1, 2, 3 or 4 $R^7$;
$R^3$ is hydrogen, $C_1$-$C_6$ alkyl, or halo($C_1$-$C_6$ alkyl);
$R^4$ and $R^5$ are independently halogen, —CN, —NO$_2$, $C_1$-$C_6$ alkyl, halo($C_1$-$C_6$ alkyl), —OR$^6$, —NR$^6_2$, —CO$_2$R$^6$, or —CONR$^6_2$;
X is —N(R$^8$)—, —N(R$^8$)CH$_2$—, —N(R$^8$)CHR$^8$—, —N(R$^8$)(CHR$^8$)$_{2-5}$—, or —O—;
Y=Z is —N=N— or —C(R$^8$)=C(R$^8$)—; and
$R^9$ is hydrogen, —CHR$^{6a}$, —OR$^{6a}$, —NR$^{6a}_2$, —CO$_2$R$^{6a}$, —CONR$^{6a}_2$, —CON(R$^8$)—(CH$_2$)$_{1-6}$—NR$^{6a}_2$, —N(R$^8$)CO—(CH$_2$)$_{1-6}$—NR$^{6a}_2$, —CON(R$^8$)—(CH$_2$)$_{1-6}$—N(R$^8$)COR$^{6a}$, —N(R$^8$)CO—(CH$_2$)$_{1-6}$—N(R$^8$)COR$^{6a}$, —CON(R$^8$)—(CH$_2$)$_{1-6}$—N(R$^8$)COR$^{10}$, or —N(R$^8$)CO—(CH$_2$)$_{1-6}$—N(R$^8$)COR$^{10}$, wherein $R^{10}$ is —CH$_2$CH$_2$(OCH$_2$CH$_2$)$_{2-50}$—N(R$^8$)COR$^{6a}$;
where each $R^6$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;
where each $R^{6a}$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;
where each $R^7$ independently is halogen, —CN, —NO$_2$, —N$_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —CO$_2$H, —COH, —CO$_2$R$^8$, or —CON(R$^8$)$_2$; and
where each $R^8$ independently is hydrogen or $C_1$-$C_6$ alkyl.

2. The compound according to claim 1, wherein $R^3$ is hydrogen.

3. The compound according to claim 1, wherein $R^1$ and $R^2$ are independently $C_1$-$C_{12}$ alkyl, optionally substituted with one to four substituents selected from halogen, —CN, —$NO_2$, $C_1$-$C_6$ alkyl, halo($C_1$-$C_6$ alkyl), —$OR^6$, —$NR^6{}_2$, —$CO_2R^6$, —$CONR^6{}_2$, $C_3$-$C_8$ cycloalkyl, $C_3$-$C_8$cycloalkenyl, aryl, heteroaryl, and heterocycle.

4. The compound according to claim 3, wherein $R^1$ and $R^2$ are independently unsubstituted $C_1$-$C_{12}$ alkyl.

5. The compound according to claim 1, wherein X is —NH— or —O—.

6. The compound according to claim 1, wherein X is —$N(R^8)CH_2$—, —$N(R^8)CHR^8$—, or —$N(R^8)(CHR^8)_{2-5}$—.

7. The compound according to claim 6, wherein X is —$NHCH_2$—.

8. The compound according to claim 1, wherein $R^4$ and $R^5$ are independently selected from the group consisting of halogen, —CN, —$NO_2$, $C_1$-$C_6$ alkyl, halo($C_1$-$C_6$ alkyl), —$OR^6$, and —$NR^6{}_2$.

9. The compound according to claim 1, wherein $R^4$ and $R^5$ are absent.

10. The compound according to claim 1, wherein Y=Z are —N=N—.

11. The compound according to claim 1, wherein Y=Z are —CH=CH—.

12. The compound according to claim 1, wherein $R^9$ is hydrogen, —$CO_2R^{6a}$, —$CONR^{6a}{}_2$, —$CON(R^8)$—$(CH_2)_{1-6}$—$NR^{6a}{}_2$, —$CON(R^8)$—$(CH_2)_{1-6}$—$N(R^8)COR^{6a}$, or —$CON(R^8)$—$(CH_2)_{1-6}$—$N(R^8)COR^{10}$, wherein $R^{10}$ is —$CH_2CH_2(OCH_2CH_2)_{2-50}$—$N(R^8)COR^{6a}$.

13. The compound according to claim 12, wherein $R^9$ is hydrogen, —$CO_2H$, or —CONH—$(CH_2)_2$—$NH_2$.

14. The compound according to claim 13, wherein $R^9$ is —CONH—$(CH_2)_2$—$NH_2$.

15. The compound according to claim 12, wherein $R^9$ is —CONH—$(CH_2)_2$—$NHCOR^{10}$, wherein $R^{10}$ is —$CH_2CH_2$$(OCH_2CH_2)_{2-50}$—$NHCOR^{6a}$, and $R^{6a}$ is heterocycle($C_1$-$C_6$ alkyl) or heteroaryl($C_1$-$C_6$ alkyl).

16. The compound according to claim 15, wherein $R^9$ is

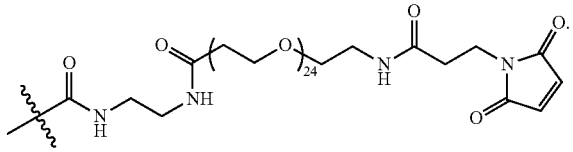

17. The compound according to claim 1, wherein
$R^1$ and $R^2$ are independently $C_1$-$C_{12}$ alkyl, halo($C_1$-$C_{12}$ alkyl), $C_2$-$C_{12}$ alkenyl, or $C_2$-$C_{12}$ alkynyl, each optionally substituted with 1, 2, 3 or 4 substituents selected from halogen, —CN, —$NO_2$, —$OR^6$, —$NR^6{}_2$, —$CO_2R^6$ and —$CONR^6{}_2$;
$R^3$ is hydrogen, $C_1$-$C_6$ alkyl, or halo($C_1$-$C_6$ alkyl);
$R^4$ and $R^5$ are independently halogen, —CN, —$NO_2$, $C_1$-$C_6$ alkyl, halo($C_1$-$C_6$ alkyl), —$OR^6$, —$NR^6{}_2$, —$CO_2R^6$, or —$CONR^6{}_2$;
X is —$N(R^8)$—, —$N(R^8)CH_2$—, —$N(R^8)CHR^8$—, —$N(R^8)(CHR^8)_{2-5}$—, or —O—;
Y=Z is —N=N— or —$C(R^8)$=$C(R^8)$—; and
$R^9$ is hydrogen, —$CHR^{6a}$, —$OR^{6a}$, —$NR^{6a}{}_2$, —$CO_2R^{6a}$, —$CONR^{6a}{}_2$, —$CON(R^8)$—$(CH_2)_{1-6}$—$NR^{6a}{}_2$, —$N(R^8)CO$—$(CH_2)_{1-6}$—$NR^{6a}{}_2$, —$CON(R^8)$—$(CH_2)_{1-6}$—$N(R^8)COR^{6a}$, —$N(R^8)CO$—$(CH_2)_{1-6}$—N$(R^8)COR^{6a}$, —$CON(R^8)$—$(CH_2)_{1-6}$—$N(R^8)COR^{10}$, or —$N(R^8)CO$—$(CH_2)_{1-6}$—$N(R^8)COR^{10}$, wherein $R^{10}$ is —$CH_2CH_2(OCH_2CH)_{2-50}$—$N(R^8)COR^{6a}$;
where each $R^6$ independently is hydrogen, $C_1$-$C_6$ alkyl or halo($C_1$-$C_6$ alkyl), wherein each alkyl is optionally substituted with 1, 2, 3 or 4 $R^7$, or two $R^6$ with the nitrogen to which they are attached form a heterocycle optionally substituted with 1, 2, 3 or 4 $R^7$;
where each $R^{6a}$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl)-, $C_3$-$C_8$cycloalkyl($C_1$-$C_6$ alkyl)-, aryl($C_1$-$C_6$ alkyl)-, heteroaryl($C_1$-$C_6$ alkyl)-, or heterocycle($C_1$-$C_6$ alkyl)-, wherein each alkyl, cycloalkyl, aryl, heteroaryl, and heterocycle is optionally substituted with 1, 2, 3 or 4 $R^7$, or two $R^6$ with the nitrogen to which they are attached form a heterocycle optionally substituted with 1, 2, 3 or 4 $R^7$;
where each $R^7$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —$CO_2H$, —COH, —$CO_2R^8$, or —$CON(R^8)_2$; and
wherein each $R^8$ is independently hydrogen or $C_1$-$C_6$ alkyl.

18. The compound according to claim 1, which is:

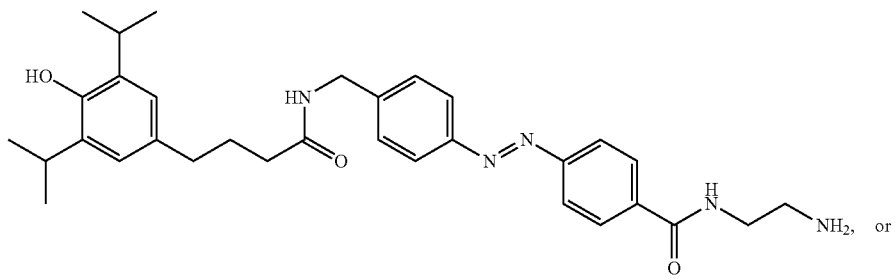

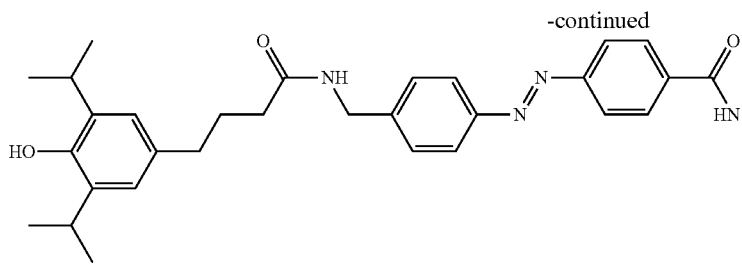

-continued

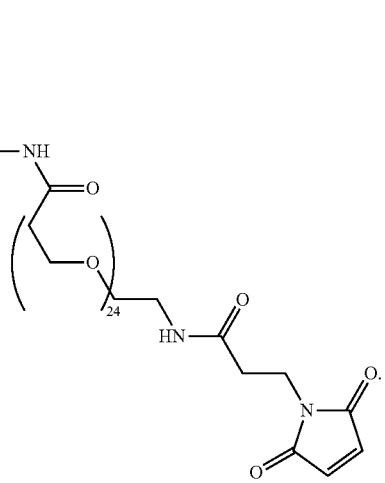

19. A pharmaceutical composition comprising a compound or a pharmaceutically acceptable salt of claim 1 and an acceptable carrier, excipient and/or diluent.

20. A method of activating a GABA receptor comprising administering an effective amount of a compound or a pharmaceutically acceptable salt of claim 1.

21. The method of claim 20 wherein said GABA receptor is a $GABA_A$.

22. A method of treating a disease of hyperexcitability comprising administering an effective amount of a compound or a pharmaceutically acceptable salt of claim 1.

23. The method of claim 22 wherein said hyperexcitability disease is epilepsy.

24. A method of treating a retinal neurodegenerative disease comprising administering an effective amount of a compound or a pharmaceutically acceptable salt of claim 1.

25. The method of claim 24 wherein said retinal neurodegenerative disease is macular degeneration.

26. A nanoscale neuromodulator platform apparatus for activating membrane receptors of a postsynaptic neuron in response to light, said apparatus comprising:
    an effector comprising a portion of a compound or pharmaceutically acceptable salt according to claim 1, which is:

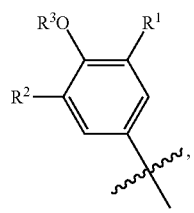

a photoswitch,
said photoswitch having a first configuration and second configuration, said first configuration being adapted to operatively approximate said effector with a postsynaptic receptor such that the receptor is activated;
said second configuration maintaining said effector remote from said operative approximation with the postsynaptic receptor such that the receptor remains unactivated;
said photoswitch being mediated between said first configuration and said second configuration by exposure to a preconfigured range of electromagnetic radiation;
an anchor, said anchor being adapted to attach the apparatus to a native postsynaptic receptor area; and
a linker between said effector, said photoswitch and said anchor, said linker maintaining said effector within a range of the receptor sufficient for said effector to operatively approximate with the receptor when said photoswitch is in said first configuration.

* * * * *